(12) United States Patent
Kim et al.

(10) Patent No.: US 12,103,934 B2
(45) Date of Patent: Oct. 1, 2024

(54) HETEROCYCLIC COMPOUND, ORGANIC LIGHT EMITTING DIODE COMPRISING SAME, COMPOSITION FOR ORGANIC LAYER OF ORGANIC LIGHT EMITTING DIODE, AND METHOD FOR MANUFACTURING ORGANIC LIGHT EMITTING DIODE

(71) Applicant: LT MATERIALS CO., LTD., Yongin (KR)

(72) Inventors: Mi-Jin Kim, Yongin (KR); Jun-Tae Mo, Yongin (KR); Ji-Yoon Byun, Yongin (KR); Yong-Hui Lee, Yongin (KR); Jong-Su Lee, Yongin (KR); Young-Seok No, Yongin (KR); Dong-Jun Kim, Yongin (KR)

(73) Assignee: LT MATERIALS CO., LTD., Yongin-si (KR)

( * ) Notice: Subject to any disclaimer, the term of this patent is extended or adjusted under 35 U.S.C. 154(b) by 647 days.

(21) Appl. No.: 17/282,091

(22) PCT Filed: Oct. 2, 2019

(86) PCT No.: PCT/KR2019/012895
§ 371 (c)(1),
(2) Date: Apr. 1, 2021

(87) PCT Pub. No.: WO2020/071778
PCT Pub. Date: Apr. 9, 2020

(65) Prior Publication Data
US 2021/0395263 A1 Dec. 23, 2021

(30) Foreign Application Priority Data
Oct. 2, 2018 (KR) .................. 10-2018-0117901

(51) Int. Cl.
*C07D 493/00* (2006.01)
*C07D 491/048* (2006.01)
(Continued)

(52) U.S. Cl.
CPC ....... *C07D 493/00* (2013.01); *C07D 491/048* (2013.01); *C07D 513/04* (2013.01);
(Continued)

(58) Field of Classification Search
None
See application file for complete search history.

(56) References Cited

U.S. PATENT DOCUMENTS

| 4,356,429 | A | 10/1982 | Tang |
| 8,652,654 | B2 | 2/2014 | Inoue et al. |

(Continued)

FOREIGN PATENT DOCUMENTS

| CN | 103936653 A | 7/2014 |
| CN | 107250132 A | 10/2017 |

(Continued)

OTHER PUBLICATIONS

International Search Report (PCT/ISA/210) issued in PCT/KR2019/012895 mailed on Jan. 10, 2020.
(Continued)

*Primary Examiner* — Jeffrey D Washville
(74) *Attorney, Agent, or Firm* — Birch, Stewart, Kolasch & Birch, LLP

(57) ABSTRACT

The present specification provides a heterocyclic compound represented by Chemical Formula 1, an organic light emitting device comprising the same, a composition for an organic material layer of an organic light emitting device, and a method for manufacturing an organic light emitting device.

17 Claims, 2 Drawing Sheets

(51) Int. Cl.
*C07D 513/04* (2006.01)
*H10K 50/11* (2023.01)
*H10K 71/00* (2023.01)
*H10K 85/60* (2023.01)
*H10K 101/30* (2023.01)

(52) U.S. Cl.
CPC ......... *H10K 85/626* (2023.02); *H10K 85/654* (2023.02); *H10K 85/6572* (2023.02); *H10K 85/6574* (2023.02); *H10K 50/11* (2023.02); *H10K 71/00* (2023.02); *H10K 2101/30* (2023.02)

(56) References Cited

U.S. PATENT DOCUMENTS

| | | | |
|---|---|---|---|
| 9,876,181 | B2 | 1/2018 | Parham et al. |
| 10,734,588 | B2 | 8/2020 | Park et al. |
| 2015/0060833 | A1 | 3/2015 | Kwon et al. |
| 2017/0062736 | A1* | 3/2017 | Parham ............... H10K 85/6572 |
| 2017/0207399 | A1 † | 7/2017 | Parham |
| 2018/0037548 | A1 | 2/2018 | Sugino et al. |
| 2019/0047991 | A1 | 2/2019 | Jung et al. |
| 2020/0119285 | A1 | 4/2020 | No et al. |
| 2020/0123133 | A1 | 4/2020 | No et al. |
| 2020/0381629 | A1 | 12/2020 | No et al. |
| 2022/0165961 | A1 | 5/2022 | Parham et al. |

FOREIGN PATENT DOCUMENTS

| | | |
|---|---|---|
| CN | 107973786 A | 5/2018 |
| JP | 2017-524707 A | 8/2017 |
| KR | 10-2010-0023783 A | 3/2010 |
| KR | 10-2013-0100264 A | 9/2013 |
| KR | 10-2018-0010144 A | 1/2018 |
| KR | 20180010144 A † | 1/2018 |
| KR | 10-2018-0041607 A | 4/2018 |
| KR | 20180041607 A † | 4/2018 |
| KR | 10-2018-0045798 A | 5/2018 |
| KR | 20180045798 A † | 5/2018 |
| KR | 20180051355 A † | 5/2018 |
| TW | 201141990 A1 | 12/2011 |
| WO | WO 2015/165563 A1 | 11/2015 |
| WO | WO 2018/084423 A2 | 5/2018 |
| WO | WO 2018/092927 A1 | 5/2018 |
| WO | 18174678 A1 † | 9/2018 |
| WO | 18174679 A1 † | 9/2018 |
| WO | 18174681 A1 † | 9/2018 |
| WO | WO 2018/174678 A1 | 9/2018 |
| WO | WO 2018/174679 A1 | 9/2018 |
| WO | WO 2018/174681 A1 | 9/2018 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4" -Tris(3-methylphenylphenylamino)triphenylamine (m-MTDATA), as Hole-Transport Materials", Advanced Materials vol. 6 No. 9 1994 pp. 677-679.

Extended European Search Report for European Application No. 19869166.9, dated Jul. 12, 2022.

European Office Action for Europe App 19889186.9, dated Jan. 24, 2024.

\* cited by examiner
† cited by third party

【FIG. 1】
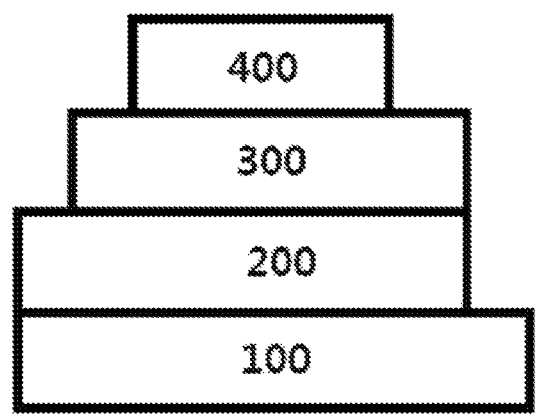
【FIG. 2】
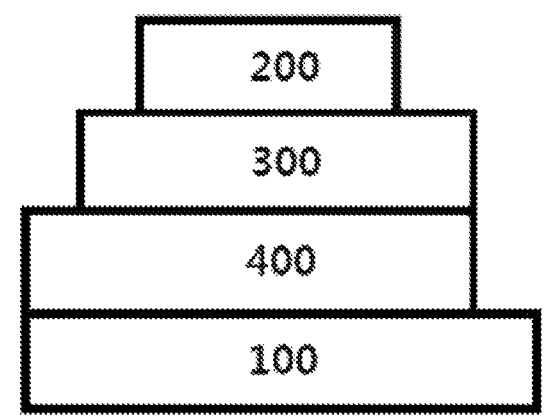

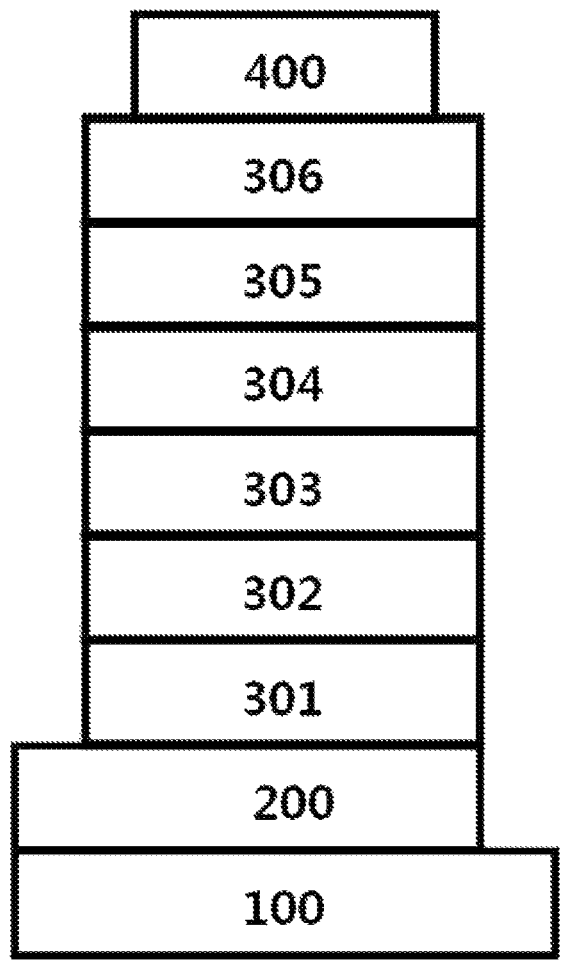
[FIG. 3]

HETEROCYCLIC COMPOUND, ORGANIC LIGHT EMITTING DIODE COMPRISING SAME, COMPOSITION FOR ORGANIC LAYER OF ORGANIC LIGHT EMITTING DIODE, AND METHOD FOR MANUFACTURING ORGANIC LIGHT EMITTING DIODE

TECHNICAL FIELD

This application claims priority to and the benefits of Korean Patent Application No. 10-2018-0117901, filed with the Korean Intellectual Property Office on Oct. 2, 2018, the entire contents of which are incorporated herein by reference. The present specification relates to a heterocyclic compound, an organic light emitting device comprising the same, a composition for an organic material layer of an organic light emitting device, and a method for manufacturing an organic light emitting device.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

Studies on an organic light emitting device comprising a compound capable of satisfying conditions required for materials usable in an organic light emitting device such as a proper energy level, electrochemical stability and thermal stability, and having a chemical structure capable of performing various roles required in an organic light emitting device depending on substituents have been required.

PRIOR ART DOCUMENTS

Patent Documents

U.S. Pat. No. 4,356,429

DISCLOSURE

Technical Problem

The present application relates to a heterocyclic compound, an organic light emitting device comprising the same, a composition for an organic material layer of an organic light emitting device, and a method for manufacturing an organic light emitting device.

Technical Solution

One embodiment of the present application provides a heterocyclic compound represented by the following Chemical Formula 1.

[Chemical Formula 1]

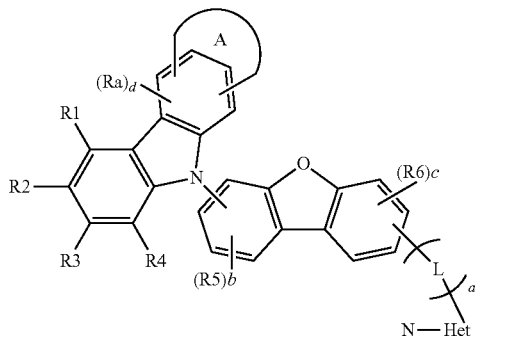

In Chemical Formula 1,

N-Het is a monocyclic or polycyclic heterocyclic group substituted or unsubstituted, and comprising one or more Ns, L is a direct bond; a substituted or unsubstituted arylene group; or a substituted or unsubstituted heteroarylene group, a is an integer of 1 to 3, and when a is 2 or greater, Ls are the same as or different from each other, A is a substituted or unsubstituted aryl ring; or a substituted or unsubstituted heteroaryl ring, Ra is selected from the group consisting of hydrogen; a substituted or unsubstituted aryl group; and a substituted or unsubstituted heteroaryl group, or two or more groups adjacent to each other bond to each other to form a substituted or unsubstituted aliphatic or aromatic hydrocarbon ring or heteroring, d is an integer of 0 to 2, and when d is 2, two or more Ras are the same as or different from each other, and R1 to R6 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, b and c are each an integer of 1 to 3, and when b is 2 or greater, R5s are the same as or different from each other, and when c is 2 or greater, R6s are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise one or more of the heterocyclic compound represented by Chemical Formula 1.

Another embodiment of the present application provides a composition for an organic material layer of an organic light emitting device, the composition comprising the heterocyclic compound of Chemical Formula 1 and a compound represented by the following Chemical Formula 14; or two types of the heterocyclic compound of Chemical Formula 1.

[Chemical Formula 14]

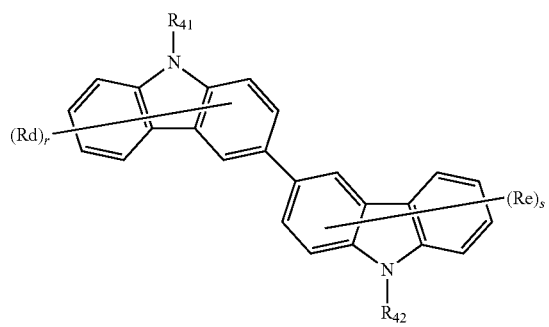

In Chemical Formula 14, $R_1$ and $R_{42}$ are the same as or different from each other, and each independently a substituted or unsubstituted aryl group; or a substituted or unsubstituted heteroaryl group, Rd and Re are the same as or different from each other, and each independently hydrogen; or a substituted or unsubstituted aryl group, and r and s are an integer of 0 to 7.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like in an organic light emitting device. Particularly, the compound can be used as a light emitting layer material of an organic light emitting device. For example, the compound can be used alone as a light emitting material, or the compound can be used as a light emitting material using two compounds together, and can be used as a host material of a light emitting layer.

Particularly, in a compound of Chemical Formula 1, one side benzene ring in the dibenzofuran structure is substituted with an N-containing ring, and the other side benzene ring not substituted with the N-containing ring in the dibenzofuran structure is substituted with a carbazole structure, and as a result, a structure of more stable electron stability is obtained, and proper energy level and thermal stability are provided to a device. Using the compounds of Chemical Formula 1, an organic light emitting device having improved lifetime, driving stability and efficiency can be manufactured.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode Mode for Disclosure Herein, the present application will be described in detail.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

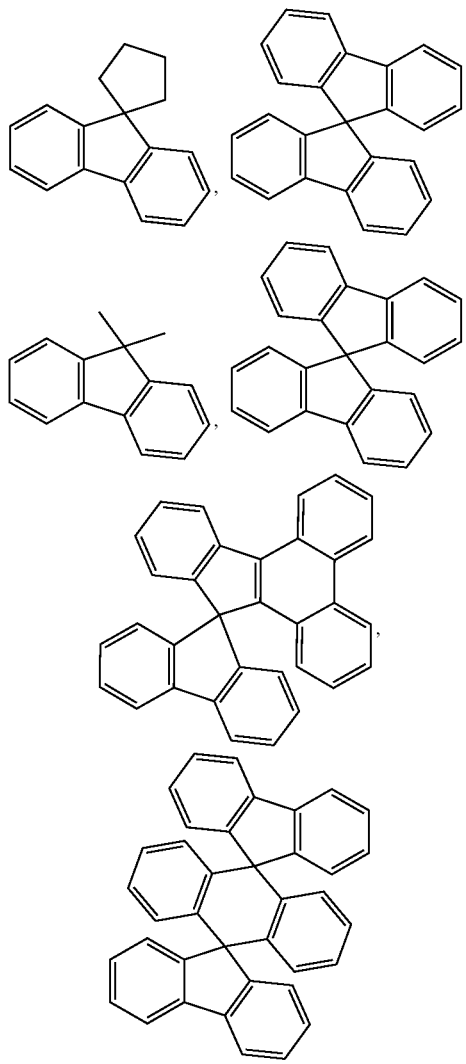

and the like may be included, however, the structure is not limited thereto.

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b] carbazolyl group, an indolinyl group, a 10,11-dihydrodibenzo[b,f]azepine group, a 9,10-dihydroacridinyl group, a phenanthrazinyl group, a phenothiazinyl group, a phthalazinyl group, a naphthylidinyl group, a phenanthrolinyl group, a benzo [c][1,2,5]thiadiazolyl group, a 5,10-dihydrobenzo [b,e][1,4]azasilinyl, a pyrazolo [1,5-c]quinazolinyl group, a pyrido[1,2-b]indazolyl group, a pyrido[1,2-a]imidazo[1,2-e] indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, the phosphine oxide group is represented by —P(=O) R$_{101}$R$_{102}$, and R$_{101}$ and R$_{102}$ are the same as or different from each other and may be each independently a substituted formed with at least one of hydrogen; deuterium; a halogen group; an alkyl group; an alkenyl group; an alkoxy group; a cycloalkyl group; an aryl group; and a heterocyclic group. Specific examples of the phosphine oxide group may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that adjacent groups may form, the structures included as examples of the cycloalkyl group, the cycloheteroalkyl group, the aryl group and the heteroaryl group described above may be used except for those that are not monovalent.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R''; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

In one embodiment of the present application, Chemical Formula 1 may be represented by one of the following Chemical Formulae 2 to 5.

[Chemical Formula 2]

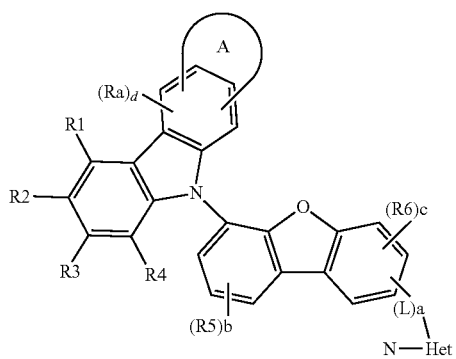

[Chemical Formula 3]

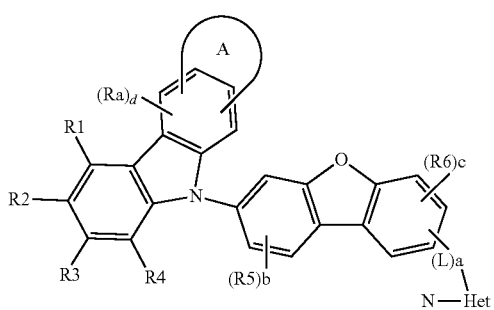

[Chemical Formula 4]

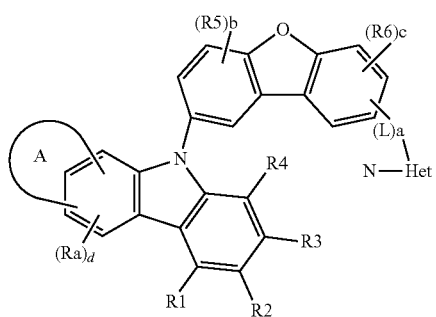

[Chemical Formula 5]

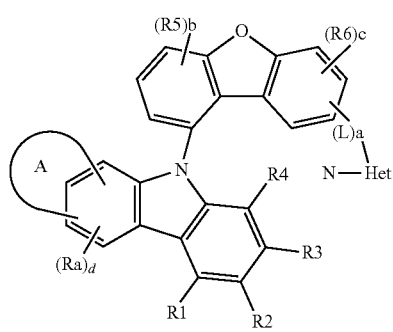

In Chemical Formulae 2 to 5,

N-Het, L, A, Ra, R1 to R6, a, b, c and d have the same definitions as in Chemical Formula 1.

In one embodiment of the present application, Chemical Formula 1 may be represented by any one of the following Chemical Formulae 6 to 13.

[Chemical Formula 6]

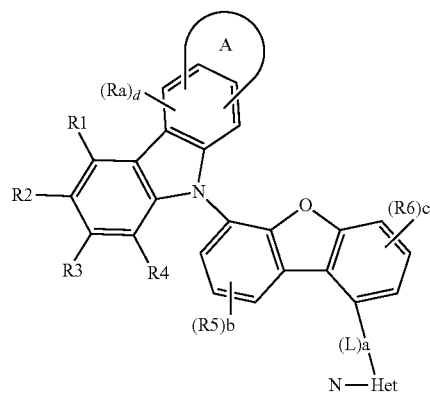

[Chemical Formula 7]

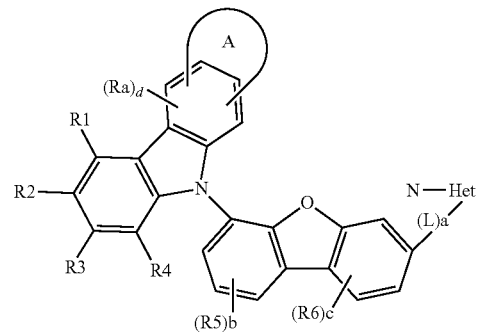

[Chemical Formula 8]

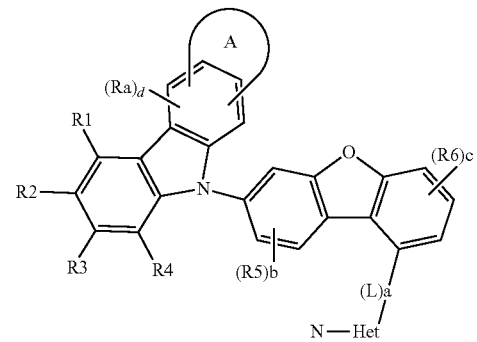

[Chemical Formula 9]

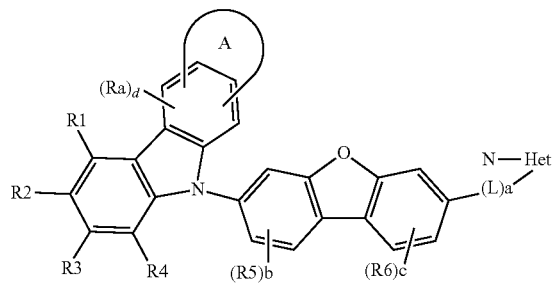

-continued
[Chemical Formula 10]
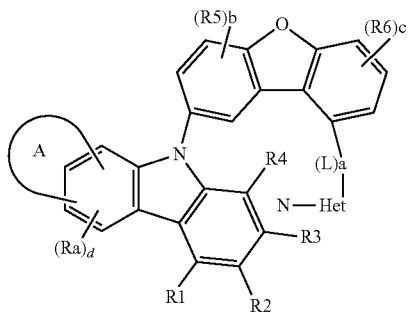
[Chemical Formula 11]
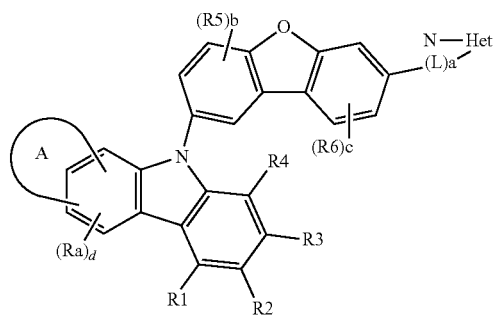
[Chemical Formula 12]
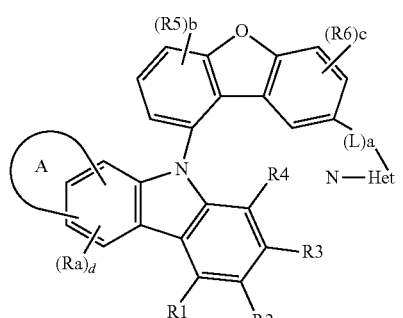
[Chemical Formula 13]
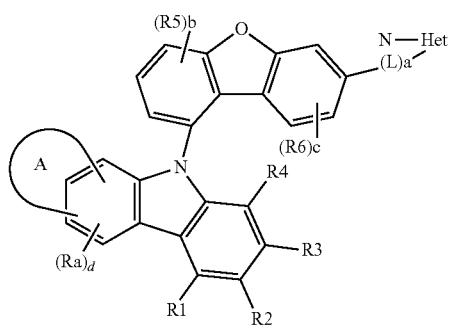
In Chemical Formulae 6 to 13,
N-Het, L, A, Ra, R1 to R6, a, b, c and d have the same definitions as in Chemical Formula 1.
In one embodiment of the present application, R3 R4
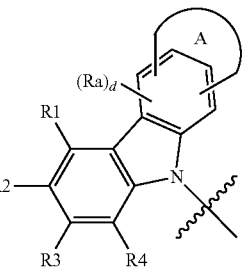
may be represented by any one of the following Chemical Formulae 1-1 to 1-5.
[Chemical Formula 1-1]
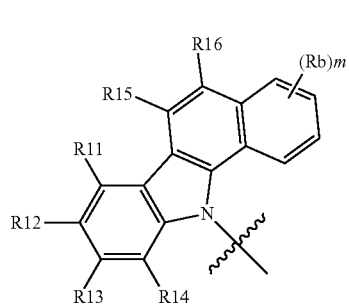
[Chemical Formula 1-2]
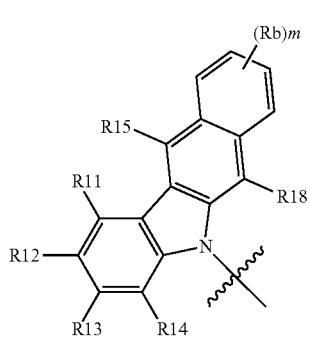
[Chemical Formula 1-3]
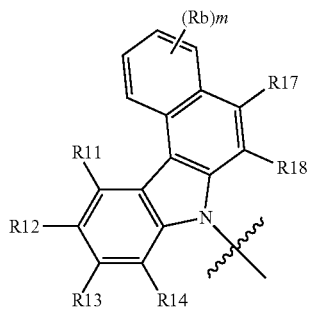

[Chemical Formula 1-4]

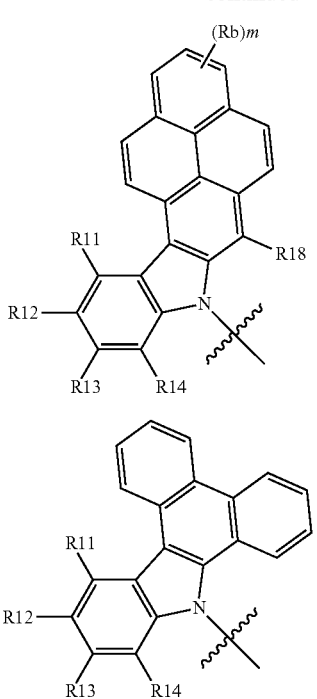

[Chemical Formula 1-5]

In Chemical Formulae 1-1 to 1-5,

R11 to R14 are the same as or different from each other, and each independently selected from the group consisting of hydrogen; a substituted or unsubstituted alkyl group; a substituted or unsubstituted aryl group; and a substituted or unsubstituted heteroaryl group, or two or more groups adjacent to each other bond to each other to form a substituted or unsubstituted aliphatic or aromatic hydrocarbon ring or heteroring, R15 to R18 are the same as or different from each other, and each independently hydrogen; a substituted or unsubstituted alkyl group; a substituted or unsubstituted aryl group or a substituted or unsubstituted heteroaryl group, and Rb is selected from the group consisting of hydrogen; and a substituted or unsubstituted aryl group, or two or more groups adjacent to each other bond to each other to form a substituted or unsubstituted aliphatic or aromatic hydrocarbon ring or heteroring, m is an integer of 1 to 4, n is an integer of 1 to 3, and when m and n are 2 or greater, Rbs are the same as or different from each other.

In Chemical Formulae 1-1 to 1-5,

means a position linked to Chemical Formula 1.

In one embodiment of the present application, N-Het is a monocyclic or polycyclic heteroring substituted or unsubstituted, and comprising one or more Ns.

In another embodiment, N-Het is a monocyclic or polycyclic heteroring unsubstituted or substituted with one or more substituents selected from the group consisting of an aryl group and a heteroaryl group, and comprising one or more Ns.

In another embodiment, N-Het is a monocyclic or polycyclic C2 to C60 heteroring unsubstituted or substituted with one or more substituents selected from the group consisting of a C6 to C60 aryl group, and comprising one or more Ns.

In another embodiment, N-Het a monocyclic or polycyclic C2 to C60 heteroring unsubstituted or substituted with one or more substituents selected from the group consisting of a C6 to C60 aryl group, and comprising one or more and three or less Ns.

In another embodiment, N-Het is a monocyclic or polycyclic C2 to C40 heteroring unsubstituted or substituted with one or more substituents selected from the group consisting of a C6 to C40 aryl group, and comprising one or more and 3 or less Ns.

In another embodiment, N-Het is a monocyclic or polycyclic heteroring unsubstituted or substituted with one or more substituents selected from the group consisting of a phenyl group, a biphenyl group and a naphthyl group, and comprising one or more Ns.

In another embodiment, N-Het is a monocyclic or polycyclic heteroring unsubstituted or substituted with one or more substituents selected from the group consisting of a phenyl group, a biphenyl group and a naphthyl group, and comprising one or more and three or less Ns.

In another embodiment, N-Het may be a triazine group unsubstituted or substituted with one or more substituents selected from the group consisting of a phenyl group, a biphenyl group and a naphthyl group; benzo[4,5]thieno[3,2-d]pyrimidine unsubstituted or substituted with one or more substituents selected from the group consisting of a phenyl group, a biphenyl group and a naphthyl group; benzofuro[3,2-d]pyrimidine unsubstituted or substituted with one or more substituents selected from the group consisting of a phenyl group, a biphenyl group and a naphthyl group; benzofuro[2,3-d]pyrimidine unsubstituted or substituted with one or more substituents selected from the group consisting of a phenyl group, a biphenyl group and a naphthyl group; or benzo [4,5]thieno [3,2-d]pyrimidine unsubstituted or substituted with one or more substituents selected from the group consisting of a phenyl group, a biphenyl group and a naphthyl group.

In one embodiment of the present application, N-Het may be represented by any one of the following Chemical Formulae 2-1 to 2-3.

[Chemical Formula 2-1]

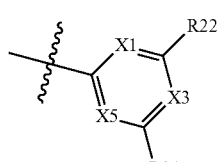

[Chemical Formula 2-2]

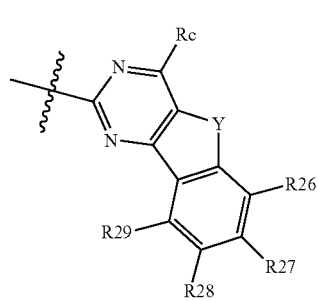

-continued

[Chemical Formula 2-3]

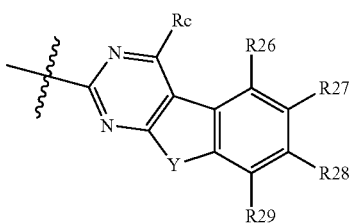

In Chemical Formulae 2-1 to 2-3,
X1 is N or CR21, X3 is N or CR23, and X5 is N or CR25, at least one of X1 to X3 is N,
Y is O; or S,
Rc is hydrogen; or a substituted or unsubstituted aryl group, and
R21 to R29 are the same as or different from each other, and each independently hydrogen; a substituted or unsubstituted alkyl group; a substituted or unsubstituted aryl group; or a substituted or unsubstituted heteroaryl group.

In Chemical Formulae 2-1 to 2-3,

means a position linked to L of Chemical Formula 1.

In one embodiment of the present application, Chemical Formula 2-1 may be selected from among the following structural formulae.

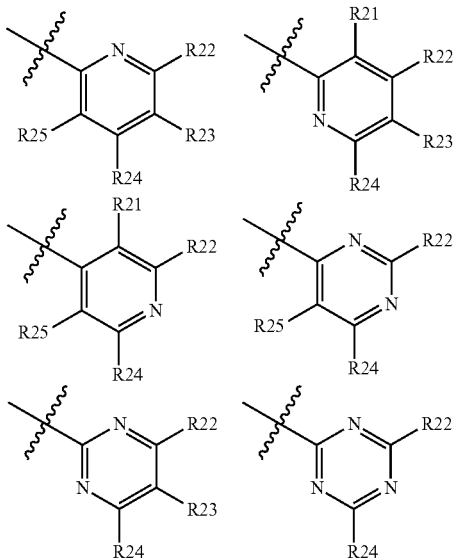

In the structural formulae,
R21 to R25 have the same definitions as in Chemical Formula 2-1.

In one embodiment of the present application, L may be a direct bond; a substituted or unsubstituted arylene group; or a substituted or unsubstituted heteroarylene group.

In another embodiment, L may be a direct bond; a substituted or unsubstituted C6 to C60 arylene group; or a substituted or unsubstituted C2 to C60 heteroarylene group.

In another embodiment, L may be a direct bond; a substituted or unsubstituted C6 to C40 arylene group; or a substituted or unsubstituted C2 to C40 heteroarylene group.

In another embodiment, L may be a direct bond; a C6 to C40 arylene group; or a C2 to C40 heteroarylene group.

In another embodiment, L may be a direct bond.

In one embodiment of the present application, A may be a substituted or unsubstituted aryl ring; or a substituted or unsubstituted heteroaryl ring.

In another embodiment, A may be a substituted or unsubstituted C6 to C60 aryl ring; or a substituted or unsubstituted C2 to C60 heteroaryl ring.

In another embodiment, A may be a substituted or unsubstituted C6 to C40 aryl ring; or a substituted or unsubstituted C2 to C40 heteroaryl ring.

In another embodiment, A may be a substituted or unsubstituted C6 to C40 aryl ring.

In another embodiment, A may be a substituted or unsubstituted benzene ring or a substituted or unsubstituted naphthyl ring.

In one embodiment of the present application, A having a substituted or unsubstituted C6 to C40 aryl ring means comprising an unsubstituted C6 to C40 aryl ring; or a substituted C6 to C40 aryl ring, and substituents in the substituted C6 to C40 aryl ring comprises a fused type obtained by bonding to adjacent groups.

In other words, the substituted C6 to C40 aryl ring may have a substituent in a fused ring type by bonding to Ra in Chemical Formula 1.

In one embodiment of the present application, Ra is selected from the group consisting of hydrogen; a substituted or unsubstituted aryl group; and a substituted or unsubstituted heteroaryl group, or two or more groups adjacent to each other may bond to each other to form a substituted or unsubstituted aliphatic or aromatic hydrocarbon ring or heteroring.

In another embodiment, Ra is selected from the group consisting of hydrogen; a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aromatic hydrocarbon ring.

In another embodiment, Ra is selected from the group consisting of hydrogen; and a substituted or unsubstituted C6 to C60 aryl group, or two or more groups adjacent to each other may bond to each other to form a substituted or unsubstituted C6 to C60 aromatic hydrocarbon ring.

In another embodiment, Ra is selected from the group consisting of hydrogen; and a substituted or unsubstituted C6 to C40 aryl group, or two or more groups adjacent to each other may bond to each other to form a substituted or unsubstituted C6 to C40 aromatic hydrocarbon ring.

In another embodiment, Ra is selected from the group consisting of hydrogen; and a C6 to C40 aryl group, or two or more groups adjacent to each other may bond to each other to form a C6 to C40 aromatic hydrocarbon ring.

In another embodiment, Ra is hydrogen; a phenyl group; a biphenyl group; a naphthyl group; or an anthracenyl group, or two or more groups adjacent to each other may bond to each other to form a benzene ring.

In one embodiment of the present application, R1 to R4 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic or aromatic hydrocarbon ring or heteroring.

In another embodiment, R1 to R4 are the same as or different from each other, and each independently selected from the group consisting of hydrogen; a substituted or unsubstituted aryl group; and a substituted or unsubstituted heteroaryl group, or two or more groups adjacent to each other may bond to each other to form a substituted or unsubstituted aliphatic or aromatic hydrocarbon ring or heteroring.

In another embodiment, R1 to R4 are the same as or different from each other, and each independently selected from the group consisting of hydrogen; and a substituted or unsubstituted C6 to C60 aryl group, or two or more groups adjacent to each other may bond to each other to form a substituted or unsubstituted C6 to C60 aromatic hydrocarbon ring.

In another embodiment, R1 to R4 are the same as or different from each other, and each independently selected from the group consisting of hydrogen; and a substituted or unsubstituted C6 to C40 aryl group, or two or more groups adjacent to each other may bond to each other to form a substituted or unsubstituted C6 to C40 aromatic hydrocarbon ring.

In another embodiment, R1 to R4 are the same as or different from each other, and each independently selected from the group consisting of hydrogen; and a C6 to C40 aryl group, or two or more groups adjacent to each other may bond to each other to form a C6 to C40 aromatic hydrocarbon ring.

In another embodiment, R1 to R4 are the same as or different from each other, and each independently selected from the group consisting of hydrogen; and a phenyl group, or two or more groups adjacent to each other may bond to each other to form benzene ring.

In one embodiment of the present application, R5 and R6 may be hydrogen.

In one embodiment of the present application, R11 to R14 are the same as or different from each other, and each independently selected from the group consisting of hydrogen; a substituted or unsubstituted alkyl group; a substituted or unsubstituted aryl group; and a substituted or unsubstituted heteroaryl group, or two or more groups adjacent to each other may bond to each other to form a substituted or unsubstituted aliphatic or aromatic hydrocarbon ring or heteroring.

In another embodiment, R11 to R14 are the same as or different from each other, and each independently selected from the group consisting of hydrogen; and a substituted or unsubstituted C6 to C60 aryl group, or two or more groups adjacent to each other may bond to each other to form a substituted or unsubstituted C6 to C60 aromatic hydrocarbon ring.

In another embodiment, R11 to R14 are the same as or different from each other, and each independently selected from the group consisting of hydrogen; and a substituted or unsubstituted C6 to C40 aryl group, or two or more groups adjacent to each other may bond to each other to form a substituted or unsubstituted C6 to C40 aromatic hydrocarbon ring.

In another embodiment, R11 to R14 are the same as or different from each other, and each independently selected from the group consisting of hydrogen; and a C6 to C40 aryl group, or two or more groups adjacent to each other may bond to each other to form a C6 to C40 aromatic hydrocarbon ring.

In another embodiment, R11 to R14 are the same as or different from each other, and each independently selected from the group consisting of hydrogen; and a phenyl group, or two or more groups adjacent to each other may bond to each other to form a benzene ring.

In one embodiment of the present application, R15 to R18 are the same as or different from each other, and may be each independently hydrogen; a substituted or unsubstituted alkyl group; a substituted or unsubstituted aryl group; or a substituted or unsubstituted heteroaryl group.

In another embodiment, R15 to R18 are the same as or different from each other, and may be each independently hydrogen; or a substituted or unsubstituted C6 to C60 aryl group.

In another embodiment, R15 to R18 are the same as or different from each other, and may be each independently hydrogen; or a substituted or unsubstituted C6 to C40 aryl group.

In another embodiment, R15 to R18 are the same as or different from each other, and may be each independently hydrogen; or a C6 to C40 aryl group.

In another embodiment, R15 to R18 are the same as or different from each other, and may be each independently hydrogen; or a C6 to C20 aryl group.

In another embodiment, R15 to R18 are the same as or different from each other, and may be each independently hydrogen; or a phenyl group.

In one embodiment of the present application, Rb is selected from the group consisting of hydrogen; and a substituted or unsubstituted aryl group, or two or more groups adjacent to each other may bond to each other to form a substituted or unsubstituted aliphatic or aromatic hydrocarbon ring or heteroring.

In another embodiment, Rb is hydrogen, or two or more groups adjacent to each other may bond to each other to form an aromatic hydrocarbon ring.

In another embodiment, Rb is hydrogen, or two or more groups adjacent to each other may bond to each other to form a benzene ring.

In one embodiment of the present application, Rc may be hydrogen; or a substituted or unsubstituted aryl group.

In another embodiment, Rc may be hydrogen; or a substituted or unsubstituted C6 to C60 aryl group.

In another embodiment, Rc may be hydrogen; or a substituted or unsubstituted C6 to C40 aryl group.

In another embodiment, Rc may be hydrogen; or a C6 to C40 aryl group.

In another embodiment, Rc may be hydrogen; or a C6 to C40 monocyclic or polycyclic aryl group.

In another embodiment, Rc may be hydrogen; or a C6 to C40 monocyclic aryl group.

In another embodiment, Rc may be hydrogen; a phenyl group; a biphenyl group; or a naphthyl group.

In one embodiment of the present application, R26 to R29 are the same as or different from each other, and may be each independently hydrogen; a substituted or unsubstituted alkyl group; a substituted or unsubstituted aryl group; or a substituted or unsubstituted heteroaryl group.

In another embodiment, R26 to R29 are the same as or different from each other, and may be each independently hydrogen; or a substituted or unsubstituted aryl group.

In another embodiment, R26 to R29 are the same as or different from each other, and may be each independently hydrogen; or a substituted or unsubstituted C6 to C60 aryl group.

In another embodiment, R26 to R29 may be hydrogen.

In one embodiment of the present application, R22 and R24 are the same as or different from each other, and may be each independently hydrogen; or a substituted or unsubstituted aryl group.

In another embodiment, R22 and R24 are the same as or different from each other, and may be each independently hydrogen; or a substituted or unsubstituted C6 to C60 aryl group.

In another embodiment, R22 and R24 are the same as or different from each other, and may be each independently hydrogen; or a substituted or unsubstituted C6 to C40 aryl group.

In another embodiment, R22 and R24 are the same as or different from each other, and may be each independently hydrogen; or a C6 to C40 aryl group.

In another embodiment, R22 and R24 are the same as or different from each other, and may be each independently hydrogen; a phenyl group; a biphenyl group; or a naphthyl group.

In one embodiment of the present application, X1, X3 and X5 may be N.

In one embodiment of the present application, at least two of X1, X3 and X5 may be N.

According to one embodiment of the present application, Chemical Formula 1 may be represented by any one of the following compounds, but is not limited thereto.

1

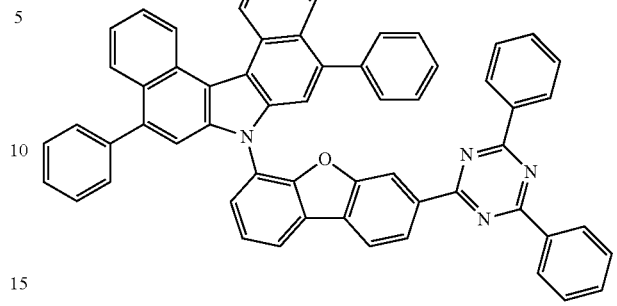

2

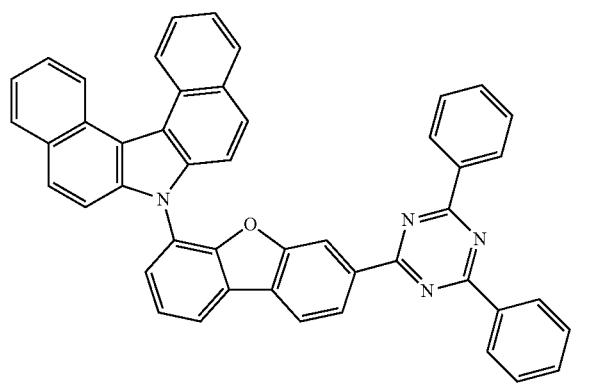

-continued

3

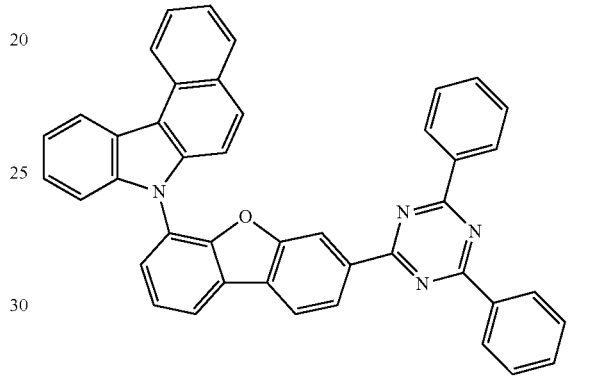

4

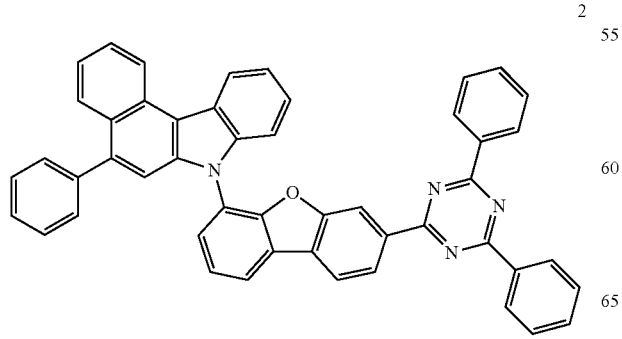

5

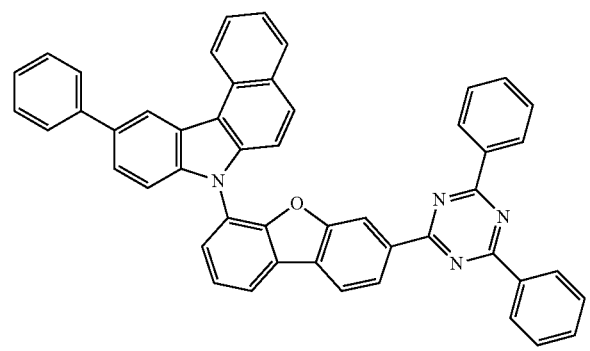

6

7
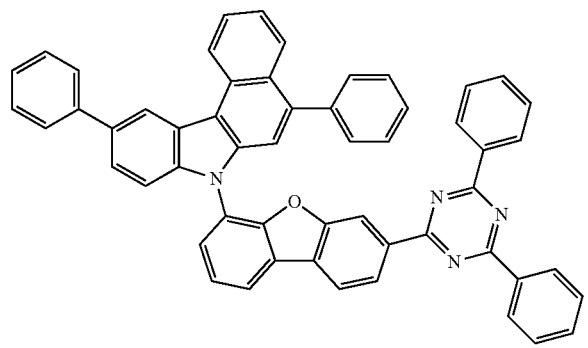
11
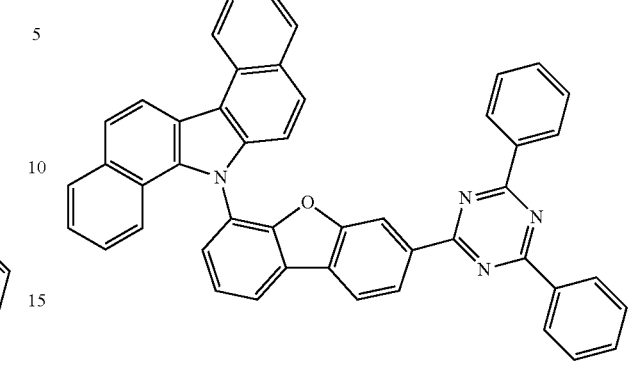
8
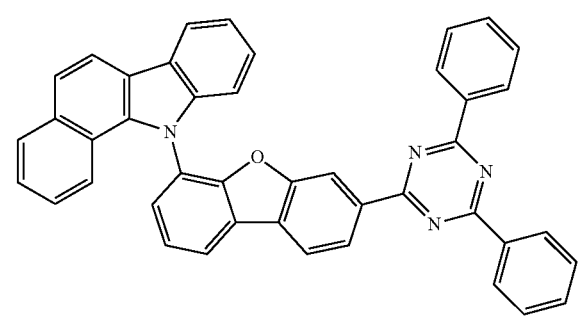
12
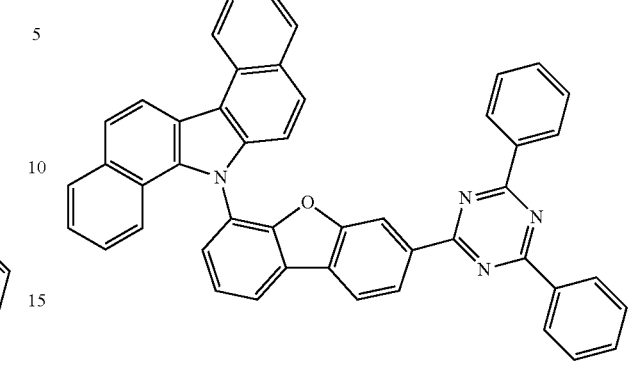
9
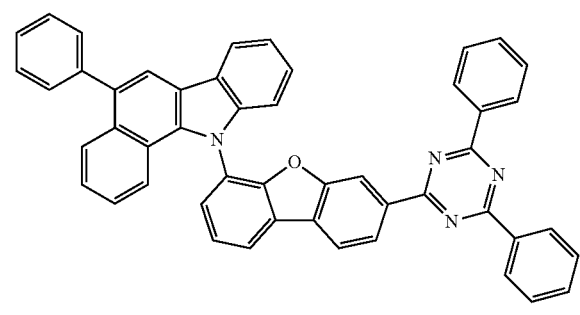
13
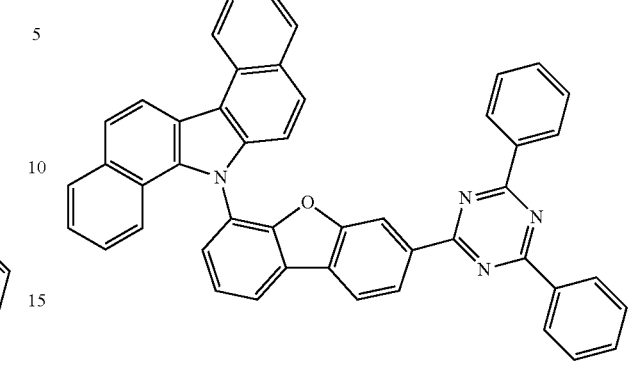
10
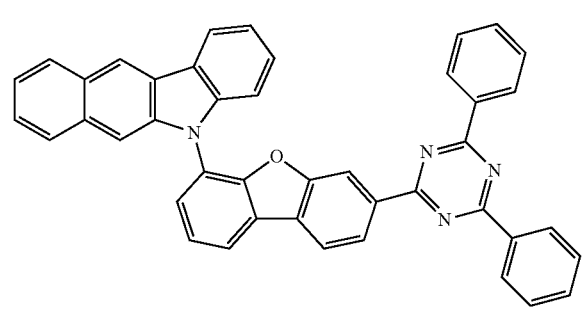
14
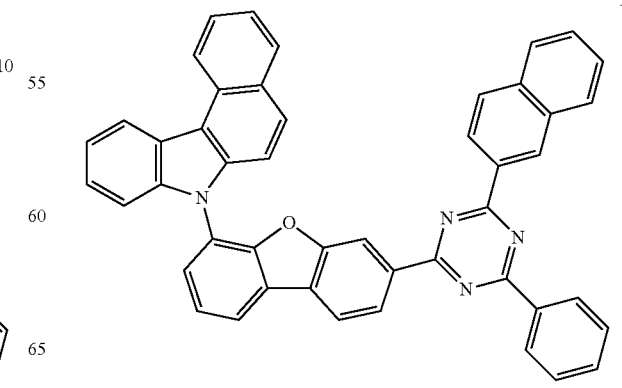

15
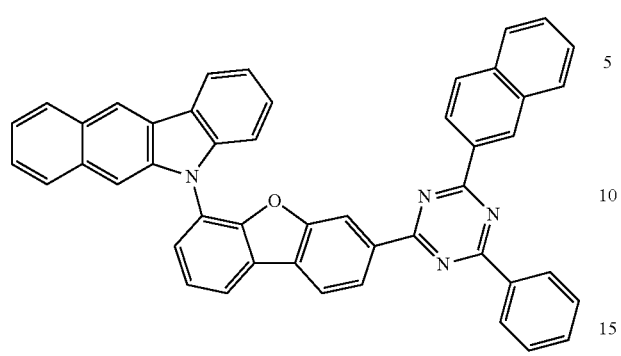
16
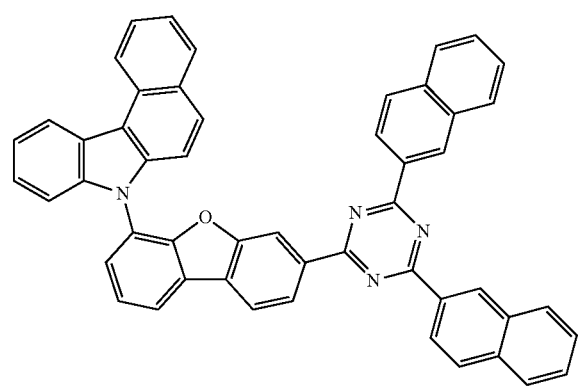
17
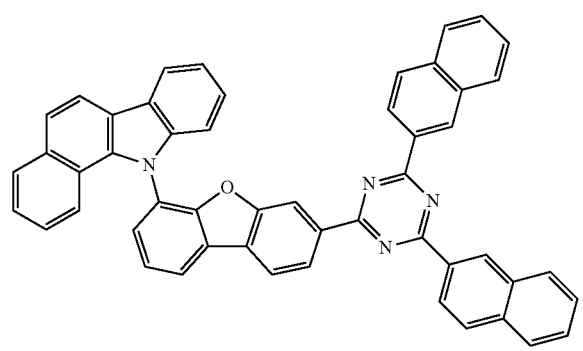
18
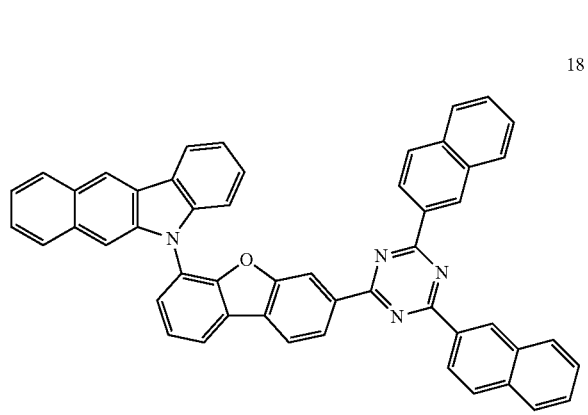
19
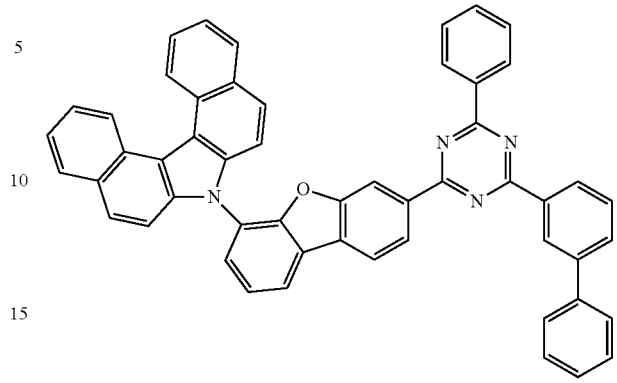
20
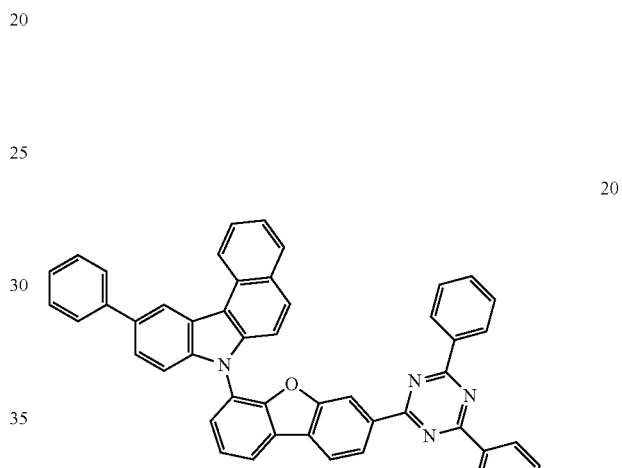
21
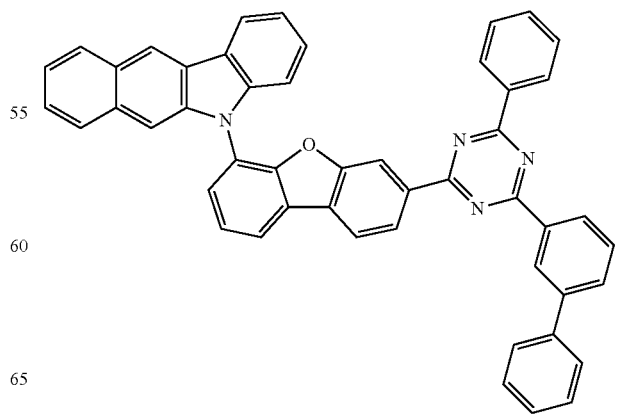

22
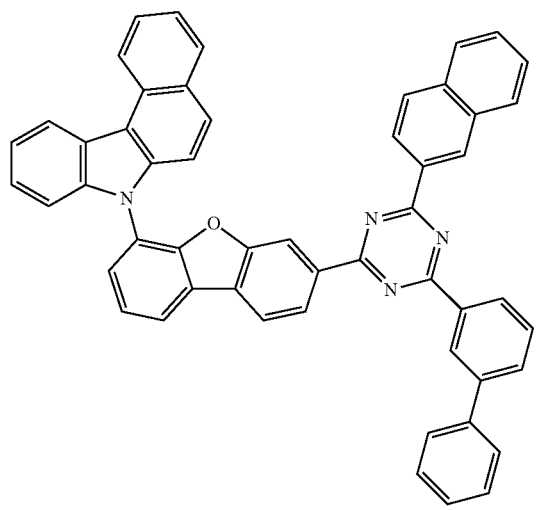
23
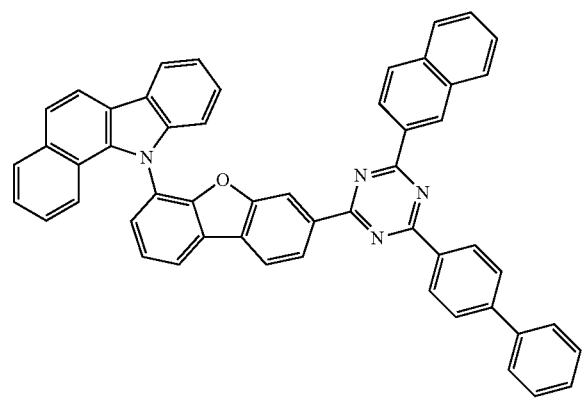
24
25
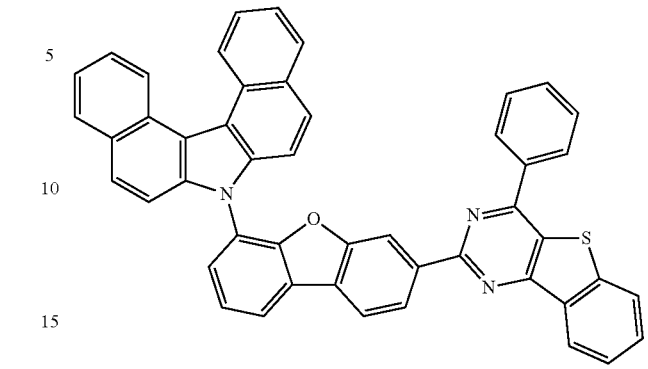
26
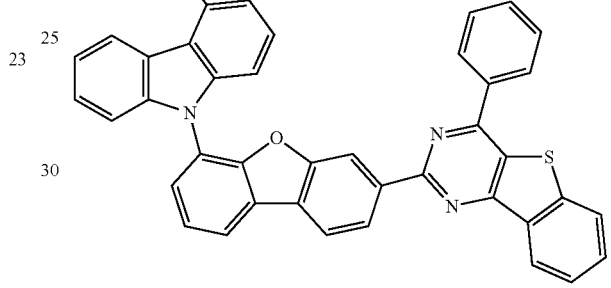
27
28
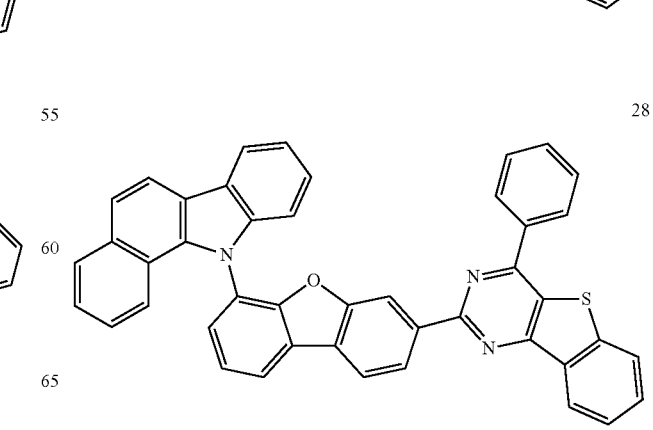

29
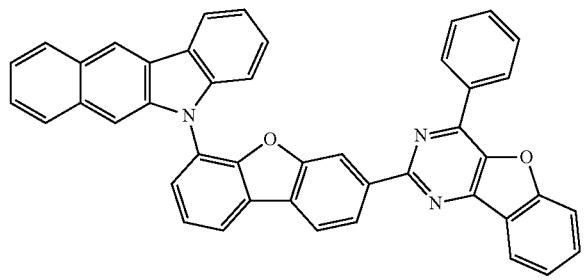
30
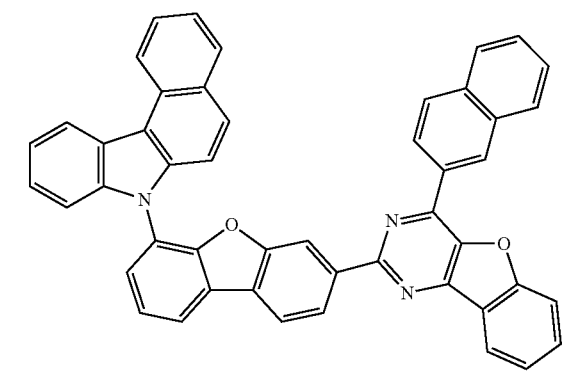
31
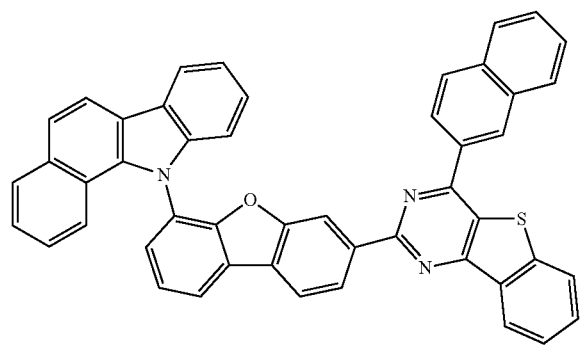
32
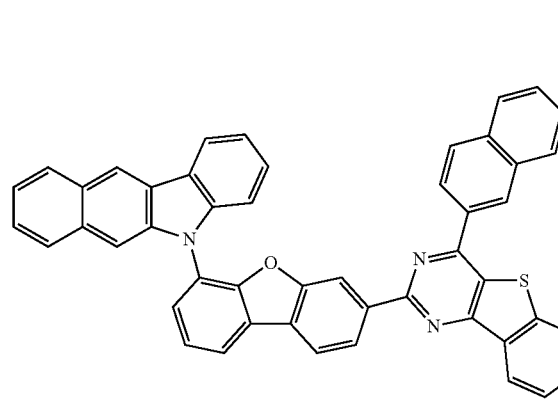
33
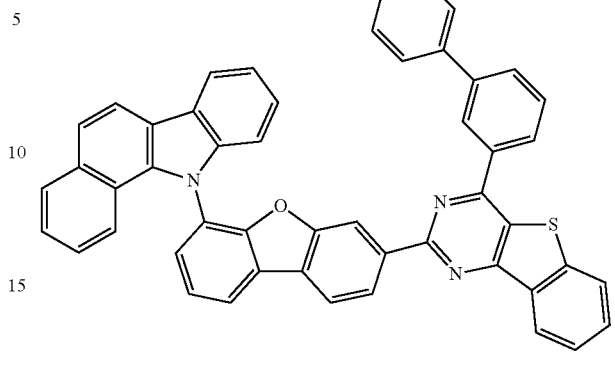
34
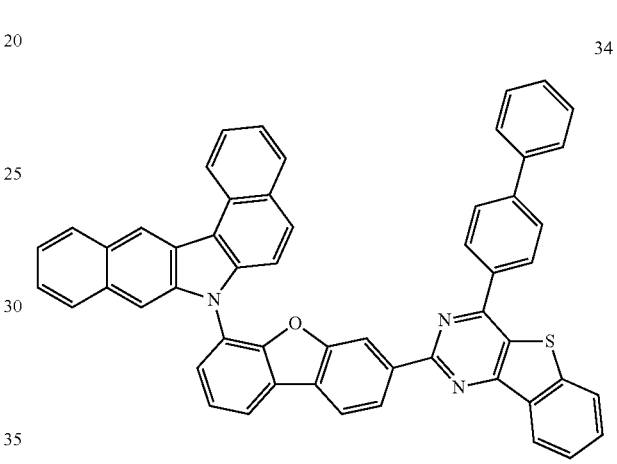
35
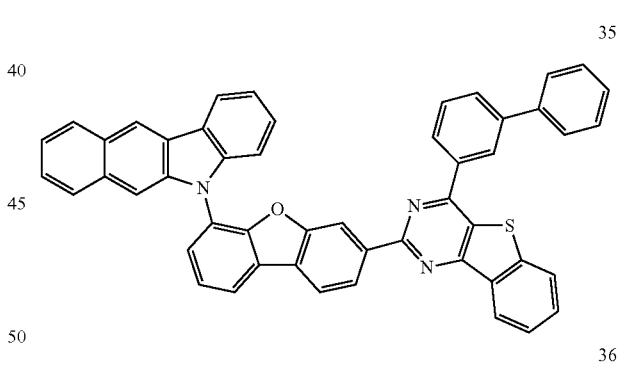
36
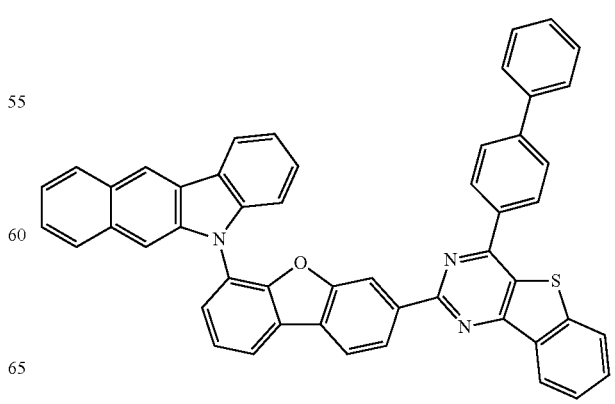

37
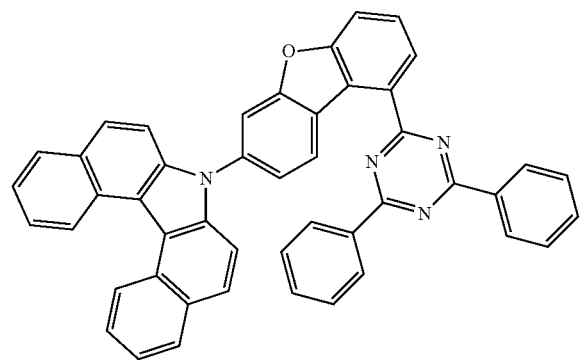
38
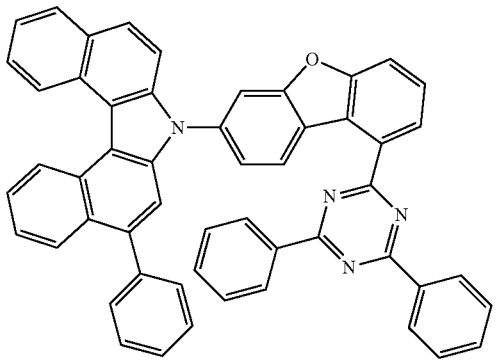
39
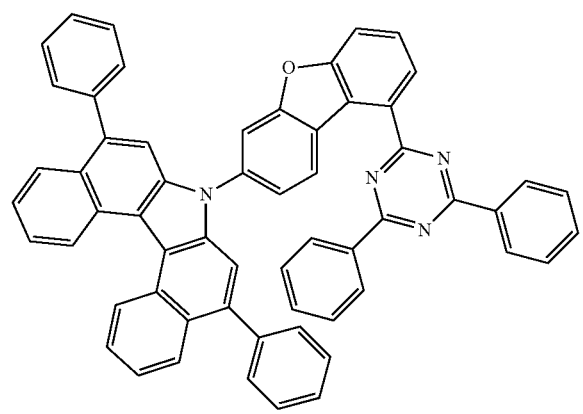
40
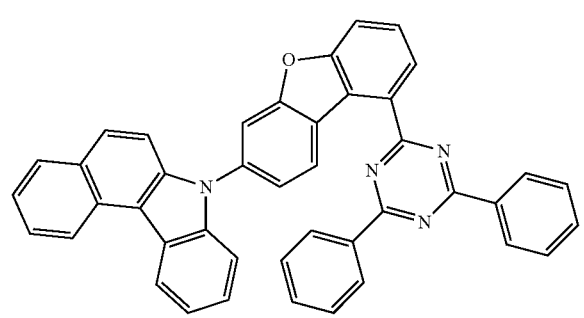
41
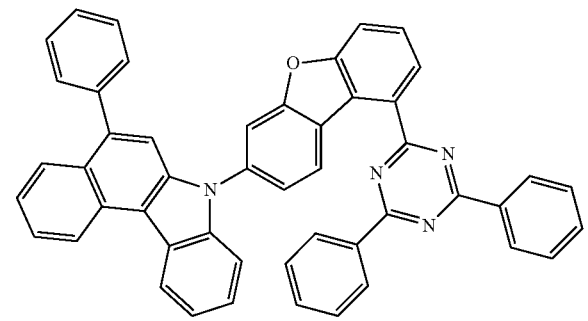
42
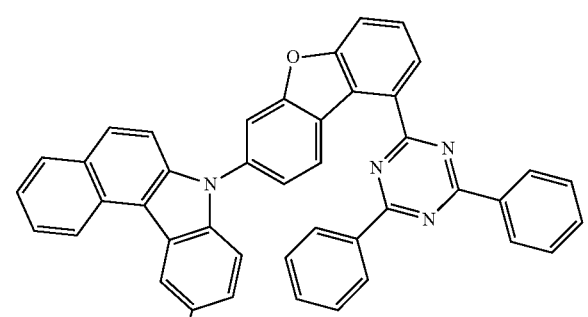
43
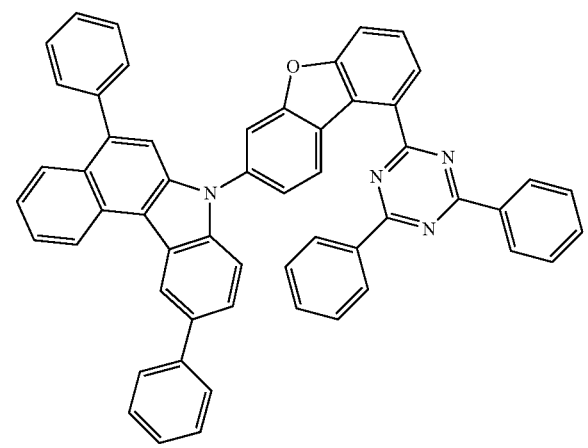

44
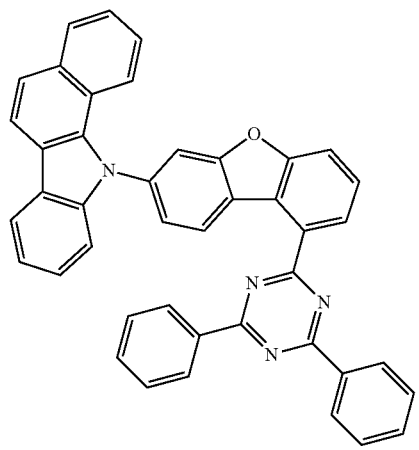
45
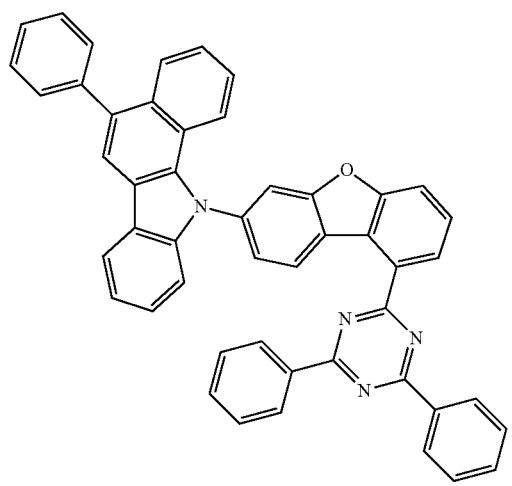
46
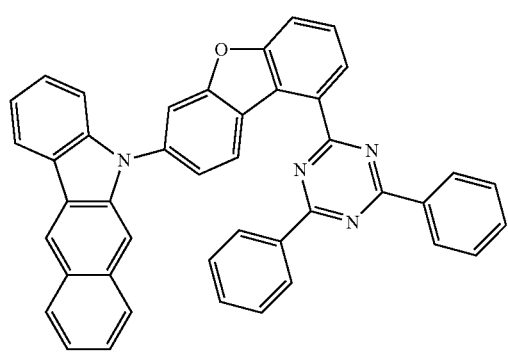
47
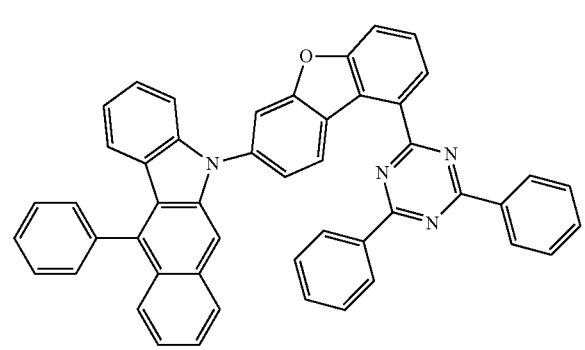
48
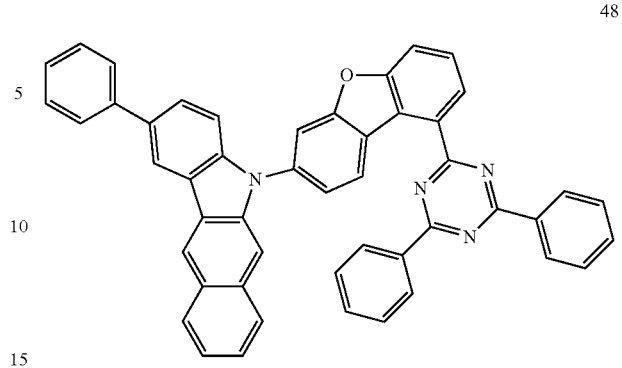
49
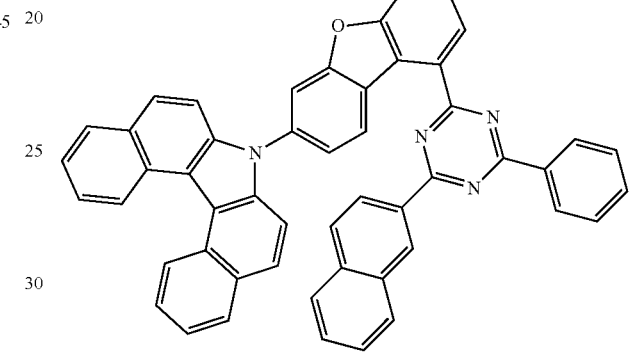
50
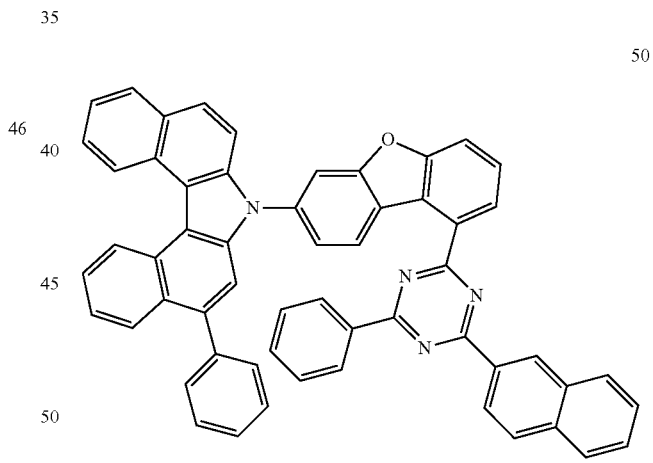
51
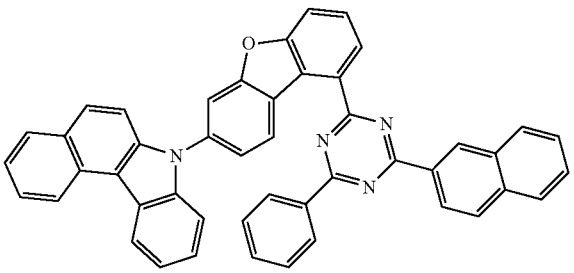

52
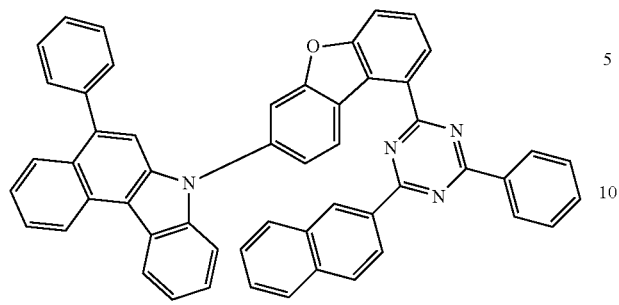
53
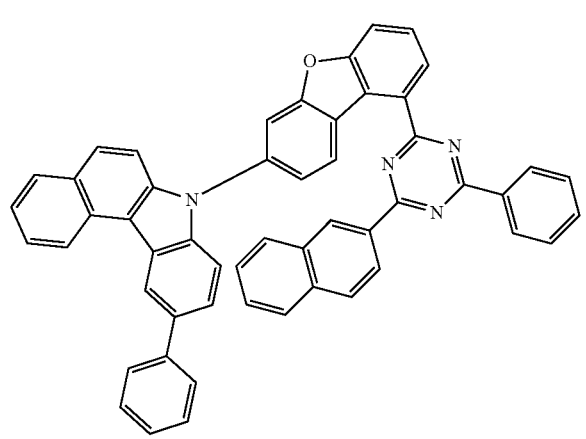
54
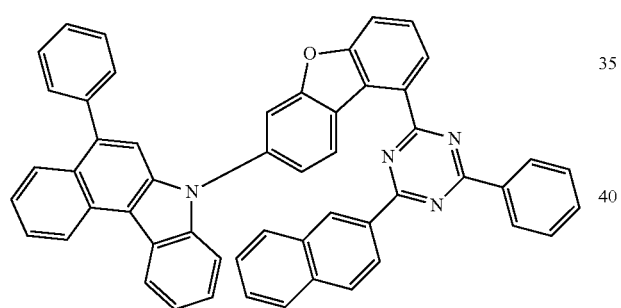
55
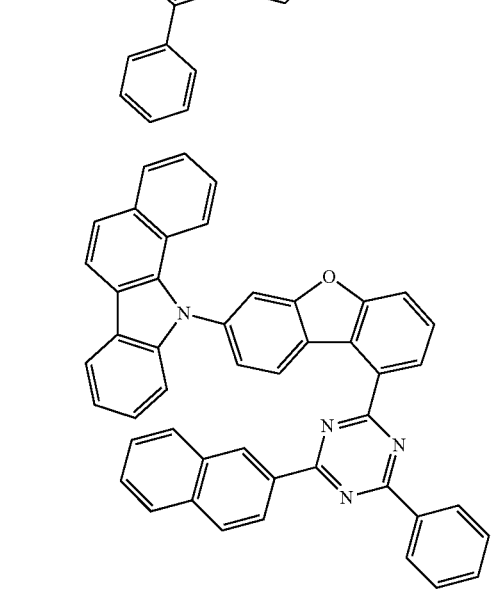
56
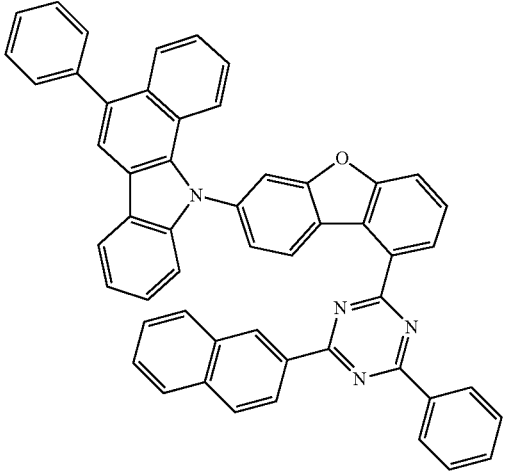
57
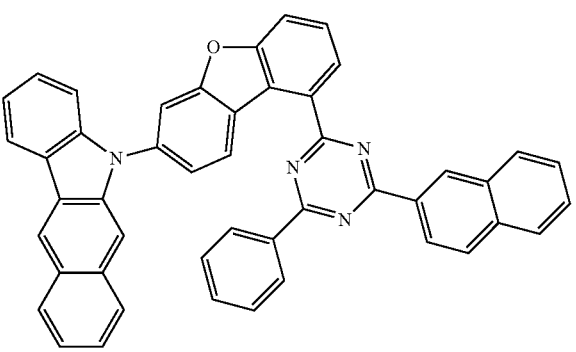
58
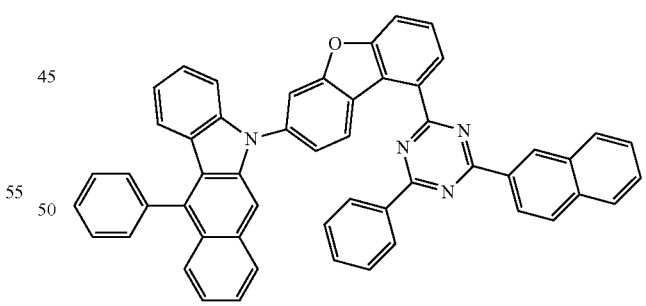
59
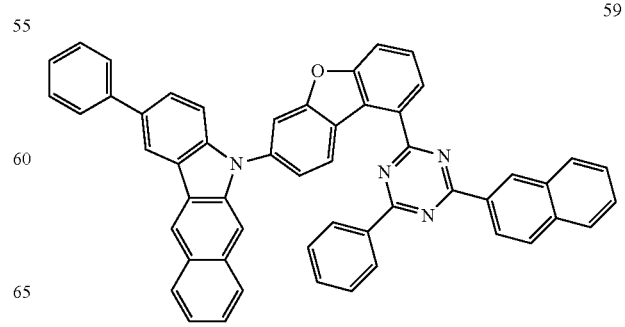

60
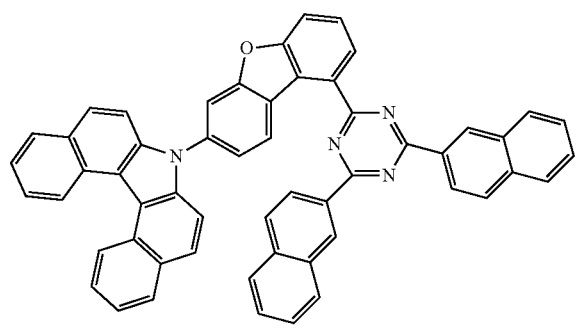
61
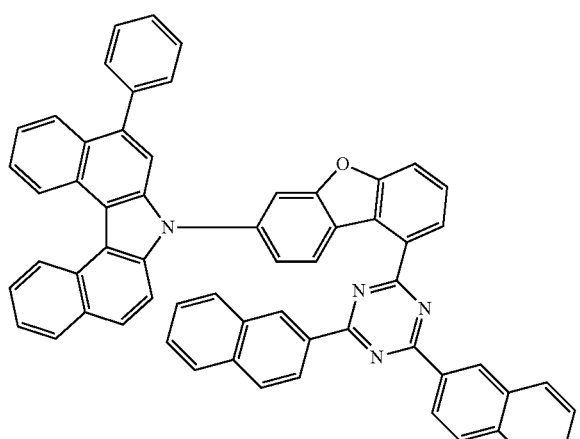
62
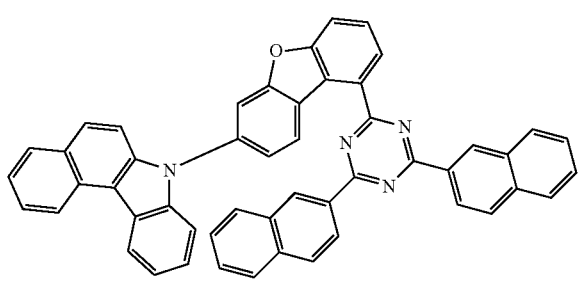
63
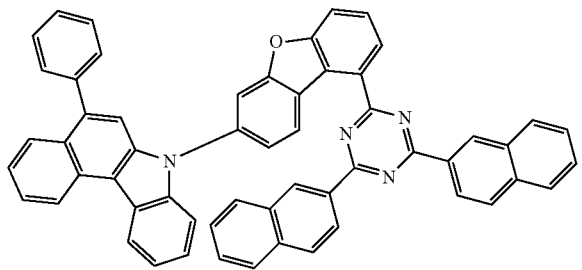
64
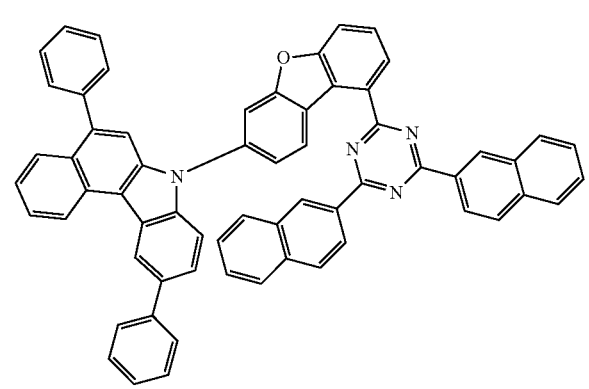
65
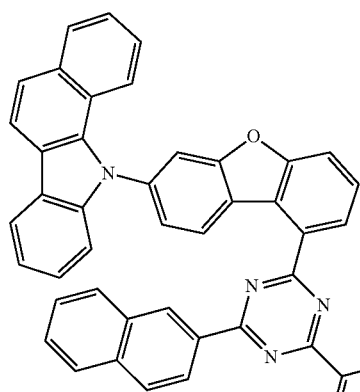
66
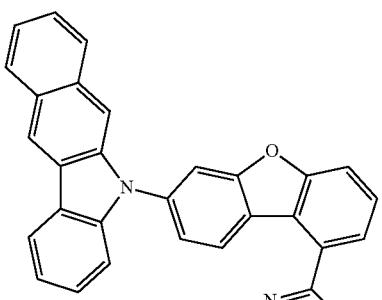
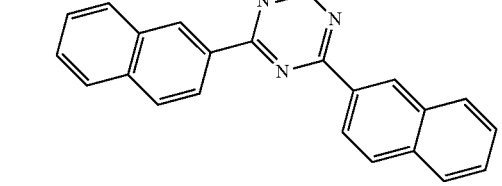

67
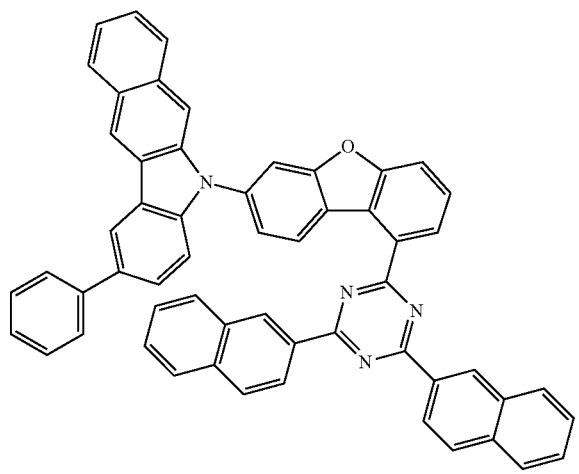
68
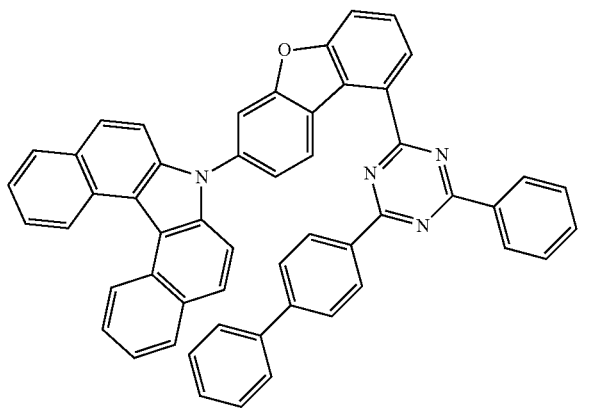
69
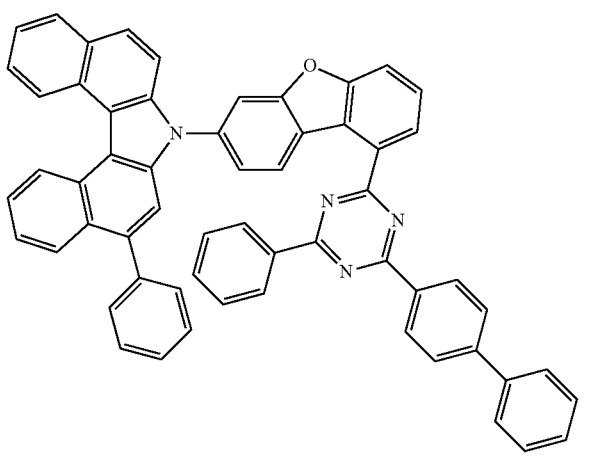
70
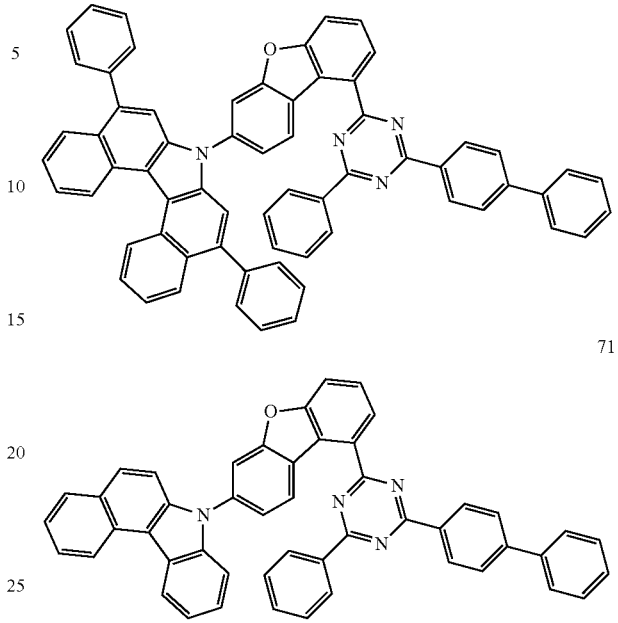
71
72
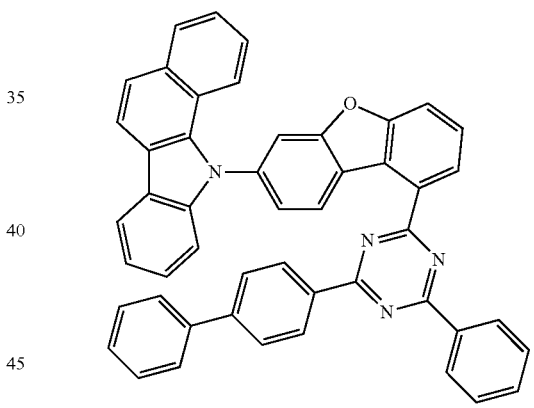
73
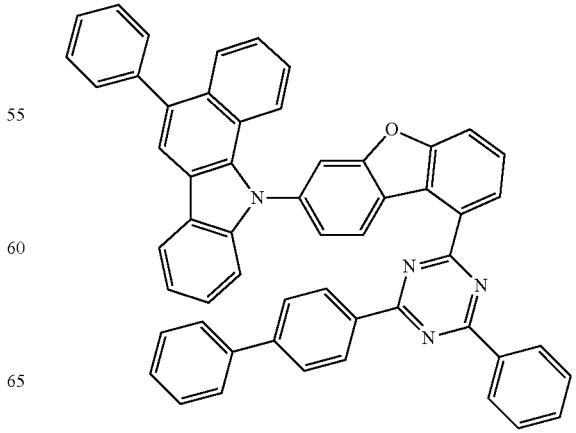

74
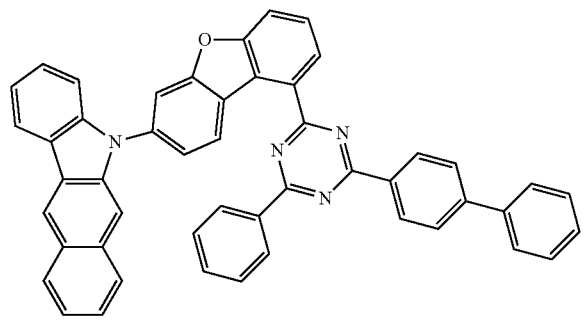
75
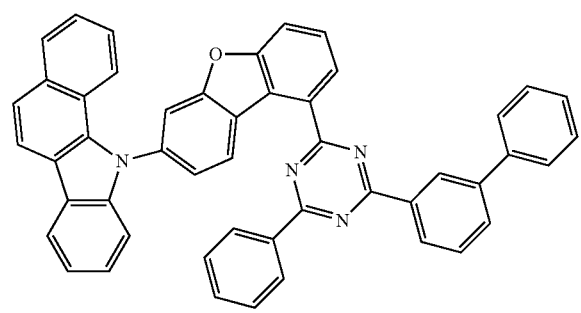
76
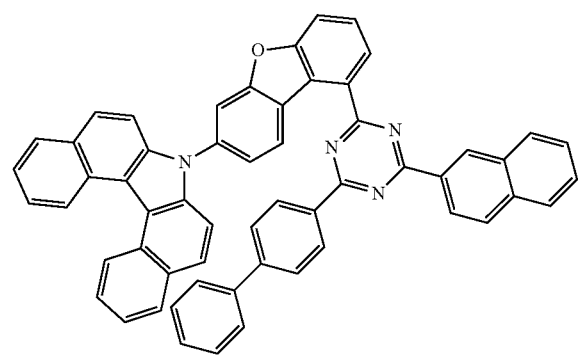
77
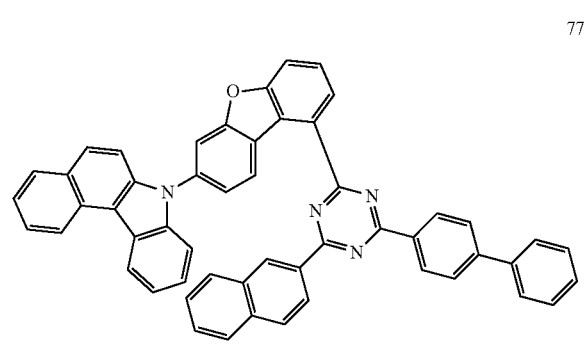
78
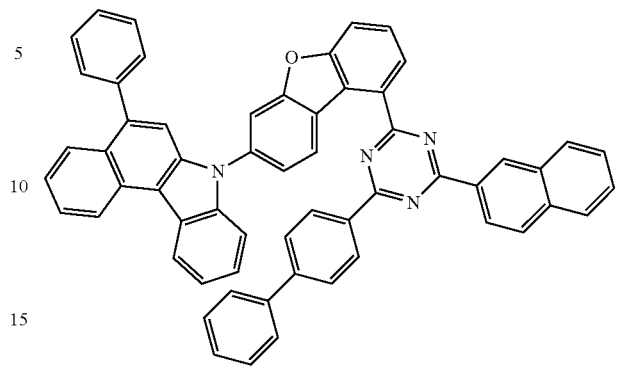
79
80
81
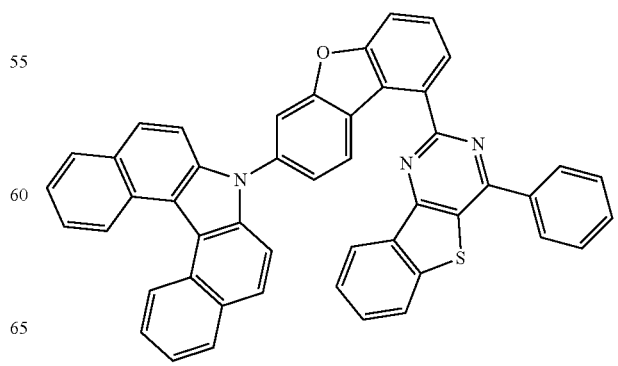

82
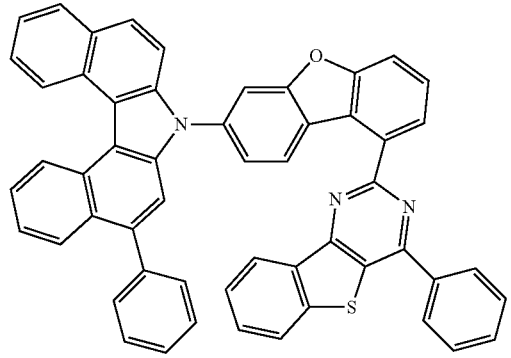
83
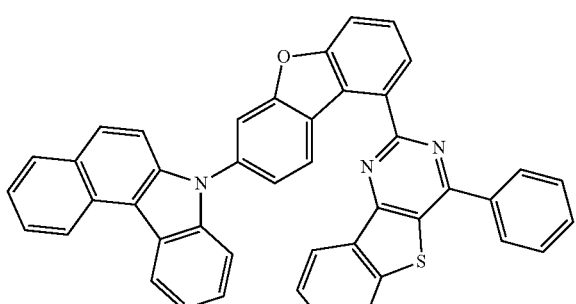
84
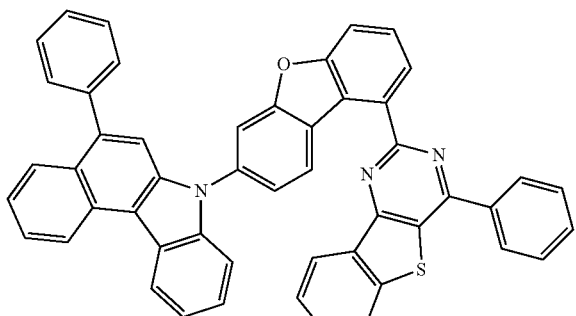
85
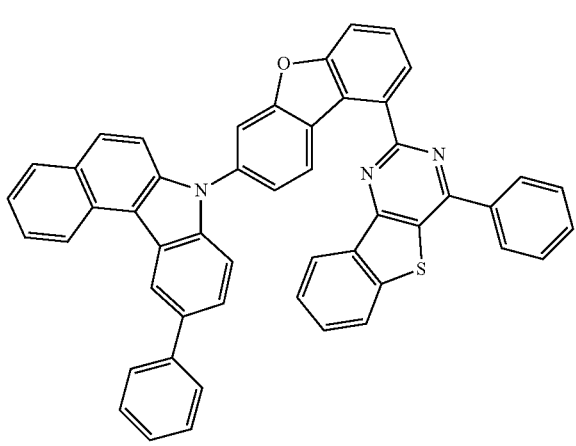
86
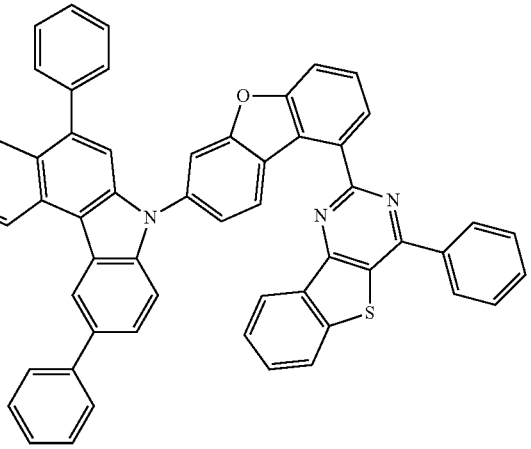
87
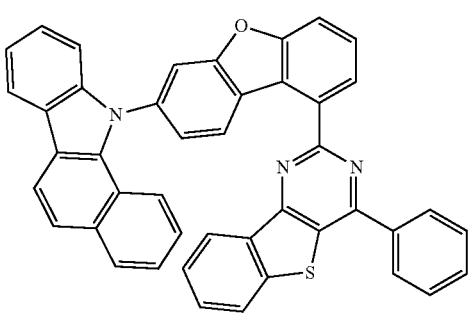
88
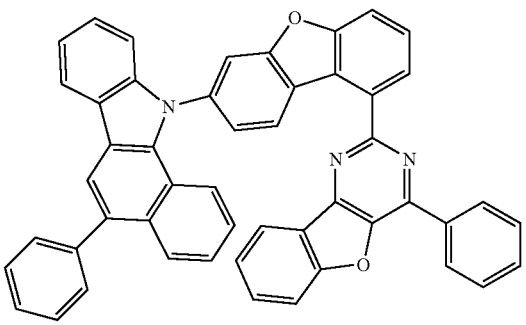
89
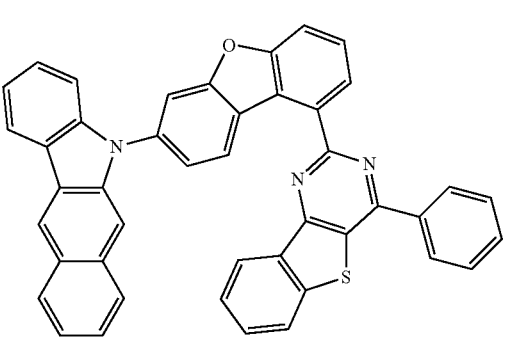

43
-continued
90
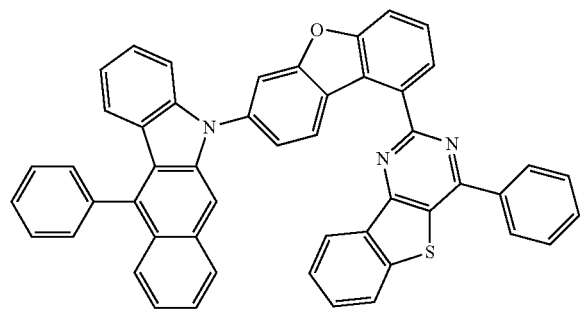
91
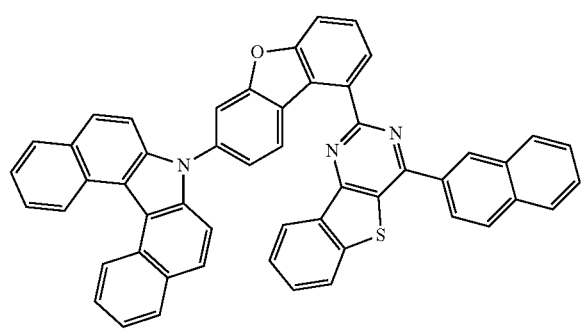
92
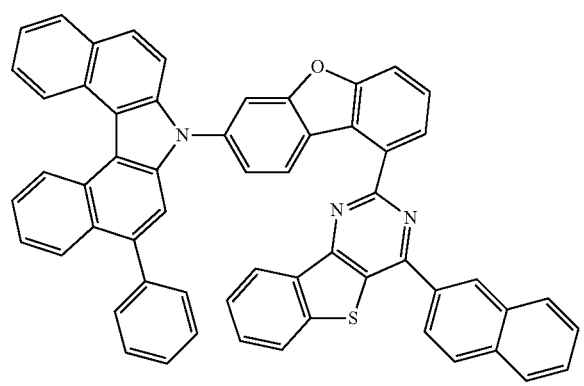
93
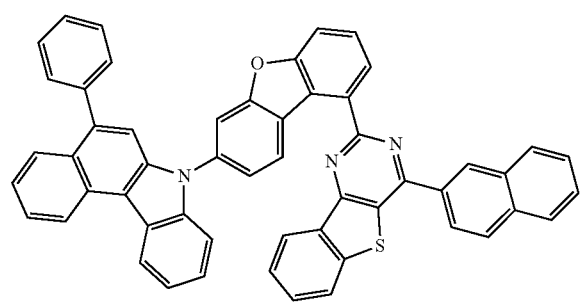
44
-continued
94
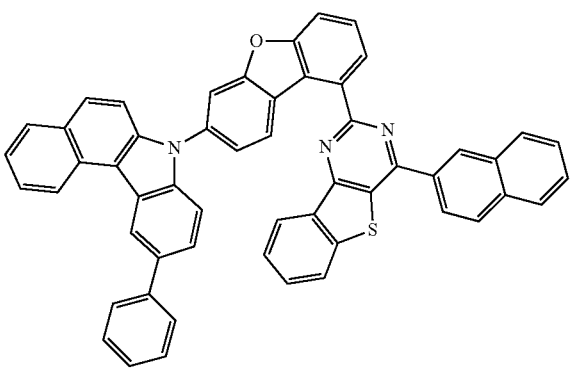
95
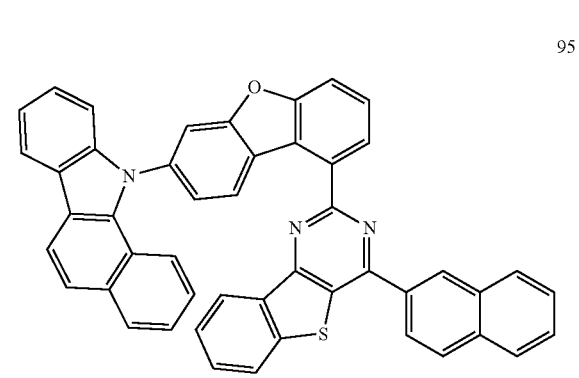
96
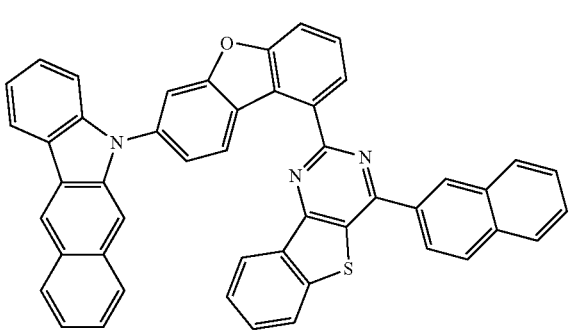
97
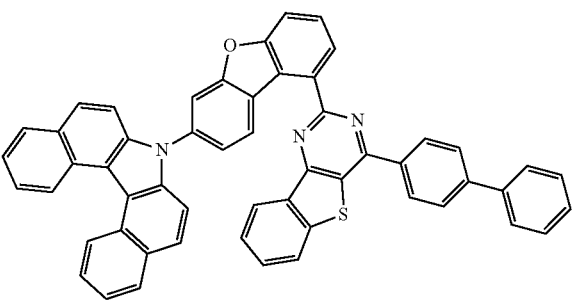

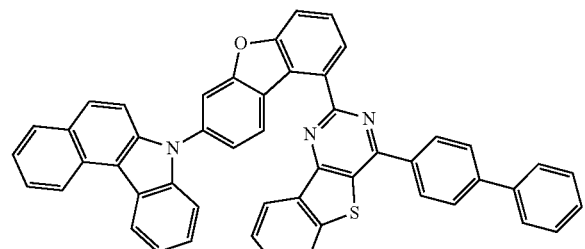
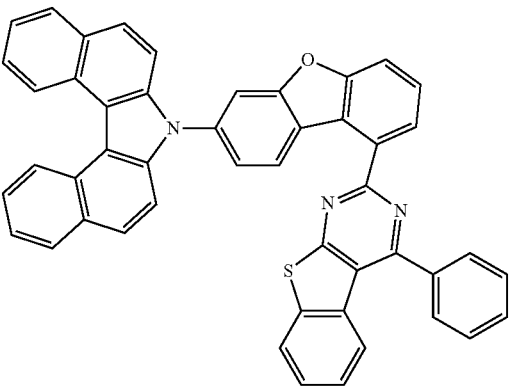
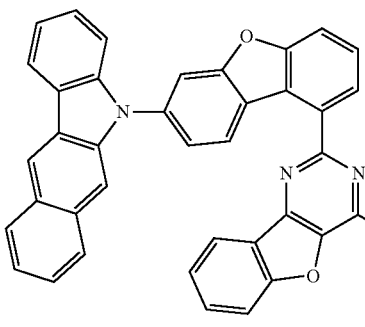
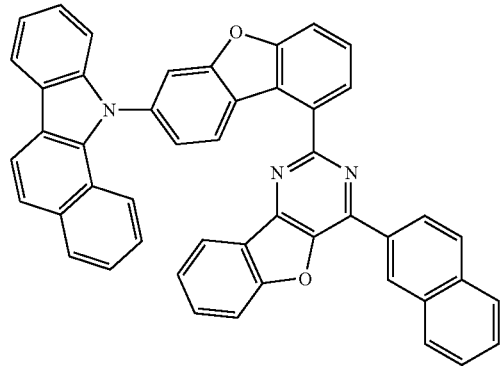
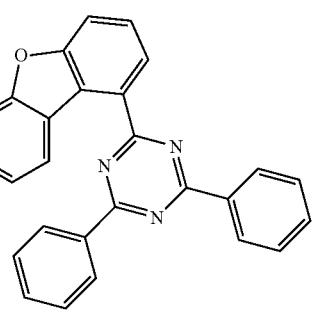

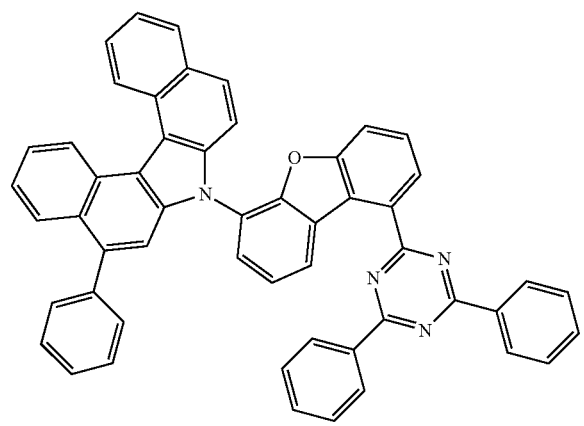
106
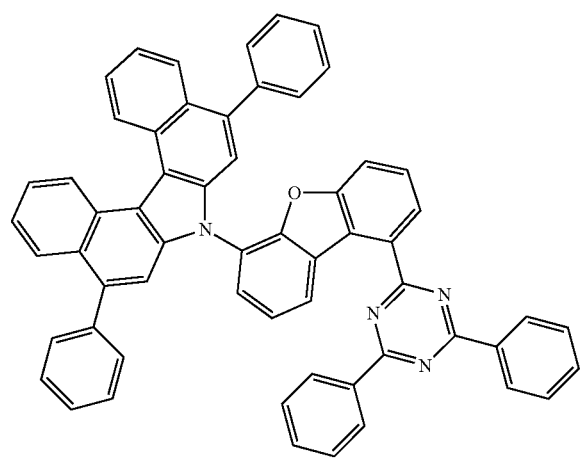
107
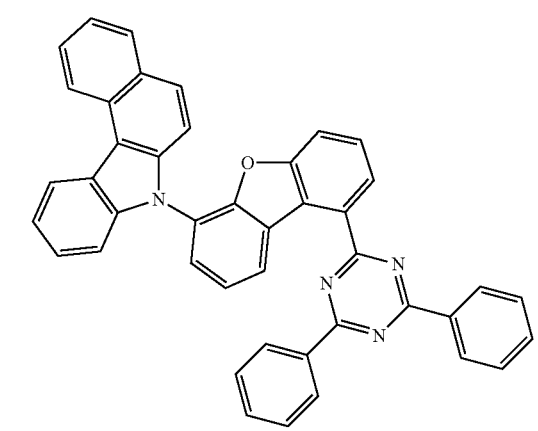
108
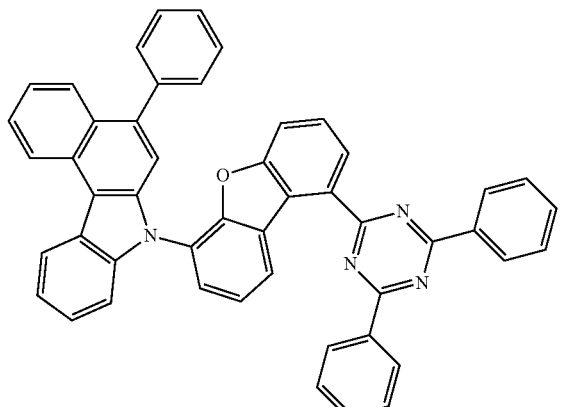
109
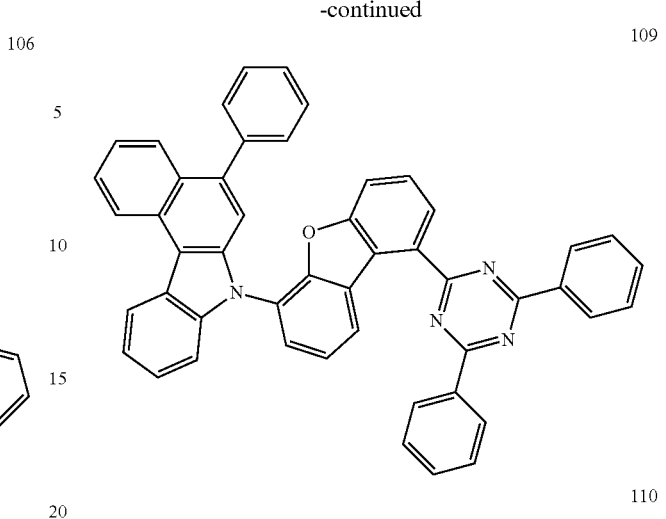
110
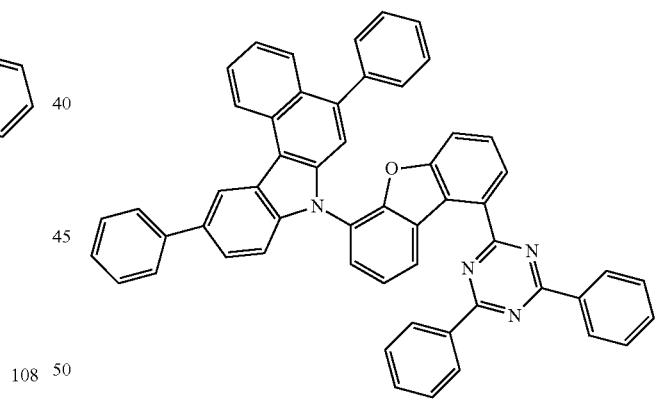
111
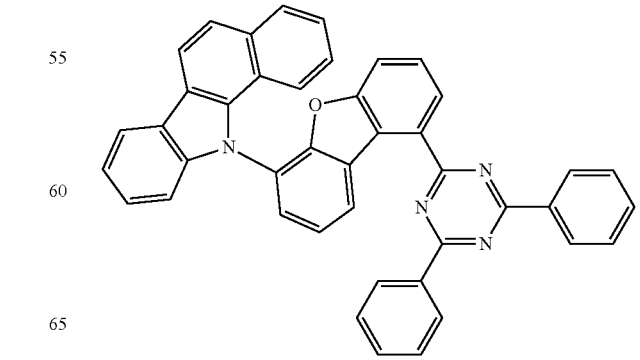
112

113
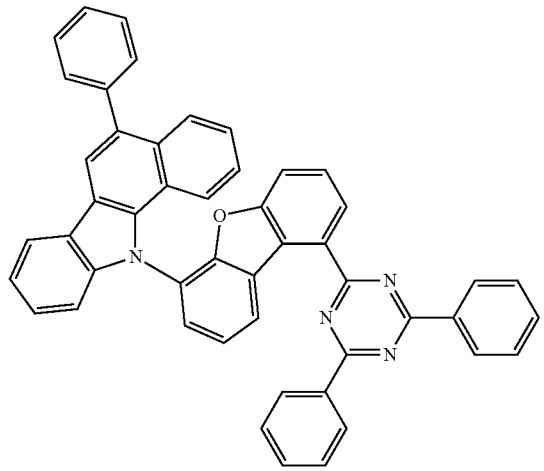
114
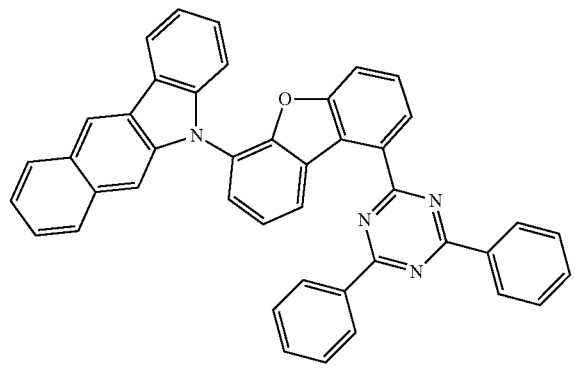
115
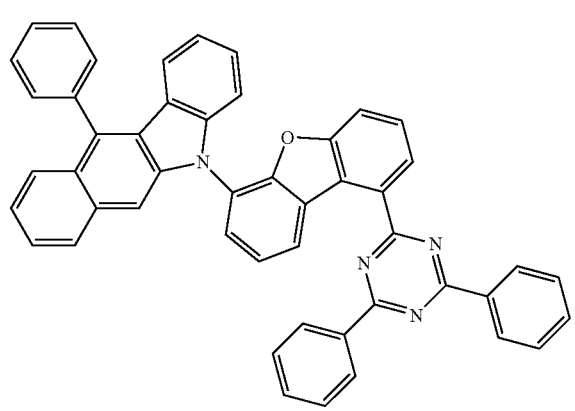
116
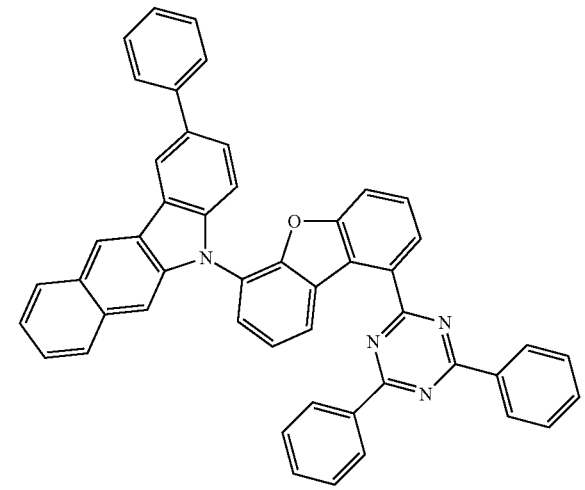
117
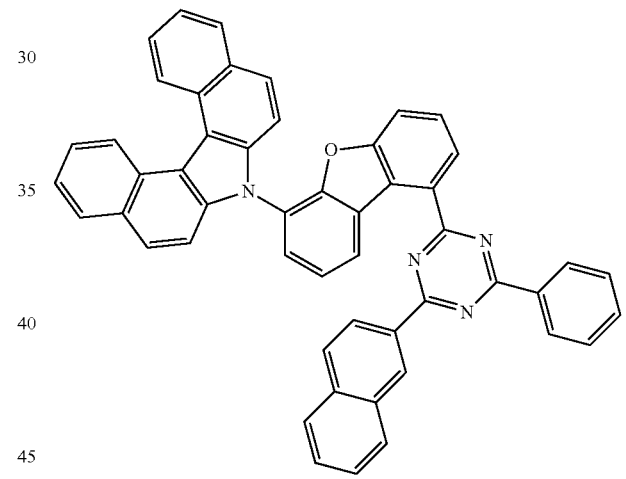
118
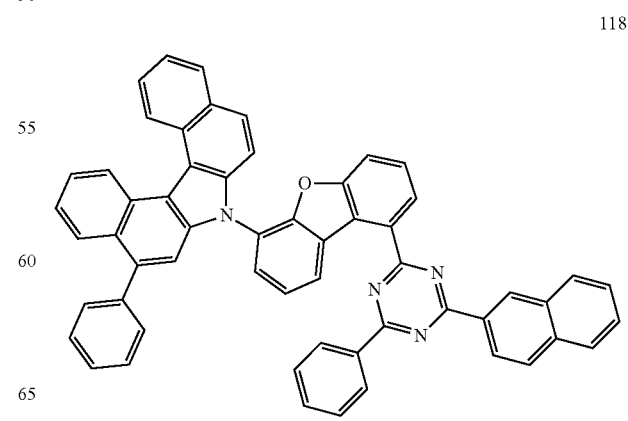

119
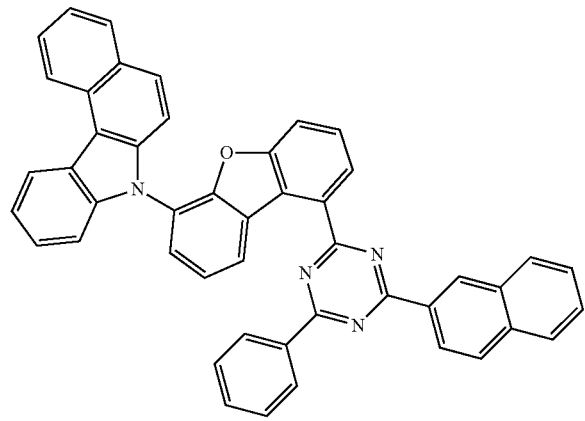
120
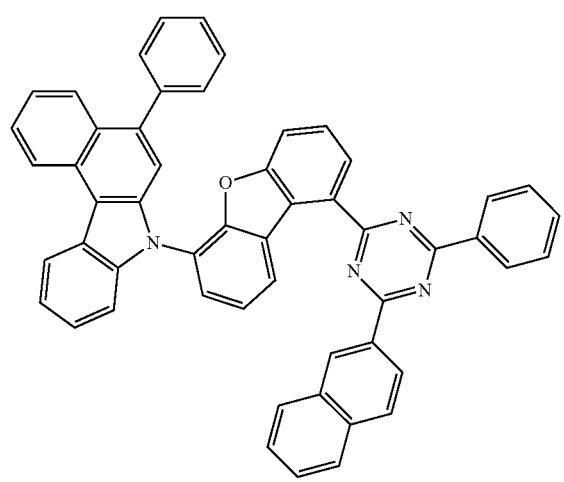
121
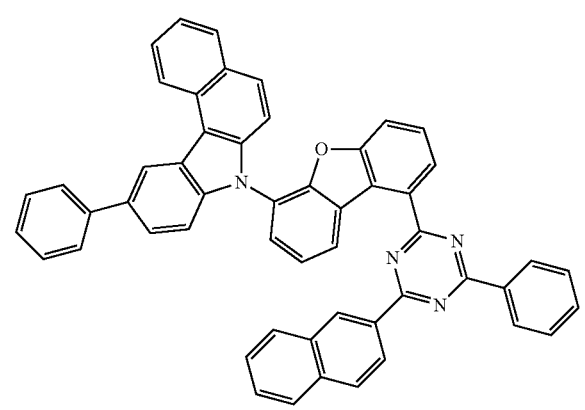
122
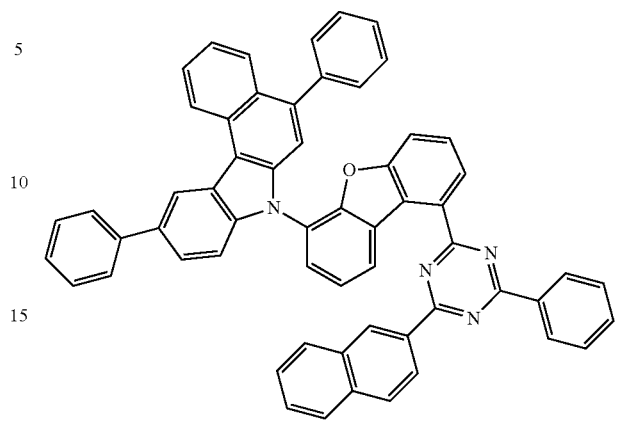
123
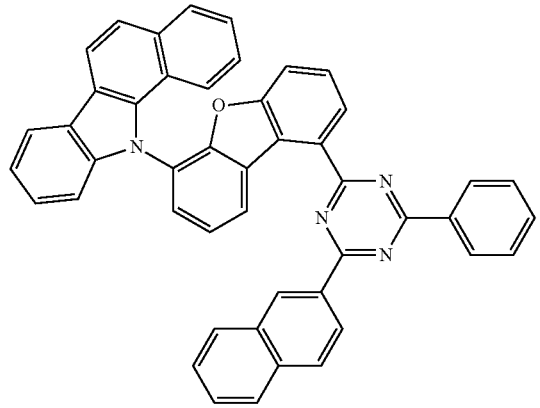
124
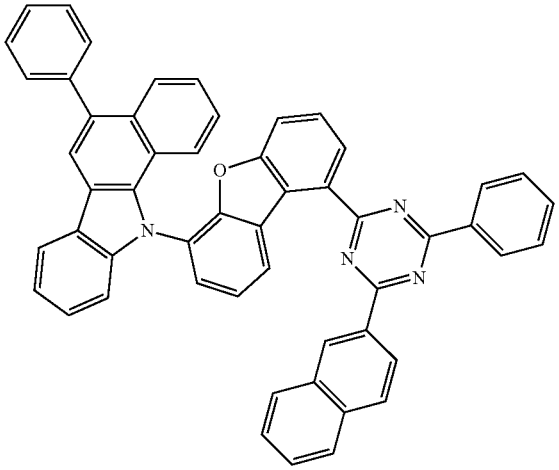

125
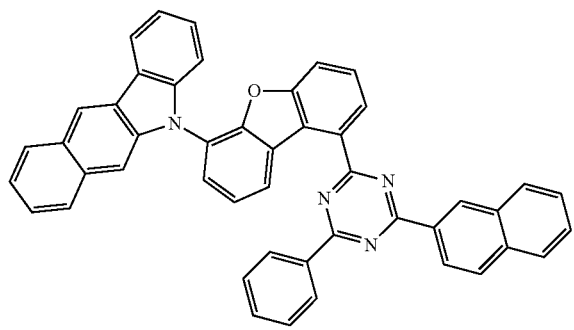
126
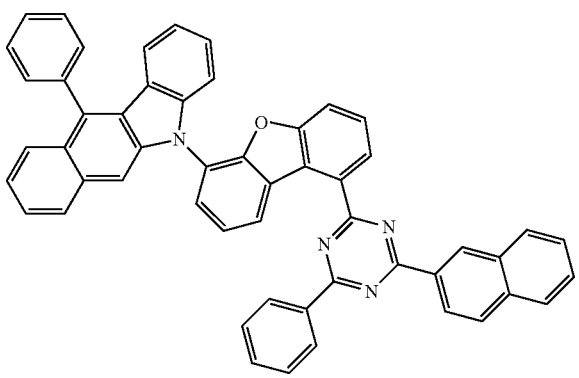
127
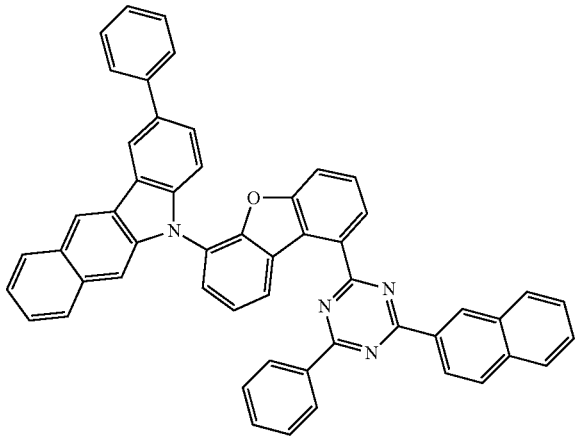
128
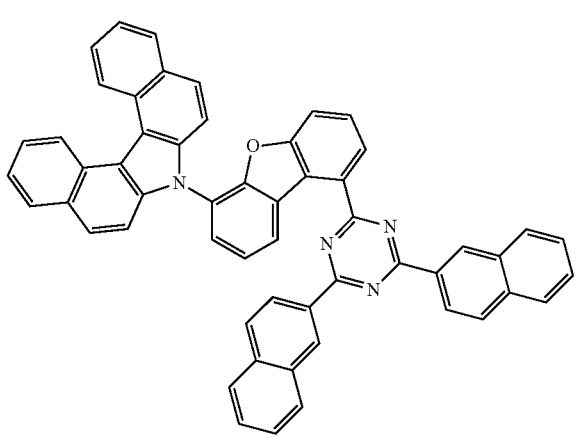
129
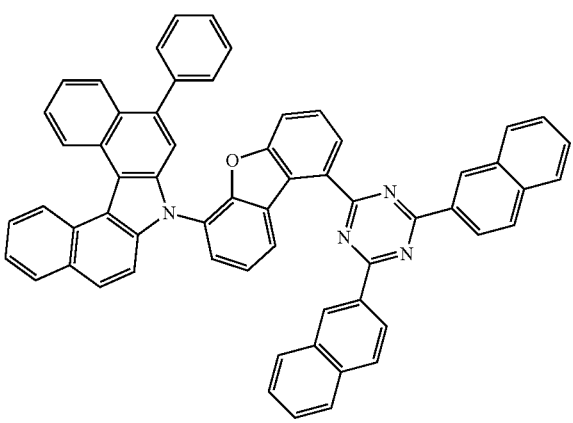
130
131
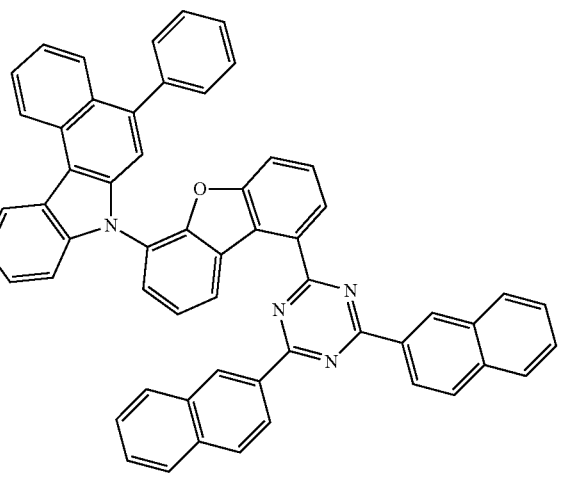

-continued
132
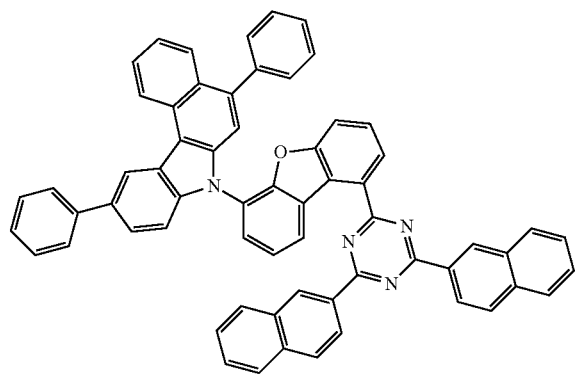
133
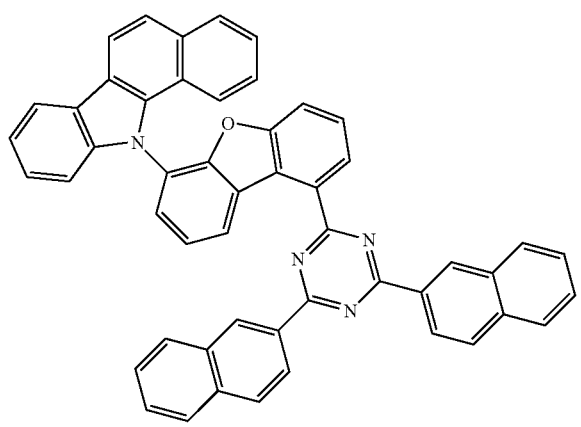
134
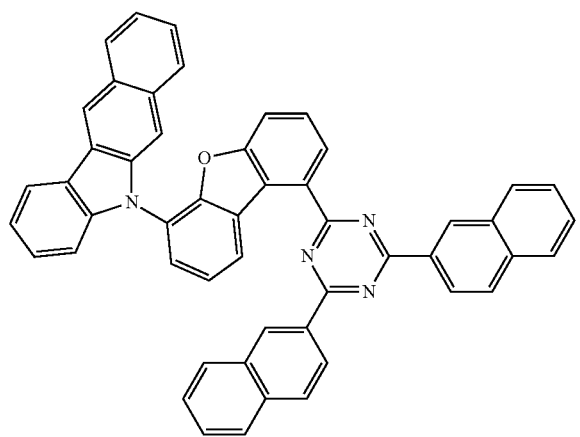
-continued
135
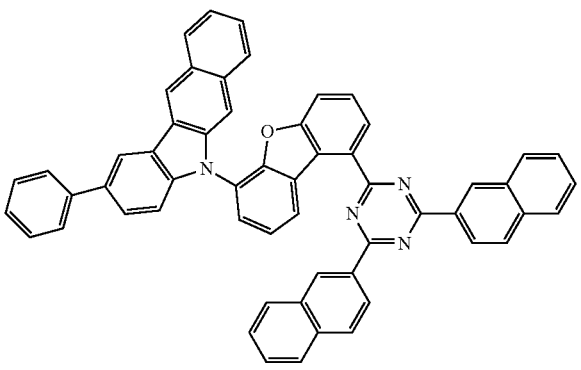
136
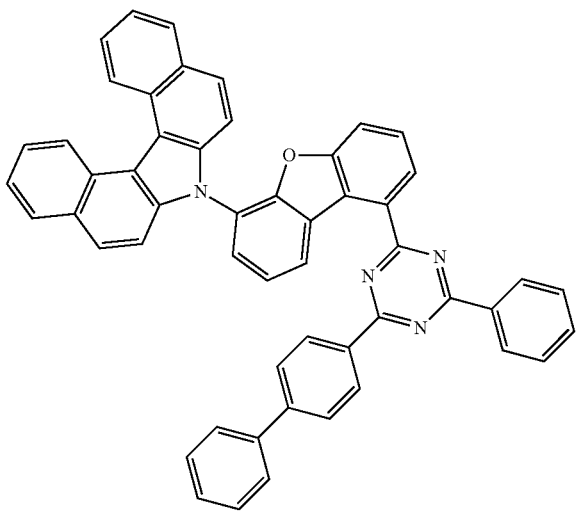
137
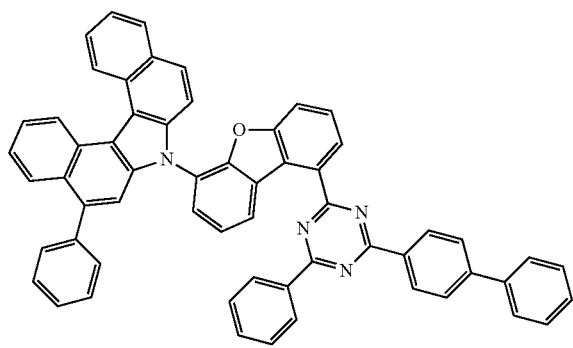

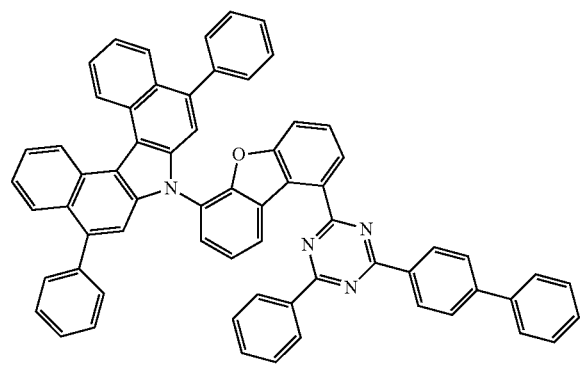
138
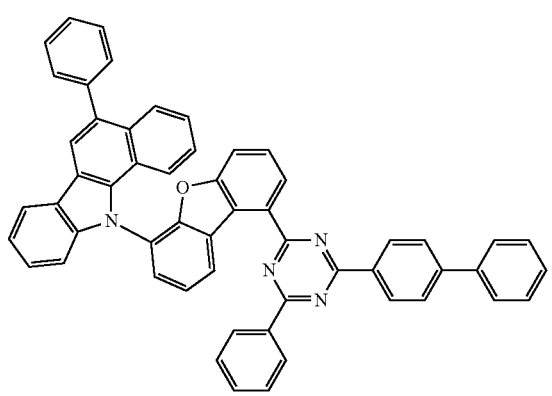
141
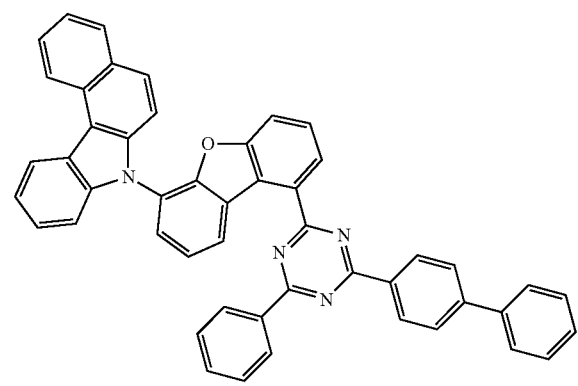
139
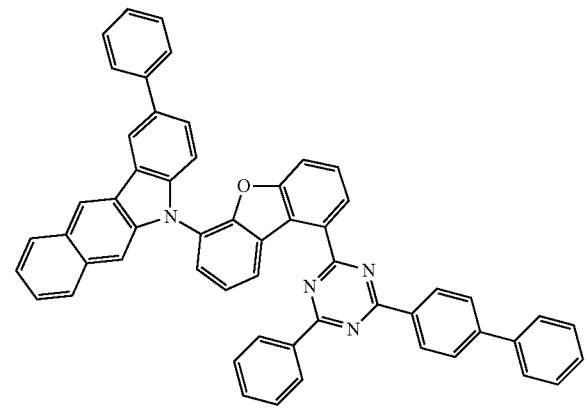
142
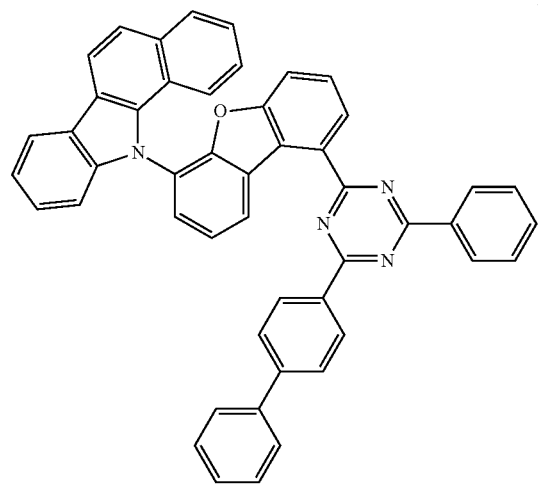
140
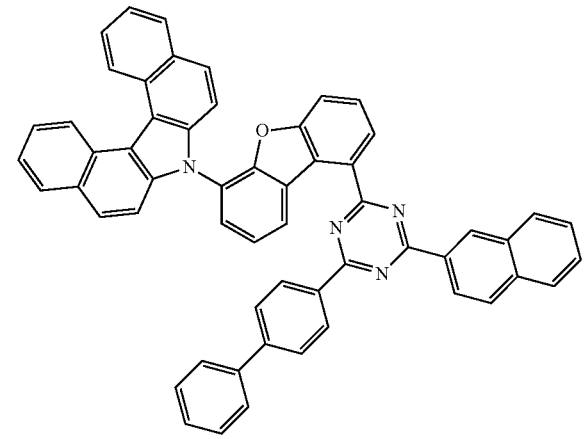
143
144

145
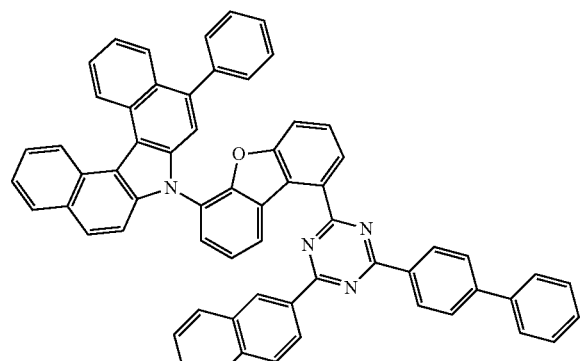
146
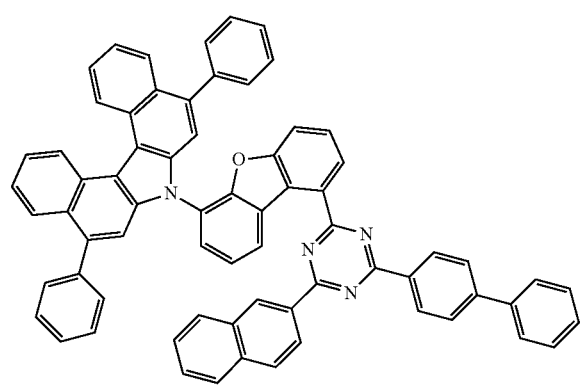
147
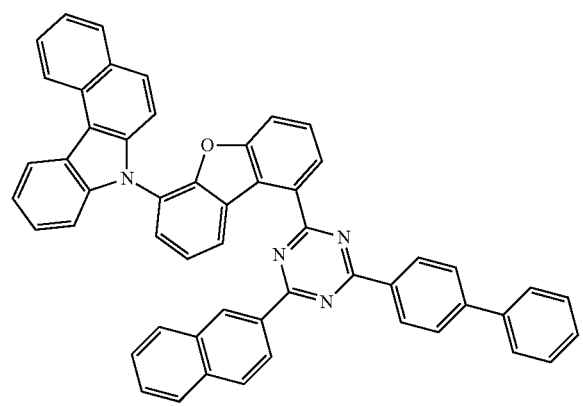
148
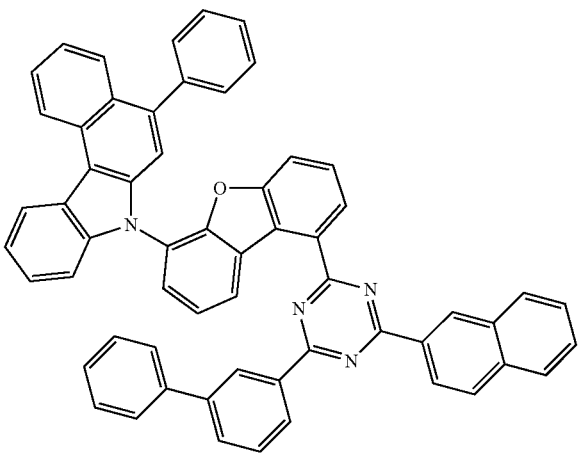
149
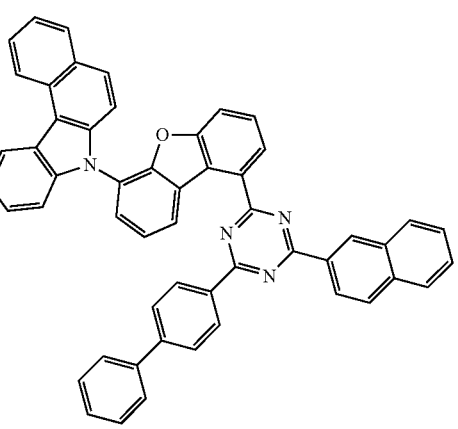
150
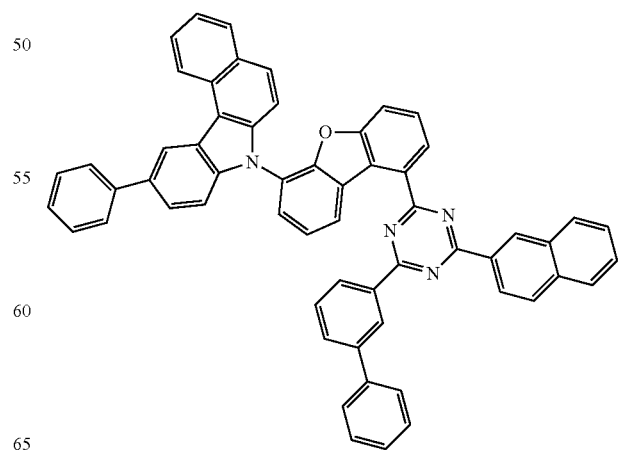

151
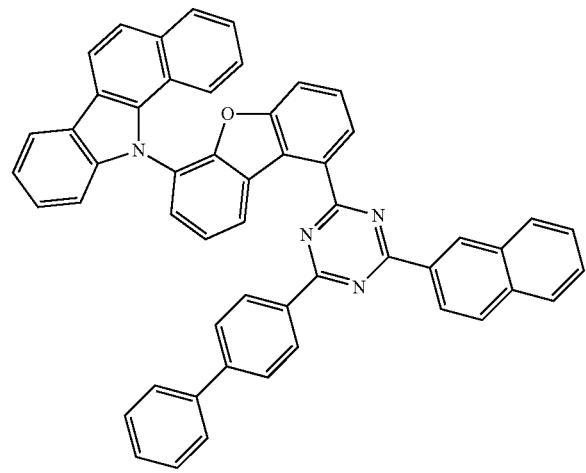
152
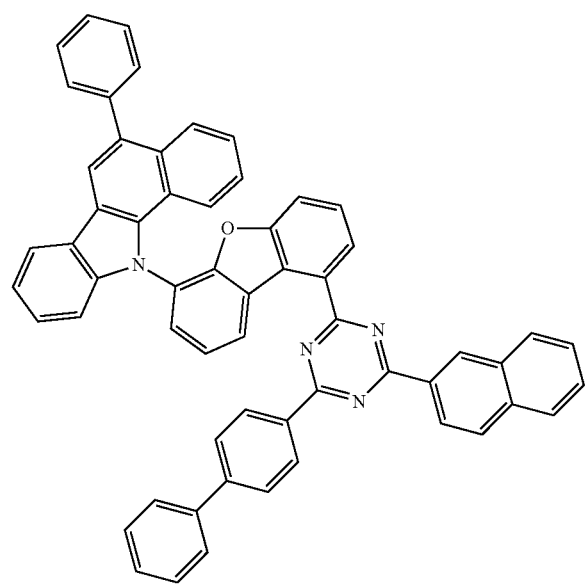
153
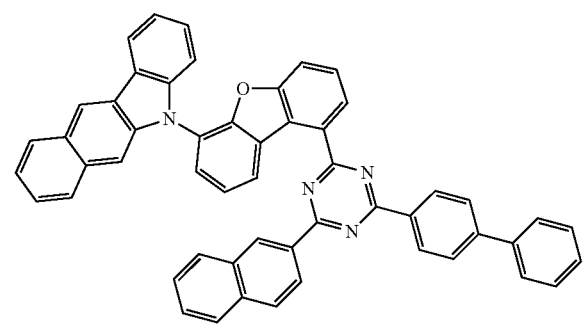
154
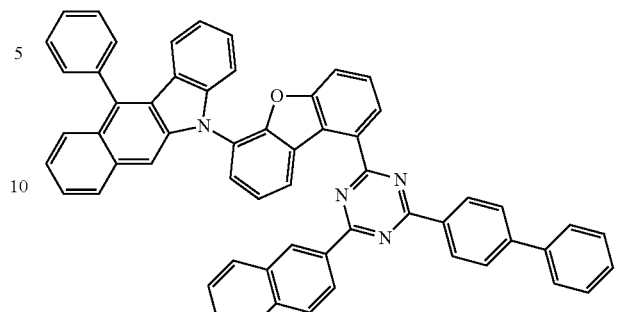
155
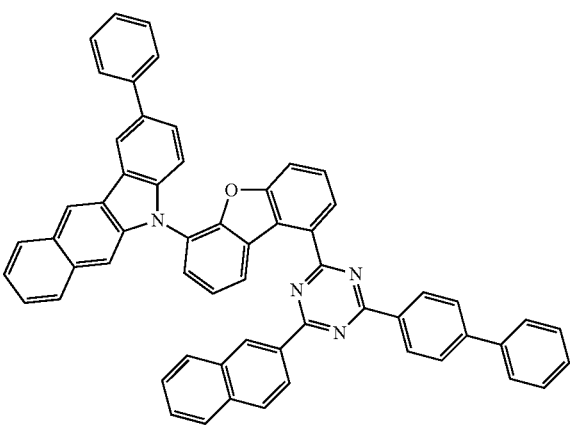
156
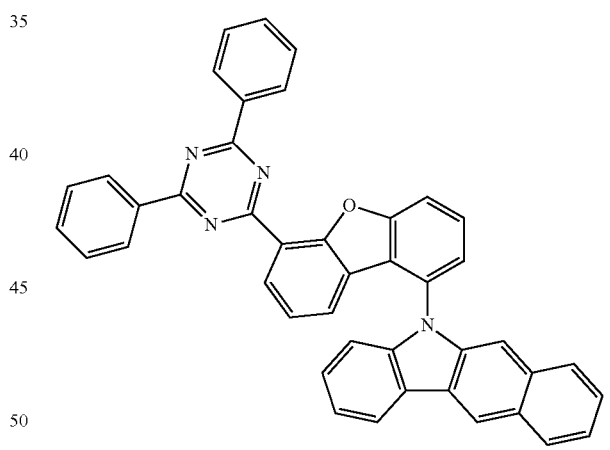
157
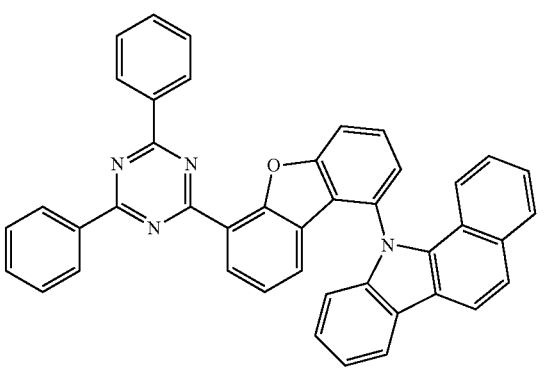

158
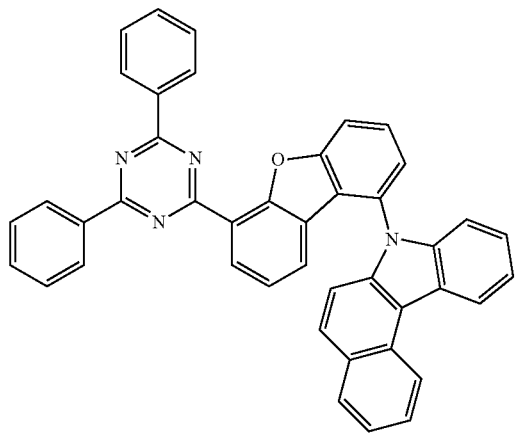
159
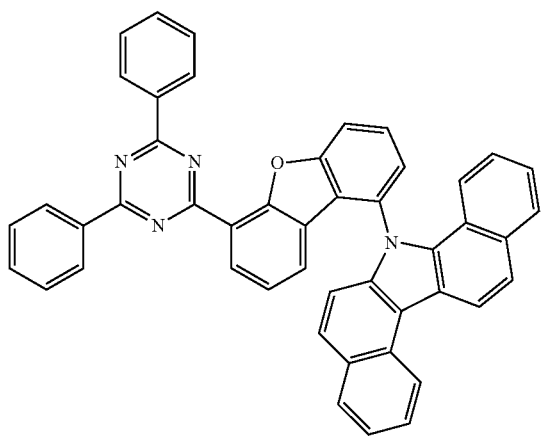
160
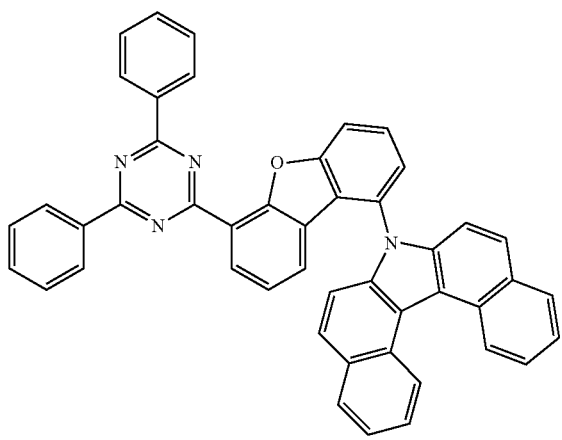
161
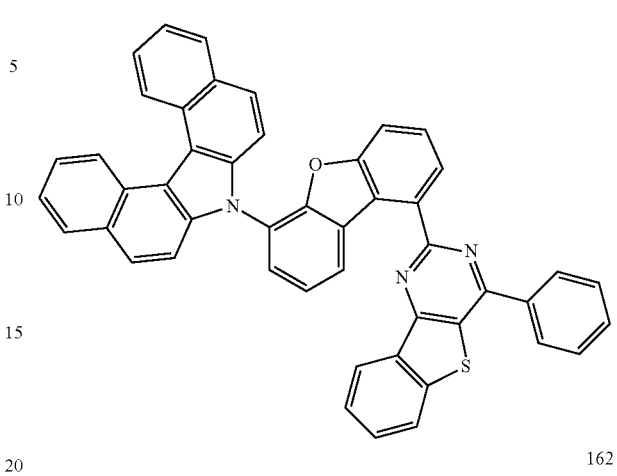
162
163
164
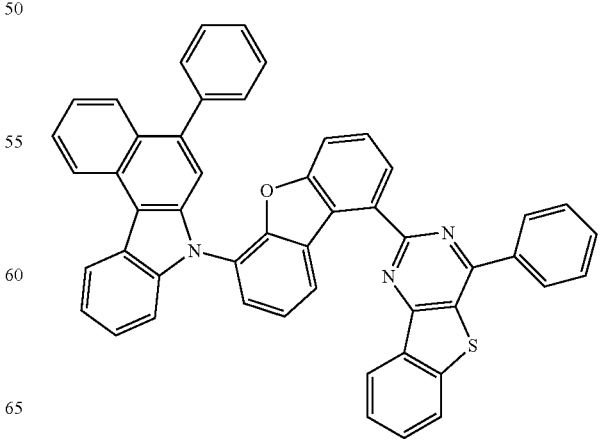

165
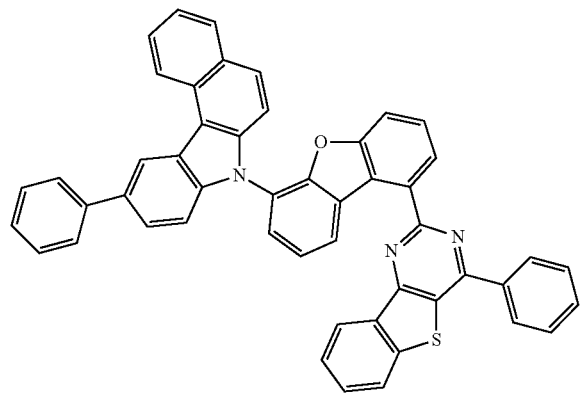
166
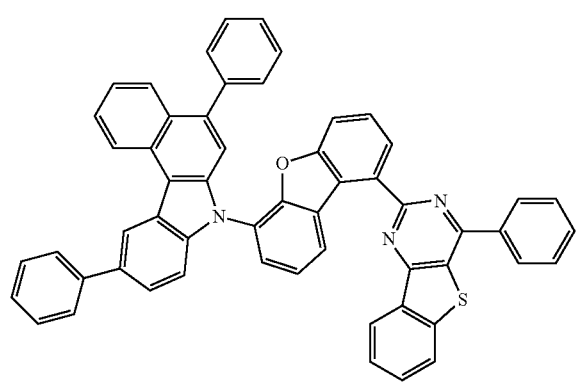
167
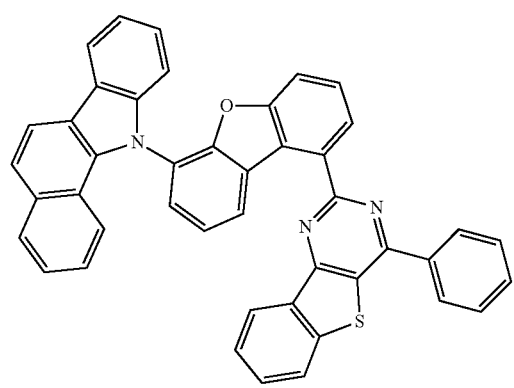
168
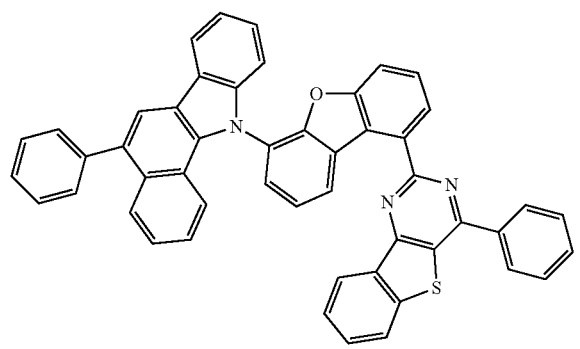
169
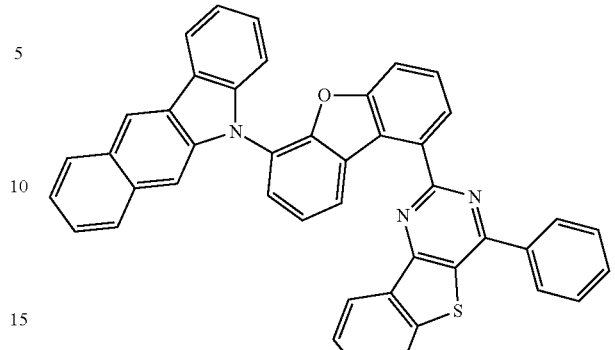
170
171
172
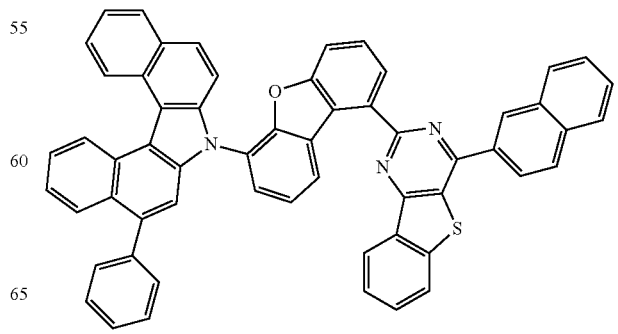

173
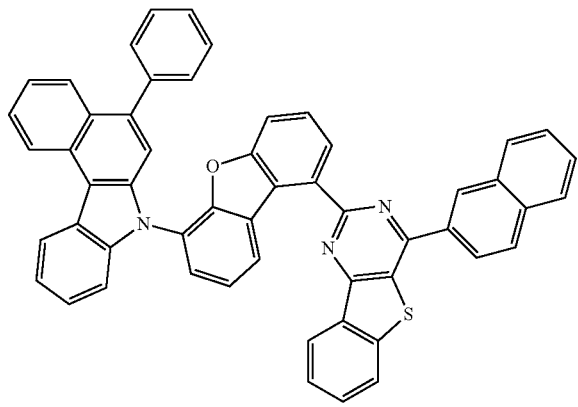
174
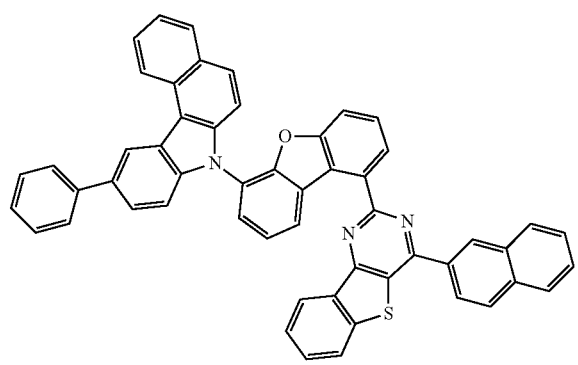
175
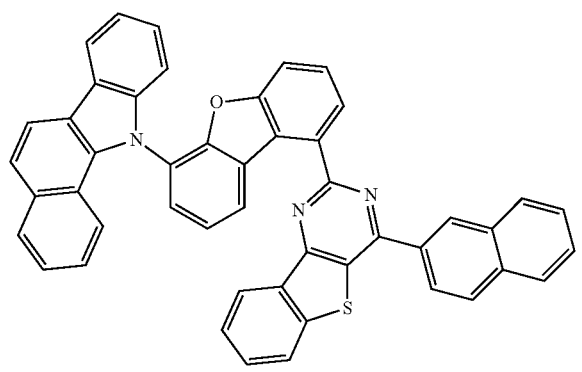
176
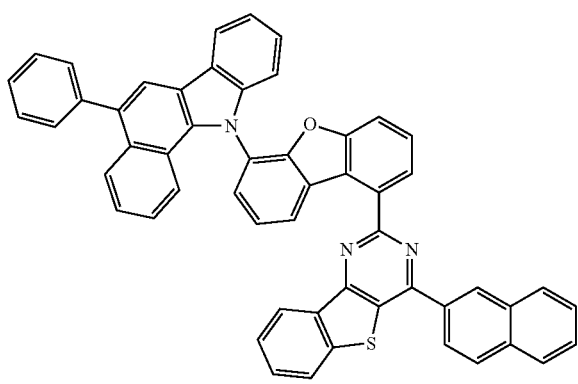
177
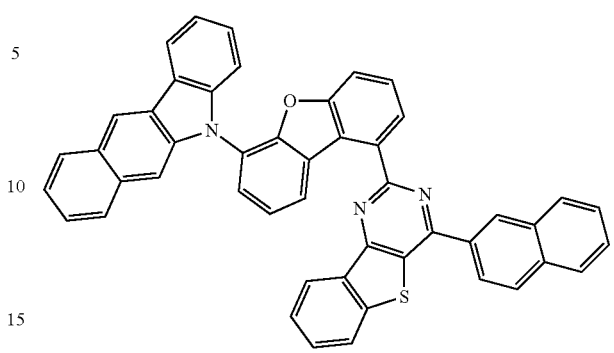
178
179
180

181
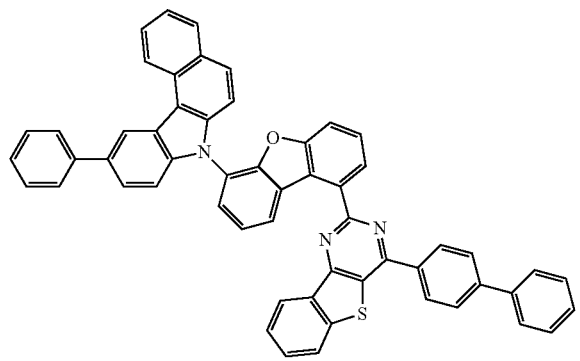
182
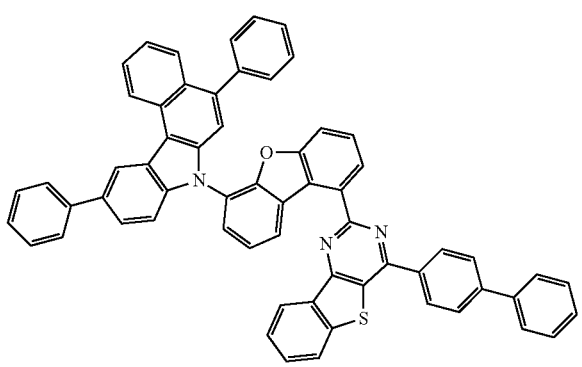
183
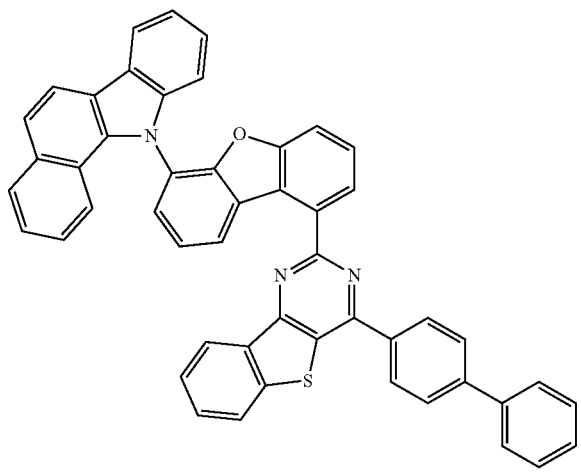
184
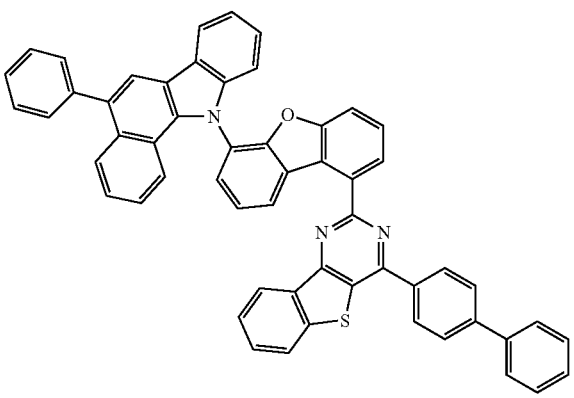
185
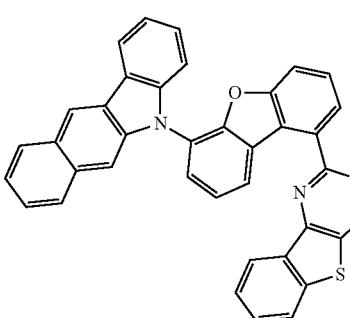
186
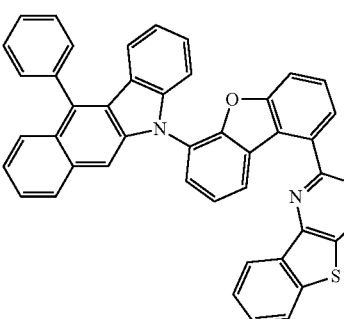
187
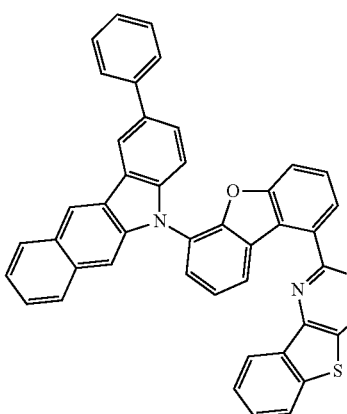

188
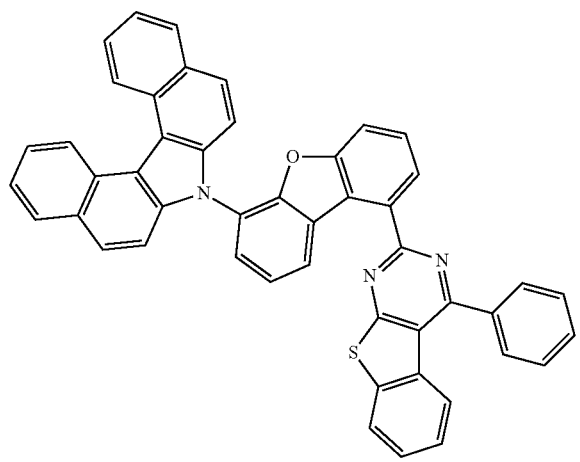
189
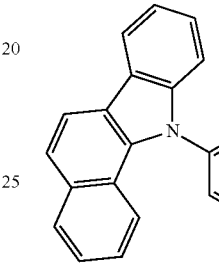
190
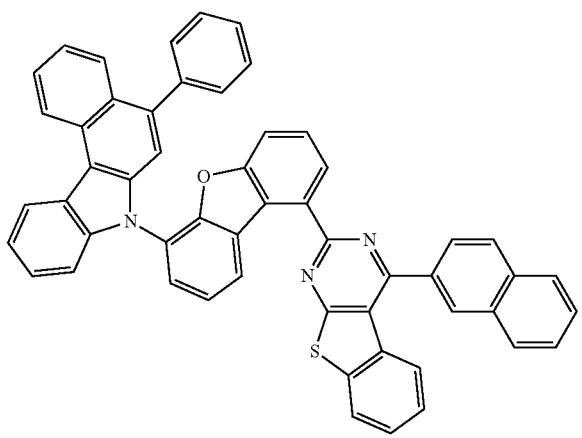
191
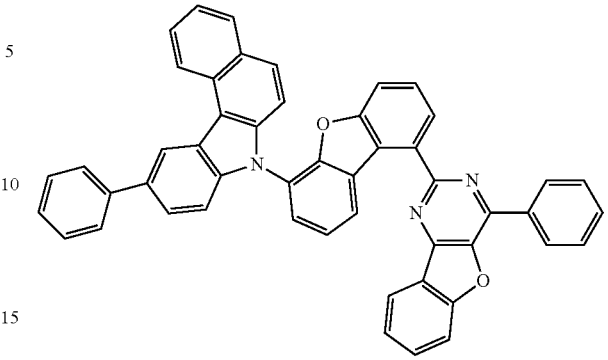
192
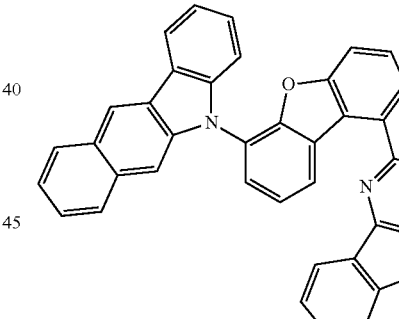
193
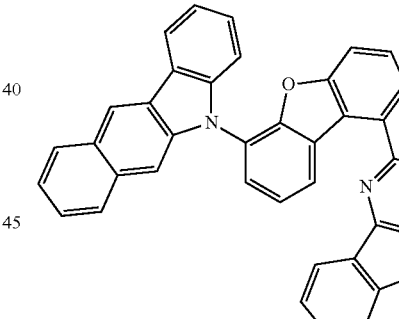
194
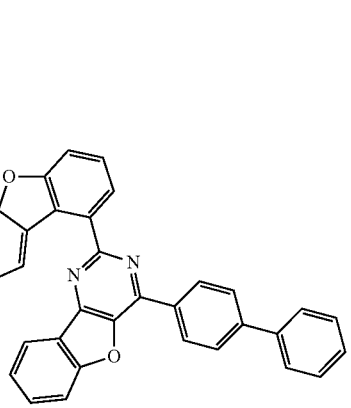

195
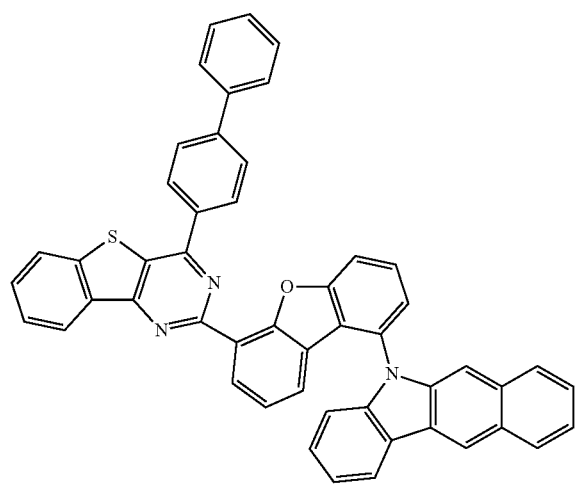
196
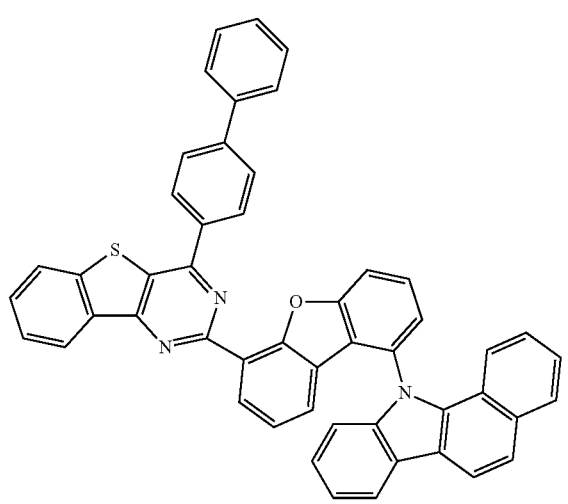
197
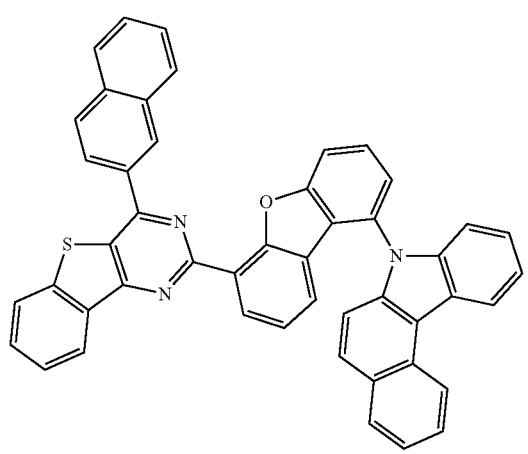
198
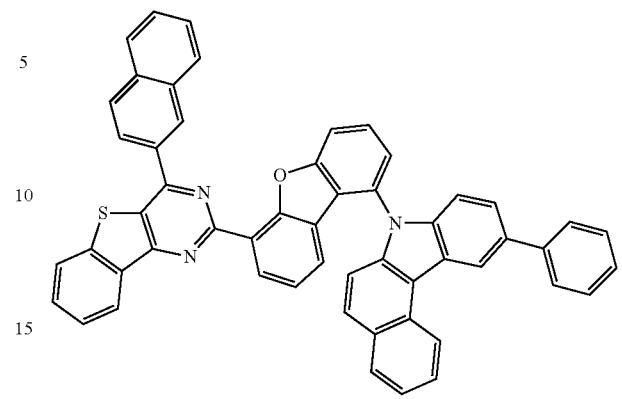
199
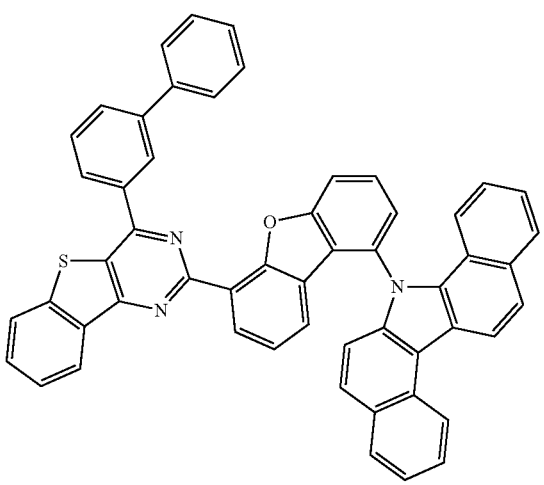
200
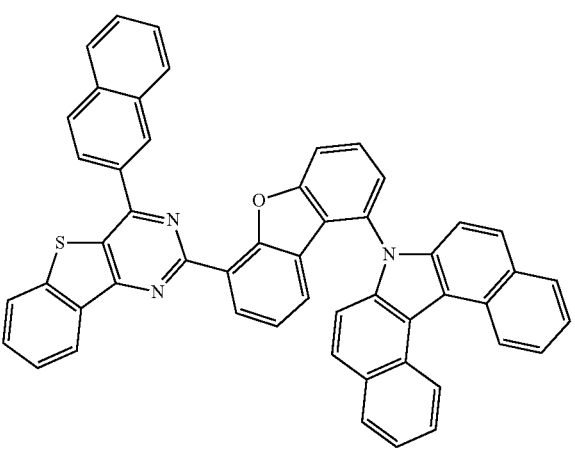

201 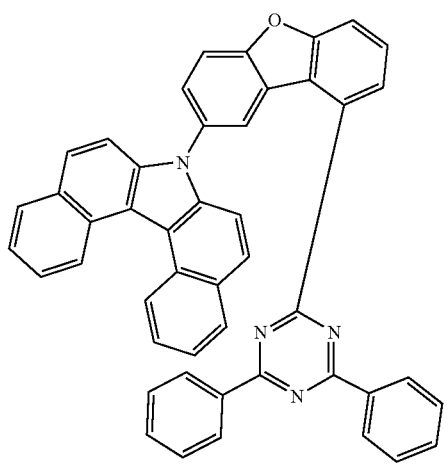
202 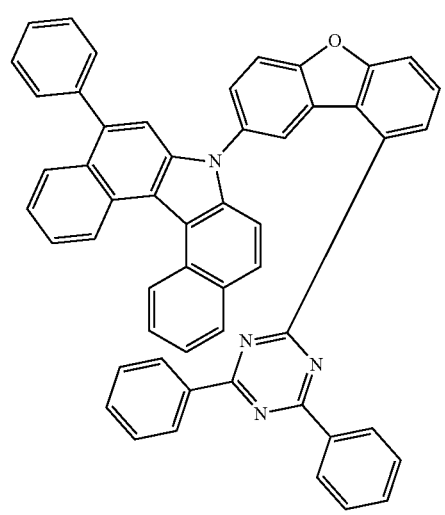
203 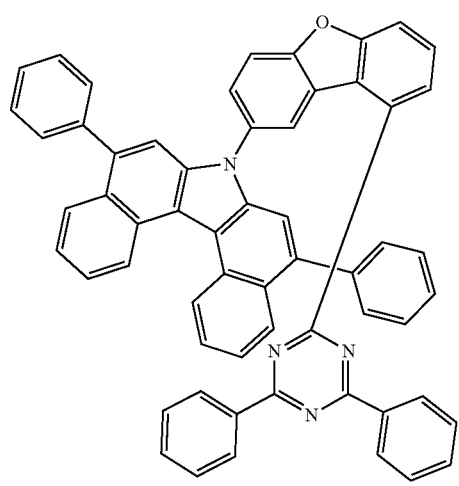
204 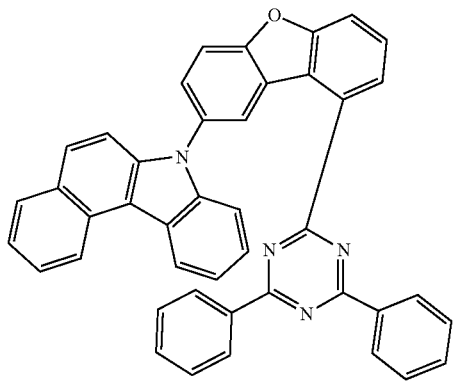
205 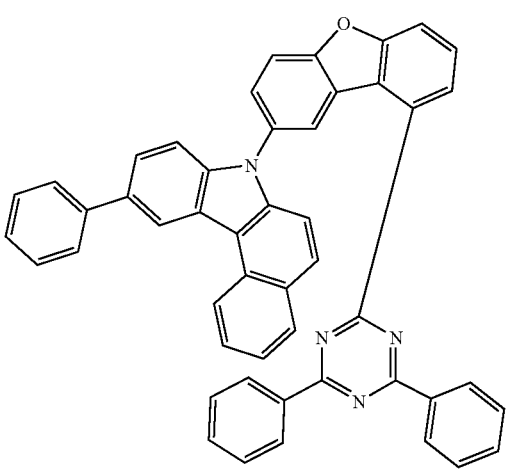
206

-continued
207
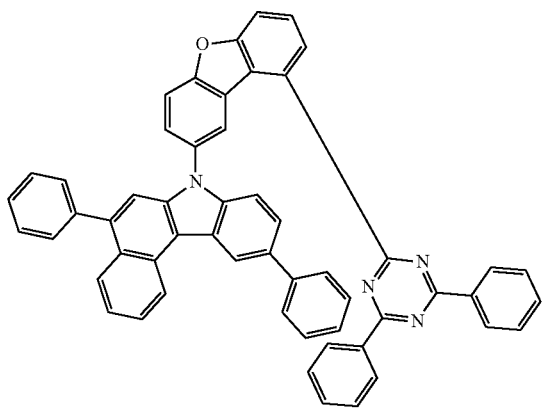
208
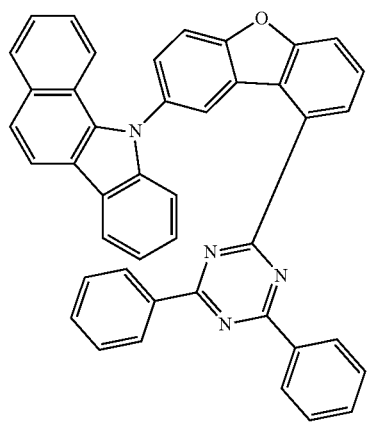
209
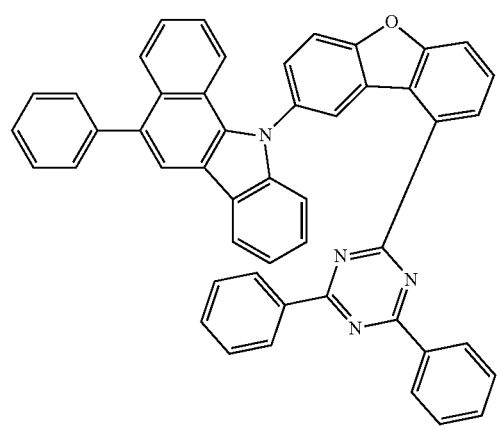
-continued
210
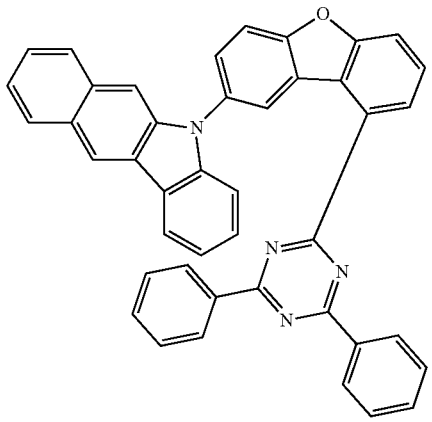
211
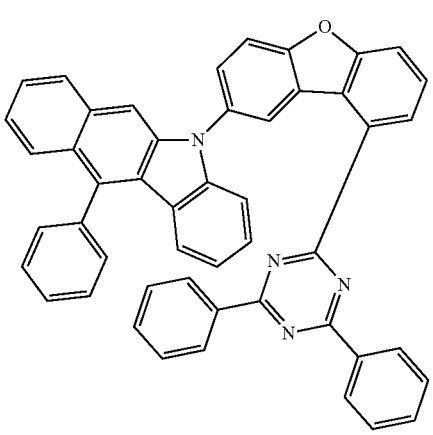
212
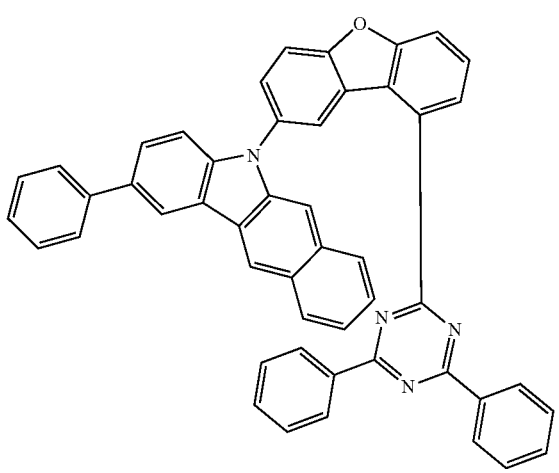

213
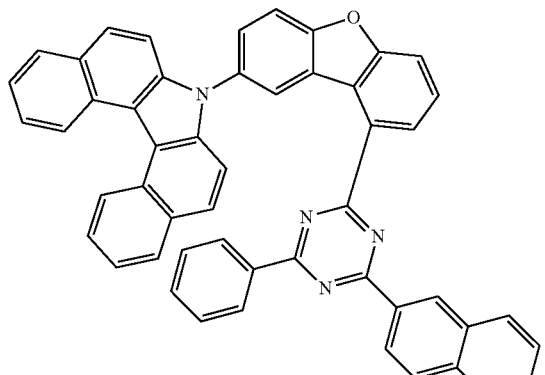
214
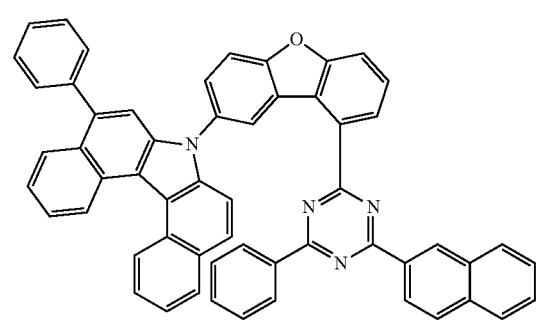
215
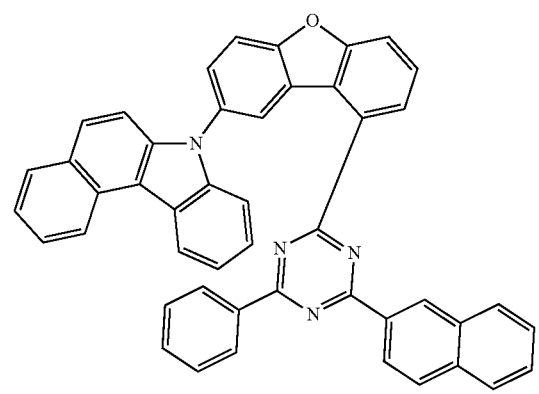
216
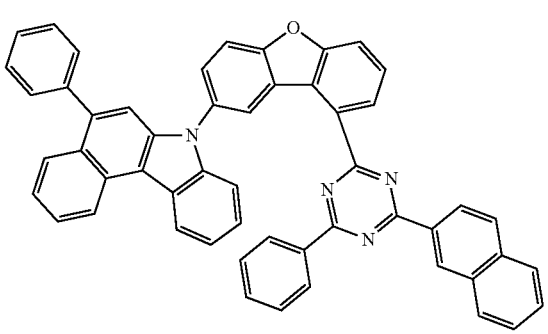
217
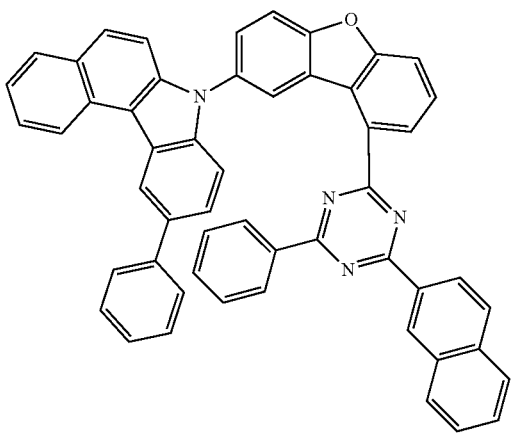
218
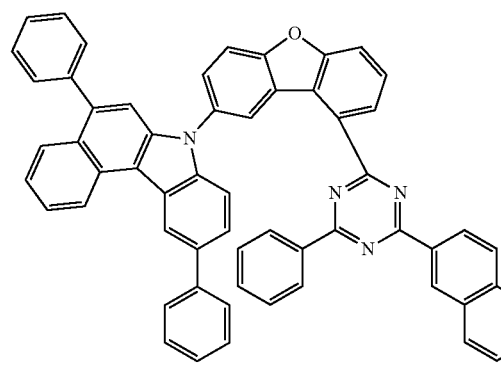
219
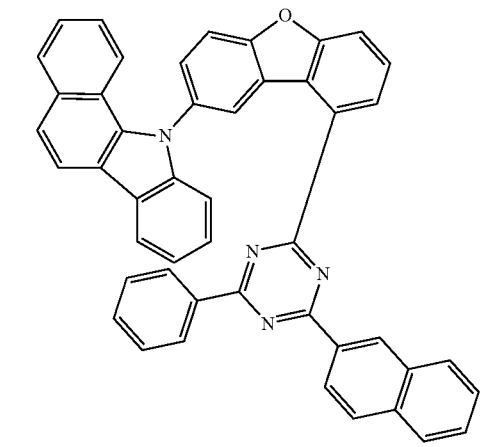

81
-continued
220
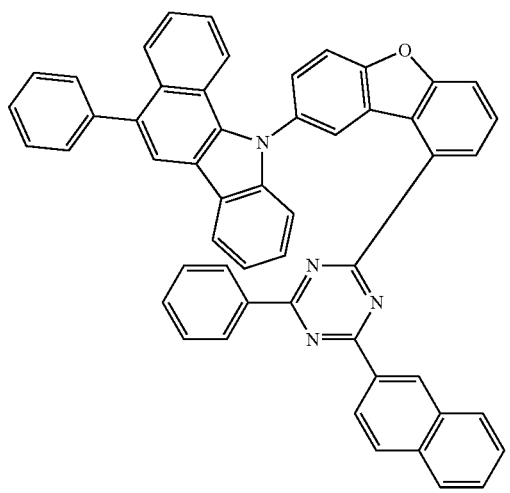
221
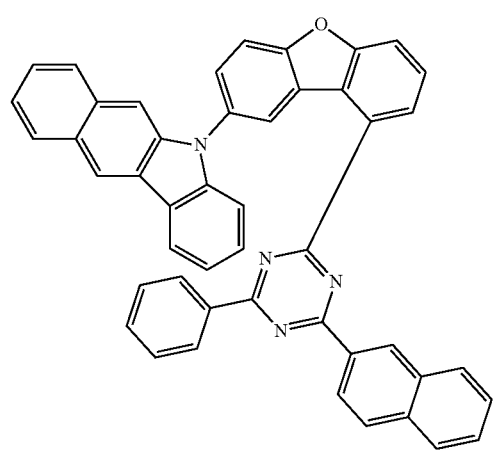
222
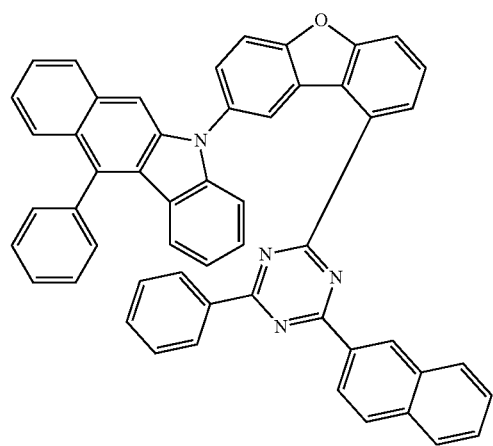
82
-continued
223
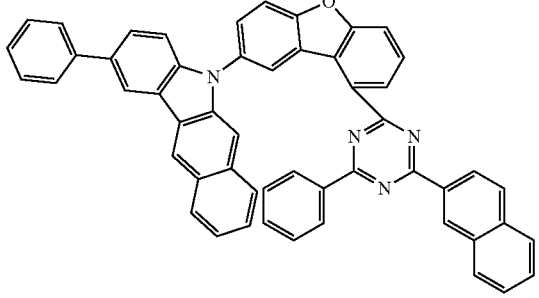
224
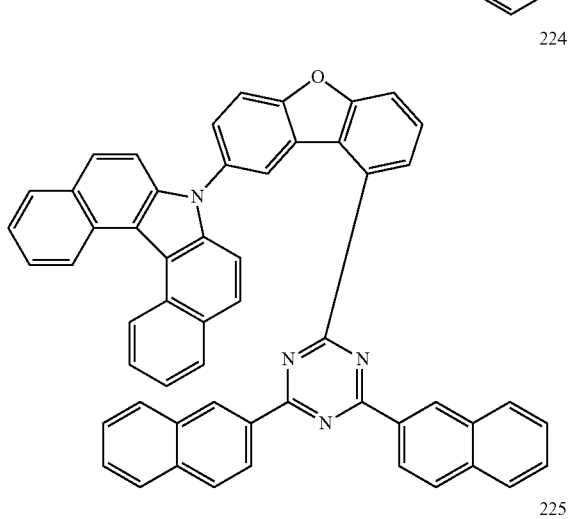
225
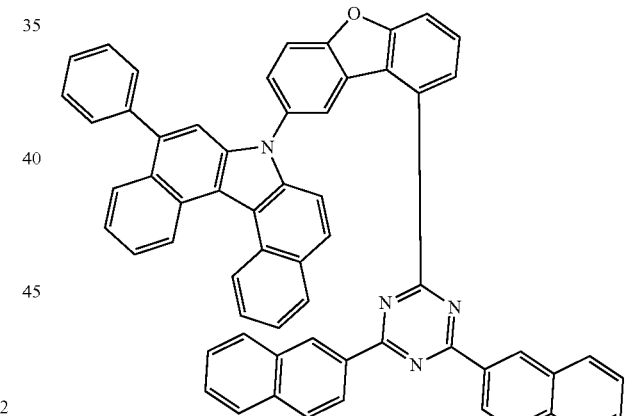
226
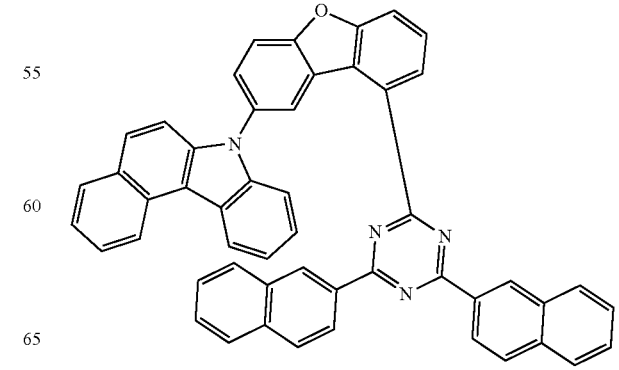

227
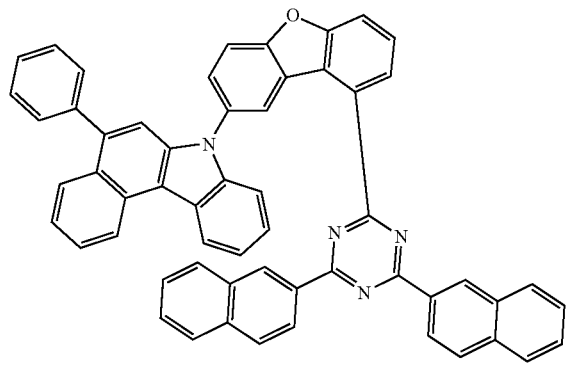
228
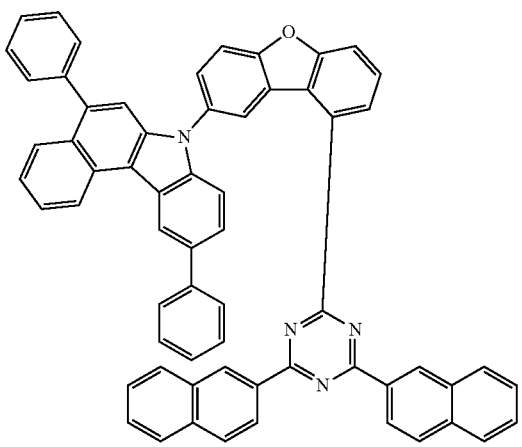
229
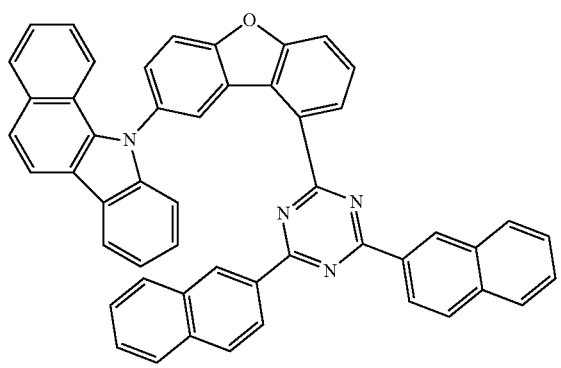
230
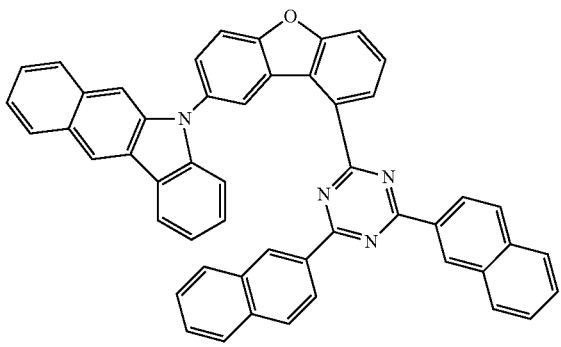
231
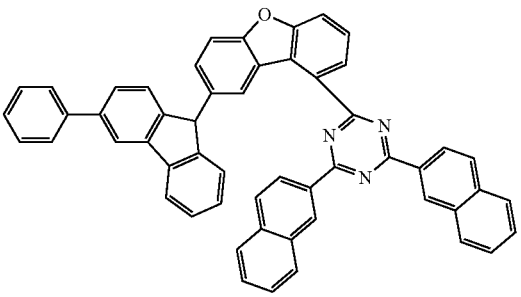
232
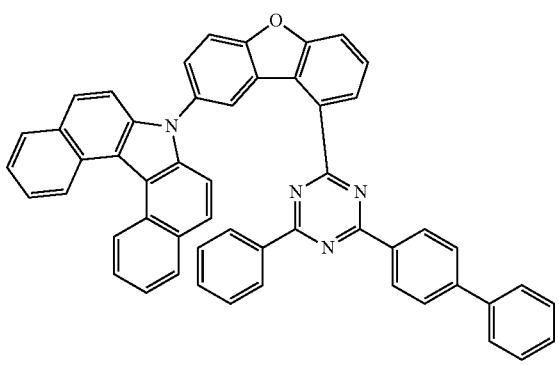
233
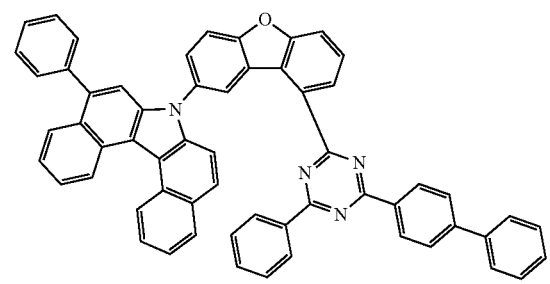
234
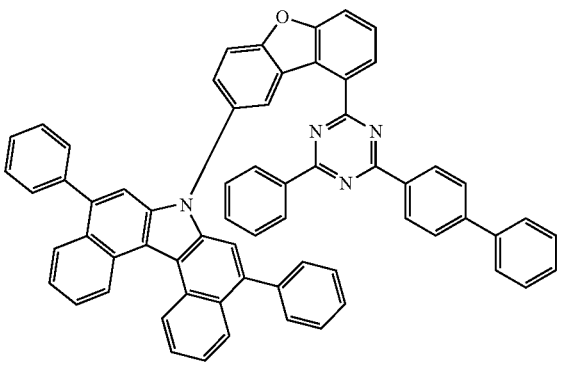

235
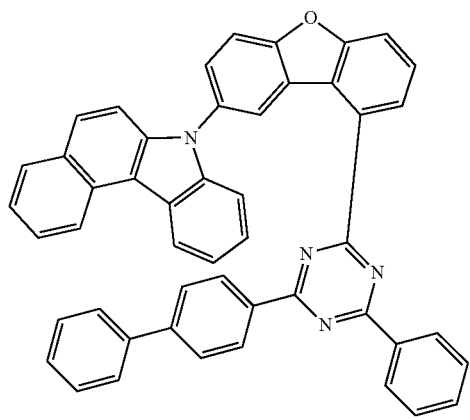
236
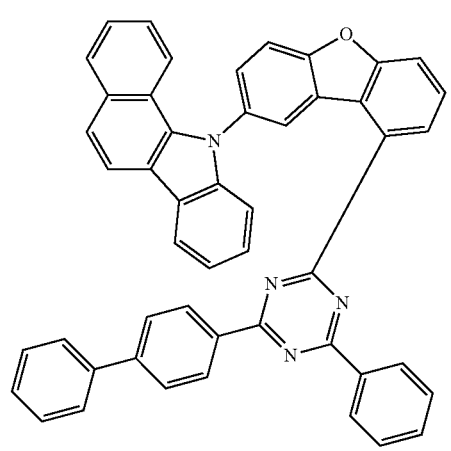
237
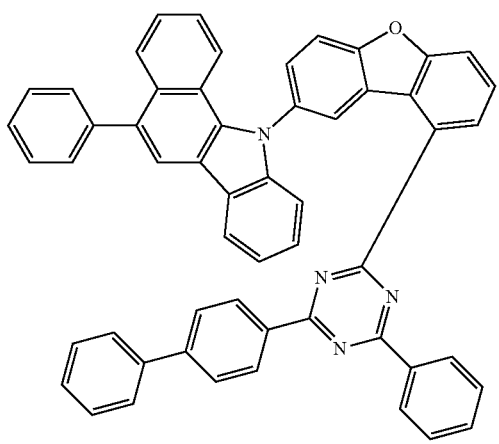
238
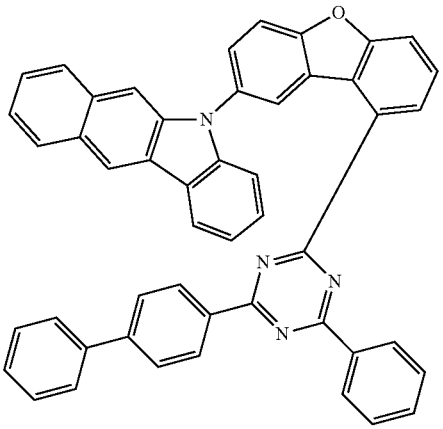
239
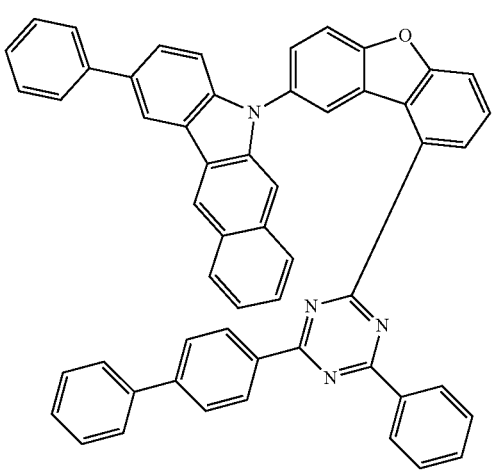
240
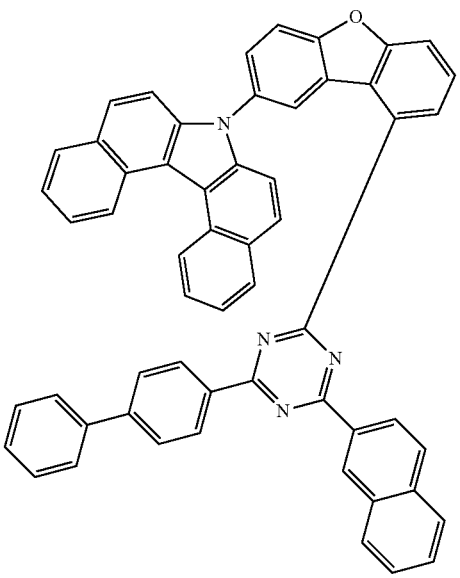

241
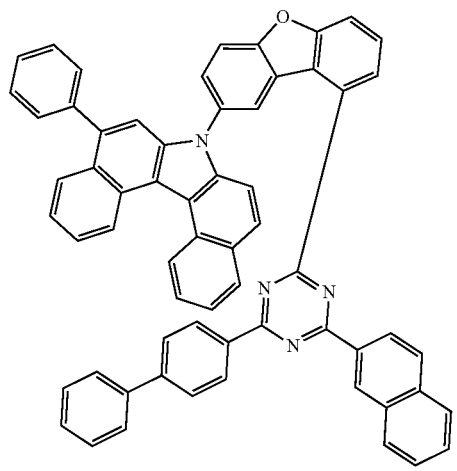
242
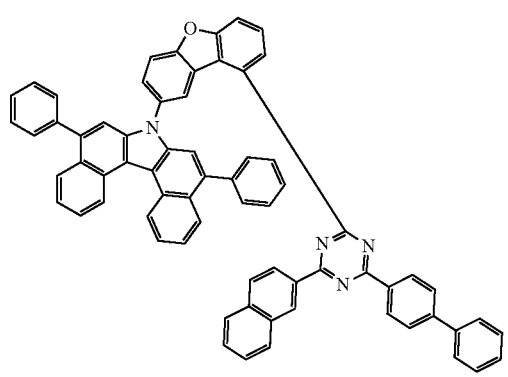
243
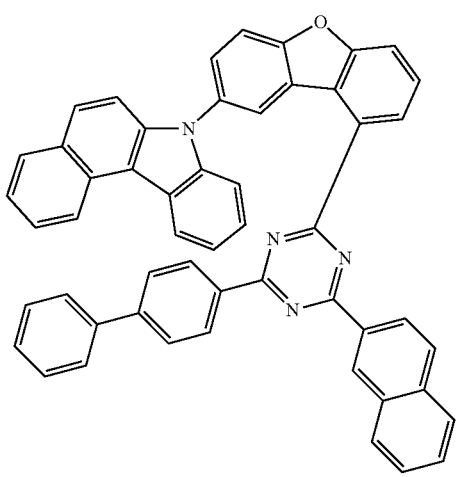
244
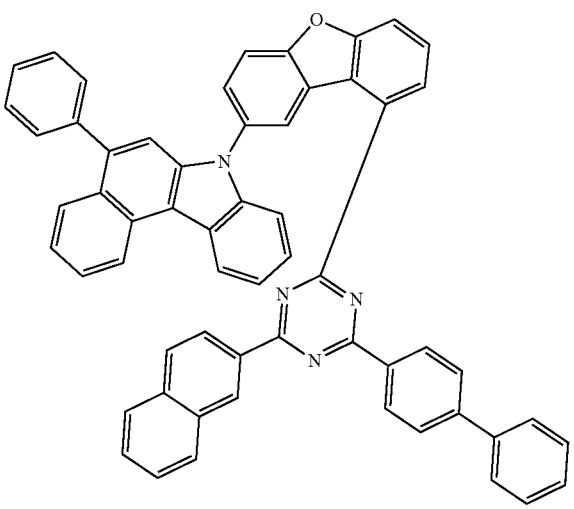
245
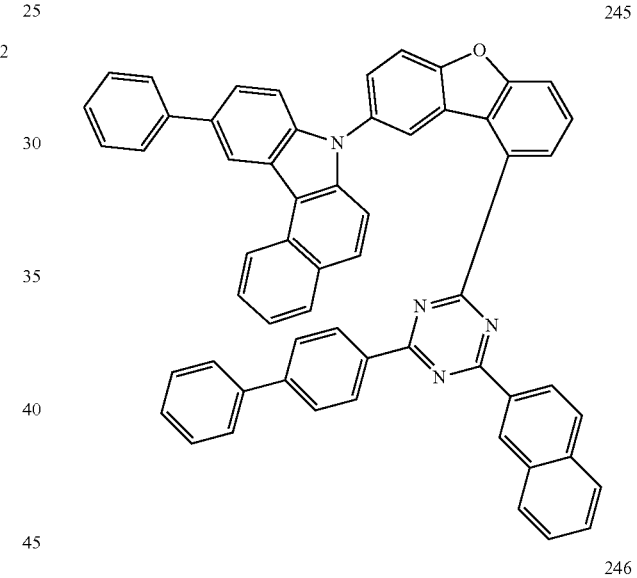
246
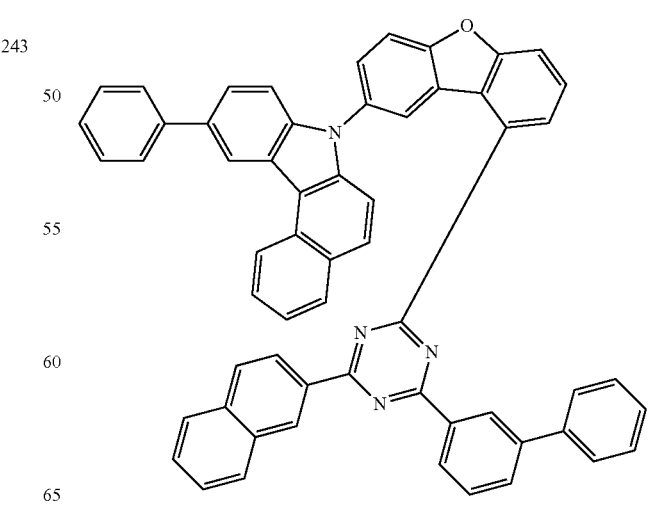

247 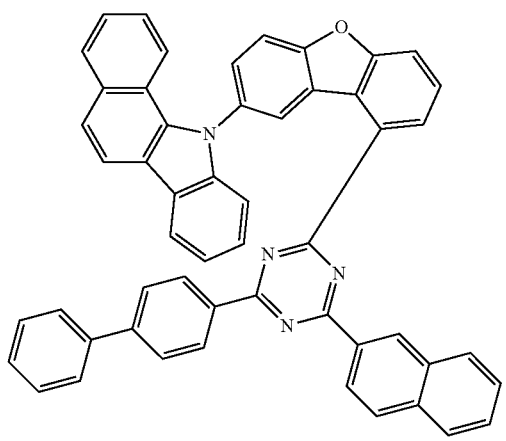
248 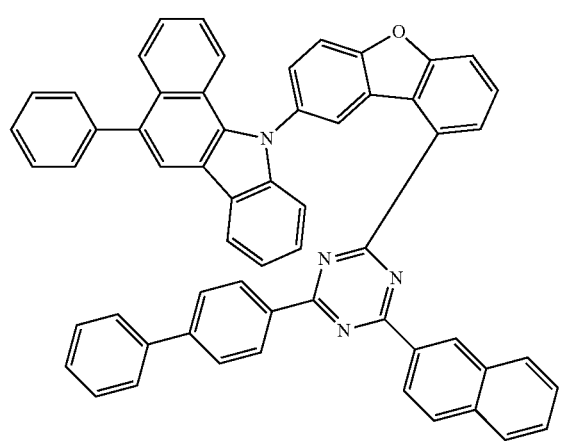
249 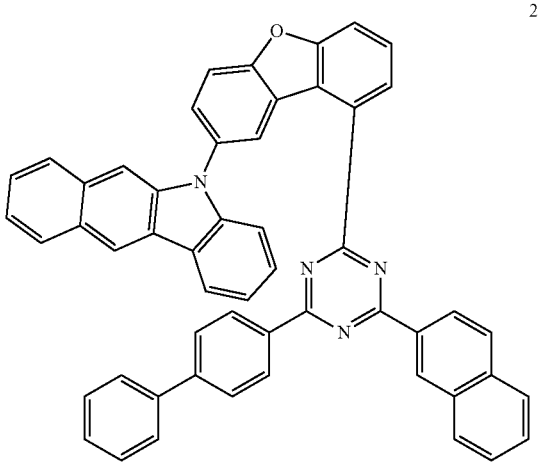
250 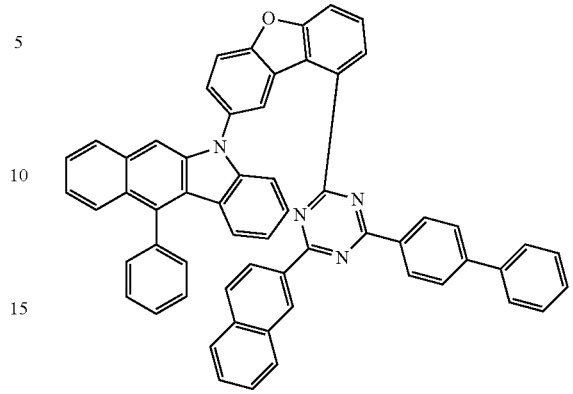
251 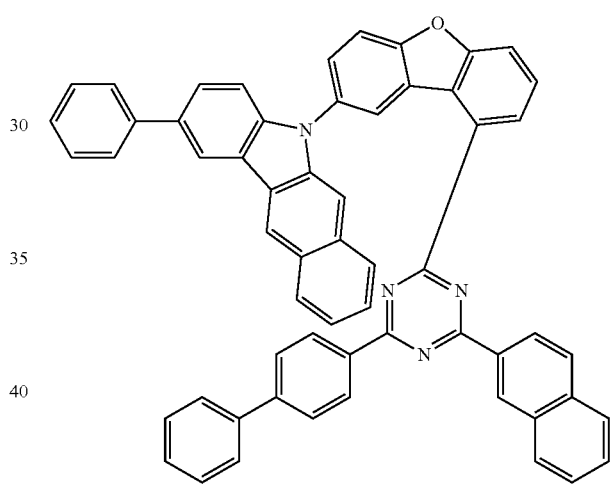
252 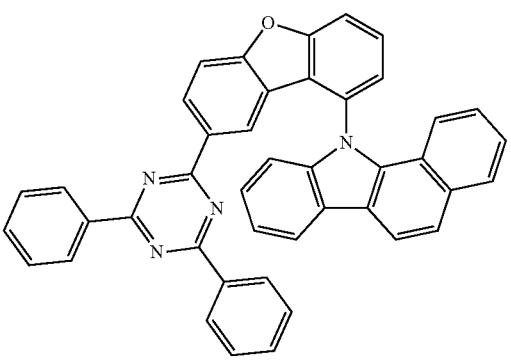

253
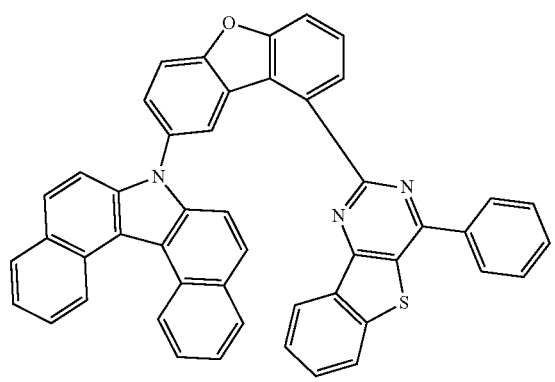
254
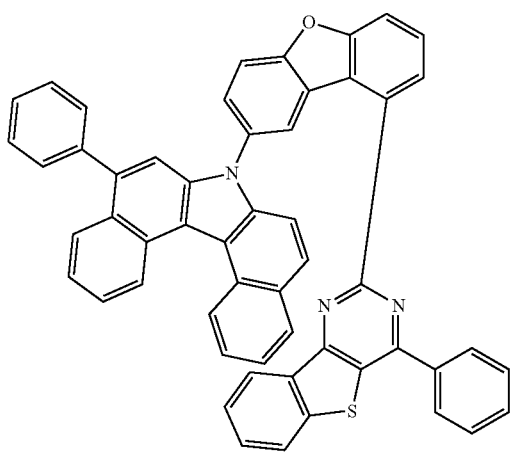
255
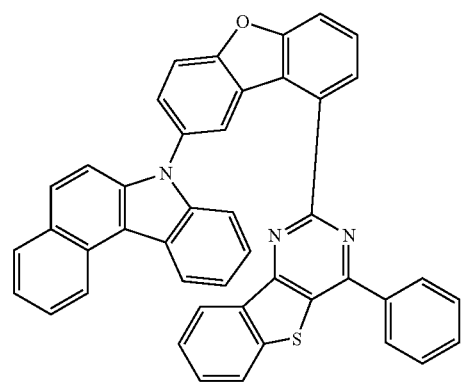
256
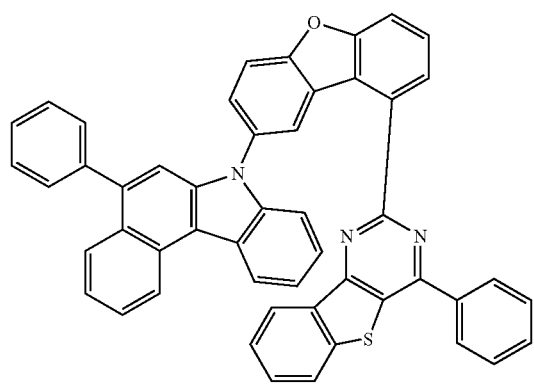
257
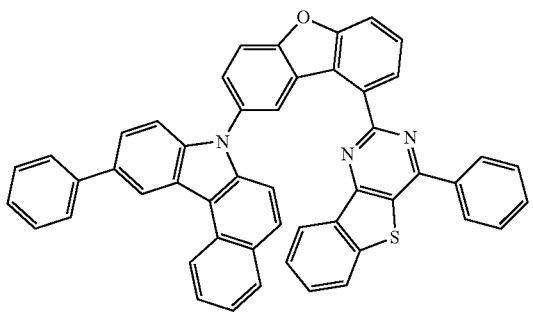
258
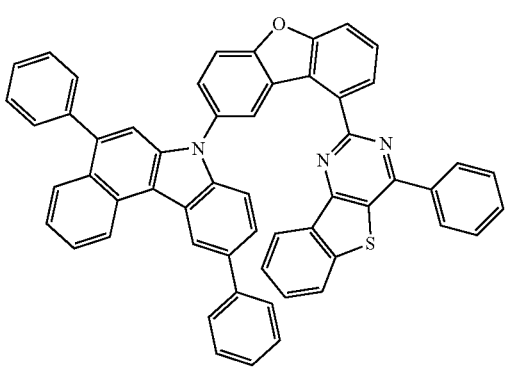
259
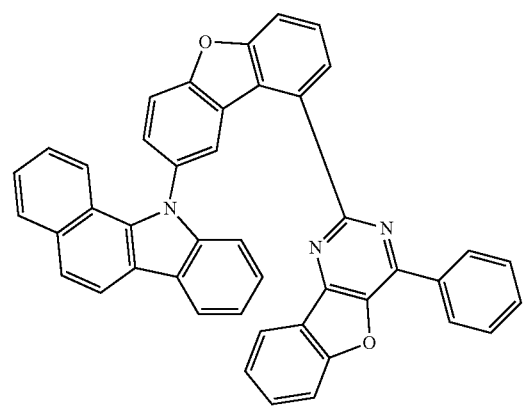
260
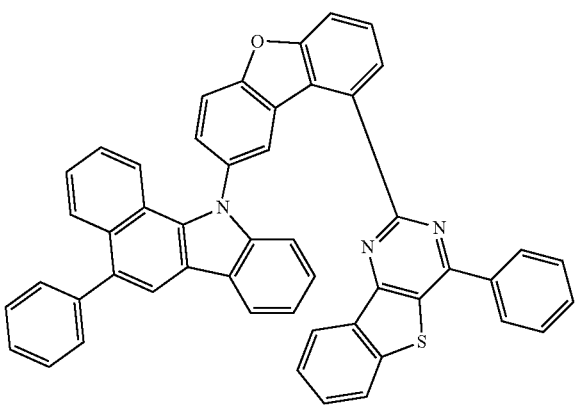

261
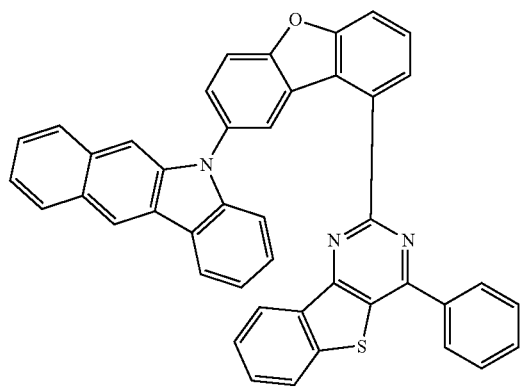
262
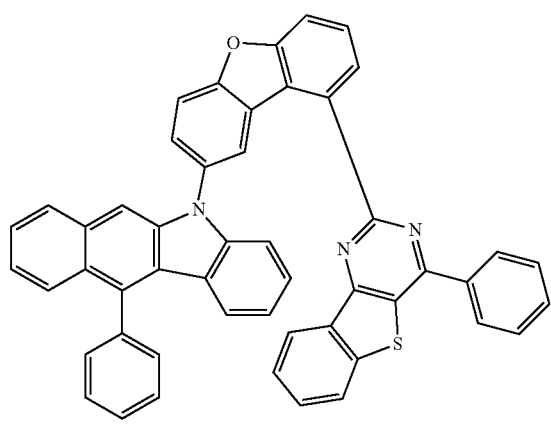
263
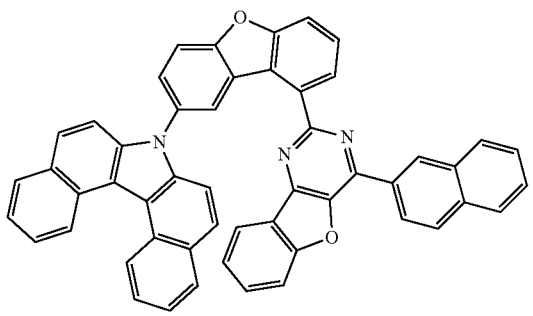
264
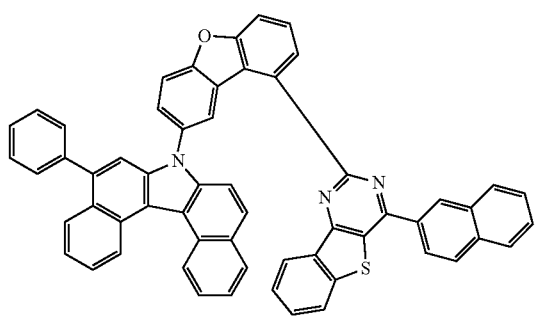
265
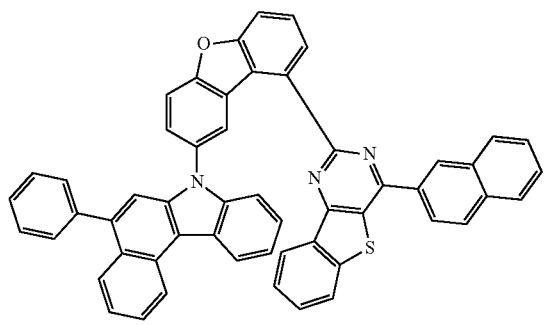
266
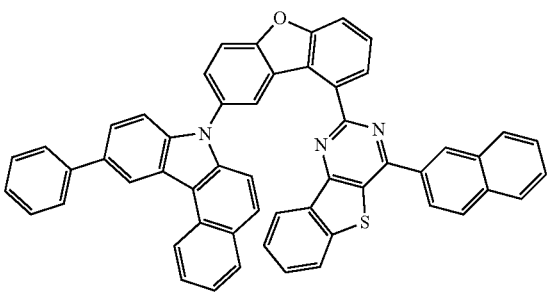
267
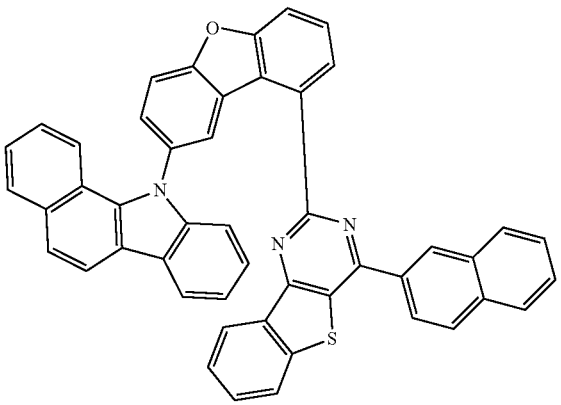
268
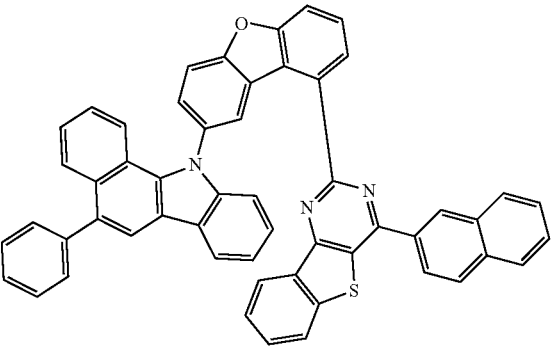

269
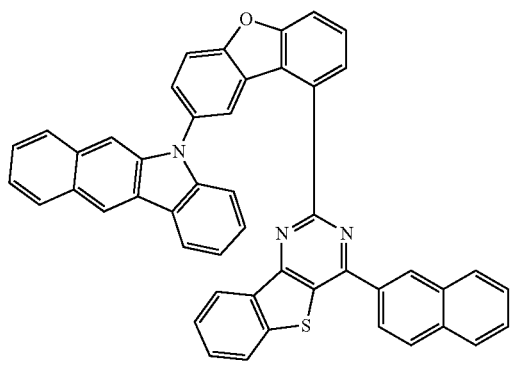
270
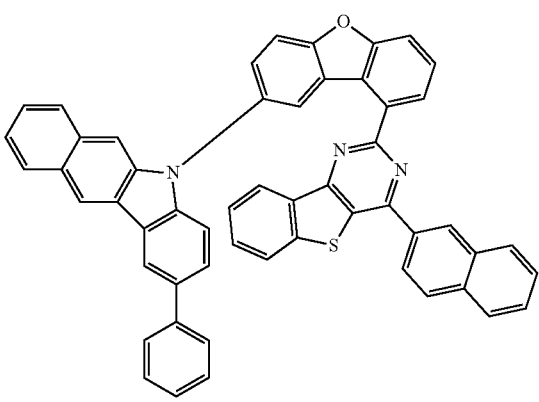
271
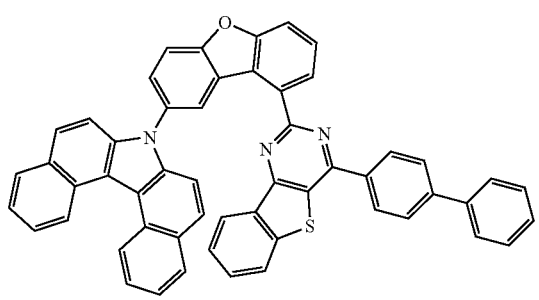
272
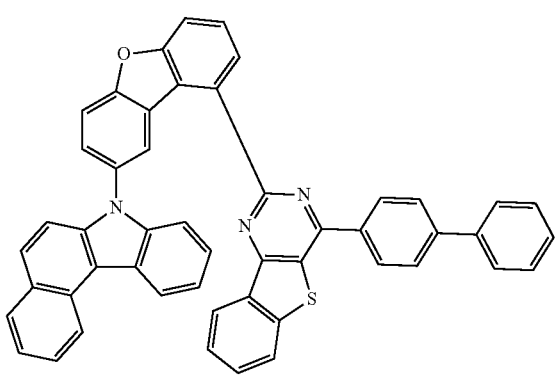
273
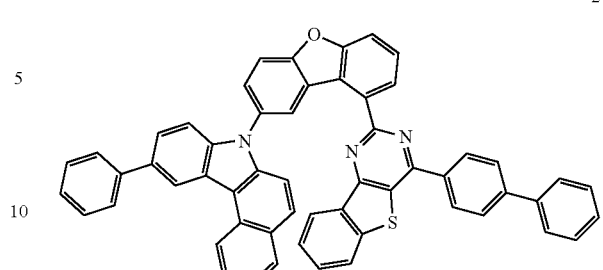
274
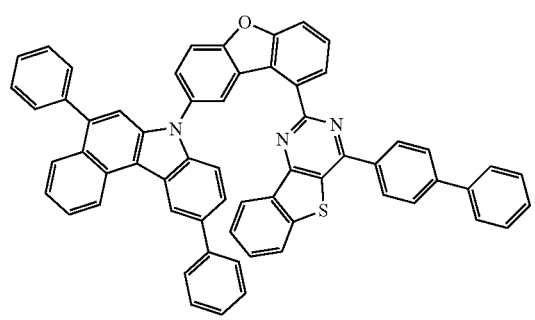
275
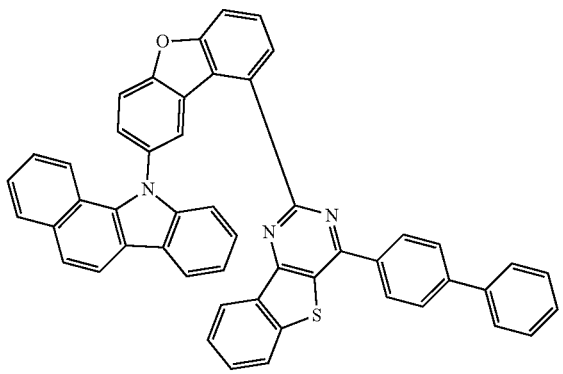
276
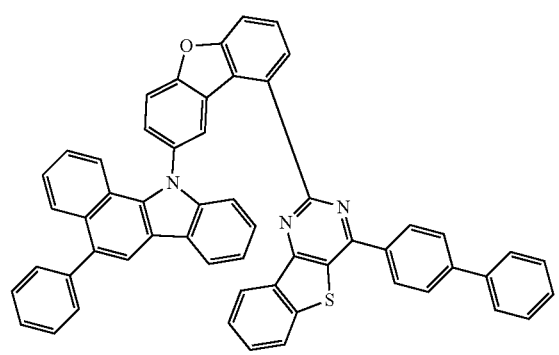

277
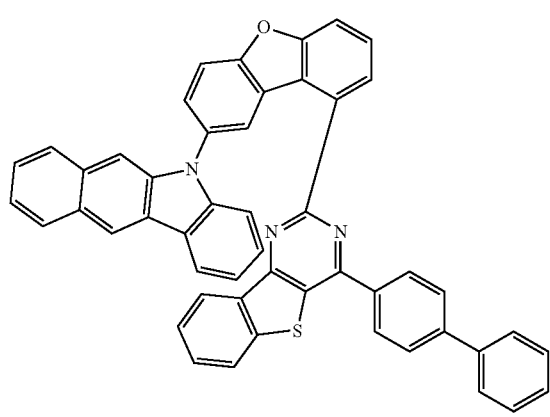
278
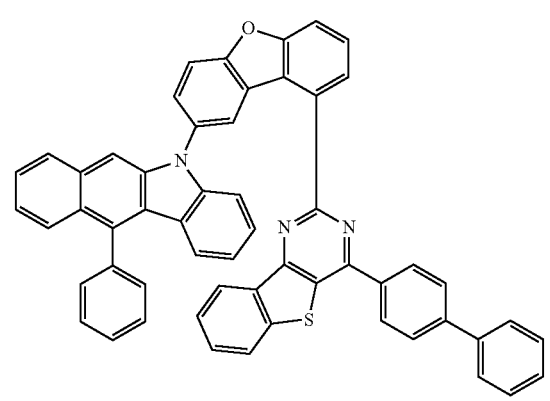
279
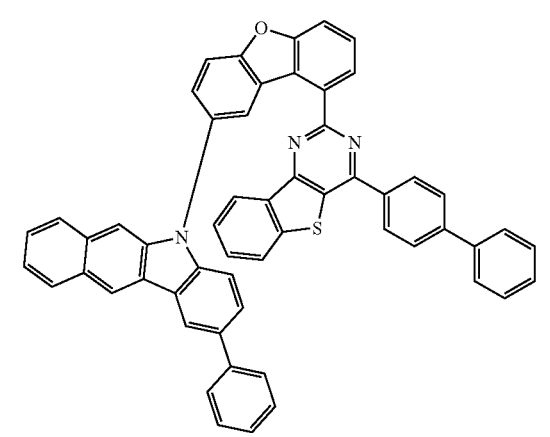
280
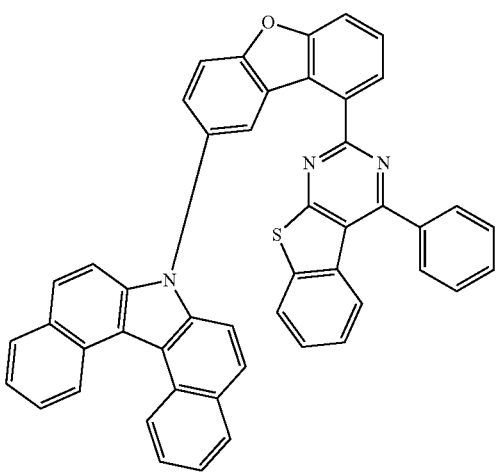
281
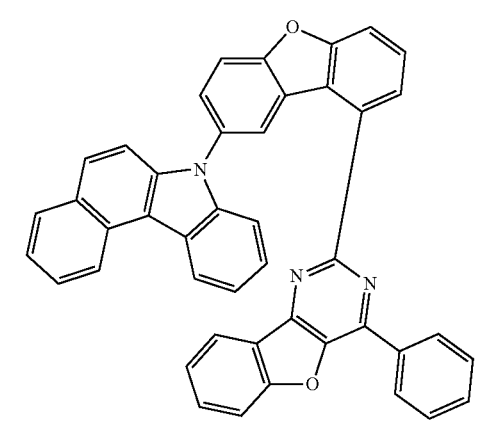
282
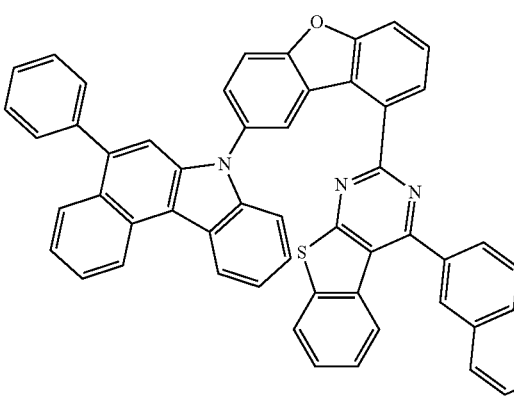
283
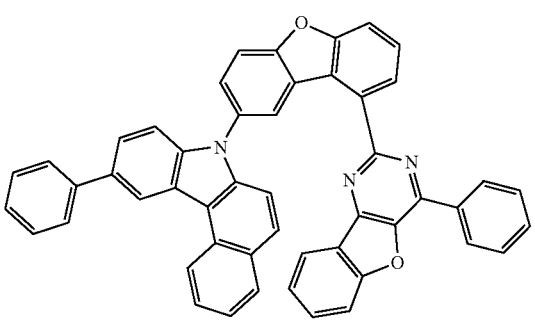

284
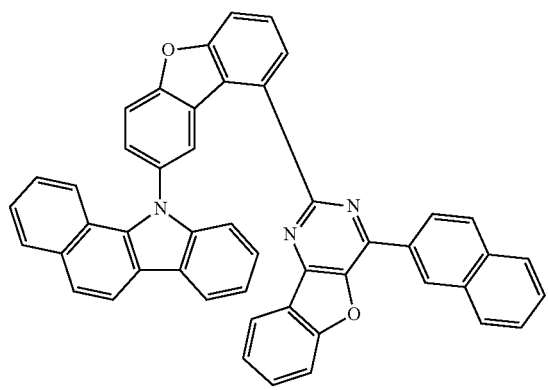
285
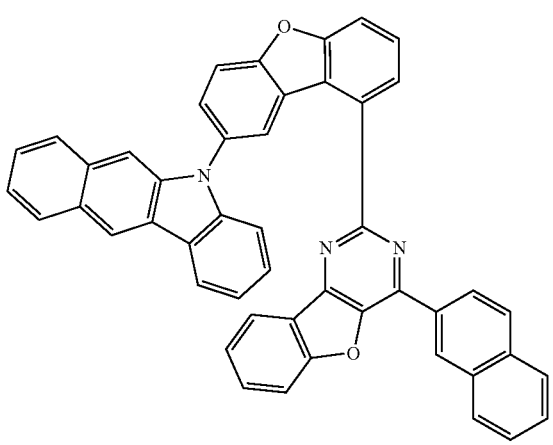
286
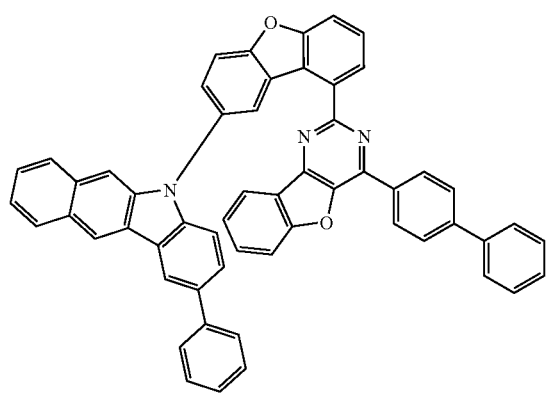
287
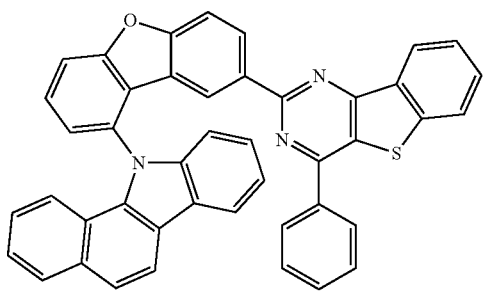
288
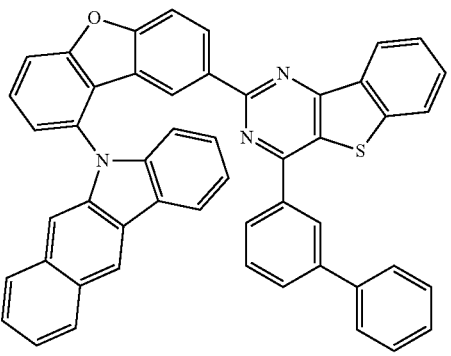
289
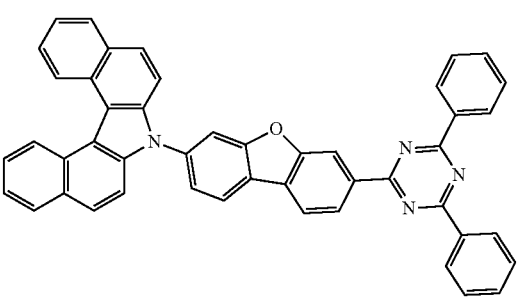
290
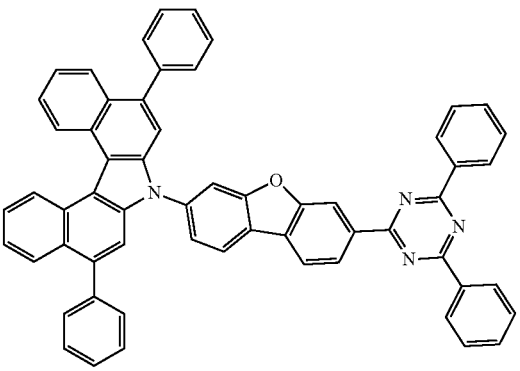
291
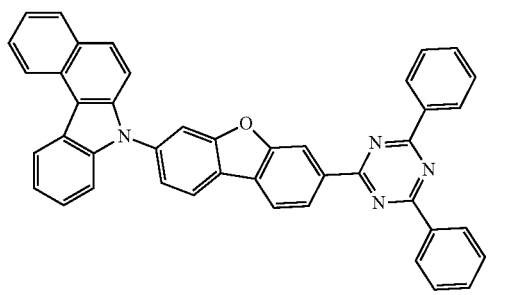

101
-continued
292
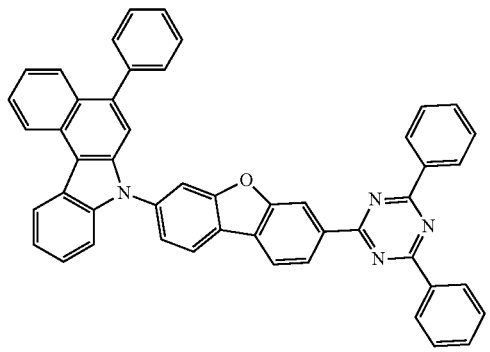
293
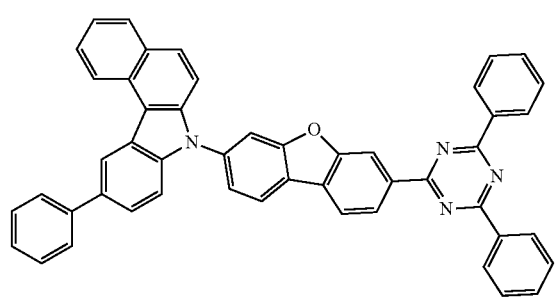
294
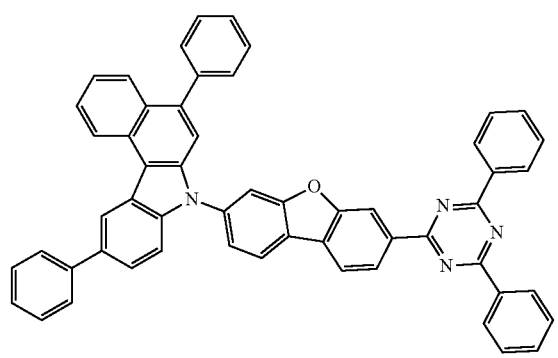
295
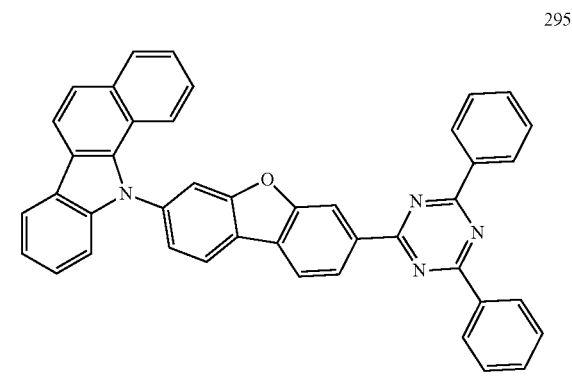
102
-continued
296
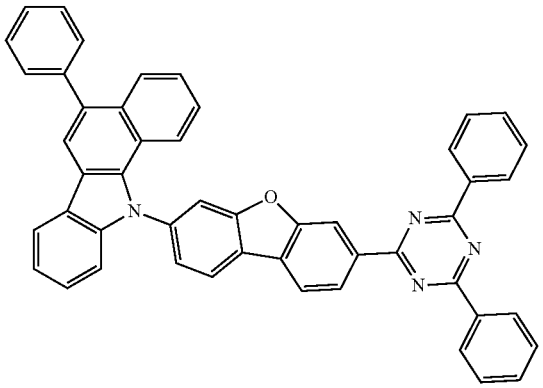
297
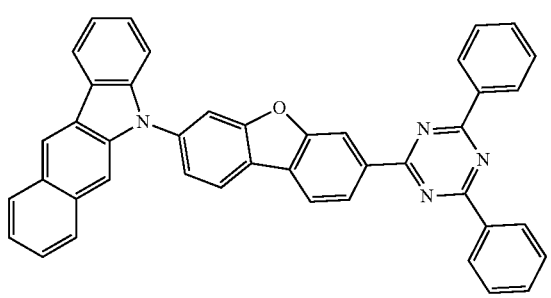
298
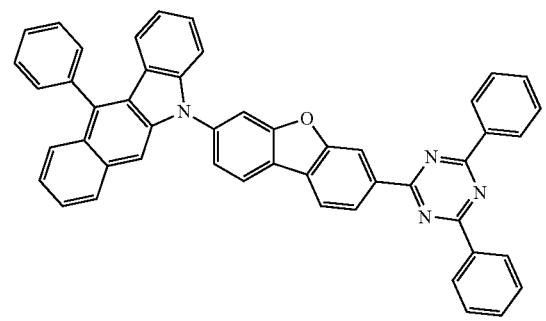
299
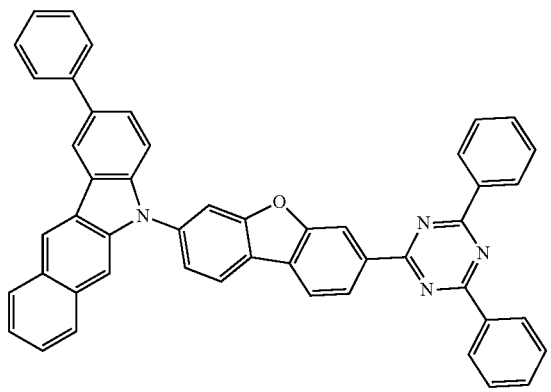

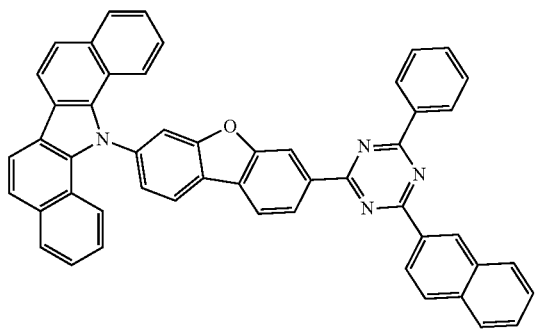
300
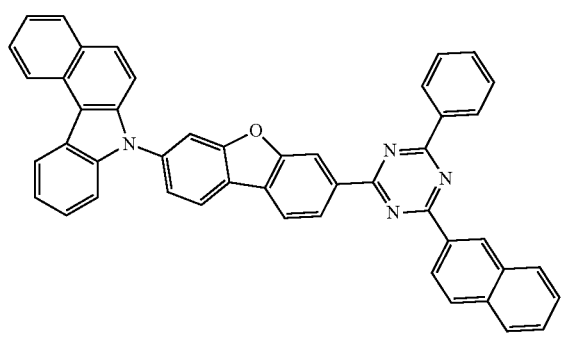
301
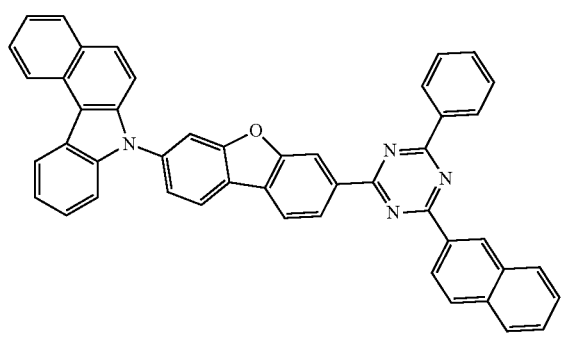
302
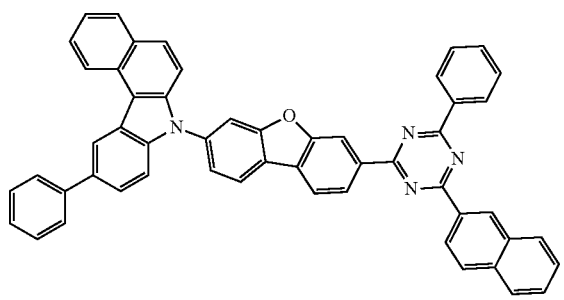
303
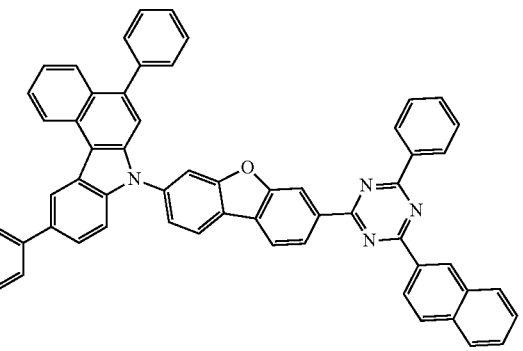
304
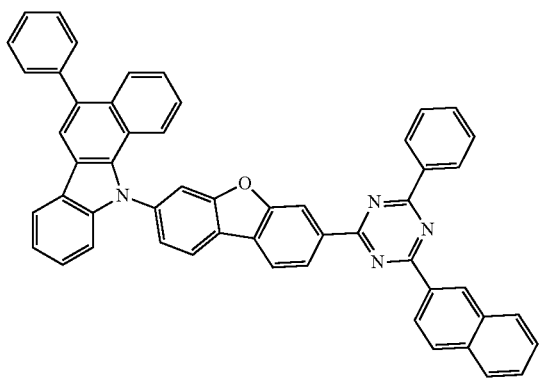
305
306
307

308
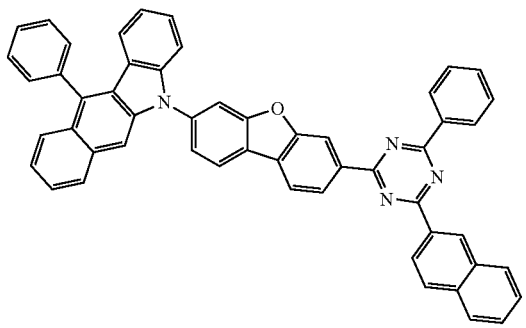
309
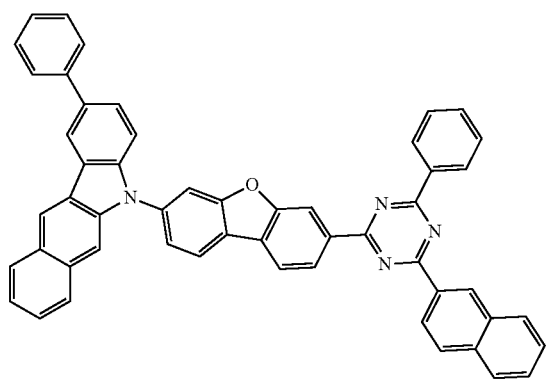
310
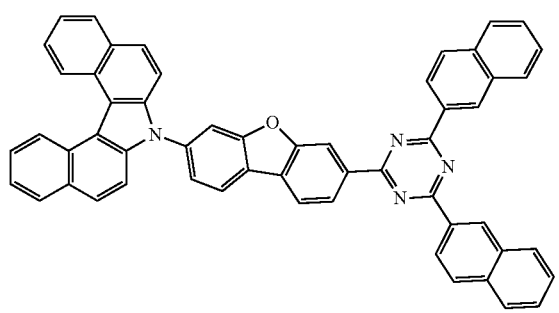
311
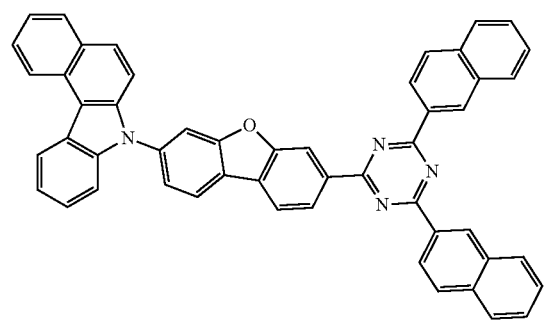
312
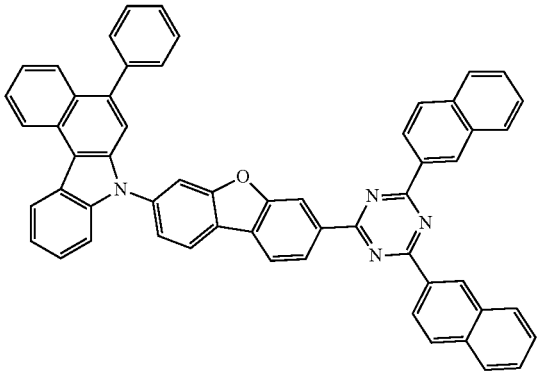
313
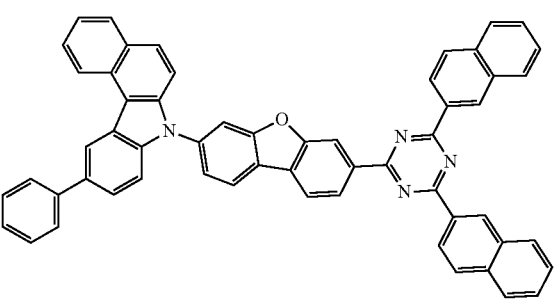
314
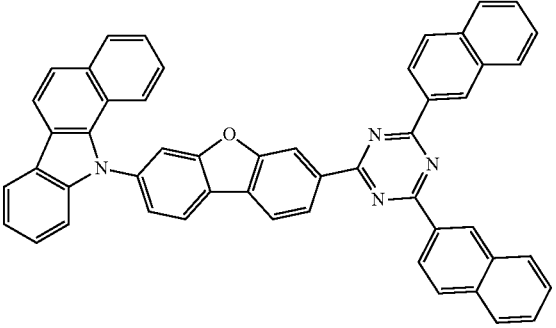
315
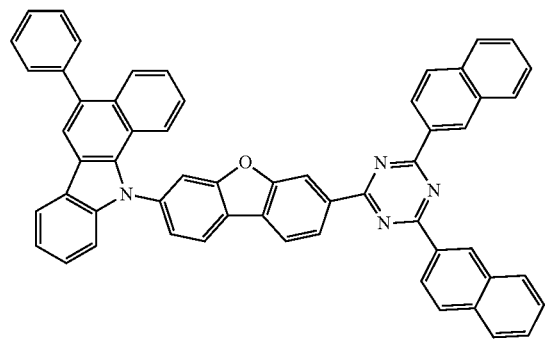

316
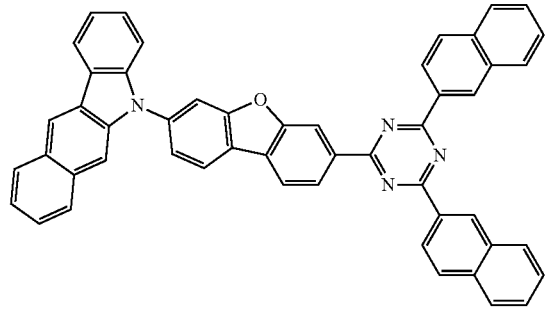
317
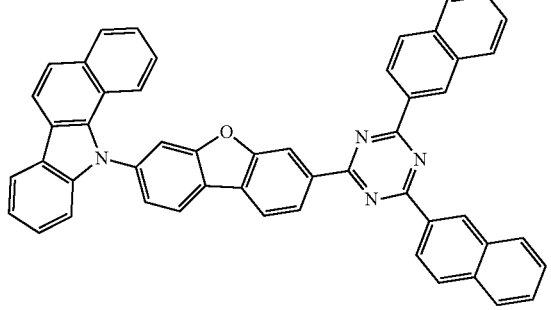
318
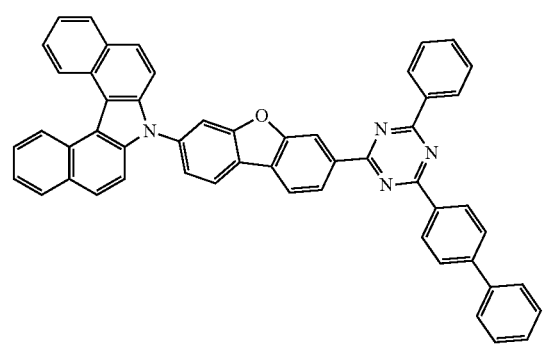
319
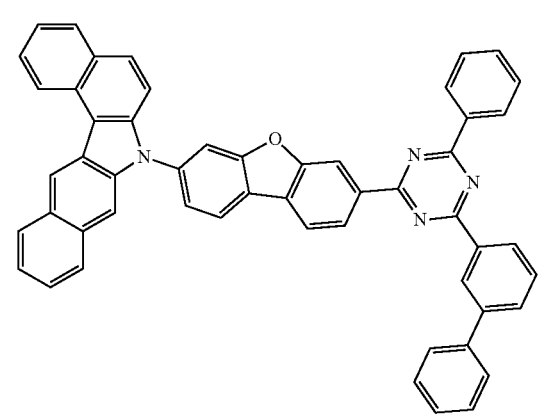
320
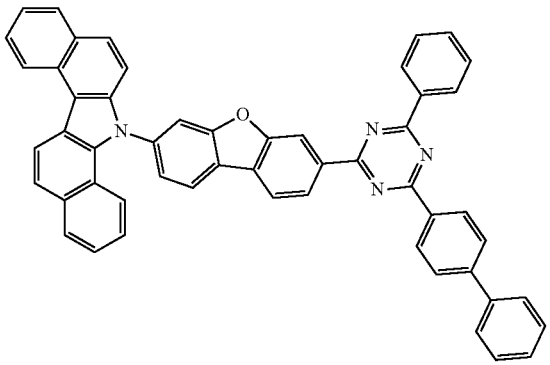
321
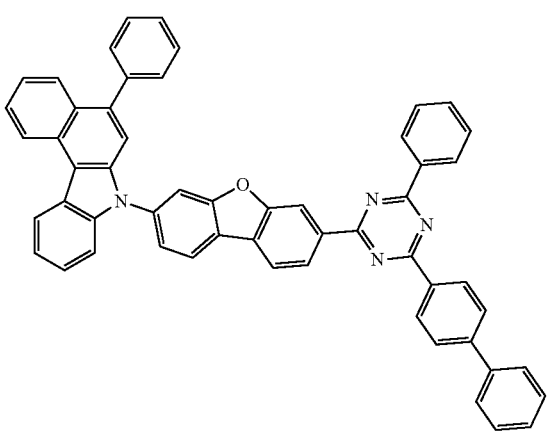
322
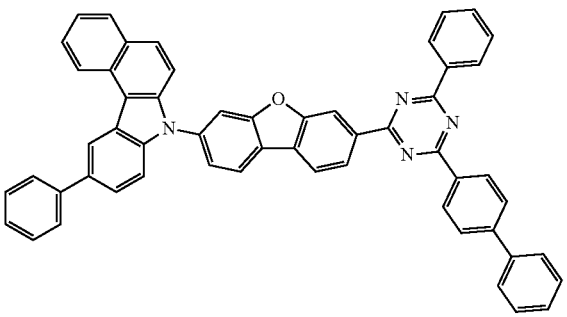
323
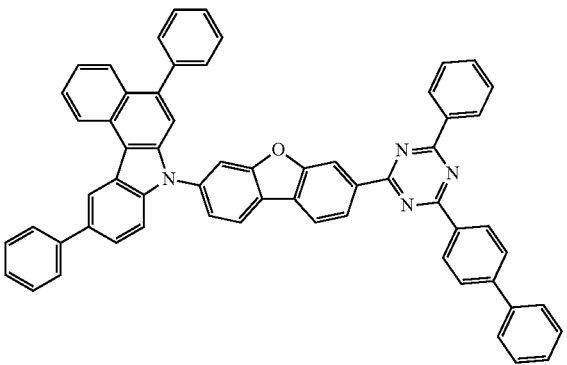

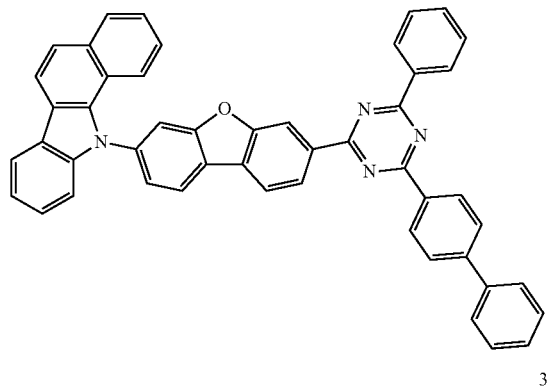
324
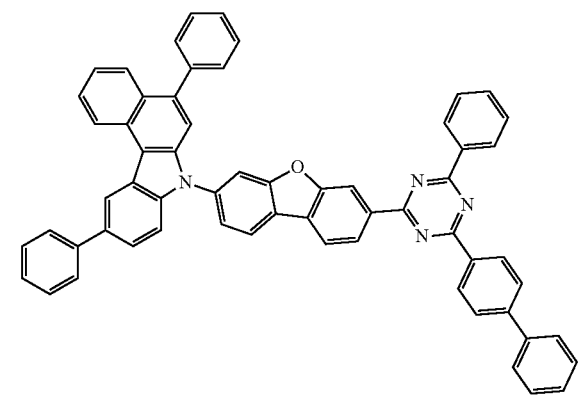
328
325
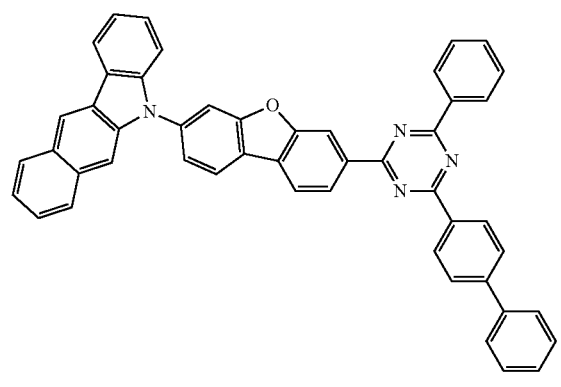
329
326
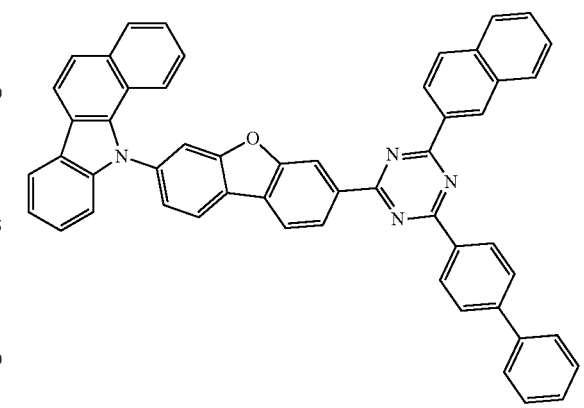
327
330

331
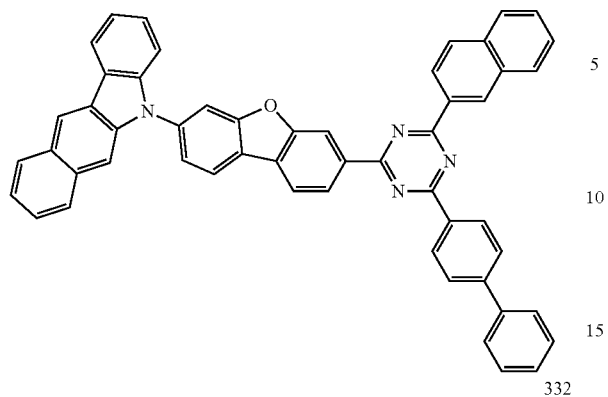
332
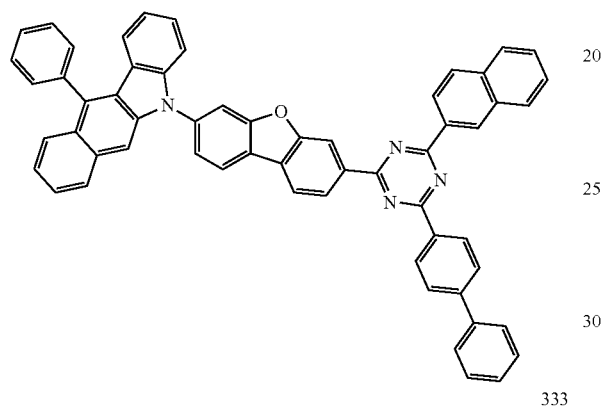
333
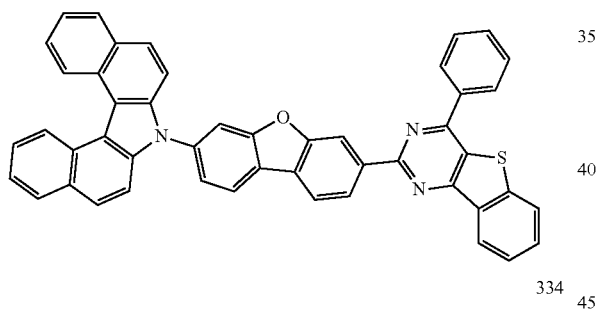
334
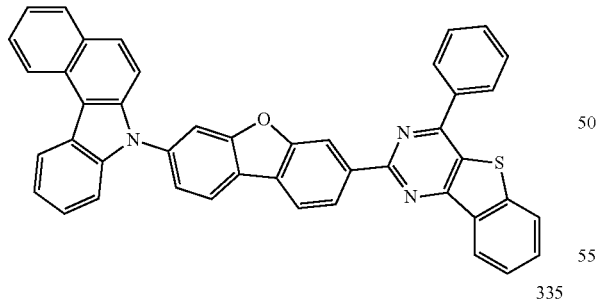
335
336
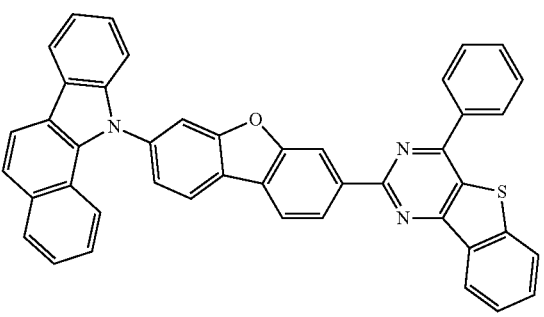
337
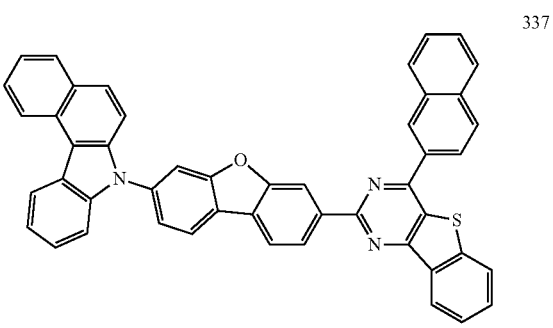
338
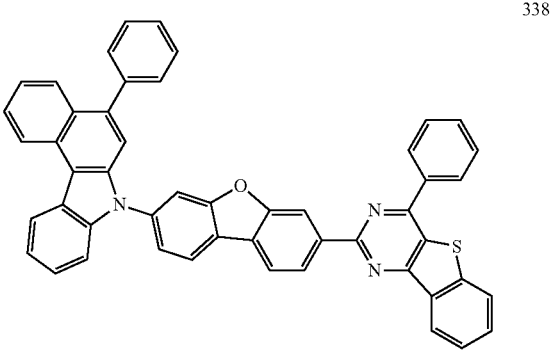
339
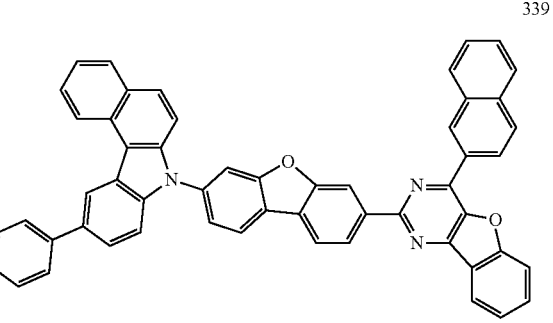

340
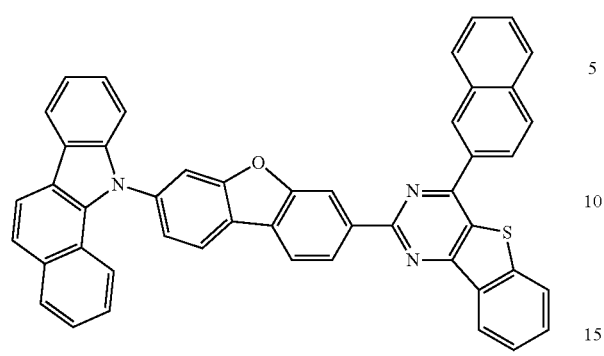
341
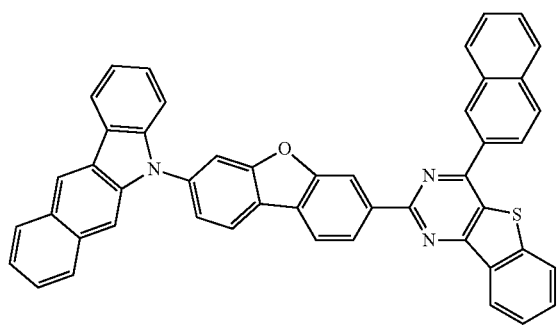
342
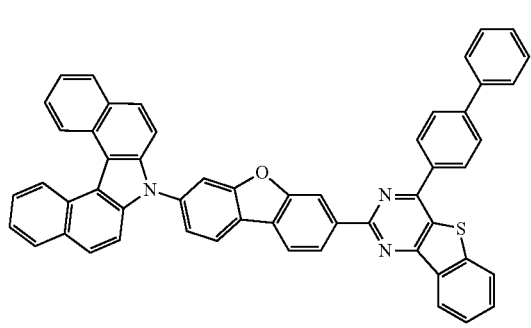
343
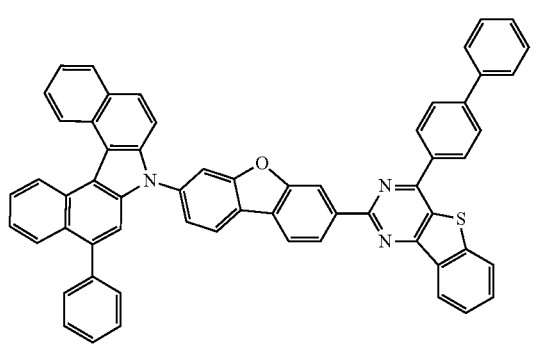
344
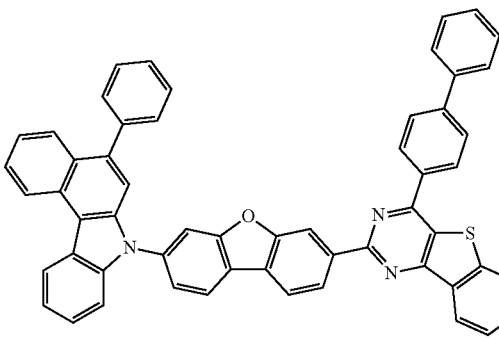
345
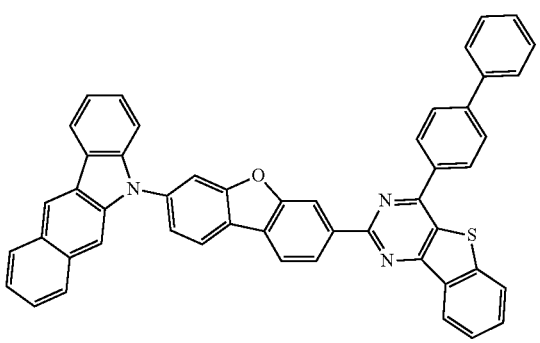
346
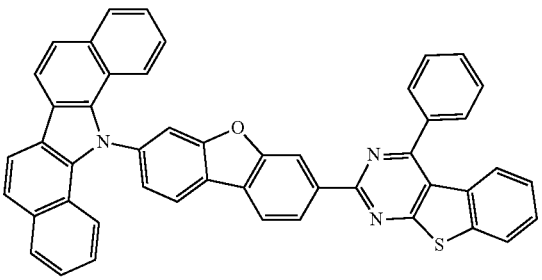
347
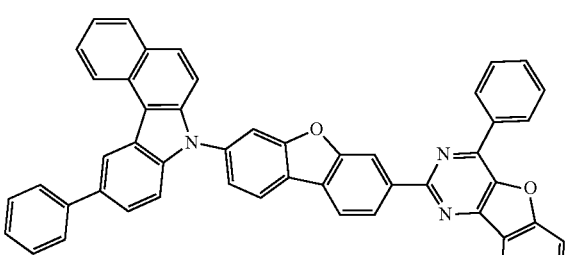
348
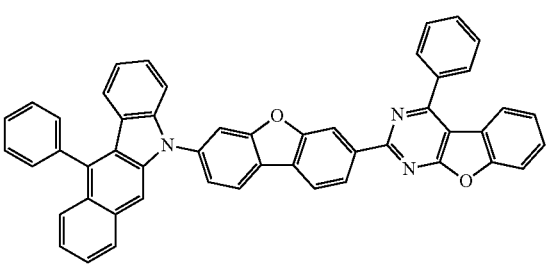

349
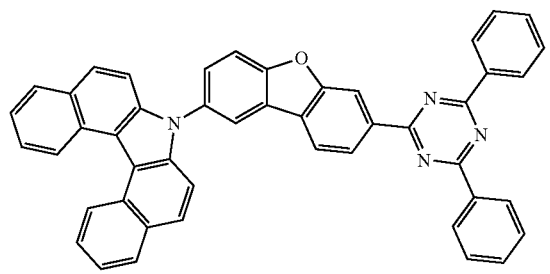
350
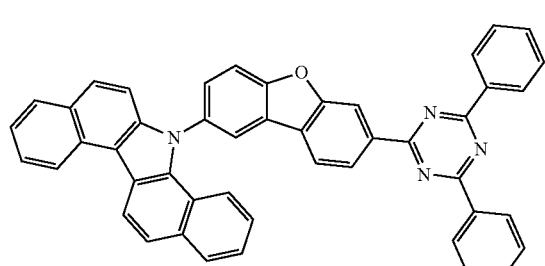
351
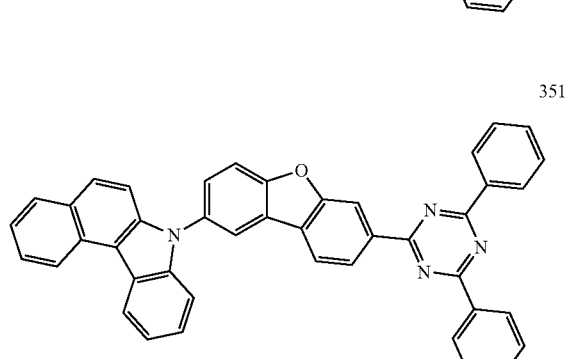
352
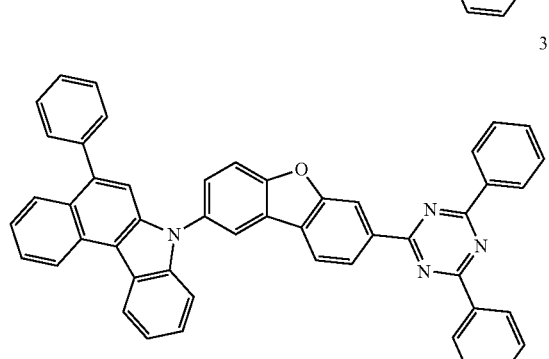
353
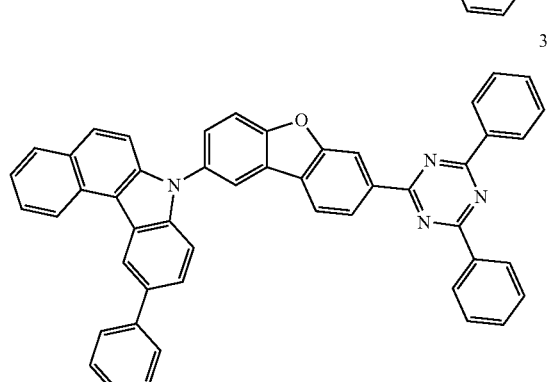
354
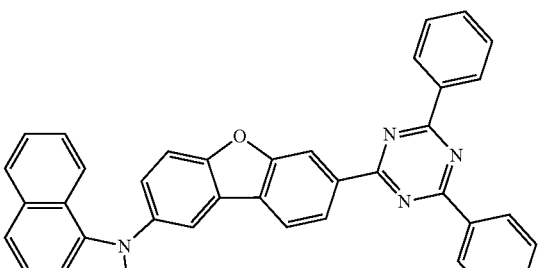
355
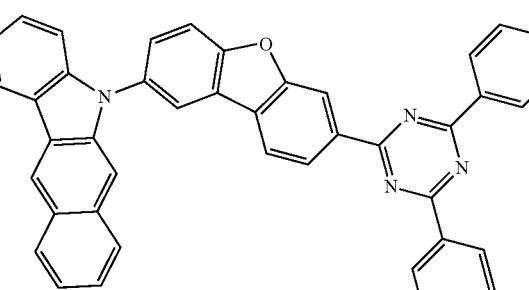
356
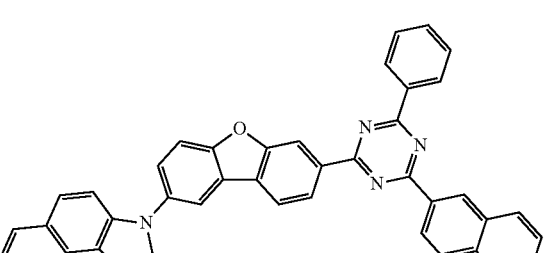
357
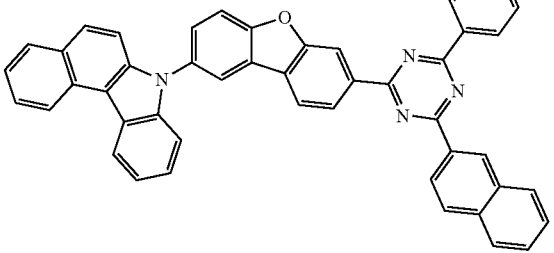

358
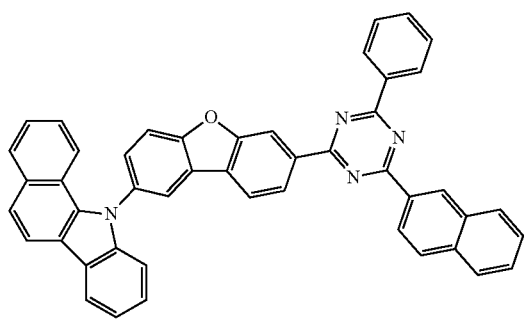
359
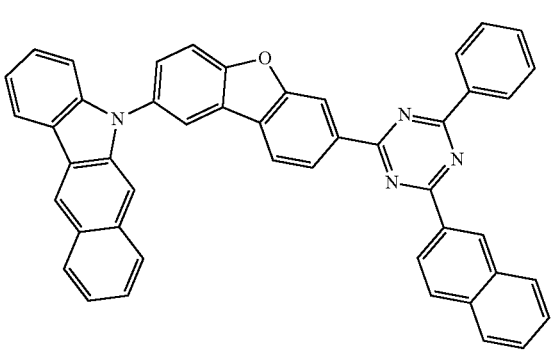
360
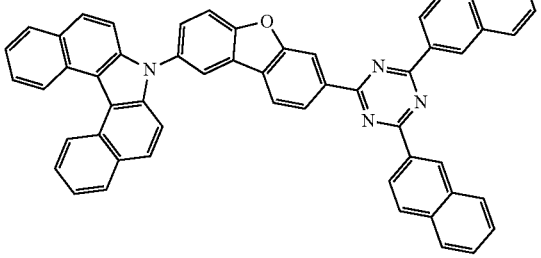
361
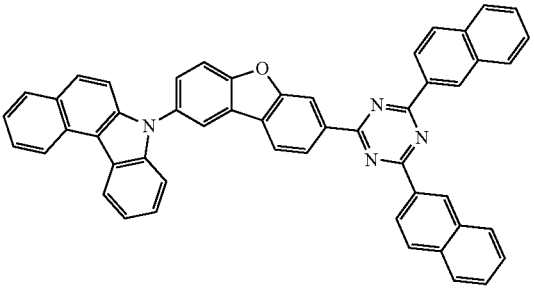
362
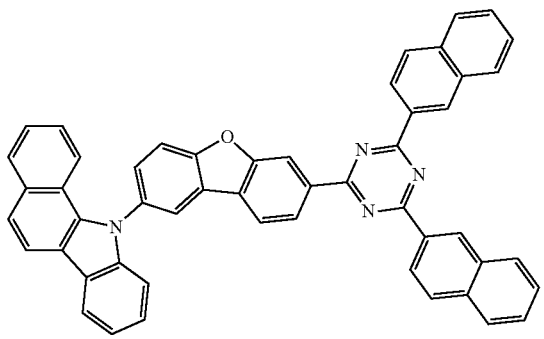
363
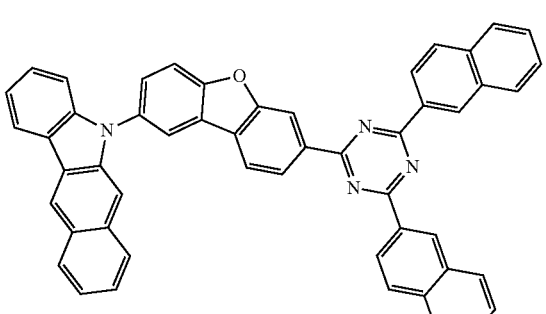
364
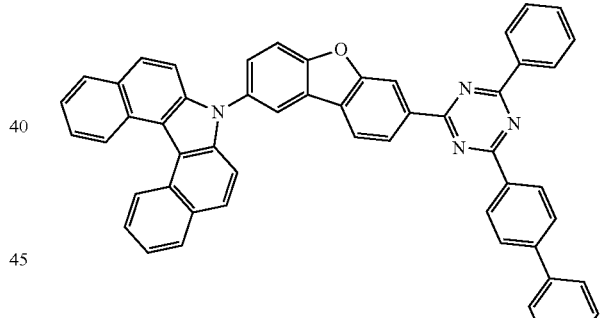
365

-continued
366
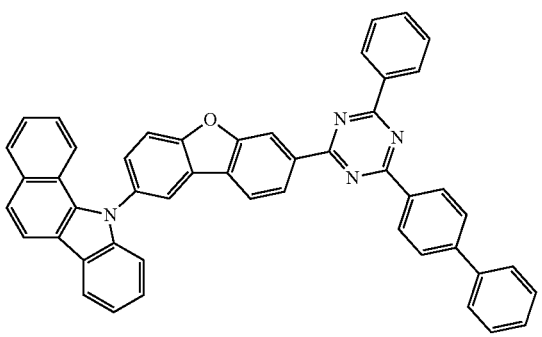
367
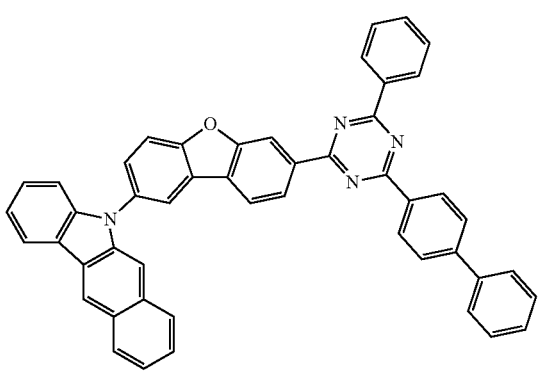
368
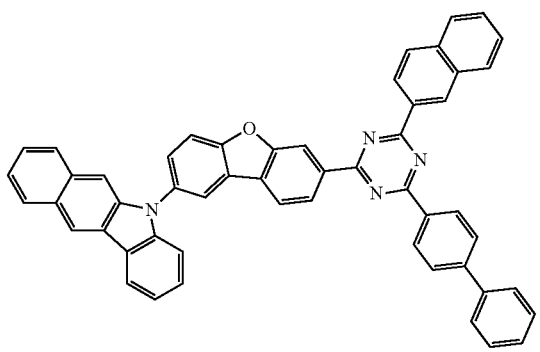
369
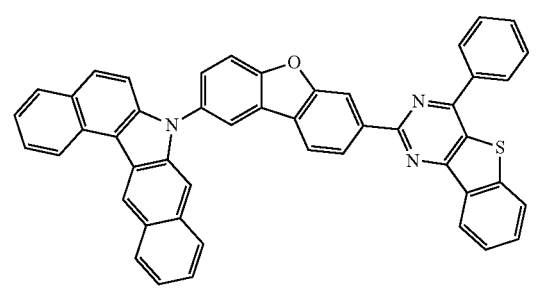
-continued
370
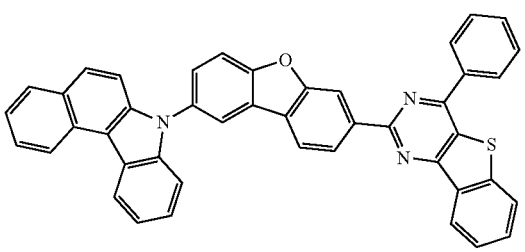
371
372
373
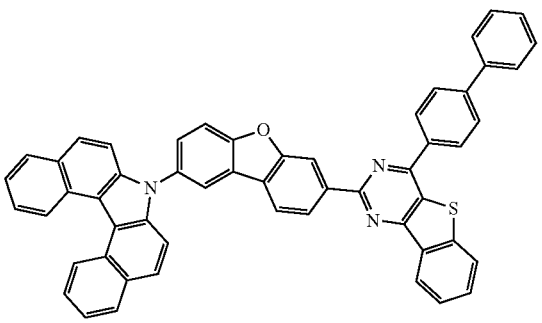

374

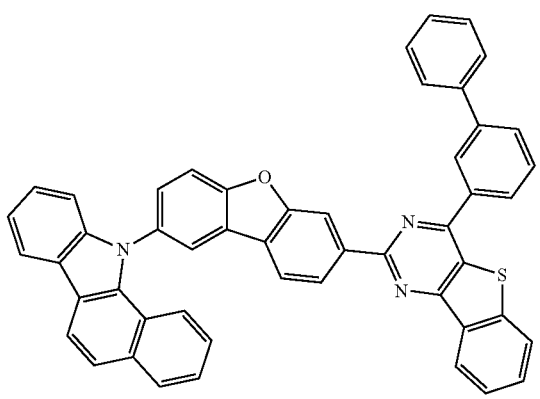

375

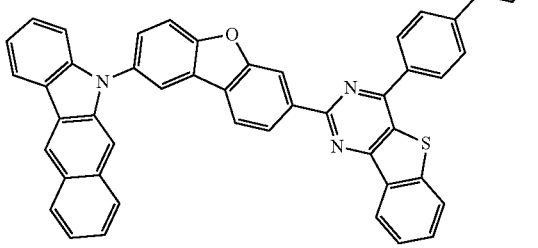

376

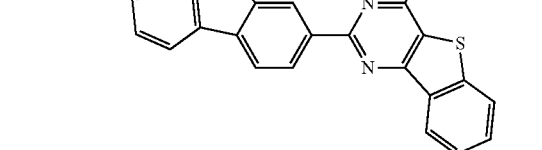

377

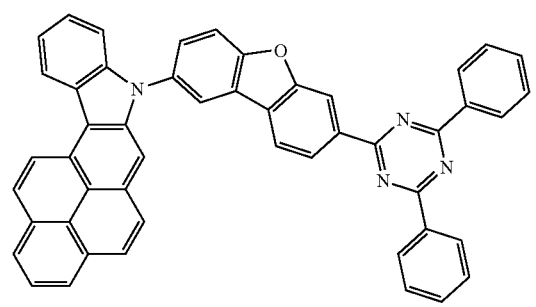

378

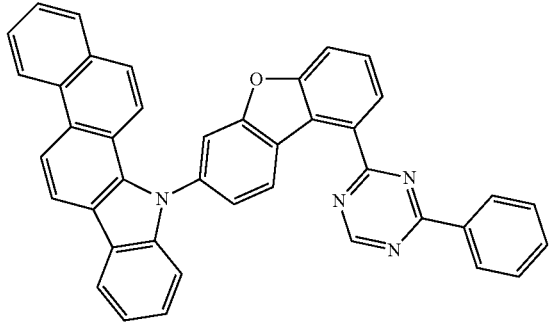

379

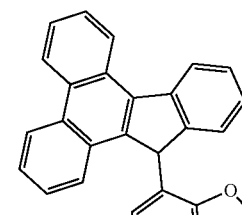

380

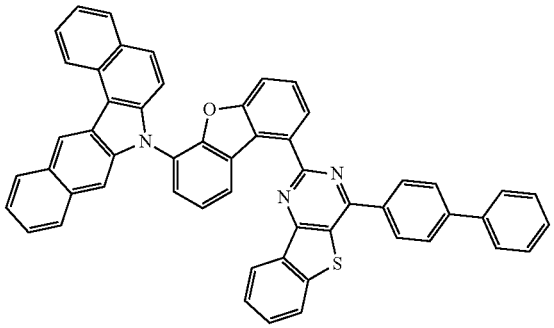

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise one or more of the heterocyclic compound according to Chemical Formula 1.

Another embodiment provides an organic light emitting device comprising a first electrode; a second electrode provided opposite to the first electrode; and one or more organic material layers provided between the first electrode and the second electrode, wherein one or more layers of the organic material layers comprise one of the heterocyclic compound according to Chemical Formula 1.

Another embodiment provides an organic light emitting device comprising a first electrode; a second electrode provided opposite to the first electrode; and one or more organic material layers provided between the first electrode and the second electrode, wherein one or more layers of the organic material layers comprise two of the heterocyclic compound according to Chemical Formula 1.

When comprising two or more of the heterocyclic compound in the organic light emitting device, types of the heterocyclic compound may be the same as or different from each other.

Specific details on the heterocyclic compound represented by Chemical Formula 1 are the same as the descriptions provided above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a blue light emitting layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a green light emitting layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a red light emitting layer of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer may comprise a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

As another example, the organic material layer comprising the heterocyclic compound comprises the heterocyclic compound represented by Chemical Formula 1 as a host, and may be used together with an iridium-based dopant.

In the organic light emitting device of the present disclosure, the organic material layer comprises an electron injection layer or an electron transfer layer, and the electron transfer layer or the electron injection layer may comprise the heterocyclic compound.

In another organic light emitting device, the organic material layer comprises an electron blocking layer or a hole blocking layer, and the electron blocking layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In the organic light emitting device according to one embodiment of the present application, the organic material layer may further comprise a compound of the following Chemical Formula 14.

[Chemical Formula 14]

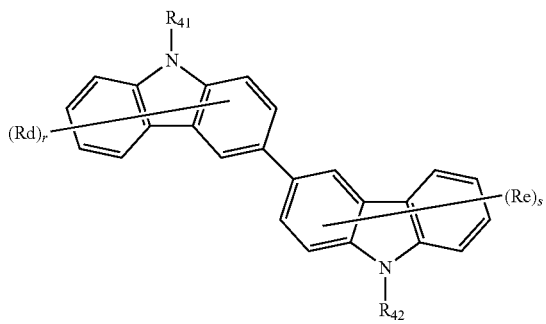

In Chemical Formula 14, $R_4$ and $R_{42}$ are the same as or different from each other, and each independently a substituted or unsubstituted aryl group; or a substituted or unsubstituted heteroaryl group, Rd and Re are the same as or different from each other, and each independently hydrogen; or a substituted or unsubstituted aryl group, and r and s are an integer of 0 to 7.

In one embodiment of the present application, Rd and Re may be hydrogen.

In the organic light emitting device according to one embodiment of the present application, Chemical Formula 14 may be included in a light emitting layer among the organic material layers.

In the organic light emitting device according to one embodiment of the present application, Chemical Formula 14 may be included in a light emitting layer among the organic material layers, and specifically, may be used as a host material of the light emitting layer.

In one embodiment of the present application, the host material of the light emitting layer of the organic light emitting device may comprise both the heterocyclic compound of Chemical Formula 1 and the compound of Chemical Formula 14.

One embodiment of the present application provides a composition for an organic material layer of an organic light emitting device comprising the heterocyclic compound represented by Chemical Formula 1 and the compound represented by Chemical Formula 14; or two types of the heterocyclic compound represented by Chemical Formula 1.

Another embodiment provides a composition for an organic material layer of an organic light emitting device comprising two different types of the heterocyclic compound represented by Chemical Formula 1.

Another embodiment provides a composition for an organic material layer of an organic light emitting device comprising the compound represented by Chemical Formula 1 and the compound represented by Chemical Formula 14.

In the composition, a weight ratio of the heterocyclic compound represented by Chemical Formula 1:the heterocyclic compound represented by Chemical Formula 1 may be from 1:10 to 10:1, 1:8 to 8:1, 1:5 to 5:1, and 1:2 to 2:1, however, the weight ratio is not limited thereto.

The heterocyclic compound represented by Chemical Formula 1 in the composition may be a different type.

In the composition, a weight ratio of the heterocyclic compound represented by Chemical Formula 1:the heterocyclic compound represented by Chemical Formula 14 may be from 1:10 to 10:1, 1:8 to 8:1, 1:5 to 5:1, and 1:3 to 3:1, however, the weight ratio is not limited thereto.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

In one embodiment of the present application, the forming of organic material layers is forming by premixing the heterocyclic compound and the heterocyclic compound of Chemical Formula 14; or two types of the heterocyclic compound, and using a thermal vacuum deposition method.

The pre-mixing means, before depositing the heterocyclic compound represented by Chemical Formula 1 and the compound represented by Chemical Formula 14; or two different types of the heterocyclic compound represented by Chemical Formula 1 on the organic material layer, mixing the materials in advance and placing and mixing the result in one supply source.

The pre-mixed material may be referred to as the composition for an organic material layer according to one embodiment of the present application.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly [3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4', 4"-tri[phenyl (m-tolyl) amino]triphenylamine (m-MTDATA) or 1,3,5-tris [4-(3-methylphenylphenylamino) phenyl]benzene (m-MTDAPB) described in the literature [Advanced Material, 6, p.677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

[Preparation Example 1] Preparation of Compound 1

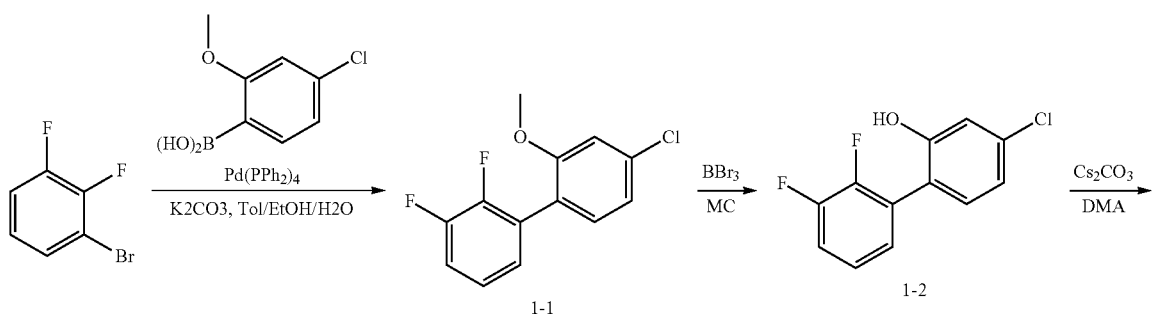

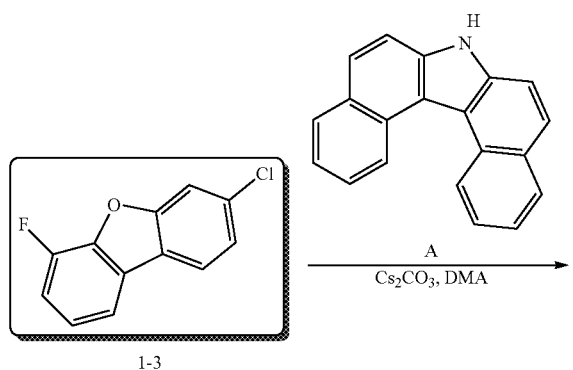

-continued

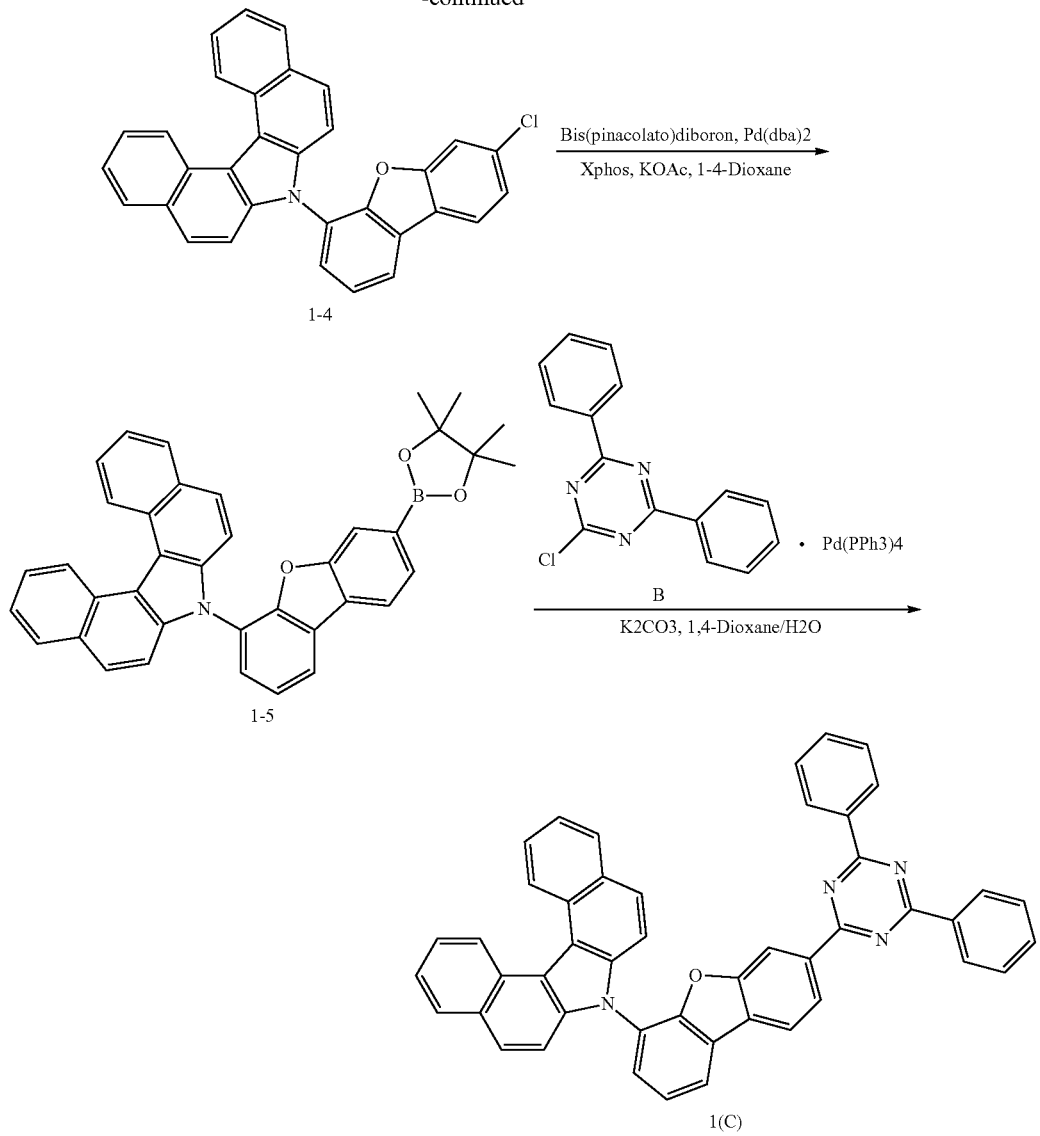

Preparation of Compound 1-1

In a one neck round bottom flask, a mixture of 1-bromo-2,3-difluorobenzene (50 g, 259 mmol), (4-chloro-2-methoxyphenyl)boronic acid (57.7 g, 310 mmol), tetrakis(triphenylphosphine)palladium(0) (29 g, 25.9 mmol), potassium carbonate (107.3 g, 777 mmol) and toluene/ethanol/water (500 ml/100 ml/100 ml) was stirred at 110° C. under reflux. The result was extracted with dichloromethane, dried using MgSO$_4$, and then purified using a silica gel column chromatography to obtain Compound 1-1 (65 g, 99%).

Preparation of Compound 1-2

In a one neck round bottom flask, a mixture of 4'-chloro-2,3-difluoro-2'-methoxy-1,1'-biphenyl (65 g, 255 mmol) and dichloromethane (1000 ml) was cooled to 0° C. After adding BBr$_3$ (48 mL, 500 mmol) dropwise thereto, the temperature was raised to room temperature, and the result was stirred for 2 hours. After terminating the reaction with distilled water, the result was extracted with dichloromethane, and dried using MgSO$_4$. Compound 1-2 (49 g, 80%) was obtained using a silica gel column chromatography purification method.

Preparation of Compound 1-3

In a one neck round bottom flask, a dimethylacetamide (500 ml) mixture of 4-chloro-2',3'-difluoro-[1,1'-biphenyl]-2-ol (49 g, 203 mmol) and Cs$_2$CO$_3$ (331 g, 1018 mmol) was stirred at 120° C. The result was cooled to room temperature, filtered, and after removing the solvent of the filtrate, Compound 1-3 (39.4 g, 88%) was obtained using a silica gel column chromatography purification method.

Preparation of Compound 1-4

In a one neck round bottom flask, a dimethylacetamide (100 ml) mixture of 3-chloro-6-fluorodibenzo[b,d]furan (9 g, 40.7 mmol), 7H-dibenzo[c,g]carbazole (13.0 g, 48.9 mmol) and Cs$_2$CO$_3$ (66.3 g, 203.5 mmol) was stirred for 12 hours at 170° C. under reflux. The result was cooled to room temperature, filtered, and after removing the solvent of the filtrate, Compound 1-4 (13.9 g, 73%) was obtained using a silica gel column chromatography purification method.

Preparation of Compound 1-5

In a one neck round bottom flask, a 1,4-dioxane (100 ml) mixture of 7-(7-chlorodibenzo[b,d]furan-4-yl)-7H-dibenzo[c,g]carbazole (11.8 g, 25.2 mmol), bis(pinacolato)diboron (12.8 g, 50.4 mmol), XPhos (2.6 g, 5.48 mmol), potassium acetate (7.4 g, 75.6 mmol) and Pd(dba)₂ (1.45 g, 2.52 mmol) was stirred at 140° C. under reflux. The result was extracted with dichloromethane and then concentrated, and produced solids were purified by recrystallization using dichloromethane/MeOH to obtain Compound 1-5 (13.5 g, 96%).

Preparation of Compound 1

In a one neck round bottom flask, a mixture of 7-(7-(4,5,5-tetramethyl-1,3,2-dioxaborolan-2-yl)dibenzo [b,d] furan-4-yl)-7H-dibenzo[c,g]carbazole (13.5 g, 24.1 mmol), 2-chloro-4,6-diphenyl-1,3,5-triazine (7.1 g, 26.5 mmol), tetrakis(triphenylphosphine)palladium(0) (2.8 g, 2.41 mmol), potassium carbonate (9.99 g, 72.3 mmol) and 1,4-dioxane/water (150 ml/30 ml) was stirred for 3 hours at 120° C. under reflux. Solids precipitated during the reaction were filtered while hot, and purified using 1,4-dioxane, distilled water and MeOH to obtain Compound 1 (11.21 g, 70%).

The following target compounds were synthesized in the same manner as in the method for preparing Compound 1 of Preparation Example 1 except that A of the following Table 1 was used instead of 7H-dibenzo[c,g]carbazole, and B of the following Table 1 was used instead of 2-chloro-4,6-diphenyl-1,3,5-triazine.

TABLE 1

| Compound | A | B |
|---|---|---|
| 4 | (benzo[a]carbazole structure) | (2-chloro-4,6-diphenyl-1,3,5-triazine) |
| 10 | (benzo[b]carbazole structure) | (2-chloro-4,6-diphenyl-1,3,5-triazine) |
| 11 | (benzo[c]carbazole structure) | (2-chloro-4,6-diphenyl-1,3,5-triazine) |
| 21 | (benzo[a]carbazole isomer structure) | (2-chloro-4-biphenyl-6-phenyl-1,3,5-triazine) |

TABLE 1-continued
| 25 | 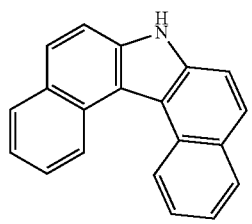 | 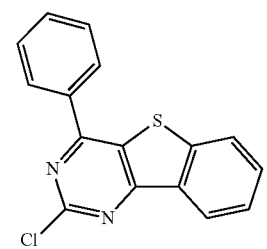 |
| --- | --- | --- |
| 26 | 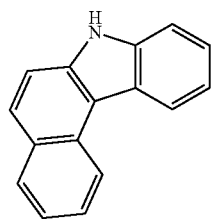 [SMILES: c1ccc2c(c1)ccc1[nH]c3ccccc3c12] | 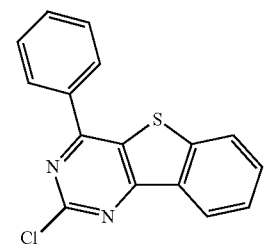 [SMILES: Clc1nc(-c2ccccc2)c2sc3ccccc3c2n1] |
| 28 | 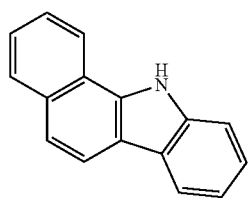 [SMILES: c1ccc2c(c1)ccc1c3ccccc3[nH]c21] | 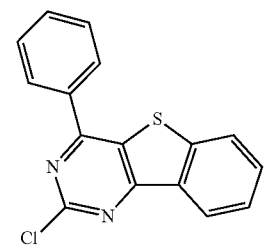 [SMILES: Clc1nc(-c2ccccc2)c2sc3ccccc3c2n1] |
| 29 | 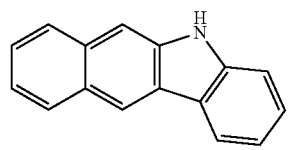 [SMILES: c1ccc2cc3c(cc2c1)[nH]c1ccccc13] | 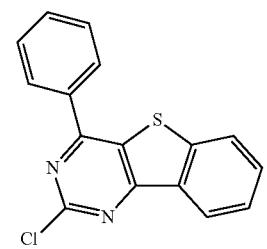 [SMILES: Clc1nc(-c2ccccc2)c2sc3ccccc3c2n1] |
| 36 |  | 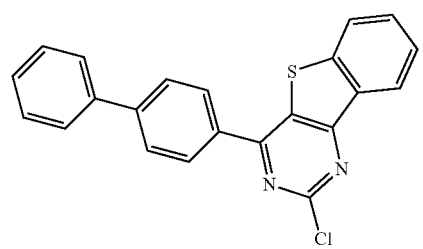 [SMILES: Clc1nc(-c2ccc(-c3ccccc3)cc2)c2sc3ccccc3c2n1] |

TABLE 1-continued

| Compound | Target Compound | Yield (%) |
|---|---|---|
| 4 | | 68 |
| 10 | | 73 |
| 11 | | 71 |
| 21 | | 69 |

TABLE 1-continued
25
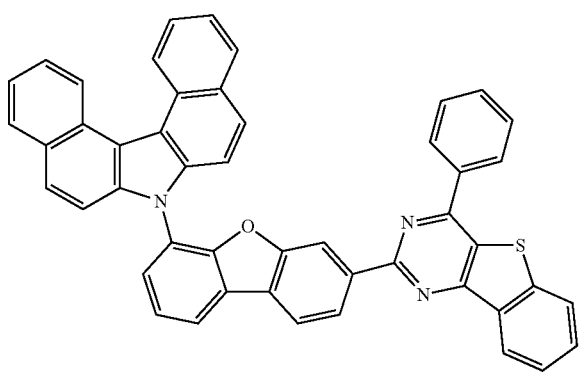 [SMILES: c1ccc(-c2nc(-c3ccc4c(c3)oc3c(-n5c6ccc7ccccc7c6c6c7ccccc7ccc65)cccc34)nc3c2sc2ccccc23)cc1]
26
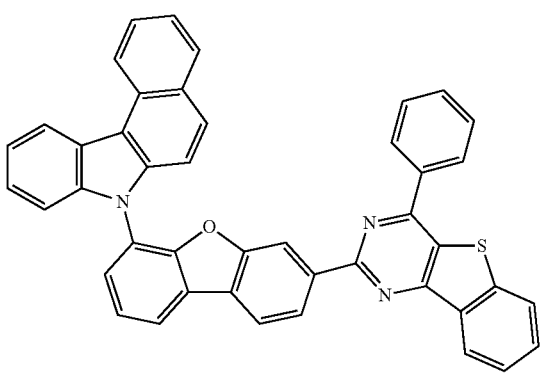 [SMILES: c1ccc(-c2nc(-c3ccc4c(c3)oc3c(-n5c6ccccc6c6c7ccccc7ccc65)cccc34)nc3c2sc2ccccc23)cc1]
28
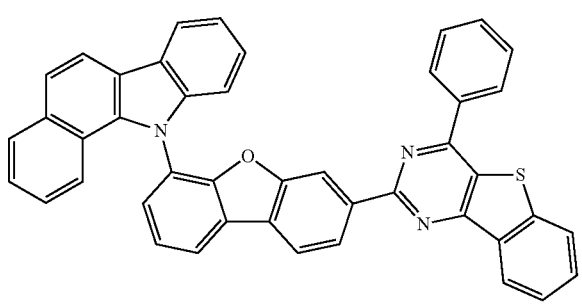 [SMILES: c1ccc(-c2nc(-c3ccc4c(c3)oc3c(-n5c6ccccc6c6ccc7ccccc7c65)cccc34)nc3c2sc2ccccc23)cc1]
29
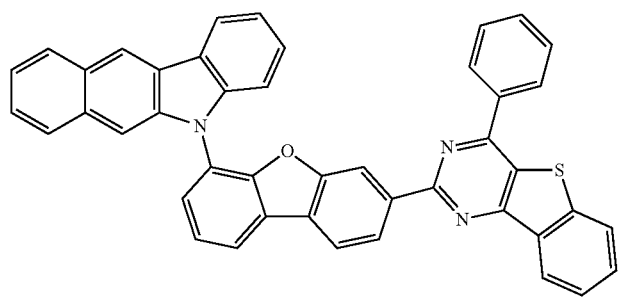 [SMILES: c1ccc(-c2nc(-c3ccc4c(c3)oc3c(-n5c6ccccc6c6cc7ccccc7cc65)cccc34)nc3c2sc2ccccc23)cc1]
66
70
69
73

TABLE 1-continued

| 36 | 79 |
|---|---|
| | 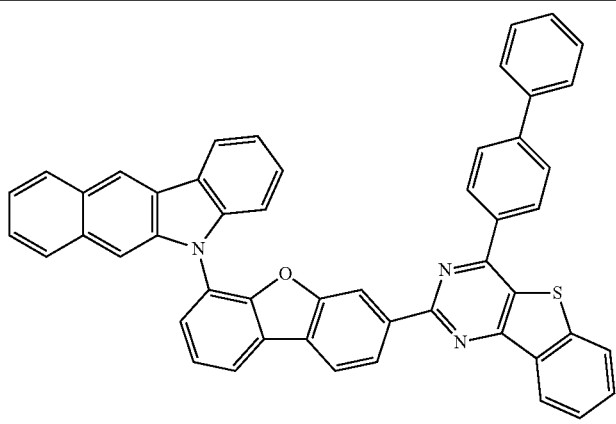 |

[Preparation Example 2] Preparation of Compound 37

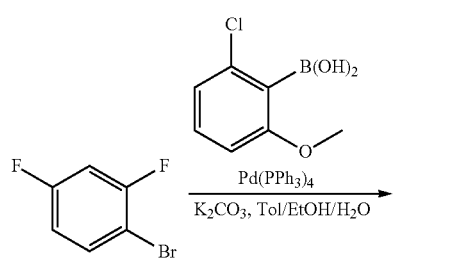

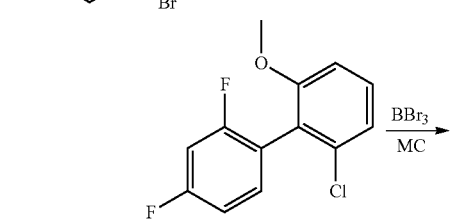

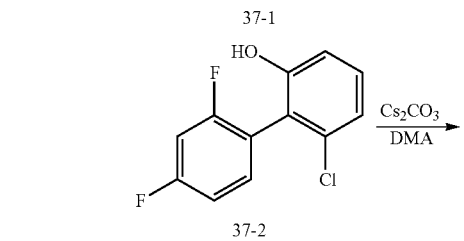

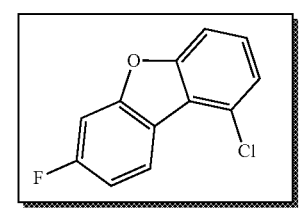

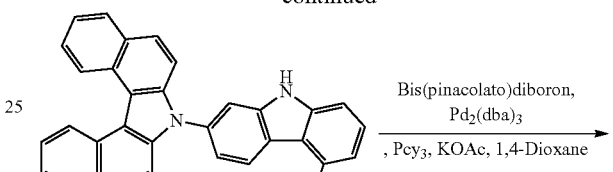

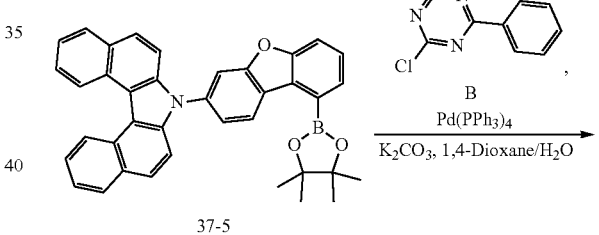

Compound 37 (10.89 g, 68%) was synthesized in the same manner as in the method for preparing Compound 1 of Preparation Example 1 except that 1-bromo-2,4-difluorobenzene was used instead of 1-bromo-2,3-difluorobenzene, and (2-chloro-6-methoxyphenyl)boronic acid was used instead of (4-chloro-2-methoxyphenyl) boronic acid.

The following target compounds were synthesized in the same manner as in the method for preparing Compound 37 of Preparation Example 2 except that A of the following Table 2 was used instead of 7H-dibenzo[c,g]carbazole, and B of the following Table 2 was used instead of 2-chloro-4,6-diphenlyl-1,3,5-triazine.

TABLE 2

| Compound | A |
|---|---|
| 44 | |
| 46 | |
| 68 | |
| 74 | |
| 76 | |
| 80 | |
| 81 | |
| 89 | |

TABLE 2-continued
| | |
|---|---|
| 95 | 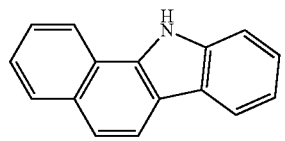 |
| 97 | 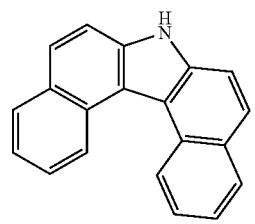 |
| 101 | 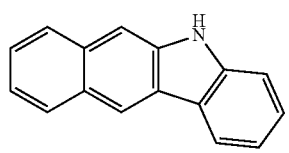 |
| Compound | B |
|---|---|
| 44 | 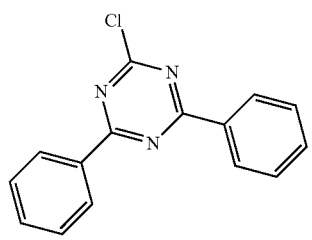 |
| 46 | 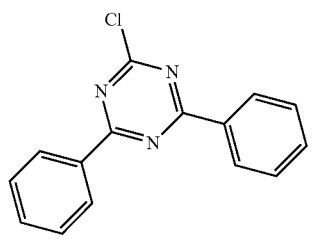 |
| 68 | 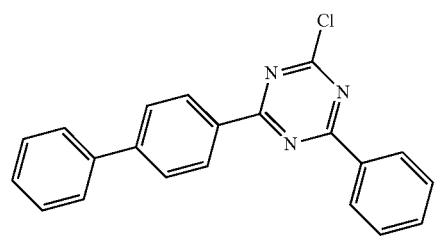 |
| 74 | 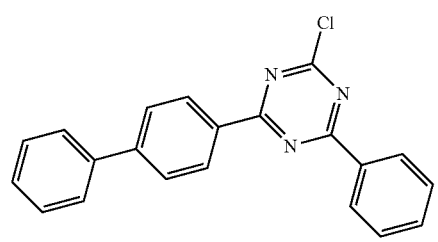 |

TABLE 2-continued
| | |
|---|---|
| 76 | 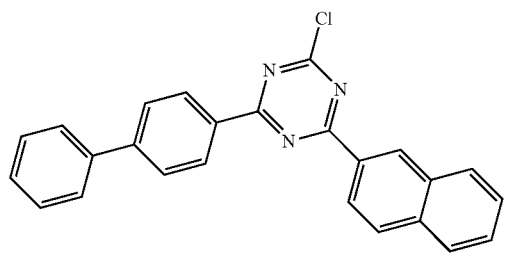 |
| 80 | 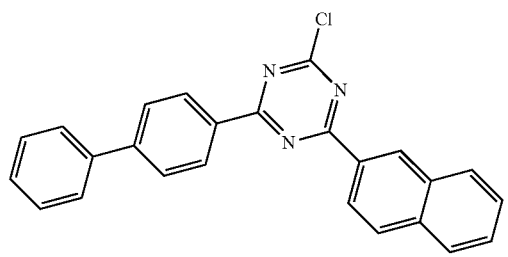 |
| 81 | 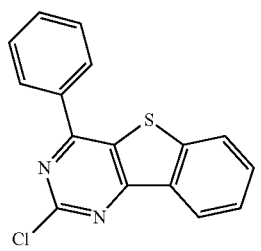 |
| 89 | 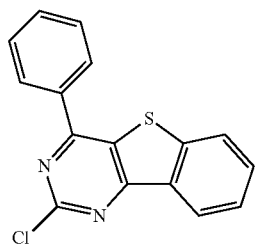 |
| 95 | 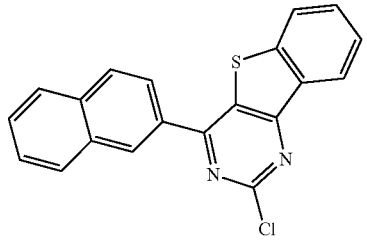 |
| 97 | 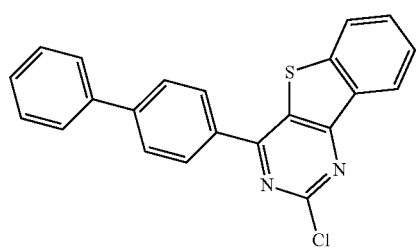 |

TABLE 2-continued
101
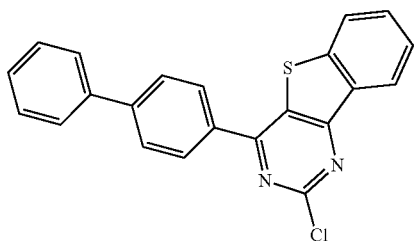 [SMILES: Clc1nc(-c2ccc(-c3ccccc3)cc2)c2sc3ccccc3c2n1]
| Compound | Target Compound | Yield (%) |
|---|---|---|
| 44 | 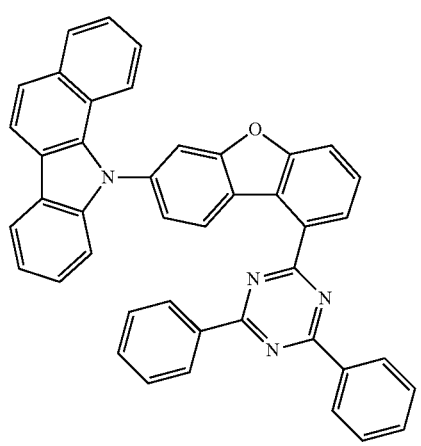 [SMILES: c1ccc(-c2nc(-c3ccccc3)nc(-c3cccc4oc5cc(-n6c7ccccc7c7ccc8ccccc8c76)ccc5c34)n2)cc1] | 64 |
| 46 | 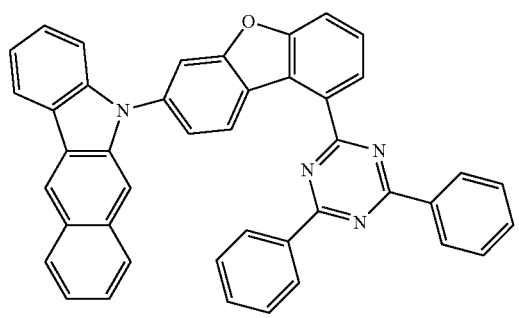 [SMILES: c1ccc(-c2nc(-c3ccccc3)nc(-c3cccc4oc5cc(-n6c7ccccc7c7cc8ccccc8cc76)ccc5c34)n2)cc1] | 68 |
| 68 | 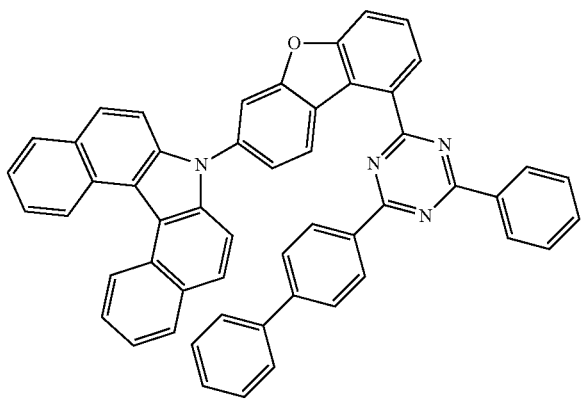 [SMILES: c1ccc(-c2ccc(-c3nc(-c4ccccc4)nc(-c4cccc5oc6cc(-n7c8ccc9ccccc9c8c8c9ccccc9ccc87)ccc6c45)n3)cc2)cc1] | 70 |

TABLE 2-continued
| 74 | 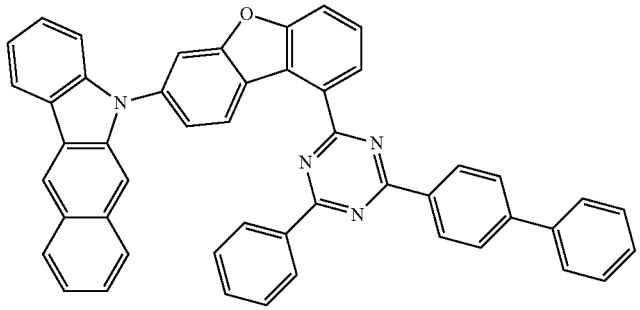 [SMILES: c1ccc(-c2ccc(-c3nc(-c4ccccc4)nc(-c4cccc5oc6cc(-n7c8ccccc8c8cc9ccccc9cc87)ccc6c45)n3)cc2)cc1] | 72 |
| 76 | 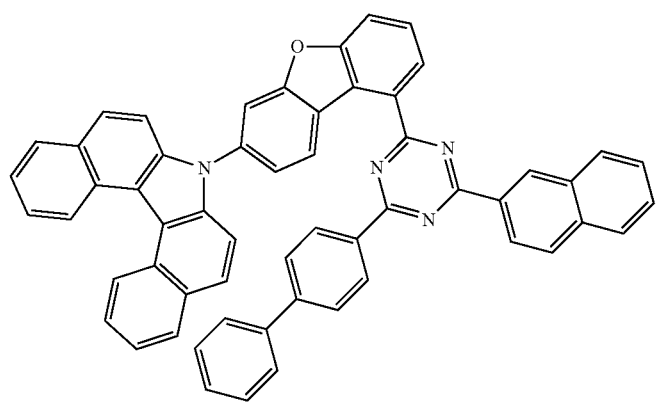 [SMILES: c1ccc(-c2ccc(-c3nc(-c4ccc5ccccc5c4)nc(-c4cccc5oc6cc(-n7c8ccc9ccccc9c8c8c9ccccc9ccc87)ccc6c45)n3)cc2)cc1] | 66 |
| 80 | 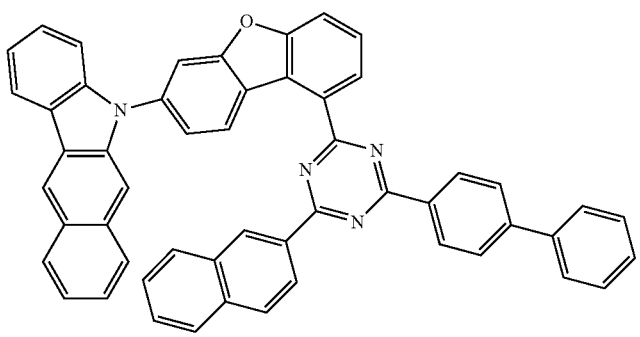 [SMILES: c1ccc(-c2ccc(-c3nc(-c4ccc5ccccc5c4)nc(-c4cccc5oc6cc(-n7c8ccccc8c8cc9ccccc9cc87)ccc6c45)n3)cc2)cc1] | 65 |
| 81 | 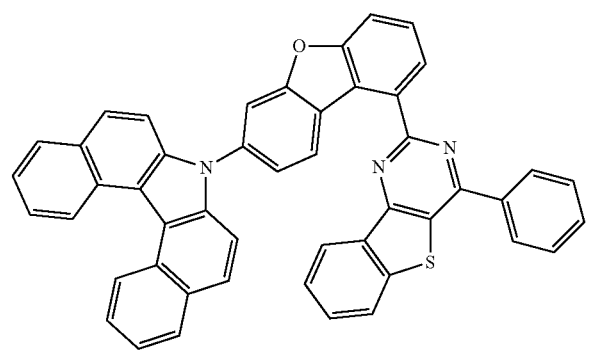 [SMILES: c1ccc(-c2nc(-c3cccc4oc5cc(-n6c7ccc8ccccc8c7c7c8ccccc8ccc76)ccc5c34)nc3c2sc2ccccc23)cc1] | 67 |

TABLE 2-continued
| | | |
|---|---|---|
| 89 | 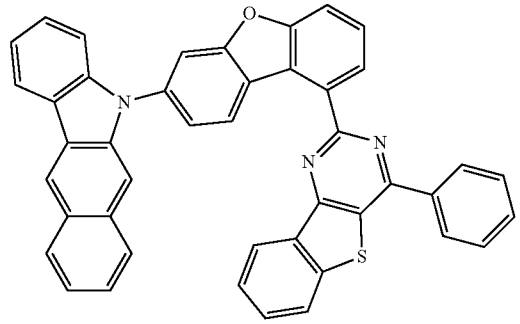 [SMILES: c1ccc(-c2nc(-c3cccc4oc5cc(-n6c7ccccc7c7cc8ccccc8cc76)ccc5c34)nc3c2sc2ccccc23)cc1] | 71 |
| 95 | 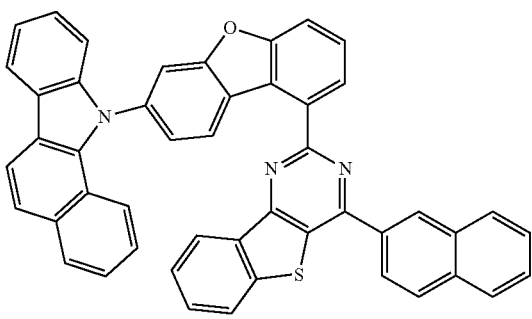 [SMILES: c1ccc2cc(-c3nc(-c4cccc5oc6cc(-n7c8ccccc8c8ccc9ccccc9c87)ccc6c45)nc4c3sc3ccccc34)ccc2c1] | 72 |
| 97 | 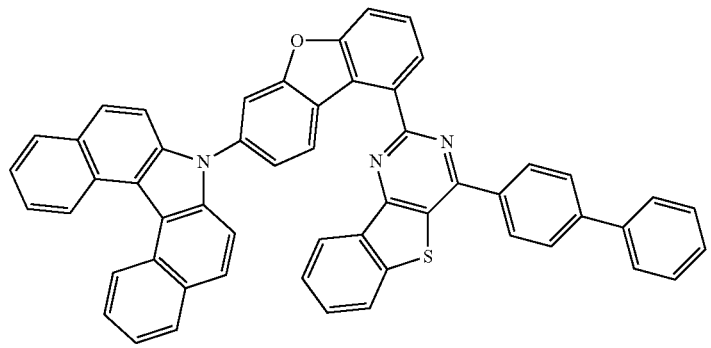 [SMILES: c1ccc(-c2ccc(-c3nc(-c4cccc5oc6cc(-n7c8ccc9ccccc9c8c8c9ccccc9ccc87)ccc6c45)nc4c3sc3ccccc34)cc2)cc1] | 69 |
| 101 | 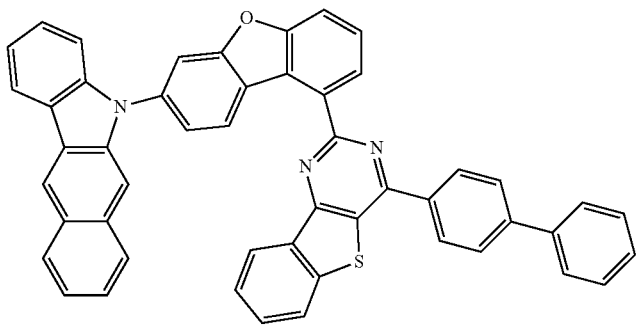 [SMILES: c1ccc(-c2ccc(-c3nc(-c4cccc5oc6cc(-n7c8ccccc8c8cc9ccccc9cc87)ccc6c45)nc4c3sc3ccccc34)cc2)cc1] | 70 |

[Preparation Example 3] Preparation of Compound 105

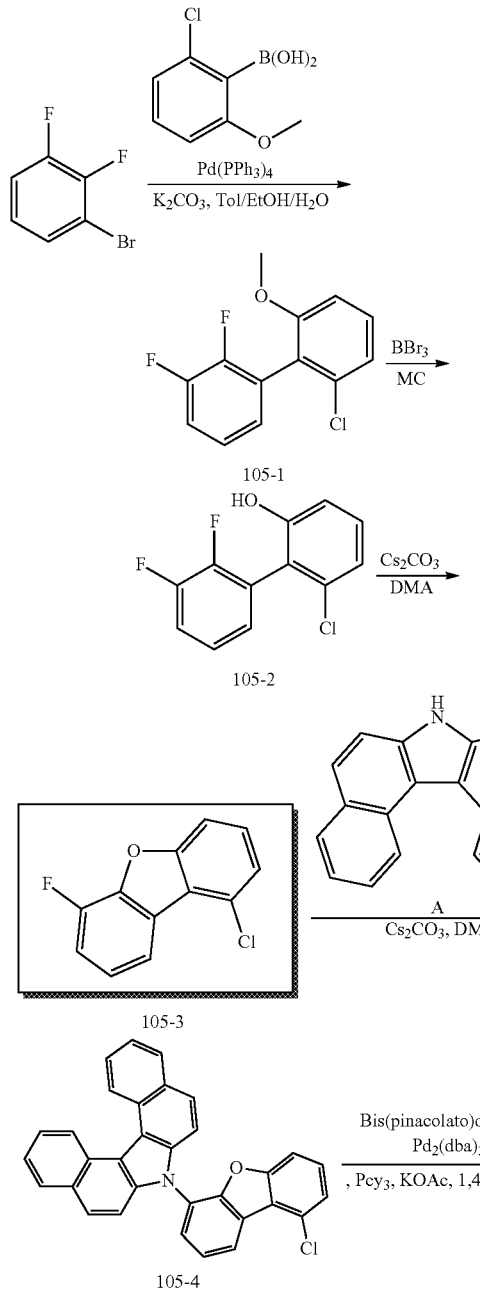

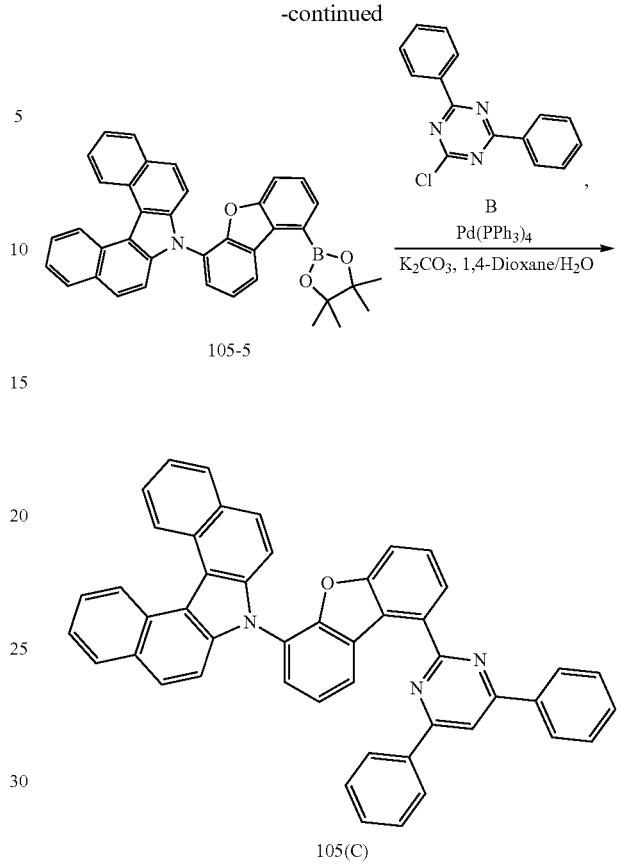

Target Compound 105 (13.13 g, 82%) was obtained in the same manner as in the method for preparing Compound 1 of Preparation Example 1 except that (2-chloro-6-methoxyphenyl)boronic acid was used instead of (4-chloro-2-methoxyphenyl) boronic acid.

The following target compounds of Table 3 were synthesized in the same manner as in the method for preparing Compound 105 of Preparation Example 3 except that A of the following Table 3 was used instead of 7H-dibenzo[c,g]carbazole, and B of the following Table 3 was used instead of 2-chloro-4,6-diphenyl-1,3,5-triazine.

Particularly, the dibenzofuran linker of Compounds 156, 160, 195 and 200 of the following Table 3 was prepared in the same manner as in the method for preparing Compound 105 of Preparation Example 3, except that 1-bromo-3-chloro-2-fluorobenzene was used instead of 1-bromo-2,3-difluorobenzene, and (2-fluoro-6-methoxyphenyl)boronic acid was used instead of (2-chloro-6-methoxyphenyl) boronic acid.

TABLE 3

| Compound | A |
| --- | --- |
| 114 | |

TABLE 3-continued
| | |
|---|---|
| 119 | 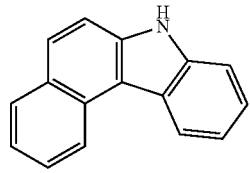 |
| 125 | 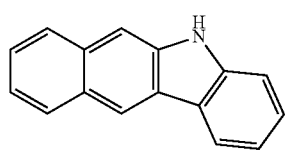 |
| 130 | 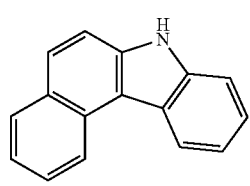 |
| 136 | 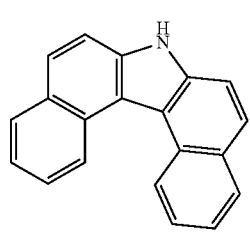 |
| 140 | 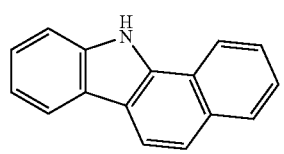 |
| 142 | 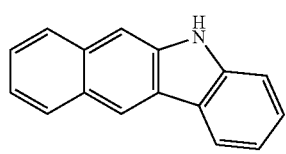 |
| 147 | 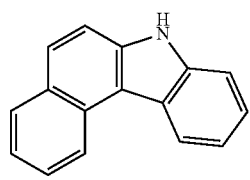 |
| 156 | 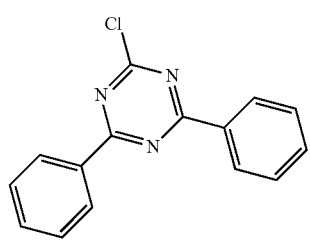 |

TABLE 3-continued
| | |
|---|---|
| 160 | 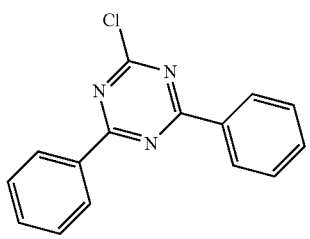 |
| 161 | 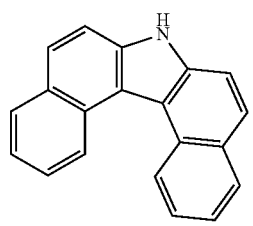 |
| 169 | 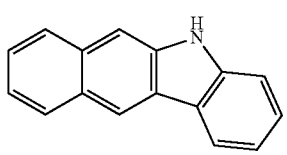 |
| 175 | 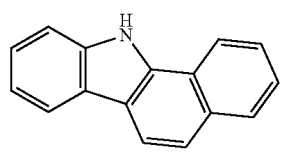 |
| 179 | 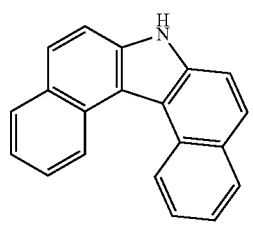 |
| 185 | 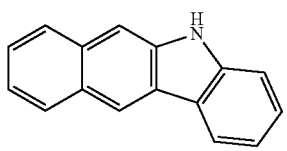 |
| 195 | 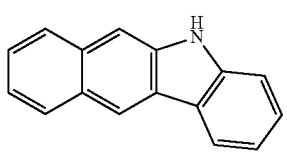 |
| 200 | 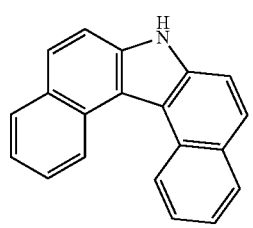 |

TABLE 3-continued
| Compound | B |
|---|---|
| 114 | 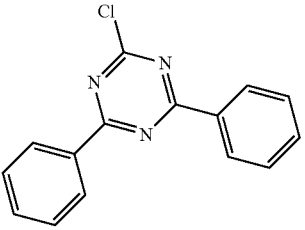 |
| 119 | 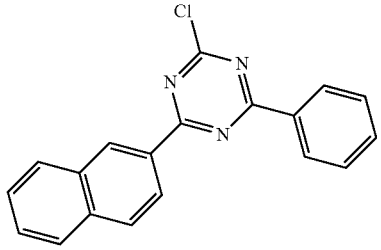 |
| 125 | 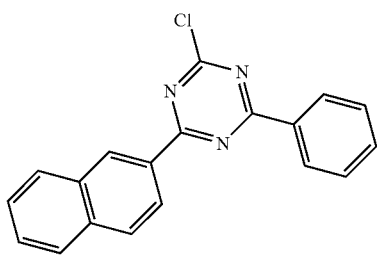 |
| 130 | 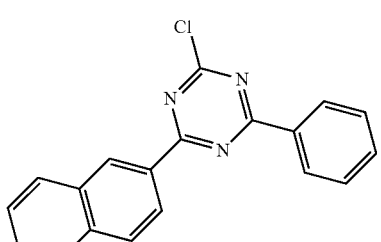 |
| 136 | 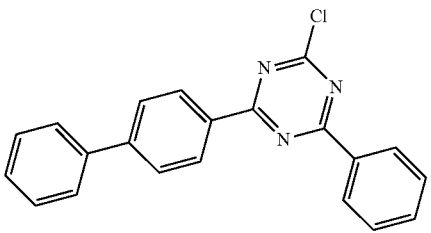 |
| 140 | 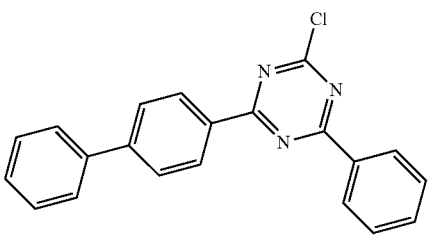 |

TABLE 3-continued
142 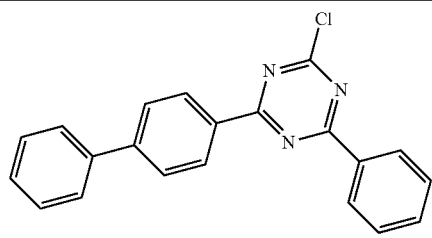
147 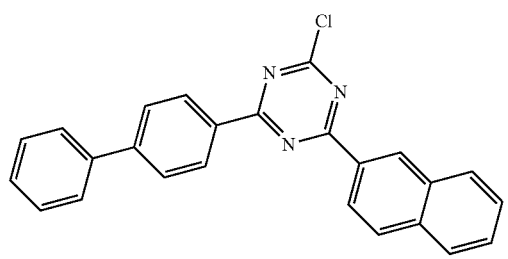 [SMILES: Clc1nc(-c2ccc(-c3ccccc3)cc2)nc(-c2ccc3ccccc3c2)n1]
156 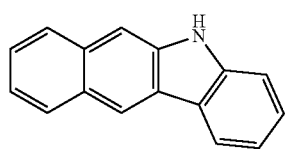 [SMILES: c1ccc2cc3c(cc2c1)[nH]c1ccccc13]
160 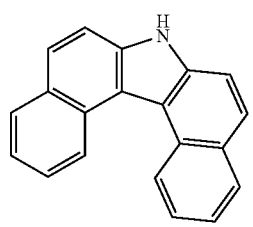 [SMILES: c1ccc2c(c1)ccc1[nH]c3ccc4ccccc4c3c12]
161 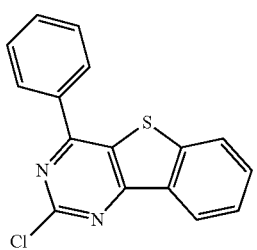 [SMILES: Clc1nc(-c2ccccc2)c2sc3ccccc3c2n1]
169 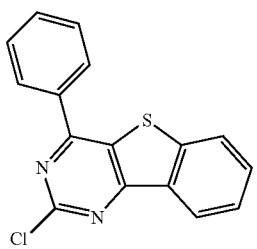 [SMILES: Clc1nc(-c2ccccc2)c2sc3ccccc3c2n1]
175 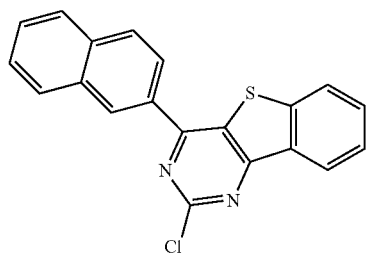 [SMILES: Clc1nc(-c2ccc3ccccc3c2)c2sc3ccccc3c2n1]

TABLE 3-continued
179 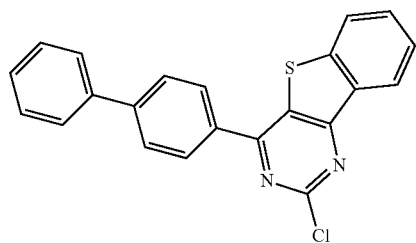 [SMILES: Clc1nc(-c2ccc(-c3ccccc3)cc2)c2sc3ccccc3c2n1]
185 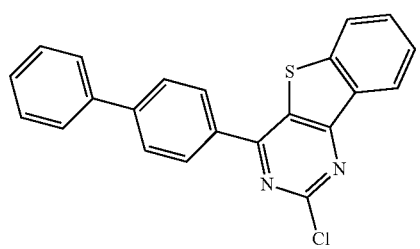 [SMILES: Clc1nc(-c2ccc(-c3ccccc3)cc2)c2sc3ccccc3c2n1]
195 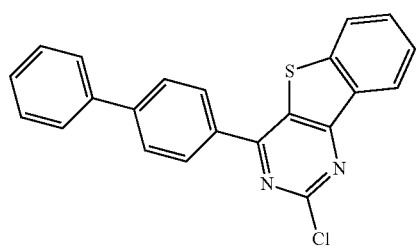 [SMILES: Clc1nc(-c2ccc(-c3ccccc3)cc2)c2sc3ccccc3c2n1]
200 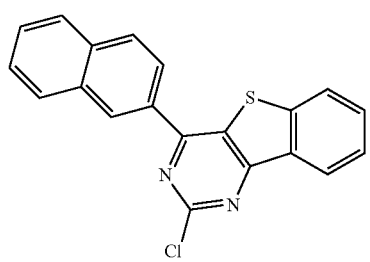 [SMILES: Clc1nc(-c2ccc3ccccc3c2)c2sc3ccccc3c2n1]
| Compound | C | Yield (%) |
|---|---|---|
| 114 | 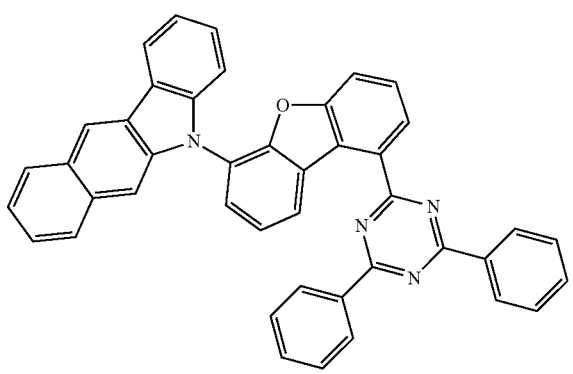 | 81 |

TABLE 3-continued
| | | |
|---|---|---|
| 119 | 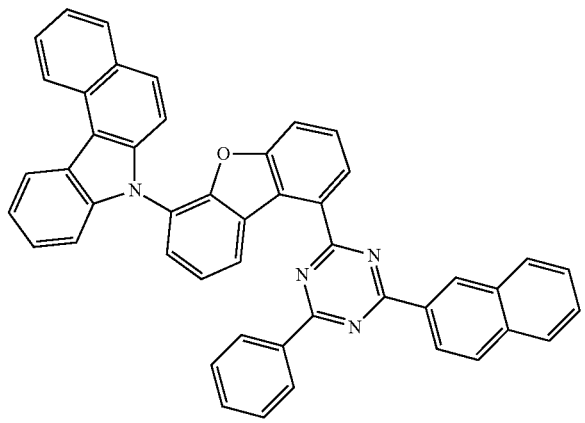 | 80 |
| 125 | 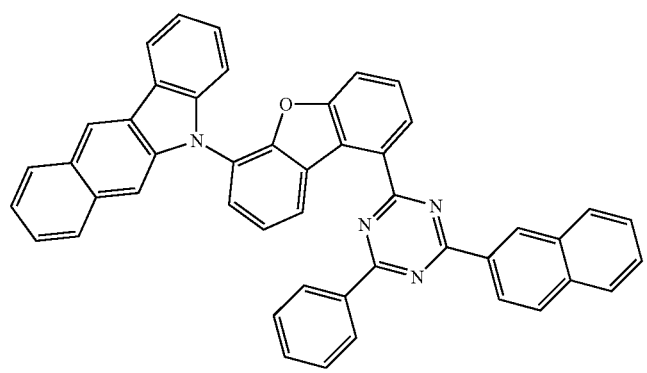 | 83 |
| 130 | 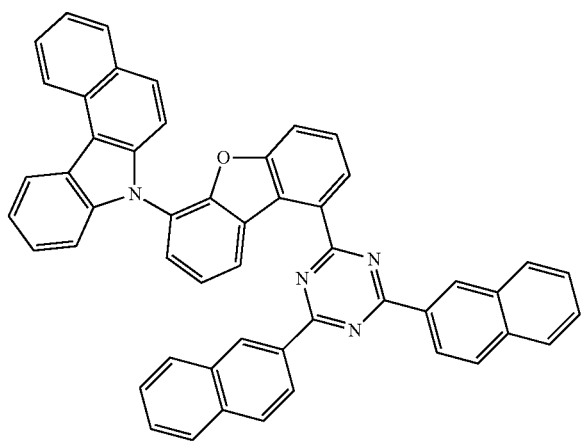 | 79 |

TABLE 3-continued
136
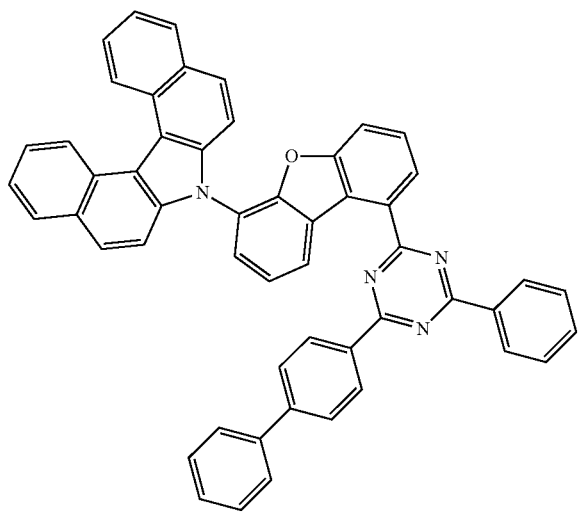 [SMILES: c1ccc(-c2ccc(-c3nc(-c4ccccc4)nc(-c4cccc5oc6c(-n7c8ccc9ccccc9c8c8c9ccccc9ccc87)cccc6c45)n3)cc2)cc1]
80
140
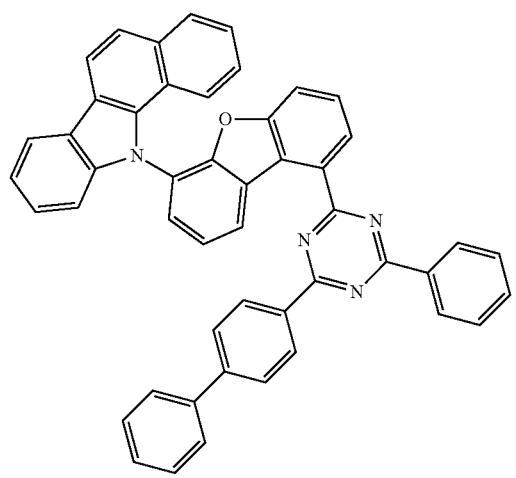 [SMILES: c1ccc(-c2ccc(-c3nc(-c4ccccc4)nc(-c4cccc5oc6c(-n7c8ccccc8c8ccc9ccccc9c87)cccc6c45)n3)cc2)cc1]
79
142
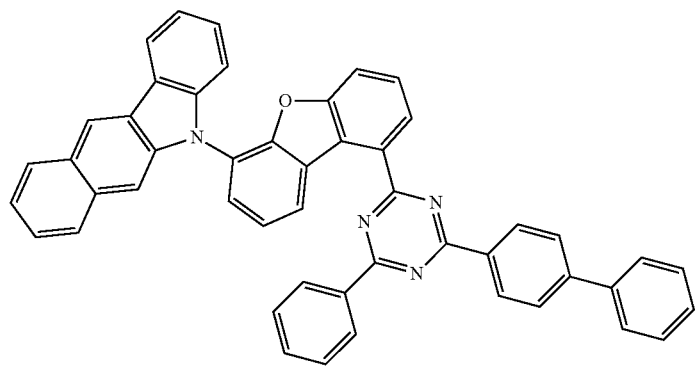 [SMILES: c1ccc(-c2ccc(-c3nc(-c4ccccc4)nc(-c4cccc5oc6c(-n7c8ccccc8c8cc9ccccc9cc87)cccc6c45)n3)cc2)cc1]
76

TABLE 3-continued
147
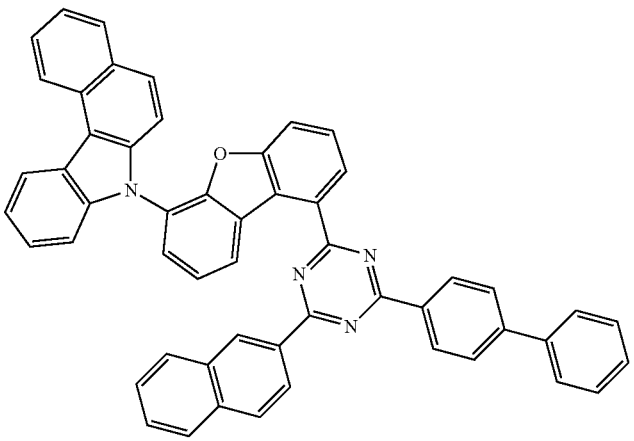 [SMILES: c1ccc(-c2ccc(-c3nc(-c4ccc5ccccc5c4)nc(-c4cccc5oc6c(-n7c8ccccc8c8c9ccccc9ccc87)cccc6c45)n3)cc2)cc1]
81
156
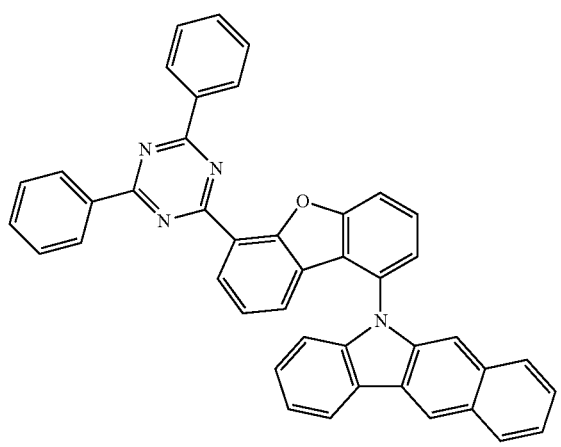 [SMILES: c1ccc(-c2nc(-c3ccccc3)nc(-c3cccc4c3oc3cccc(-n5c6ccccc6c6cc7ccccc7cc65)c34)n2)cc1]
69
160
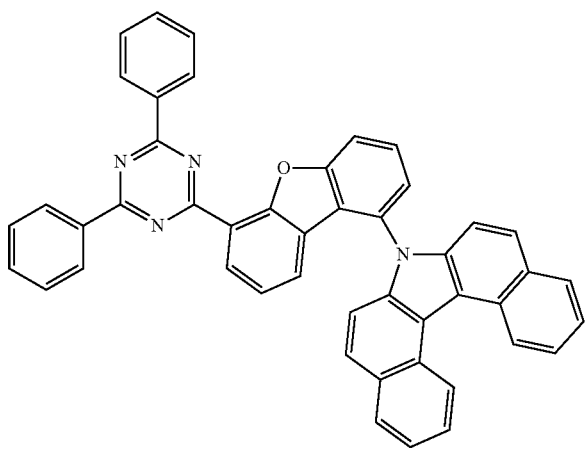 [SMILES: c1ccc(-c2nc(-c3ccccc3)nc(-c3cccc4c3oc3cccc(-n5c6ccc7ccccc7c6c6c7ccccc7ccc65)c34)n2)cc1]
68

TABLE 3-continued
| 161 | 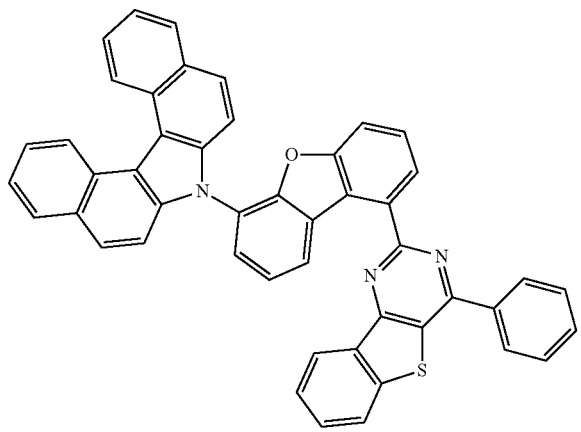 | 70 |
| 169 | 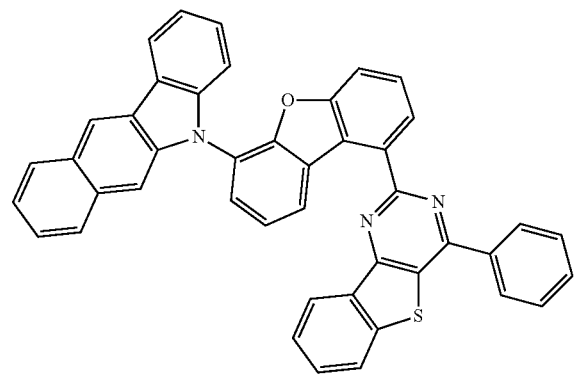 | 76 |
| 175 | 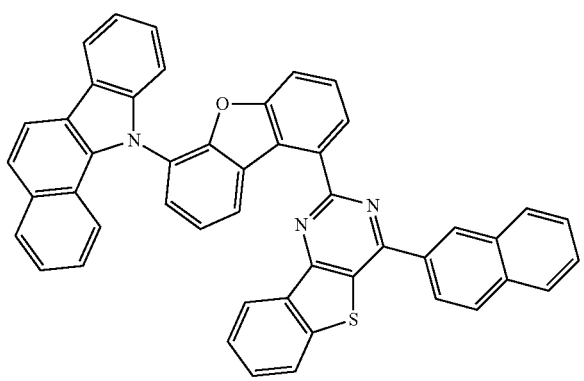 | 77 |
| 179 | 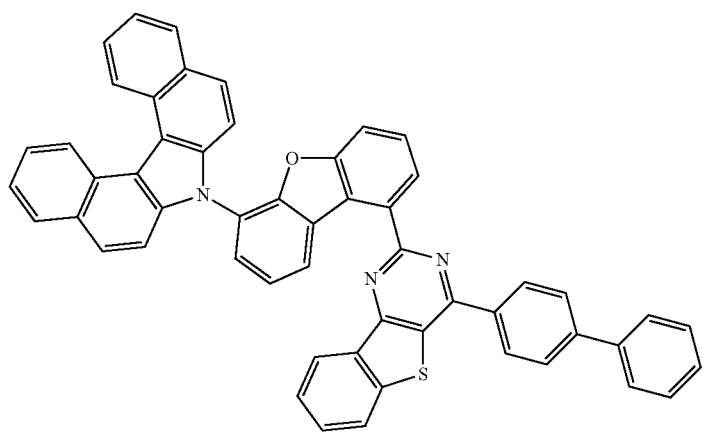 | 80 |

TABLE 3-continued
185
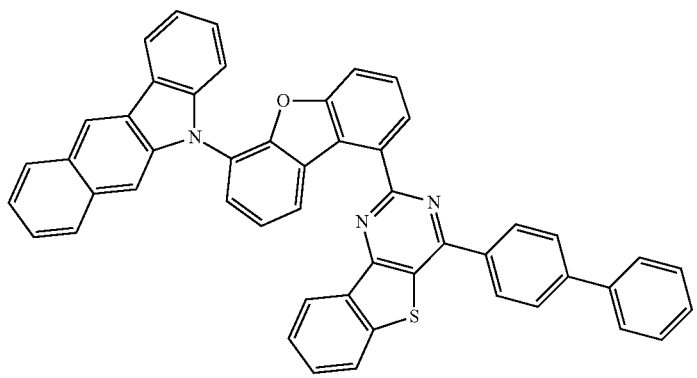 [SMILES: c1ccc(-c2ccc(-c3nc(-c4cccc5oc6c(-n7c8ccccc8c8cc9ccccc9cc87)cccc6c45)nc4c3sc3ccccc34)cc2)cc1]
83
195
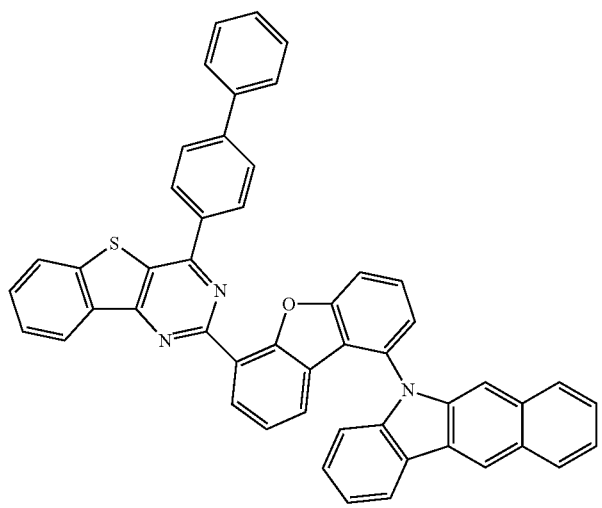 [SMILES: c1ccc(-c2ccc(-c3nc(-c4cccc5c4oc4cccc(-n6c7ccccc7c7cc8ccccc8cc76)c45)nc4c3sc3ccccc34)cc2)cc1]
66
200
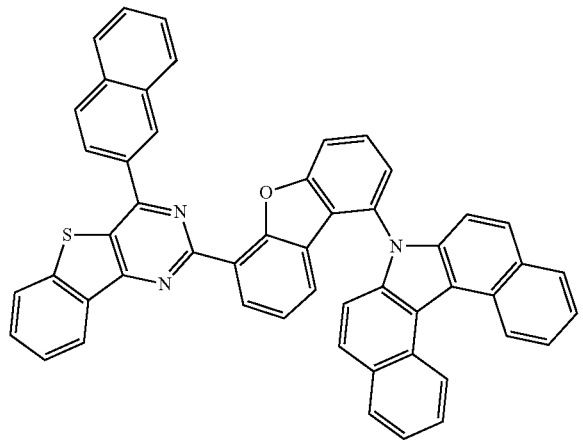 [SMILES: c1ccc2cc(-c3nc(-c4cccc5c4oc4cccc(-n6c7ccc8ccccc8c7c7c8ccccc8ccc76)c45)nc4c3sc3ccccc34)ccc2c1]
68

[Preparation Example 4] Preparation of Compound 201

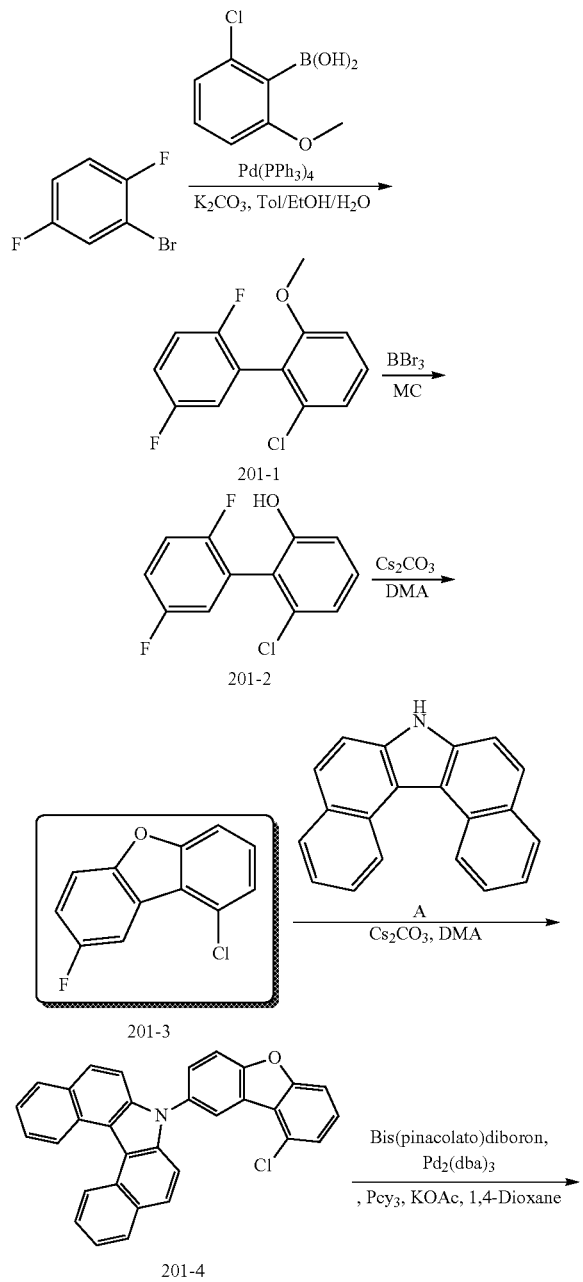

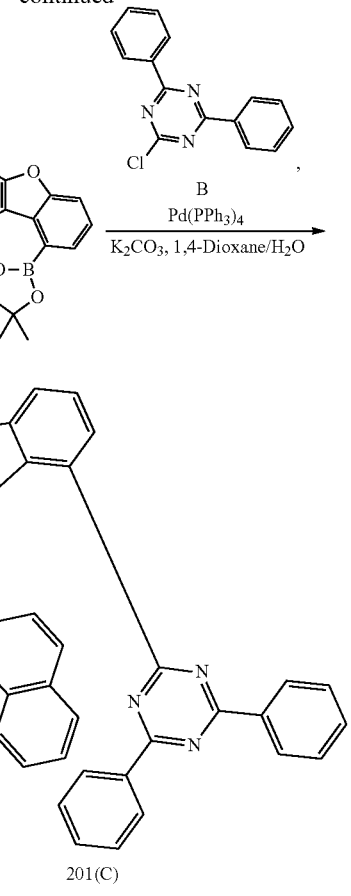

Target Compound 201 (10.09 g, 63%) was obtained in the same manner as in the method for preparing Compound 1 of Preparation Example 1 except that 2-bromo-1,4-difluorobenzene was used instead of 1-bromo-2,3-difluorobenzene, and (2-chloro-6-methoxyphenyl)boronic acid was used instead of (4-chloro-2-methoxyphenyl) boronic acid.

The following target compounds of Table 4 were synthesized in the same manner as in the method for preparing Compound 201 of Preparation Example 4 except that A of the following Table 4 was used instead of 7H-dibenzo[c,g]carbazole, and B of the following Table 4 was used instead of 2-chloro-4,6-diphenyl-1,3,5-triazine.

Particularly, the dibenzofuran linker of the following 252 structure was prepared in the same manner as in the method for preparing Compound 201 of Preparation Example 4, except that 2-bromo-4-chloro-1-fluorobenzene was used instead of 2-bromo-1,4-difluorobenzene, and (2-fluoro-6-methoxyphenyl)boronic acid was used instead of (2-chloro-6-methoxyphenyl)boronic acid.

TABLE 4

| Compound | A |
| --- | --- |
| 204 | |

TABLE 4-continued
| | |
|---|---|
| 210 | 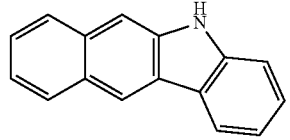 |
| 221 | 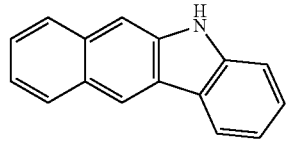 |
| 232 | 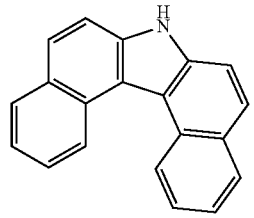 |
| 236 | 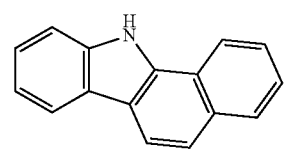 |
| 238 | 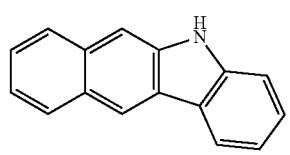 |
| 240 | 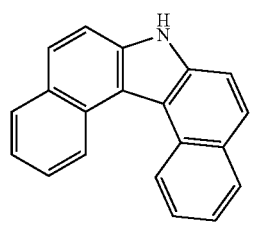 |
| 252 | 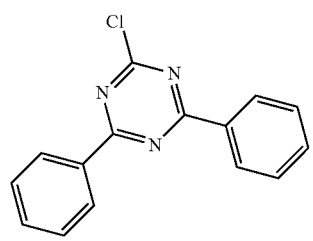 |
| 253 | 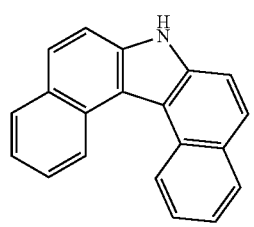 |

TABLE 4-continued
| | |
|---|---|
| 259 | 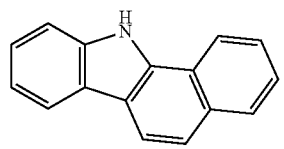 |
| 271 | 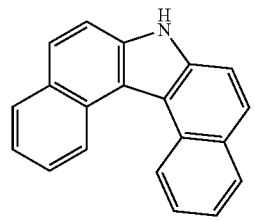 |
| 277 | 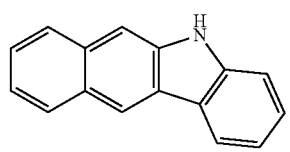 |
| 280 | 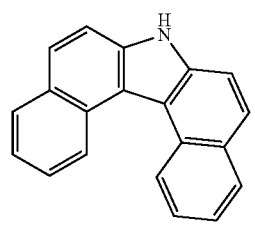 |
| 288 | 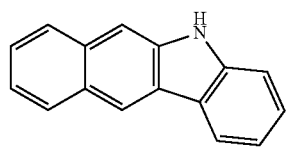 |
| Compound | B |
|---|---|
| 204 | 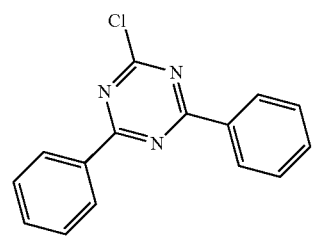 |
| 210 | 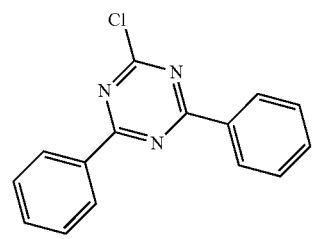 |

TABLE 4-continued
221
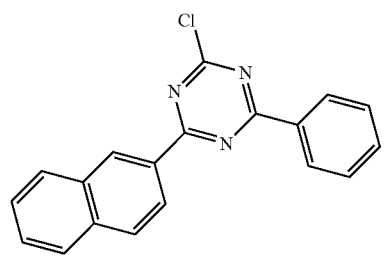 [SMILES: Clc1nc(-c2ccccc2)nc(-c2ccc3ccccc3c2)n1]
232
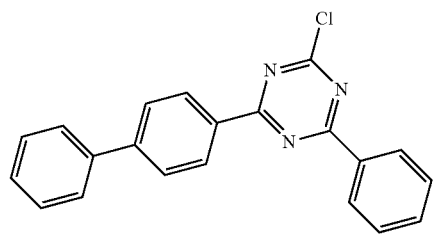 [SMILES: Clc1nc(-c2ccccc2)nc(-c2ccc(-c3ccccc3)cc2)n1]
236
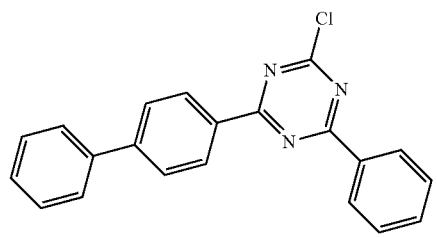 [SMILES: Clc1nc(-c2ccccc2)nc(-c2ccc(-c3ccccc3)cc2)n1]
238
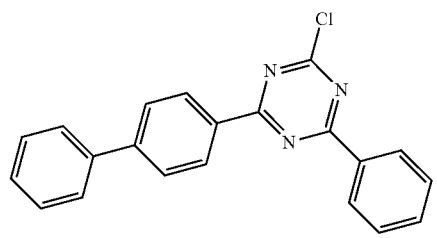 [SMILES: Clc1nc(-c2ccccc2)nc(-c2ccc(-c3ccccc3)cc2)n1]
240
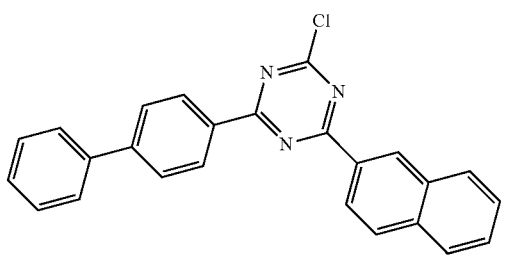 [SMILES: Clc1nc(-c2ccc(-c3ccccc3)cc2)nc(-c2ccc3ccccc3c2)n1]
252
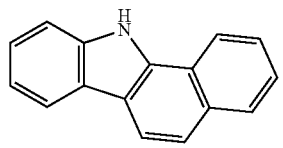 [SMILES: c1ccc2c(c1)ccc1c3ccccc3[nH]c21]
253
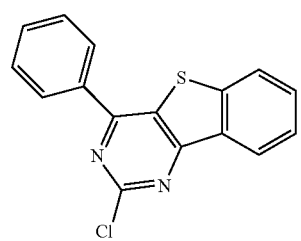 [SMILES: Clc1nc(-c2ccccc2)c2sc3ccccc3c2n1]

TABLE 4-continued
259 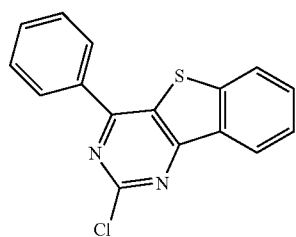 [SMILES: Clc1nc(-c2ccccc2)c2sc3ccccc3c2n1]
271 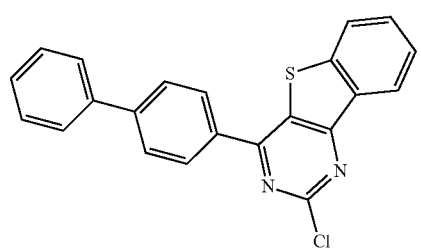 [SMILES: Clc1nc(-c2ccc(-c3ccccc3)cc2)c2sc3ccccc3c2n1]
277 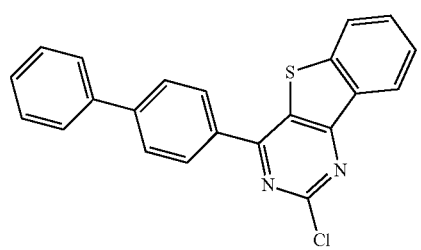 [SMILES: Clc1nc(-c2ccc(-c3ccccc3)cc2)c2sc3ccccc3c2n1]
280 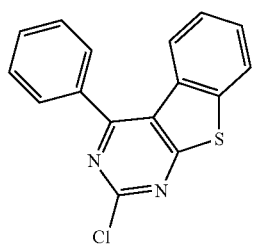 [SMILES: Clc1nc(-c2ccccc2)c2c(n1)sc1ccccc12]
288 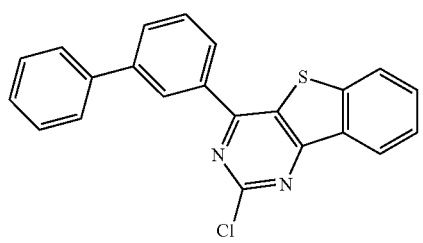 [SMILES: Clc1nc(-c2cccc(-c3ccccc3)c2)c2sc3ccccc3c2n1]

TABLE 4-continued

| Compound | C | Yield (%) |
|---|---|---|
| 204 | | 65 |
| 210 | | 66 |
| 221 | | 63 |

TABLE 4-continued
232 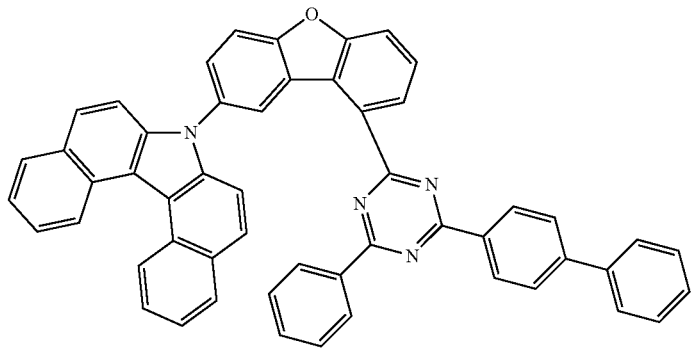 [SMILES: c1ccc(-c2ccc(-c3nc(-c4ccccc4)nc(-c4cccc5oc6ccc(-n7c8ccc9ccccc9c8c8c9ccccc9ccc87)cc6c45)n3)cc2)cc1] 62
236 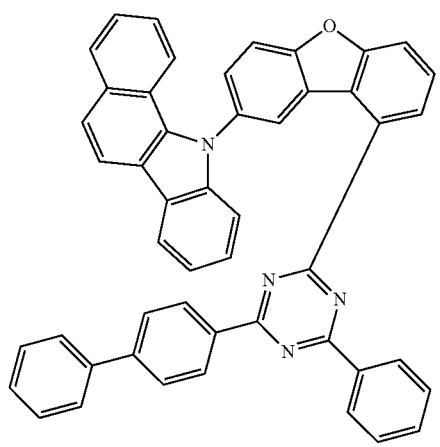 [SMILES: c1ccc(-c2ccc(-c3nc(-c4ccccc4)nc(-c4cccc5oc6ccc(-n7c8ccccc8c8ccc9ccccc9c87)cc6c45)n3)cc2)cc1] 60
238 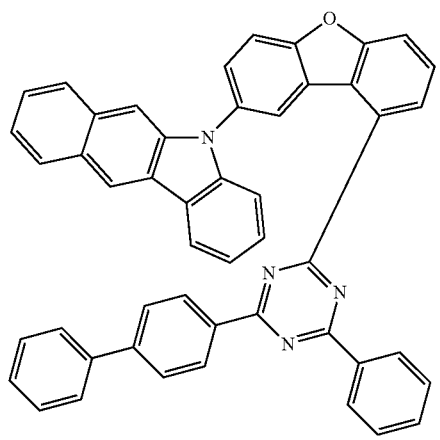 [SMILES: c1ccc(-c2ccc(-c3nc(-c4ccccc4)nc(-c4cccc5oc6ccc(-n7c8ccccc8c8cc9ccccc9cc87)cc6c45)n3)cc2)cc1] 65

TABLE 4-continued
| 240 | 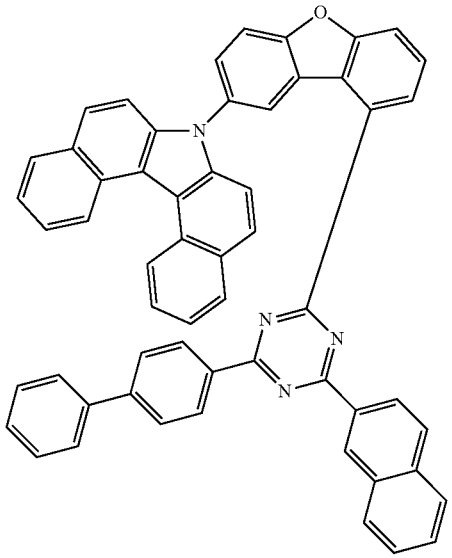 | 59 |
| 252 | 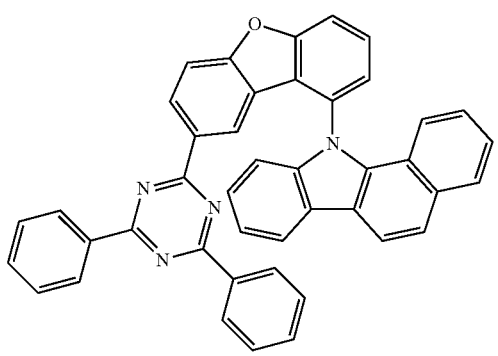 | 63 |
| 253 | 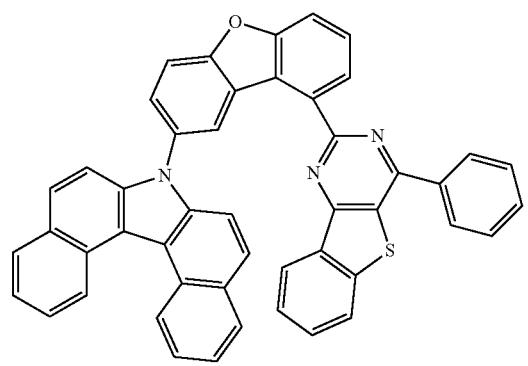 | 63 |

TABLE 4-continued
| 259 | 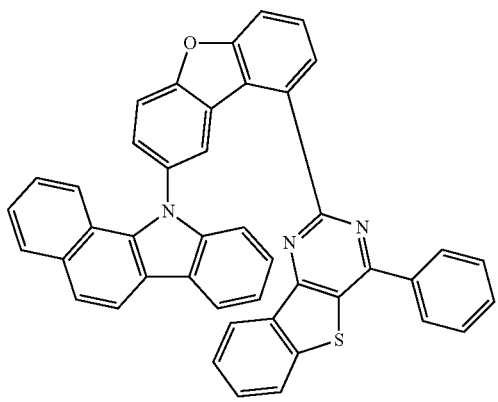 | 61 |
| 271 | 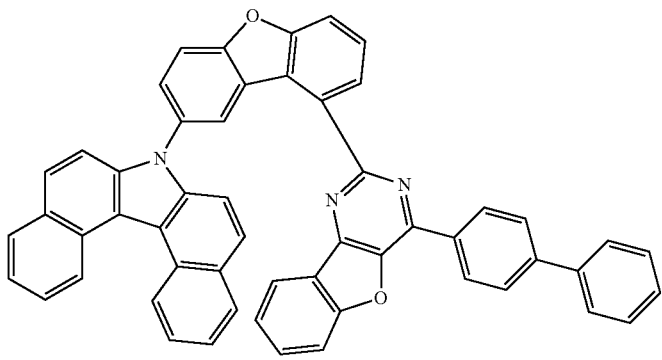 | 67 |
| 277 | 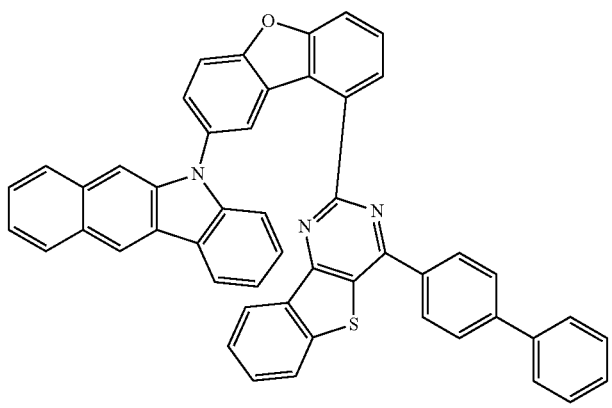 | 56 |
| 280 | 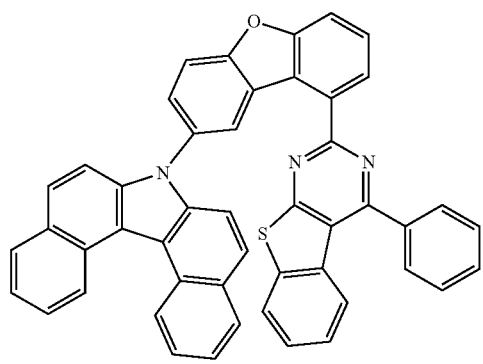 | 66 |

TABLE 4-continued
| 288 | 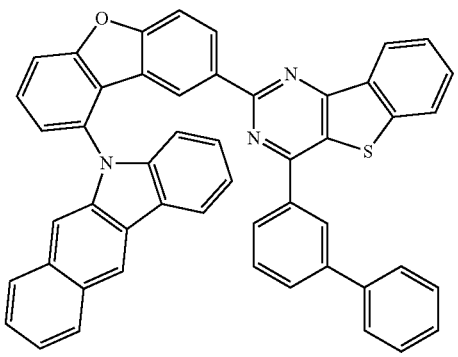 | 57 |
[Preparation Example 5] Preparation of Compound 289
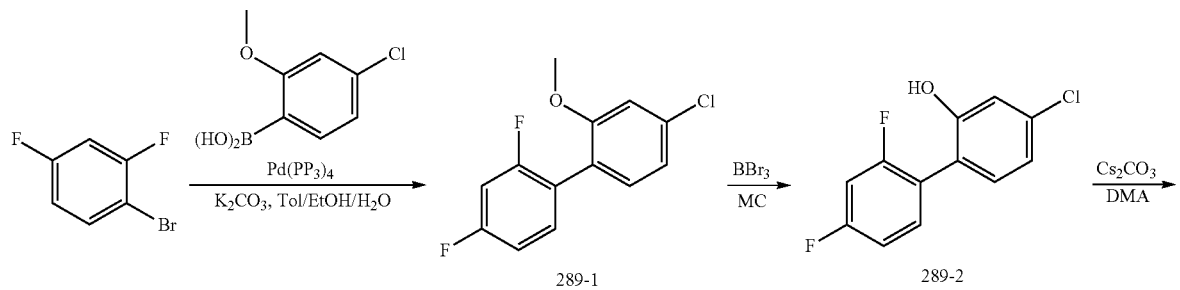
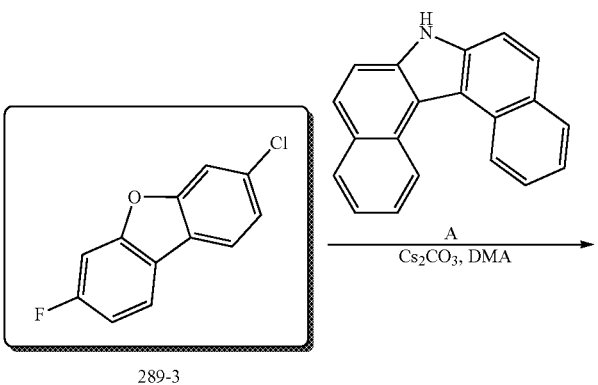
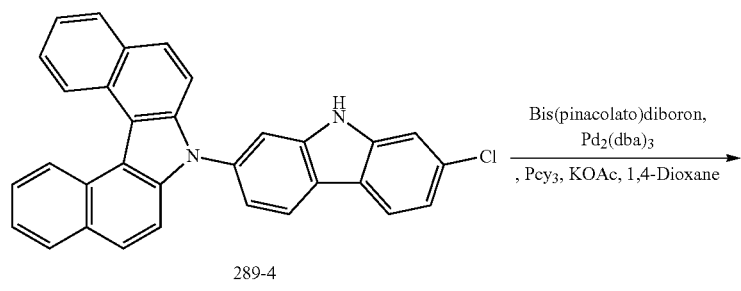

-continued

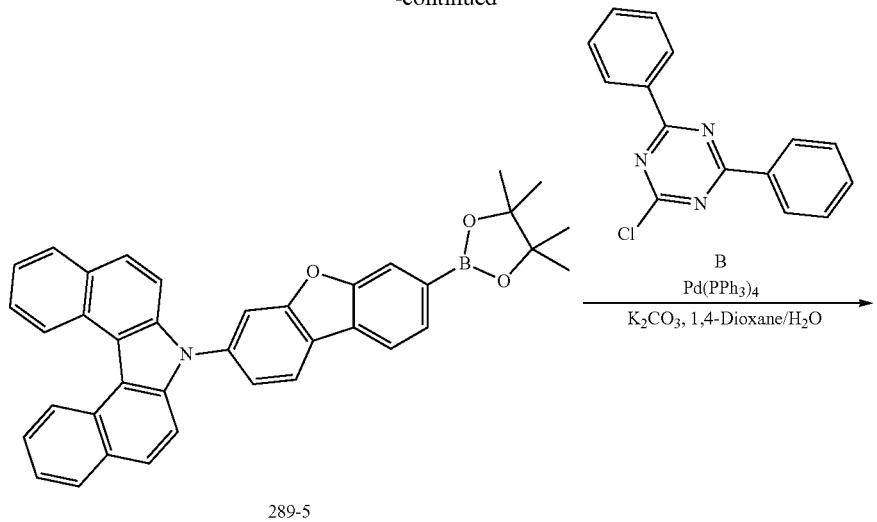

289-5

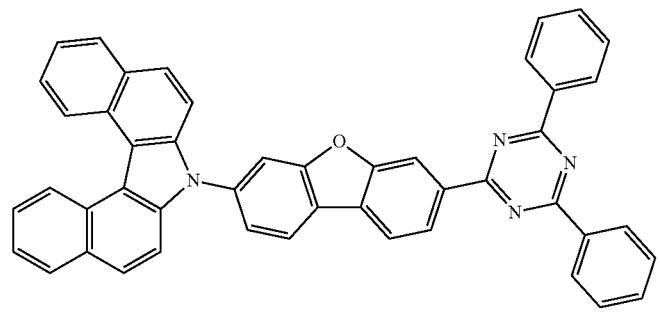

289(C)

Target Compound 289 (13.61 g, 85%) was obtained in the same manner as in the method for preparing Compound 1 of Preparation Example 1 except that 1-bromo-2,4-difluorobenzene was used instead of 1-bromo-2,3-difluorobenzene.

The following target compounds of Table 5 were synthesized in the same manner as in the method for preparing Compound 289 of Preparation Example 5 except that A of the following Table 5 was used instead of 7H-dibenzo[c,g]carbazole, and B of the following Table 5 was used instead of 2-chloro-4,6-diphenyl-1,3,5-triazine.

TABLE 5

| Compound | A |
|---|---|
| 297 | |
| 307 | |

TABLE 5-continued
| | |
|---|---|
| 318 | 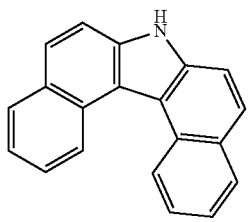 |
| 320 | 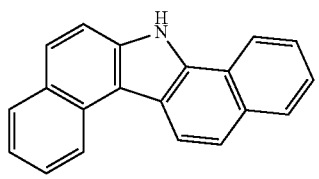 |
| 324 | 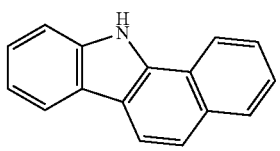 |
| 325 | 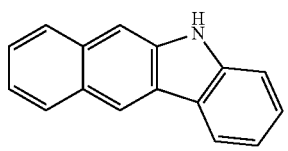 |
| 330 | 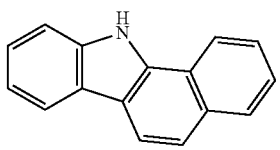 |
| 333 | 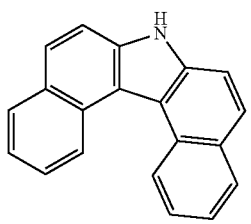 |
| 340 | 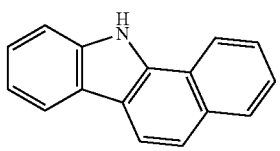 |
| 342 | 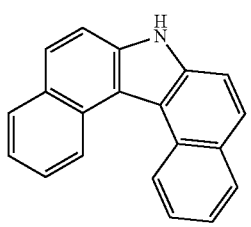 |

TABLE 5-continued
| Compound | B |
|---|---|
| 297 | 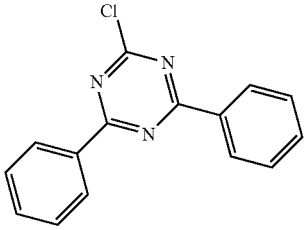 |
| 307 | 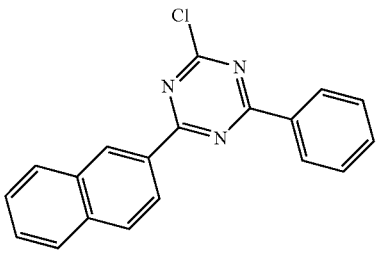 |
| 318 | 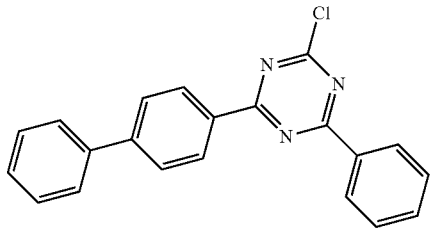 |
| 320 | 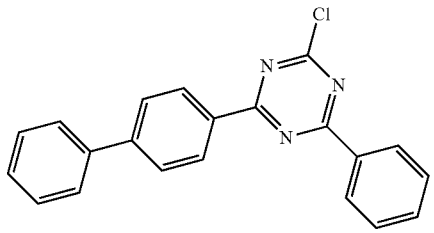 |
| 324 | 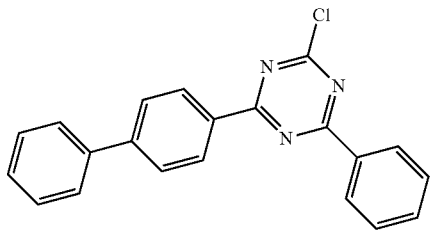 |
| 325 | 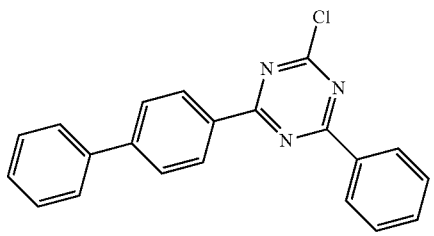 |

TABLE 5-continued
330 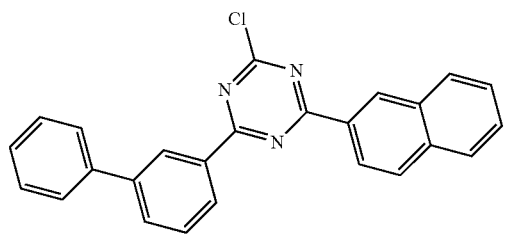 [SMILES: Clc1nc(-c2cccc(-c3ccccc3)c2)nc(-c2ccc3ccccc3c2)n1]
333 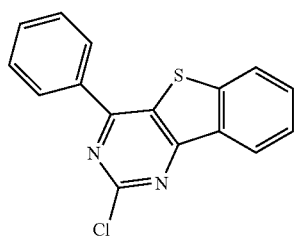 [SMILES: Clc1nc(-c2ccccc2)c2sc3ccccc3c2n1]
340 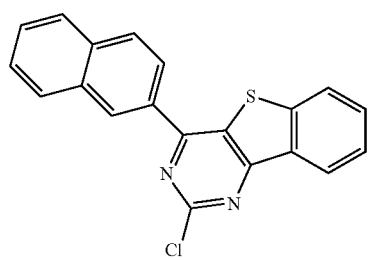 [SMILES: Clc1nc(-c2ccc3ccccc3c2)c2sc3ccccc3c2n1]
342 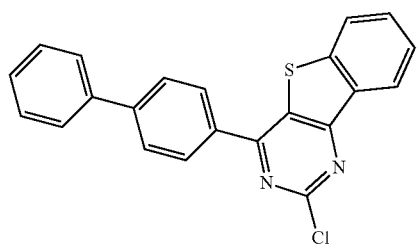 [SMILES: Clc1nc(-c2ccc(-c3ccccc3)cc2)c2sc3ccccc3c2n1]
| Compound | C | Yield (%) |
|---|---|---|
| 297 | 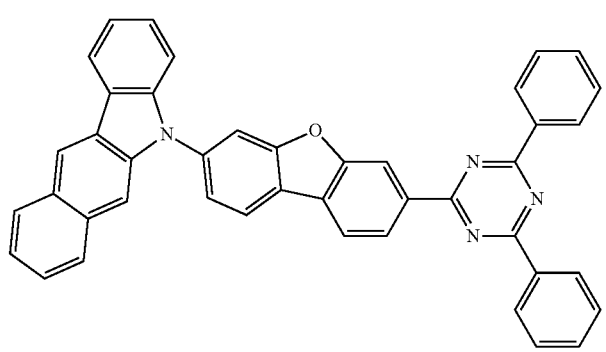 | 83 |

TABLE 5-continued
307 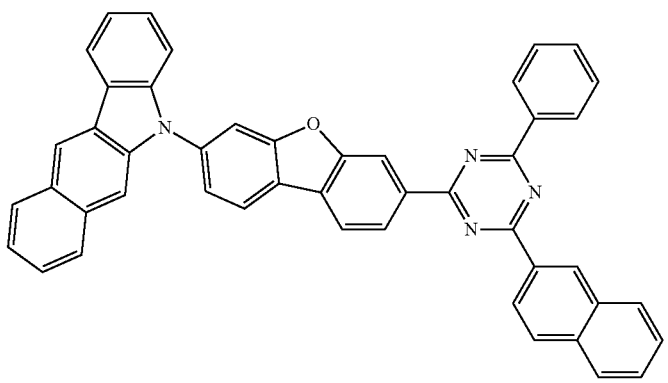 [SMILES: c1ccc(-c2nc(-c3ccc4ccccc4c3)nc(-c3ccc4c(c3)oc3cc(-n5c6ccccc6c6cc7ccccc7cc65)ccc34)n2)cc1] 83
318 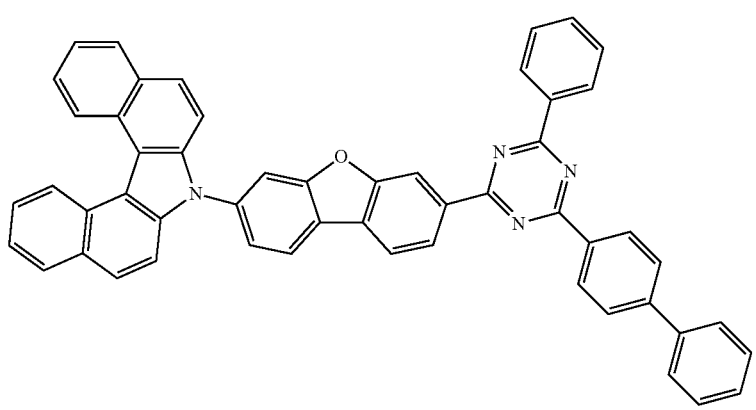 [SMILES: c1ccc(-c2ccc(-c3nc(-c4ccccc4)nc(-c4ccc5c(c4)oc4cc(-n6c7ccc8ccccc8c7c7c8ccccc8ccc76)ccc45)n3)cc2)cc1] 80
320 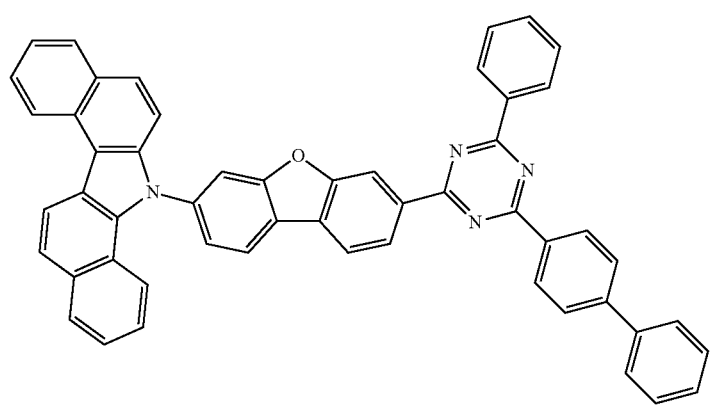 [SMILES: c1ccc(-c2ccc(-c3nc(-c4ccccc4)nc(-c4ccc5c(c4)oc4cc(-n6c7ccc8ccccc8c7c7ccc8ccccc8c76)ccc45)n3)cc2)cc1] 83
324 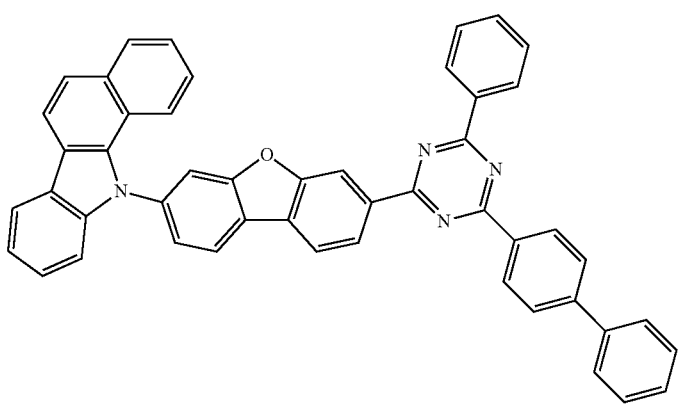 [SMILES: c1ccc(-c2ccc(-c3nc(-c4ccccc4)nc(-c4ccc5c(c4)oc4cc(-n6c7ccccc7c7ccc8ccccc8c76)ccc45)n3)cc2)cc1] 86

TABLE 5-continued
| 325 | 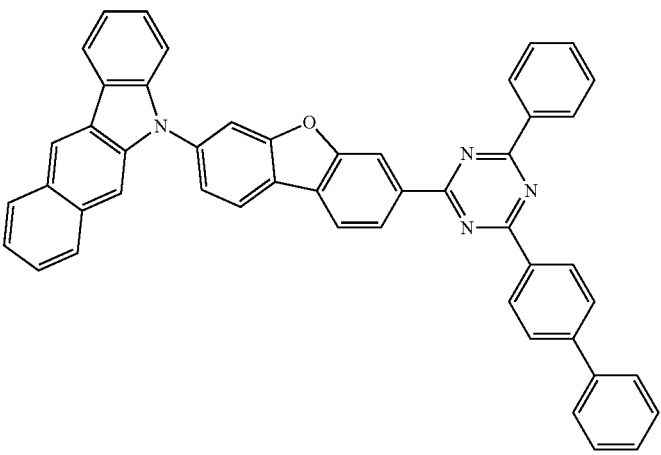 | 87 |
| 330 | 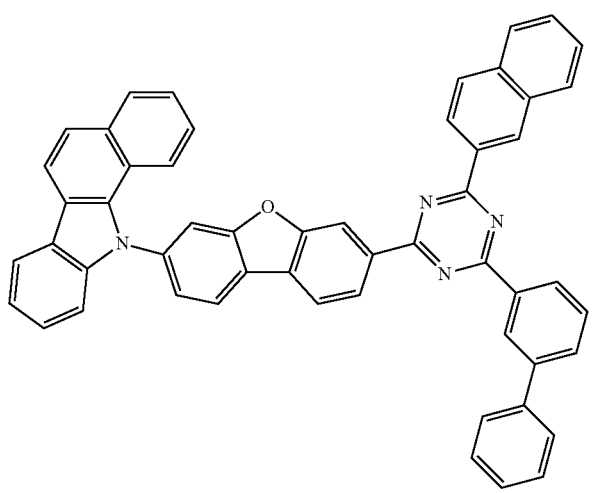 | 84 |
| 333 | 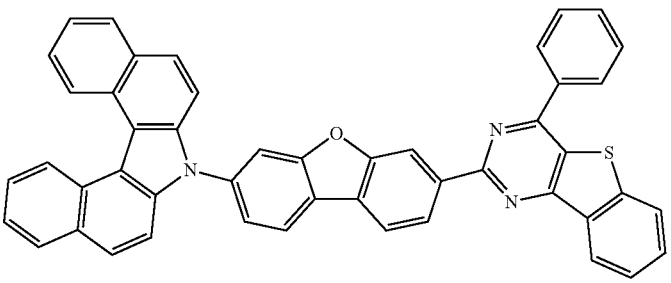 | 84 |
| 340 | 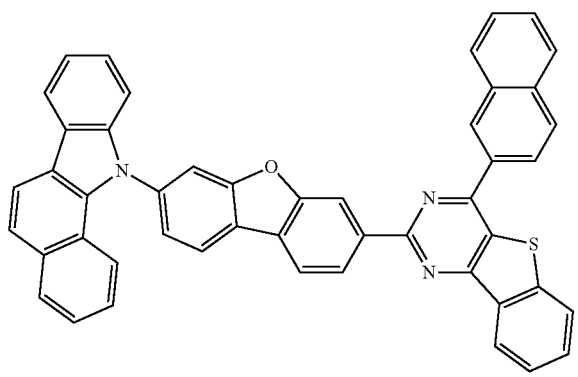 | 84 |

TABLE 5-continued
342
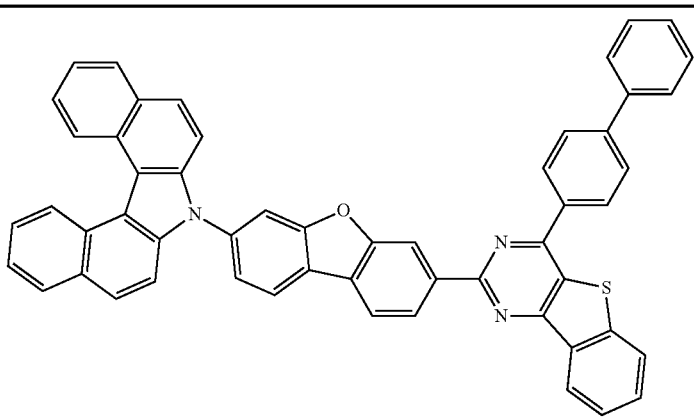
83
[Preparation Example 6] Preparation of Compound 349
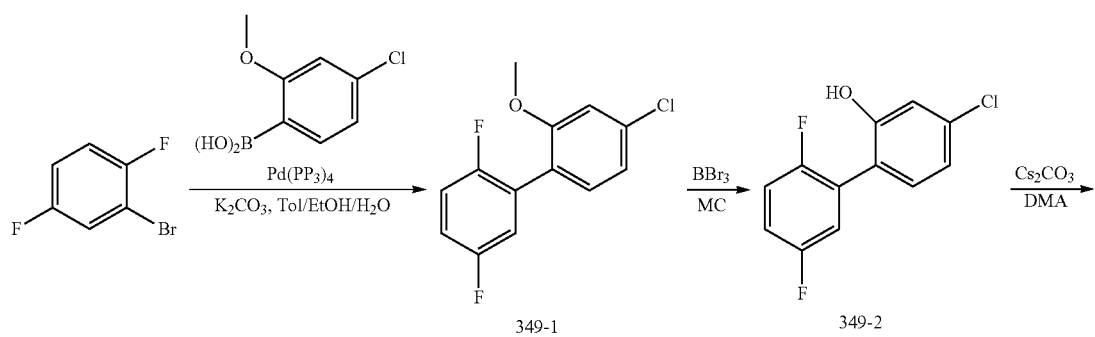
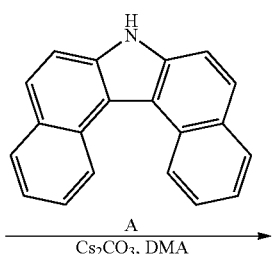

-continued

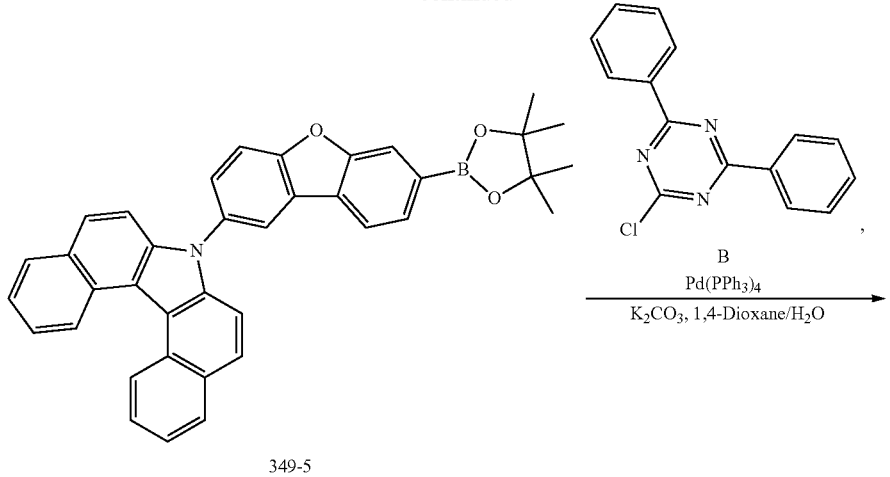
349-5

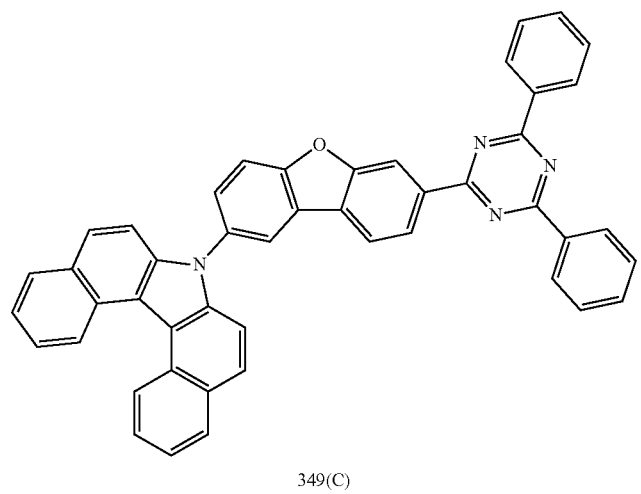 [SMILES: c1ccc(-c2nc(-c3ccccc3)nc(-c3ccc4c(c3)oc3ccc(-n5c6ccc7ccccc7c6c6c7ccccc7ccc65)cc34)n2)cc1]
349(C)

Target Compound 349 (12.97 g, 81%) was obtained in the same manner as in the method for preparing Compound 1 of Preparation Example 1 except that 2-bromo-1,4-difluorobenzene was used instead of 1-bromo-2,3-difluorobenzene.

The following target compounds of Table 6 were synthesized in the same manner as in the method for preparing Compound 349 of Preparation Example 6 except that A of the following Table 6 was used instead of 7H-dibenzo[c,g]carbazole, and B of the following Table 6 was used instead of 2-chloro-4,6-diphenyl-1,3,5-triazine.

TABLE 6

| Compound | A | B |
|---|---|---|
| 354 | | |

TABLE 6-continued
| | | |
|---|---|---|
| 355 | 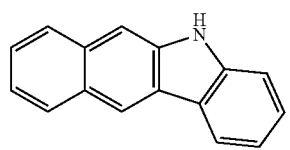 | 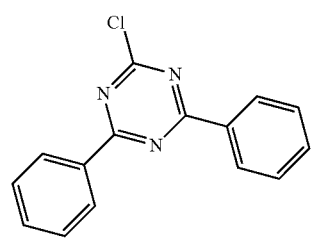 |
| 359 | 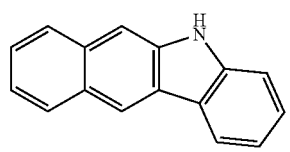 | 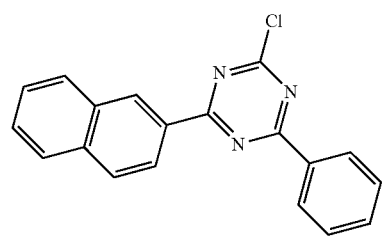 |
| 364 | 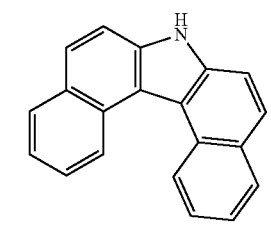 | 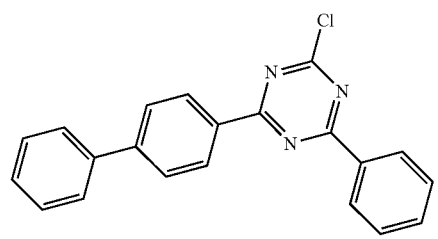 |
| 367 | 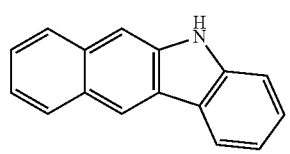 | 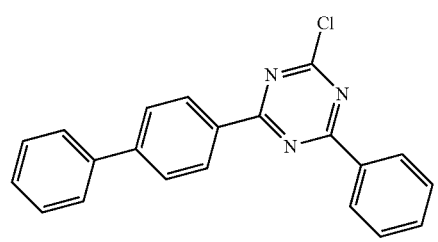 |
| 373 | 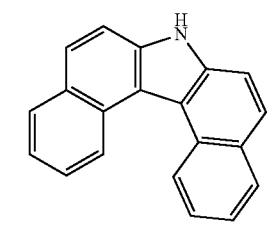 | 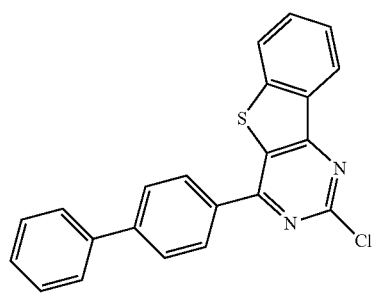 |
| 374 | 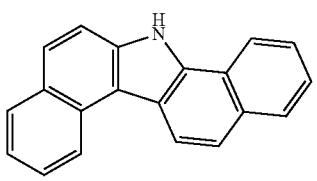 | 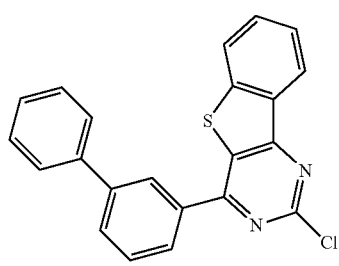 |

TABLE 6-continued
| 376 | 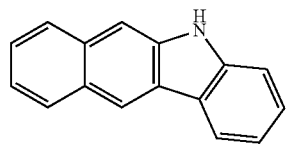 | 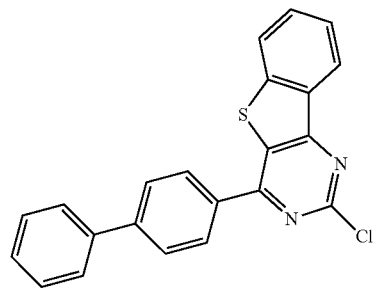 |
| Compound | C | Yield (%) |
|---|---|---|
| 354 | 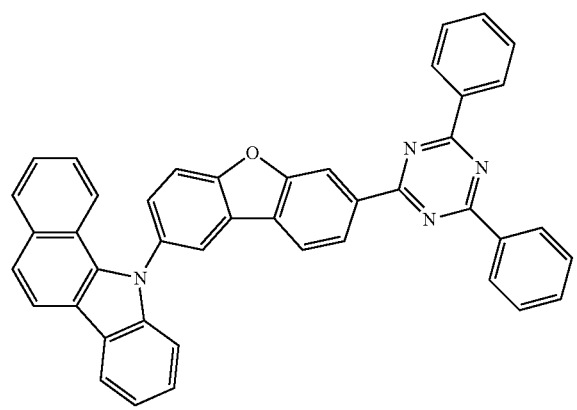 | 79 |
| 355 | 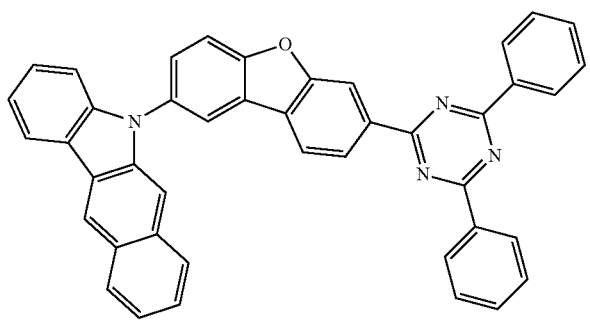 | 76 |
| 359 | 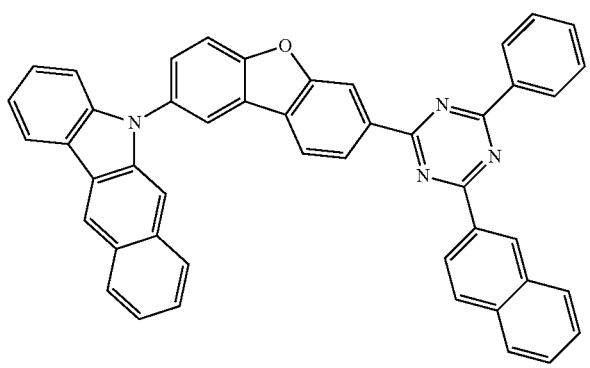 | 81 |

TABLE 6-continued
| 364 | 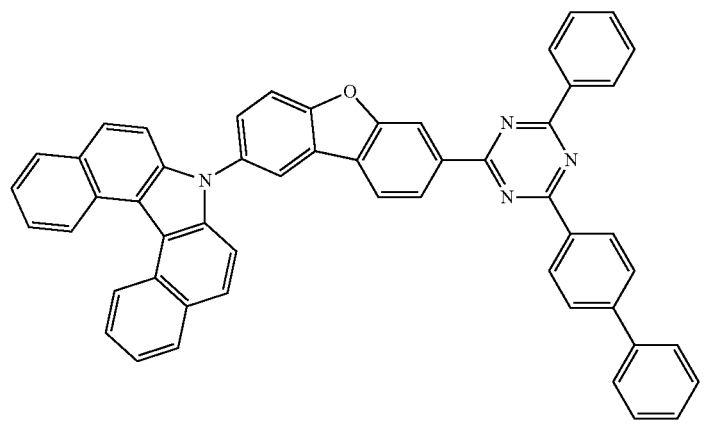 | 80 |
| 367 | 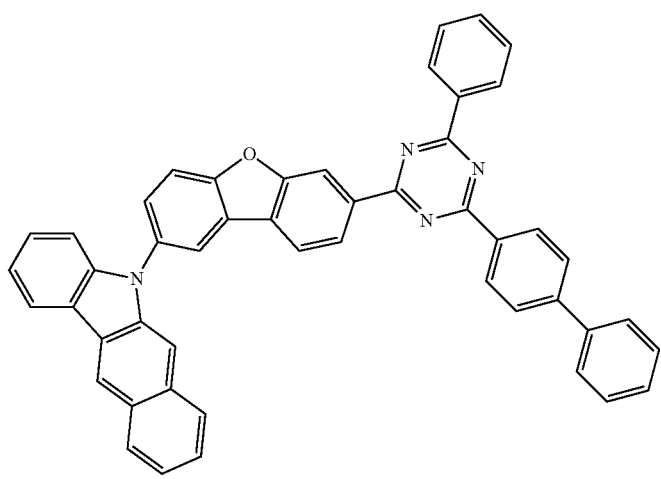 | 80 |
| 373 | 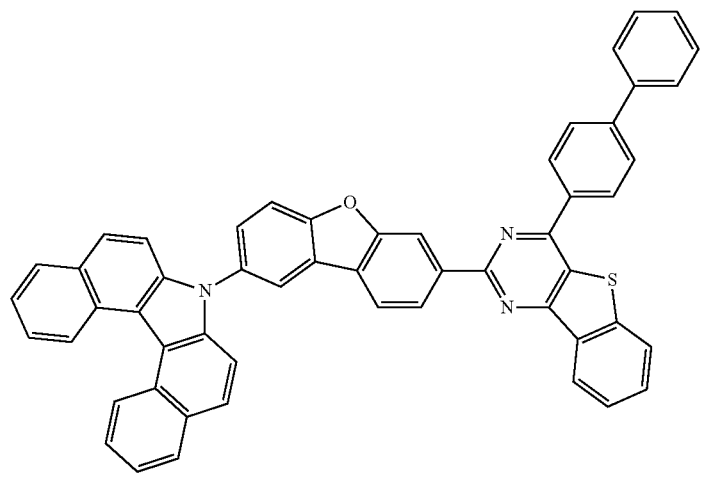 | 81 |

| 374 | 83 |

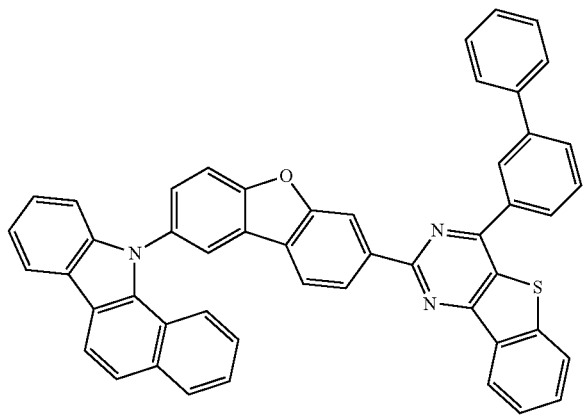 [SMILES: c1ccc(-c2cccc(-c3nc(-c4ccc5c(c4)oc4ccc(-n6c7ccccc7c7ccc8ccccc8c76)cc45)nc4c3sc3ccccc34)c2)cc1]

| 376 | 89 |

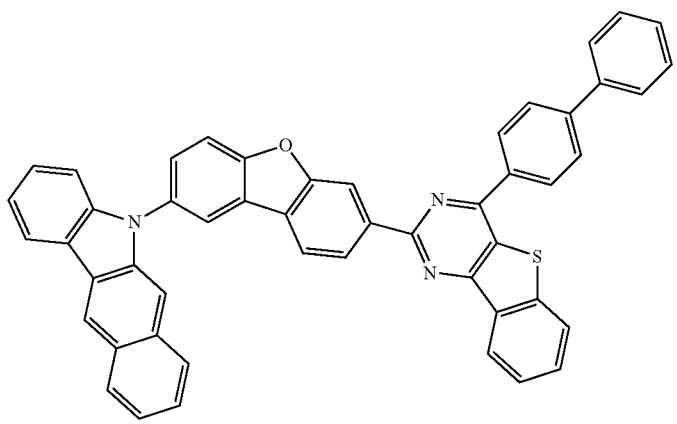 [SMILES: c1ccc(-c2ccc(-c3nc(-c4ccc5c(c4)oc4ccc(-n6c7ccccc7c7cc8ccccc8cc76)cc45)nc4c3sc3ccccc34)cc2)cc1]

Compounds 1 to 376 other than the compounds described in Preparation Examples 1 to 6 and Tables 1 to 6 were also prepared in the same manner as in the methods for preparing the compounds described in the preparation examples described above.

Synthesis identification data for the compounds prepared above are as described in the following [Table 7] and [Table 8].

TABLE 7

| Compound | $^1$H NMR (CDCl$_3$, 200 Mz) |
|---|---|
| 1 | δ = 8.54(d, 2H), 8.28(d, 4H), 8.16(d, 2H), 7.96-7.89(m, 4H), 7.75-7.63(m, 8H), 7.51-7.41(m, 7H), 7.32(t, 1H) |
| 4 | δ = 8.55(d, 2H), 8.28(d, 4H), 8.16(d, 1H), 7.95-7.89(q, 3H), 7.75(d, 1H), 7.67-7.63(m, 5H), 7.51-7.41(m, 7H), 7.33-7.25(m, 3H) |
| 10 | δ = 8.55(d, 1H), 8.28(d, 4H), 8.14(d, 2H), 7.95-7.89(m, 3H), 7.75(d, 1H), 7.65(m, 3H), 7.55-7.50(m, 6H), 7.41-7.25(m, 5H) |
| 11 | δ = 8.55(d, 1H), 8.28(d, 4H), 8.14(d, 3H), 7.96-7.89(m, 4H), 7.75(d, 1H), 7.67(d, 4H), 7.57-7.50(m, 7H), 7.41-7.32(m, 3H) |
| 21 | δ = 8.55(d, 1H), 8.28(d, 2H), 8.18(d, 3H), 7.95-7.89(m, 3H), 7.75(d, 1H), 7.70-7.64(m, 4H), 7.57-7.48(m, 10H), 7.41-7.25(m, 6H) |
| 25 | δ = 8.54(d, 2H), 8.16(d, 2H), 8.05-7.89(m, 6H), 7.77(d, 3H), 7.67-7.63(m, 6H), 7.52-7.41(m, 6H), 7.32(t, 1H) |
| 26 | δ = 8.54(d, 2H), 8.16(d, 1H), 8.05-7.89(m, 5H), 7.77(d, 3H), 7.67-7.63(m, 5H), 7.52-7.41(m, 6H), 7.33-7.25(m, 3H) |
| 28 | δ = 8.53(d, 2H), 8.16-8.05(m, 3H), 7.95-7.89(m, 4H), 7.77(d, 3H), 7.67-7.50(m, 9H), 7.33-7.25(m, 3H) |
| 29 | δ = 8.55(d, 1H), 8.16(d, 2H), 8.05-7.89(m, 5H), 7.79-7.64(m, 6H), 7.55-7.50(m, 6H), 7.41-7.25(m, 5H) |
| 36 | δ = 8.55(d, 1H), 8.30(d, 2H), 8.16(d, 2H), 8.05-7.85(m, 7H), 7.75-7.64(m, 4H), 7.55-7.50(m, 8H), 7.41-7.25(m, 5H) |
| 37 | δ = 8.54(d, 2H), 8.28(d, 4H), 8.16(d, 2H), 7.96-7.89(d, 3H), 7.75-7.62(m, 9H), 7.51-7.41(m, 8H) |
| 44 | δ = 8.55(d, 2H), 8.28(d, 4H), 8.16(d, 2H), 7.94(d, 2H), 7.77-7.50(m, 11H), 7.43-7.25(m, 4H) |
| 46 | δ = 8.55(d, 1H), 8.28(d, 4H), 8.16(d, 2H), 7.91(d, 1H), 7.73-7.51(m, 10H), 7.44-7.25(m, 6H) |
| 68 | δ = 8.54(d, 2H), 8.28(d, 2H), 8.16(d, 2H), 7.96-7.89(m, 5H), 7.75-7.62(m, 9H), 7.52-7.41(m, 10H), 7.25(d, 2H) |
| 74 | δ = 8.55(d, 1H), 8.28(d, 2H), 8.16(d, 2H), 7.94-7.85(m, 4H), 7.75-7.67(m, 5H), 7.55-7.51(m, 6H), 7.44-7.25(m, 8H) |
| 76 | δ = 9.09(d, 1H), 8.52(d, 3H), 8.16(d, 2H), 8.00-7.85(m, 8H), 7.75-7.41(m, 17H), 7.25(d, 2H) |
| 80 | δ = 9.09(d, 1H), 8.52(q, 2H), 8.16(d, 2H), 8.00-7.85(m, 7H), 7.75-7.41(m, 17H), 7.25(td, 3H) |
| 81 | δ = 8.54(d, 2H), 8.16(d, 2H), 8.05-7.89(m, 5H), 7.79-7.65(m, 11H), 7.50-7.41(m, 7H) |
| 89 | δ = 8.55(d, 1H), 8.16(d, 2H), 8.05-7.89(m, 4H), 7.79-7.61(m, 7H), 7.55-7.51(m, 5H), 7.40-7.25(m, 6H) |
| 95 | δ = 8.53(d, 2H), 8.34(s, 1H), 8.16-7.89(m, 10H), 7.73-7.59(m, 12H), 7.29(t, 2H) |
| 97 | δ = 8.54(d, 2H), 8.30(d, 2H), 8.16(d, 2H), 8.05-7.89(m, 7H), 7.75-7.63(m, 9H), 7.52-7.41(m, 9H) |
| 101 | δ = 8.55(d, 1H), 8.30(d, 2H), 8.16(d, 2H), 7.98-7.89(m, 6H), 7.75-7.62(m, 5H), 7.52-7.25(m, 13H) |
| 105 | δ = 8.54(d, 2H), 8.28(d, 4H), 8.16(d, 2H), 7.96-7.89(m, 3H), 7.75-7.63(m, 8H), 7.51-7.25(m, 9H) |

TABLE 7-continued

| Compound | ¹H NMR (CDCl₃, 200 Mz) |
|---|---|
| 114 | δ = 8.55(d, 1H), 8.28(d, 4H), 8.16(d, 2H), 7.92(d, 2H), 7.75-7.50(m, 10H), 7.44-7.25(m, 7H) |
| 119 | δ = 9.09(d, 1H), 8.52(d, 3H), 8.28(d, 2H), 8.16(d, 1H), 8.00-7.89(m, 5H), 7.75-7.50(m, 11H), 7.44-7.25(m, 5H) |
| 125 | δ = 9.09(d, 1H), 8.52(d, 2H), 8.28(d, 2H), 8.16(d, 2H), 8.00-7.89(m, 5H), 7.75-7.51(m, 10H), 7.44-7.25(m, 6H) |
| 130 | δ = 9.09(d, 2H), 8.52(d, 4H), 8.16(d, 2H), 8.00-7.89(m, 8H), 7.75-7.50(m, 12H), 7.33-7.25(m, 3H) |
| 136 | δ = 8.54(d, 2H), 8.28(d, 2H), 8.16(d, 2H), 7.96-7.85(m, 5H), 7.77-7.62(m, 8H), 7.52-7.25(m, 13H) |
| 140 | δ = 8.55(d, 2H), 8.28(d, 2H), 8.16(d, 2H), 7.94-7.85(m, 4H), 7.75-7.62(m, 8H), 7.57-7.51(m, 6H), 7.40-7.25(m, 6H) |
| 142 | δ = 8.55(d, 2H), 8.28(d, 2H), 8.16(d, 2H), 7.94-7.85(m, 4H), 7.75-7.62(m, 4H), 7.52-7.25(m, 17H) |
| 147 | δ = 9.09(d, 1H), 8.52(d, 3H), 8.16(d, 2H), 8.00-7.85(m, 7H), 7.75-7.59(m, 12H), 7.52-7.25(m, 8H) |
| 156 | δ = 8.55(d, 1H), 8.28(d, 4H), 8.16(d, 2H), 7.94(d, 1H), 7.83(d, 2H), 7.66(t, 3H), 7.55-7.50(m, 7H), 7.44-7.25(m, 6H) |
| 160 | δ = 8.54(d, 2H), 8.28(d, 4H), 8.16(d, 2H), 7.95(d, 2H), 7.83(d, 2H), 7.67-7.63(m, 7H), 7.51-7.38(m, 9H) |
| 161 | δ = 8.55(d, 1H), 8.16(d, 2H), 8.05-7.89(m, 5H), 7.79-7.63(m, 10H), 7.52-7.25(m, 8H) |
| 169 | δ = 8.55(d, 1H), 8.16(d, 2H), 8.05-7.89(m, 4H), 7.75-7.62(m, 6H), 7.55-7.51(m, 7H), 7.43-7.25(m, 5H) |
| 175 | δ = 8.53(d, 2H), 8.34(s, 1H), 8.16-7.89(m, 10H), 7.75-7.50(m, 11H), 7.33-7.25(m, 3H) |
| 179 | δ = 8.54(d, 2H), 8.30(d, 2H), 8.16(d, 2H), 8.05-7.85(m, 7H), 7.75-7.63(m, 8H), 7.52-7.32(m, 10H) |
| 185 | δ = 8.55(d, 1H), 8.30(d, 2H), 8.16(d, 2H), 8.05-7.85(m, 6H), 7.75-7.62(m, 4H), 7.55-7.50(m, 9H), 7.44-7.25(m, 5H) |
| 195 | δ = 8.55(d, 1H), 8.30(d, 2H), 8.16(d, 2H), 8.05-7.94(m, 3H), 7.83(d, 4H), 7.66(t, 3H), 7.55-7.25(m, 14H) |
| 200 | δ = 8.54(d, 2H), 8.34(s, 1H), 8.16(d, 2H), 8.05-7.81(m, 10H), 7.67-7.59(m, 9H), 7.52-7.38(m, 5H) |
| 201 | δ = 8.54(d, 2H), 8.27(d, 4H), 7.94(d, 2H), 7.88(s, 1H), 7.77~7.70(m, 6H), 7.65~7.55(m, 10H), 7.44(d, 2H), 7.31(d, 1H). |
| 204 | δ = 8.43(d, 2H), 8.35(d, 4H), 7.91(d, 2H), 7.82(s, 1H), 7.76~7.71(m, 6H), 7.59~7.52(m, 8H), 7.34(d, 2H), 7.21(d, 1H). |
| 210 | δ = 8.52 (d, 2H), 8.29(d, 4H), 8.04(s, 1H), 7.91(d, 2H), 7.82(s, 1H), 7.76~7.71(m, 6H), 7.59~7.52(m, 6H), 7.36(d, 2H), 7.21(d, 1H) 6.99(s, 1H). |
| 221 | δ = 8.54 (d, 2H), 8.33(d, 2H), 8.14(s, 1H), 8.03(s, 1H), 7.92(d, 2H), 7.85(d, 2H), 7.79(s, 1H), 7.75~7.71(m, 7H), 7.60~7.55(m, 6H), 7.30(d, 2H), 7.21(d, 1H) 6.99(s, 1H). |
| 232 | δ = 8.53(d, 2H), 8.28(d, 4H), 7.93(d, 2H), 7.89(s, 1H), 7.77~7.70(m, 8H), 7.66~7.56(m, 12H), 7.46(d, 2H), 7.32(d, 1H). |
| 236 | δ = 8.45(d, 2H), 8.33(d, 4H), 7.93(d, 2H), 7.84(s, 1H), 7.78~7.71(m, 8H), 7.62~7.55(m, 10H), 7.35(d, 2H), 7.20(d, 1H). |
| 238 | δ = 8.54 (d, 2H), 8.30(d, 4H), 8.05(s, 1H), 7.92(d, 2H), 7.84(s, 1H), 7.77~7.72(m, 9H), 7.65~7.58(m, 8H), 7.35(d, 2H), 7.30(d, 1H) 6.99(s, 1H). |
| 240 | δ = 8.52(d, 2H), 8.28(d, 4H), 7.93(d, 2H), 7.89(s, 1H), 7.80~7.70(m, 10H), 7.66~7.50(m, 14H), 7.46(d, 2H), 7.32(d, 1H). |
| 252 | δ = 8.82(d, 2H), 8.54(d, 4H), 8.14(d, 2H), 7.99(s, 1H), 7.80~7.71(m, 6H), 7.65~7.55(m, 8H), 7.44(d, 2H), 7.37(d, 1H). |
| 253 | δ = 8.61(d, 2H), 8.09(d, 2H), 7.99(s, 1H), 7.85~7.79(m, 9H), 7.71~7.66(m, 10H), 7.45(d, 2H), 7.32(d, 1H). |
| 259 | δ = 8.59(d, 2H), 8.05(d, 2H), 7.94(d, 1H), 7.82~7.75(m, 8H), 7.68~7.59(m, 9H), 7.31(d, 2H), 7.17(d, 1H). |
| 271 | δ = 8.54(d, 2H), 8.01(d, 2H), 7.91(s, 1H), 7.79~7.70(m, 9H), 7.65~7.60(m, 10H), 7.51~7.45(m, 6H), 7.18(d, 1H). |
| 277 | δ = 8.53 (d, 2H), 8.05(s, 1H), 7.92(d, 2H), 7.83(s, 1H), 7.79~7.71(m, 10H), 7.62~7.52(m, 9H), 7.35(d, 2H), 7.22(d, 1H) 7.00(s, 1H). |
| 280 | δ = 8.62(d, 2H), 8.10(d, 2H), 7.99(s, 1H), 7.81~7.75(m, 9H), 7.69~7.65(m, 10H), 7.45(d, 2H), 7.32(d, 1H). |
| 288 | δ = 8.43 (d, 2H), 8.11(s, 1H), 7.90(d, 2H), 7.85(s, 1H), 7.75~7.71(m, 10H), 7.60~7.52(m, 9H), 7.35(d, 2H), 7.22(d, 1H) 7.02(s, 1H). |
| 289 | δ = 8.54(d, 2H), 8.27(d, 4H), 8.08(s, 1H), 7.94(d, 2H), 7.88(s, 1H), 7.77~7.70(m, 6H), 7.65~7.55(m, 9H), 7.44(d, 2H), 7.31(d, 1H). |
| 297 | δ = 8.50 (d, 2H), 8.25(d, 4H), 8.04(s, 1H), 7.91(d, 2H), 7.82(s, 1H), 7.75~7.71(m, 6H), 7.55~7.52(m, 5H), 7.36(d, 2H), 7.18(d, 1H) 6.99(s, 1H). |
| 307 | δ = 8.48 (d, 2H), 8.21(d, 2H), 8.01(s, 1H), 7.88(d, 2H), 7.80(s, 1H), 7.74~7.69(m, 8H), 7.56~7.50(m, 7H), 7.31(d, 2H), 7.14(d, 1H) 6.99(s, 1H). |
| 318 | δ = 8.49(d, 2H), 8.20(d, 4H), 8.05(s, 1H), 7.91(d, 2H), 7.85(s, 1H), 7.76~7.70(m, 10H), 7.65~7.55(m, 9H), 7.43(d, 2H), 7.32(d, 1H). |
| 320 | δ = 8.40(d, 2H), 8.29(d, 4H), 8.03(s, 1H) 7.93(d, 1H), 7.84(s, 1H), 7.78~7.71(m, 10H), 7.62~7.55(m, 10H), 7.32(d, 2H), 7.18(d, 1H). |
| 324 | δ = 8.38(d, 2H), 8.25(d, 4H), 8.00(s, 1H), 7.95(d, 1H), 7.88(s, 1H), 7.79~7.72(m, 8H), 7.68~7.58(m, 10H), 7.28(d, 2H), 7.11(d, 1H). |
| 325 | δ = 8.50 (d, 2H), 8.25(d, 4H), 8.04(s, 1H), 7.91(d, 2H), 7.82(s, 1H), 7.75~7.71(m, 8H), 7.55~7.52(m, 7H), 7.36(d, 2H), 7.18(d, 1H) 6.99(s, 1H). |
| 330 | δ = 8.39(d, 2H), 8.26(d, 4H), 8.01(s, 1H) 7.96(d, 1H), 7.86(s, 1H), 7.78~7.71(m, 10H), 7.65~7.55(m, 10H), 7.22(d, 2H), 7.09(d, 1H). |
| 333 | δ = 8.61(d, 2H), 8.32(s, 1H), 8.10(d, 1H), 8.02(s, 1H), 7.88~7.79(m, 9H), 7.70~7.66(m, 10H), 7.44(d, 2H), 7.30(d, 1H). |
| 340 | δ = 8.42(d, 2H), 8.27(d, 2H), 8.02(s, 1H) 7.94(d, 1H), 7.87(s, 1H), 7.78~7.72(m, 8H), 7.67~7.58(m, 9H), 7.22(d, 2H), 7.08(d, 1H). |
| 342 | δ = 8.49(d, 2H), 8.30(d, 4H), 8.10(s, 1H), 7.96(d, 2H), 7.86(s, 1H), 7.76~7.70(m, 10H), 7.65~7.58(m, 8H), 7.40(d, 2H), 7.30(d, 1H). |
| 345 | δ = 8.45 (d, 2H), 8.19(d, 4H), 8.02(s, 1H), 7.95(d, 2H), 7.85(s, 1H), 7.76~7.71(m, 8H), 7.57~7.52(m, 6H), 7.32(d, 2H), 7.11(d, 1H) 6.99(s, 1H). |
| 349 | δ = 8.31(d, 2H), 8.25(d, 4H), 8.04(s, 1H), 7.95(d, 2H), 7.88(s, 1H), 7.77~7.70(m, 6H), 7.65~7.55(m, 9H), 7.44(d, 2H), 7.31(d, 1H). |
| 354 | δ = 8.42(d, 2H), 8.24(d, 4H), 8.09(s, 1H) 7.96(d, 1H), 7.83(s, 1H), 7.78~7.72(m, 6H), 7.65~7.58(m, 8H), 7.21(d, 2H), 7.05(d, 1H). |
| 355 | δ = 8.43 (d, 2H), 8.19(d, 2H), 8.02(s, 1H), 7.82(d, 2H), 7.75(s, 1H), 7.70~7.61(m, 6H), 7.52~7.45(m, 7H), 7.29(d, 2H), 7.11(d, 1H) 6.98(s, 1H). |
| 359 | δ = 8.33 (d, 2H), 8.15(d, 2H), 8.03(s, 1H), 7.88(d, 2H), 7.80(s, 1H), 7.70~7.65(m, 8H), 7.58~7.50(m, 7H), 7.13(d, 2H), 7.09(d, 1H) 6.99(s, 1H). |
| 364 | δ = 8.36(d, 2H), 8.21(d, 4H), 8.07(s, 1H), 7.99(d, 2H), 7.89(s, 1H), 7.78~7.70(m, 10H), 7.67~7.58(m, 9H), 7.45(d, 2H), 7.37(d, 1H). |
| 367 | δ = 8.29 (d, 2H), 8.20(d, 2H), 8.02(s, 1H), 7.91(d, 2H), 7.80(s, 1H), 7.78~7.71(m, 8H), 7.65~7.59(m, 10H), 7.37(d, 2H), 7.15(d, 1H) 6.99(s, 1H). |
| 373 | δ = 8.39(d, 2H), 8.30(d, 4H), 8.12(s, 1H), 7.99(d, 2H), 7.86(s, 1H), 7.76~7.71(m, 10H), 7.64~7.58(m, 8H), 7.32(d, 2H), 7.18(d, 1H). |
| 374 | δ = 8.43(d, 2H), 8.21(d, 2H), 8.05(s, 1H) 7.98(d, 1H), 7.87(s, 1H), 7.79~7.72(m, 10H), 7.65~7.58(m, 10H), 7.22(d, 2H), 7.03(d, 1H). |
| 376 | δ = 8.45 (d, 2H), 8.21(d, 4H), 8.06(s, 1H), 7.98(d, 2H), 7.87(s, 1H), 7.76~7.71(m, 8H), 7.59~7.55(m, 6H), 7.29(d, 2H), 7.12(d, 1H) 6.98(s, 1H). |

TABLE 8

| Compound | FD-Mass | Compound | FD-Mass |
| --- | --- | --- | --- |
| 1 | m/z = 664.23($C_{47}H_{28}N_4O$, 664.77) | 2 | m/z = 690.24($C_{49}H_{30}N_4O$, 690.81) |
| 3 | m/z = 816.29($C_{59}H_{36}N_4O$, 816.96) | 4 | m/z = 614.21($C_{43}H_{26}N_4O$, 614.71) |
| 5 | m/z = 690.24($C_{49}H_{30}N_4O$, 690.81) | 6 | m/z = 690.24($C_{49}H_{30}N_4O$, 690.81) |
| 7 | m/z = 766.27($C_{55}H_{34}N_4O$, 766.90) | 8 | m/z = 614.21($C_{43}H_{26}N_4O$, 614.71) |
| 9 | m/z = 690.24($C_{49}H_{30}N_4O$, 690.81) | 10 | m/z = 614.21($C_{43}H_{26}N_4O$, 614.71) |
| 11 | m/z = 664.23($C_{47}H_{28}N_4O$, 664.77) | 12 | m/z = 714.24($C_{51}H_{30}N_4O$, 714.83) |
| 13 | m/z = 790.27($C_{57}H_{34}N_4O$, 790.93) | 14 | m/z = 664.23($C_{47}H_{28}N_4O$, 664.77) |
| 15 | m/z = 664.23($C_{47}H_{28}N_4O$, 664.77) | 16 | m/z = 714.24($C_{51}H_{30}N_4O$, 714.83) |
| 17 | m/z = 714.24($C_{51}H_{30}N_4O$, 714.83) | 18 | m/z = 714.24($C_{51}H_{30}N_4O$, 714.83) |
| 19 | m/z = 740.26($C_{53}H_{32}N_4O$, 740.87) | 20 | m/z = 766.27($C_{55}H_{34}N_4O$, 766.90) |
| 21 | m/z = 690.24($C_{49}H_{30}N_4O$, 690.81) | 22 | m/z = 740.26($C_{53}H_{32}N_4O$, 740.87) |
| 23 | m/z = 740.26($C_{53}H_{32}N_4O$, 740.87) | 24 | m/z = 740.26($C_{53}H_{32}N_4O$, 740.87) |
| 25 | m/z = 693.19($C_{48}H_{27}N_3OS$, 693.82) | 26 | m/z = 643.17($C_{44}H_{25}N_3OS$, 643.76) |
| 27 | m/z = 719.20($C_{50}H_{29}N_3OS$, 719.86) | 28 | m/z = 643.17($C_{44}H_{25}N_3OS$, 643.76) |
| 29 | m/z = 643.17($C_{44}H_{25}N_3OS$, 643.76) | 30 | m/z = 693.19($C_{48}H_{27}N_3OS$, 693.82) |
| 31 | m/z = 693.19($C_{48}H_{27}N_3OS$, 693.82) | 32 | m/z = 693.19($C_{48}H_{27}N_3OS$, 693.82) |
| 33 | m/z = 719.20($C_{50}H_{29}N_3OS$, 719.86) | 34 | m/z = 769.22($C_{54}H_{31}N_3OS$, 769.92) |
| 35 | m/z = 719.20($C_{50}H_{29}N_3OS$, 719.86) | 36 | m/z = 719.20($C_{50}H_{29}N_3OS$, 719.86) |
| 37 | m/z = 664.23($C_{47}H_{28}N_4O$, 664.77) | 38 | m/z = 740.26($C_{53}H_{32}N_4O$, 740.87) |
| 39 | m/z = 816.29($C_{59}H_{36}N_4O$, 816.96) | 40 | m/z = 614.21($C_{43}H_{26}N_4O$, 614.71) |
| 41 | m/z = 690.24($C_{49}H_{30}N_4O$, 690.81) | 42 | m/z = 690.24($C_{49}H_{30}N_4O$, 690.81) |
| 43 | m/z = 766.27($C_{55}H_{34}N_4O$, 766.90) | 44 | m/z = 614.21($C_{43}H_{26}N_4O$, 614.71) |
| 45 | m/z = 690.24($C_{49}H_{30}N_4O$, 690.81) | 46 | m/z = 614.21($C_{43}H_{26}N_4O$, 614.71) |
| 47 | m/z = 690.24($C_{49}H_{30}N_4O$, 690.81) | 48 | m/z = 690.24($C_{49}H_{30}N_4O$, 690.81) |
| 49 | m/z = 714.24($C_{51}H_{30}N_4O$, 714.83) | 50 | m/z = 790.27($C_{57}H_{34}N_4O$, 790.93) |
| 51 | m/z = 664.23($C_{47}H_{28}N_4O$, 664.77) | 52 | m/z = 740.26($C_{53}H_{32}N_4O$, 740.87) |
| 53 | m/z = 740.26($C_{53}H_{32}N_4O$, 740.87) | 54 | m/z = 816.29($C_{59}H_{36}N_4O$, 816.96) |
| 55 | m/z = 664.23($C_{47}H_{28}N_4O$, 664.77) | 56 | m/z = 740.26($C_{53}H_{32}N_4O$, 740.87) |
| 57 | m/z = 664.23($C_{47}H_{28}N_4O$, 664.77) | 58 | m/z = 740.26($C_{53}H_{32}N_4O$, 740.87) |
| 59 | m/z = 740.26($C_{53}H_{32}N_4O$, 740.87) | 60 | m/z = 764.26($C_{55}H_{32}N_4O$, 764.89) |
| 61 | m/z = 840.29($C_{61}H_{36}N_4O$, 840.99) | 62 | m/z = 714.24($C_{51}H_{30}N_4O$, 714.83) |
| 63 | m/z = 790.27($C_{57}H_{34}N_4O$, 790.93) | 64 | m/z = 866.30($C_{63}H_{38}N_4O$, 867.02) |
| 65 | m/z = 714.24($C_{51}H_{30}N_4O$, 714.83) | 66 | m/z = 714.24($C_{51}H_{30}N_4O$, 714.83) |
| 67 | m/z = 790.27($C_{57}H_{34}N_4O$, 790.93) | 68 | m/z = 740.26($C_{53}H_{32}N_4O$, 740.87) |
| 69 | m/z = 816.29($C_{59}H_{36}N_4O$, 816.96) | 70 | m/z = 892.32($C_{65}H_{40}N_4O$, 893.06) |
| 71 | m/z = 690.24($C_{49}H_{30}N_4O$, 690.81) | 72 | m/z = 690.24($C_{49}H_{30}N_4O$, 690.81) |
| 73 | m/z = 766.27($C_{55}H_{34}N_4O$, 766.90) | 74 | m/z = 690.24($C_{49}H_{30}N_4O$, 690.81) |
| 75 | m/z = 690.24($C_{49}H_{30}N_4O$, 690.81) | 76 | m/z = 790.27($C_{57}H_{34}N_4O$, 790.93) |
| 77 | m/z = 740.26($C_{53}H_{32}N_4O$, 740.87) | 78 | m/z = 816.29($C_{59}H_{36}N_4O$, 816.96) |
| 79 | m/z = 816.29($C_{59}H_{36}N_4O$, 816.96) | 80 | m/z = 740.26($C_{53}H_{32}N_4O$, 740.87) |
| 81 | m/z = 693.19($C_{48}H_{27}N_3OS$, 693.82) | 82 | m/z = 769.22($C_{54}H_{31}N_3OS$, 769.92) |
| 83 | m/z = 643.17($C_{44}H_{25}N_3OS$, 643.76) | 84 | m/z = 719.20($C_{50}H_{29}N_3OS$, 719.86) |
| 85 | m/z = 719.20($C_{50}H_{29}N_3OS$, 719.86) | 86 | m/z = 795.23($C_{56}H_{33}N_3OS$, 795.96) |
| 87 | m/z = 643.17($C_{44}H_{25}N_3OS$, 643.76) | 88 | m/z = 719.20($C_{50}H_{29}N_3OS$, 719.86) |
| 89 | m/z = 643.17($C_{44}H_{25}N_3OS$, 643.76) | 90 | m/z = 719.20($C_{50}H_{29}N_3OS$, 719.86) |
| 91 | m/z = 743.20($C_{52}H_{29}N_3OS$, 743.88) | 92 | m/z = 819.23($C_{58}H_{33}N_3OS$, 819.98) |
| 93 | m/z = 769.22($C_{54}H_{31}N_3OS$, 769.92) | 94 | m/z = 769.22($C_{54}H_{31}N_3OS$, 769.92) |
| 95 | m/z = 693.19($C_{48}H_{27}N_3OS$, 693.82) | 96 | m/z = 693.19($C_{48}H_{27}N_3OS$, 693.82) |
| 97 | m/z = 769.22($C_{54}H_{31}N_3OS$, 769.92) | 98 | m/z = 719.20($C_{50}H_{29}N_3OS$, 719.86) |
| 99 | m/z = 795.23($C_{56}H_{33}N_3OS$, 795.96) | 100 | m/z = 719.20($C_{50}H_{29}N_3OS$, 719.86) |
| 101 | m/z = 719.85($C_{50}H_{29}N_3OS$, 719.20) | 102 | m/z = 693.81($C_{48}H_{27}N_3OS$, 693.19) |
| 103 | m/z = 703.78($C_{50}H_{29}N_3O_2$, 703.23) | 104 | m/z = 677.75($C_{48}H_{27}N_3O_2$, 677.21) |
| 105 | m/z = 664.75($C_{47}H_{28}N_4O$, 664.23) | 106 | m/z = 740.85($C_{53}H_{32}N_4O$, 740.26) |
| 107 | m/z = 816.94($C_{59}H_{36}N_4O$, 816.29) | 108 | m/z = 614.69($C_{43}H_{26}N_4O$, 614.21) |
| 109 | m/z = 690.79($C_{49}H_{30}N_4O$, 690.24) | 110 | m/z = 690.79($C_{49}H_{30}N_4O$, 690.24) |
| 111 | m/z = 766.88($C_{55}H_{34}N_4O$, 766.27) | 112 | m/z = 614.69($C_{43}H_{26}N_4O$, 614.21) |
| 113 | m/z = 690.79($C_{49}H_{30}N_4O$, 690.24) | 114 | m/z = 614.69($C_{43}H_{26}N_4O$, 614.21) |
| 115 | m/z = 690.79($C_{49}H_{30}N_4O$, 690.24) | 116 | m/z = 690.79($C_{49}H_{30}N_4O$, 690.24) |
| 117 | m/z = 714.81($C_{51}H_{30}N_4O$, 714.24) | 118 | m/z = 790.91($C_{57}H_{34}N_4O$, 790.27) |
| 119 | m/z = 664.75($C_{47}H_{28}N_4O$, 664.23) | 120 | m/z = 740.85($C_{53}H_{32}N_4O$, 740.26) |
| 121 | m/z = 740.85($C_{53}H_{32}N_4O$, 740.26) | 122 | m/z = 816.94($C_{59}H_{36}N_4O$, 816.29) |
| 123 | m/z = 664.75($C_{47}H_{28}N_4O$, 664.23) | 124 | m/z = 790.91($C_{57}H_{34}N_4O$, 790.27) |
| 125 | m/z = 664.75($C_{47}H_{28}N_4O$, 664.23) | 126 | m/z = 790.91($C_{57}H_{34}N_4O$, 790.27) |
| 127 | m/z = 790.91($C_{57}H_{34}N_4O$, 790.27) | 128 | m/z = 764.87($C_{55}H_{32}N_4O$, 764.26) |
| 129 | m/z = 840.96($C_{61}H_{36}N_4O$, 840.29) | 130 | m/z = 714.81($C_{51}H_{30}N_4O$, 714.24) |
| 131 | m/z = 790.91($C_{57}H_{34}N_4O$, 790.27) | 132 | m/z = 867.00($C_{63}H_{38}N_4O$, 866.30) |
| 133 | m/z = 714.81($C_{51}H_{30}N_4O$, 714.24) | 134 | m/z = 714.81($C_{51}H_{30}N_4O$, 714.24) |
| 135 | m/z = 790.91($C_{57}H_{34}N_4O$, 790.27) | 136 | m/z = 740.85($C_{53}H_{32}N_4O$, 740.26) |
| 137 | m/z = 816.94($C_{59}H_{36}N_4O$, 816.29) | 138 | m/z = 893.04($C_{65}H_{40}N_4O$, 892.32) |
| 139 | m/z = 690.79($C_{49}H_{30}N_4O$, 690.24) | 140 | m/z = 690.79($C_{49}H_{30}N_4O$, 690.24) |
| 141 | m/z = 766.88($C_{55}H_{34}N_4O$, 766.27) | 142 | m/z = 690.79($C_{49}H_{30}N_4O$, 690.24) |
| 143 | m/z = 766.88($C_{55}H_{34}N_4O$, 766.27) | 144 | m/z = 790.91($C_{57}H_{34}N_4O$, 790.27) |
| 145 | m/z = 867.00($C_{63}H_{38}N_4O$, 866.30) | 146 | m/z = 943.10($C_{69}H_{42}N_4O$, 942.34) |
| 147 | m/z = 740.85($C_{53}H_{32}N_4O$, 740.26) | 148 | m/z = 816.94($C_{59}H_{36}N_4O$, 816.29) |
| 149 | m/z = 816.94($C_{59}H_{36}N_4O$, 816.29) | 150 | m/z = 816.94($C_{59}H_{36}N_4O$, 816.29) |
| 151 | m/z = 740.85($C_{53}H_{32}N_4O$, 740.26) | 152 | m/z = 816.94($C_{59}H_{36}N_4O$, 816.29) |
| 153 | m/z = 740.85($C_{53}H_{32}N_4O$, 740.26) | 154 | m/z = 816.94($C_{59}H_{36}N_4O$, 816.29) |
| 155 | m/z = 816.94($C_{59}H_{36}N_4O$, 816.29) | 156 | m/z = 614.69($C_{43}H_{26}N_4O$, 614.21) |

TABLE 8-continued

| Compound | FD-Mass | Compound | FD-Mass |
|---|---|---|---|
| 157 | m/z = 614.69($C_{43}H_{26}N_4O$, 614.21) | 158 | m/z = 614.69($C_{43}H_{26}N_4O$, 614.21) |
| 159 | m/z = 664.75($C_{47}H_{28}N_4O$, 664.23) | 160 | m/z = 664.75($C_{47}H_{28}N_4O$, 664.23) |
| 161 | m/z = 693.81($C_{48}H_{27}N_3OS$, 693.19) | 162 | m/z = 769.91($C_{54}H_{31}N_3OS$, 769.22) |
| 163 | m/z = 643.75($C_{44}H_{25}N_3OS$, 643.17) | 164 | m/z = 719.85($C_{50}H_{29}N_3OS$, 719.20) |
| 165 | m/z = 719.85($C_{50}H_{29}N_3OS$, 719.20) | 166 | m/z = 795.95($C_{56}H_{33}N_3OS$, 795.23) |
| 167 | m/z = 643.75($C_{44}H_{25}N_3OS$, 643.17) | 168 | m/z = 719.85($C_{50}H_{29}N_3OS$, 719.20) |
| 169 | m/z = 643.75($C_{44}H_{25}N_3OS$, 643.17) | 170 | m/z = 719.85($C_{50}H_{29}N_3OS$, 719.20) |
| 171 | m/z = 743.87($C_{52}H_{29}N_3OS$, 743.20) | 172 | m/z = 819.97($C_{58}H_{33}N_3OS$, 819.23) |
| 173 | m/z = 769.91($C_{54}H_{31}N_3OS$, 769.22) | 174 | m/z = 769.91($C_{54}H_{31}N_3OS$, 769.22) |
| 175 | m/z = 693.81($C_{48}H_{27}N_3OS$, 693.19) | 176 | m/z = 769.91($C_{54}H_{31}N_3OS$, 769.22) |
| 177 | m/z = 693.81($C_{48}H_{27}N_3OS$, 693.19) | 178 | m/z = 769.91($C_{54}H_{31}N_3OS$, 769.22) |
| 179 | m/z = 769.91($C_{54}H_{31}N_3OS$, 769.22) | 180 | m/z = 719.85($C_{50}H_{29}N_3OS$, 719.20) |
| 181 | m/z = 795.95($C_{56}H_{33}N_3OS$, 795.23) | 182 | m/z = 872.04($C_{62}H_{37}N_3OS$, 871.27) |
| 183 | m/z = 719.85($C_{50}H_{29}N_3OS$, 719.20) | 184 | m/z = 795.95($C_{56}H_{33}N_3OS$, 795.23) |
| 185 | m/z = 719.85($C_{50}H_{29}N_3OS$, 719.20) | 186 | m/z = 795.95($C_{56}H_{33}N_3OS$, 795.23) |
| 187 | m/z = 795.95($C_{56}H_{33}N_3OS$, 795.23) | 188 | m/z = 693.81($C_{48}H_{27}N_3OS$, 693.19) |
| 189 | m/z = 627.69($C_{44}H_{25}N_3O_2$, 627.19) | 190 | m/z = 769.91($C_{54}H_{31}N_3OS$, 769.22) |
| 191 | m/z = 703.78($C_{50}H_{29}N_3O_2$, 703.23) | 192 | m/z = 677.75($C_{48}H_{27}N_3O_2$, 677.21) |
| 193 | m/z = 677.75($C_{48}H_{27}N_3O_2$, 677.21) | 194 | m/z = 779.88($C_{56}H_{33}N_3O_2$, 779.26) |
| 195 | m/z = 719.85($C_{50}H_{29}N_3OS$, 719.20) | 196 | m/z = 719.85($C_{50}H_{29}N_3OS$, 719.20) |
| 197 | m/z = 693.81($C_{48}H_{27}N_3OS$, 693.19) | 198 | m/z = 769.91($C_{54}H_{31}N_3OS$, 769.22) |
| 199 | m/z = 769.91($C_{54}H_{31}N_3OS$, 769.22) | 200 | m/z = 743.87($C_{52}H_{29}N_3OS$, 743.20) |
| 201 | m/z = 664.77($C_{47}H_{28}N_4O$, 664.23) | 202 | m/z = 740.87($C_{53}H_{32}N_4O$, 740.26) |
| 203 | m/z = 816.96($C_{59}H_{36}N_4O$, 816.29) | 204 | m/z = 614.71($C_{43}H_{26}N_4O$, 614.21) |
| 205 | m/z = 690.81($C_{49}H_{30}N_4O$, 690.24) | 206 | m/z = 690.81($C_{49}H_{30}N_4O$, 690.24) |
| 207 | m/z = 766.90($C_{55}H_{34}N_4O$, 766.27) | 208 | m/z = 614.71($C_{43}H_{26}N_4O$, 614.21) |
| 209 | m/z = 690.81($C_{49}H_{30}N_4O$, 690.24) | 210 | m/z = 614.71($C_{43}H_{26}N_4O$, 614.21) |
| 211 | m/z = 690.81($C_{49}H_{30}N_4O$, 690.24) | 212 | m/z = 690.81($C_{49}H_{30}N_4O$, 690.24) |
| 213 | m/z = 714.83($C_{51}H_{30}N_4O$, 714.24) | 214 | m/z = 790.93($C_{57}H_{34}N_4O$, 790.27) |
| 215 | m/z = 664.77($C_{47}H_{28}N_4O$, 664.23) | 216 | m/z = 740.87($C_{53}H_{32}N_4O$, 740.26) |
| 217 | m/z = 740.87($C_{53}H_{32}N_4O$, 740.26) | 218 | m/z = 816.96($C_{59}H_{36}N_4O$, 816.29) |
| 219 | m/z = 664.77($C_{47}H_{28}N_4O$, 664.23) | 220 | m/z = 740.87($C_{53}H_{32}N_4O$, 740.26) |
| 221 | m/z = 664.77($C_{47}H_{28}N_4O$, 664.23) | 222 | m/z = 740.87($C_{53}H_{32}N_4O$, 740.26) |
| 223 | m/z = 740.87($C_{53}H_{32}N_4O$, 740.26) | 224 | m/z = 764.89($C_{55}H_{32}N_4O$, 764.26) |
| 225 | m/z = 840.99($C_{61}H_{36}N_4O$, 840.29) | 226 | m/z = 714.83($C_{51}H_{30}N_4O$, 714.24) |
| 227 | m/z = 790.93($C_{57}H_{34}N_4O$, 790.27) | 228 | m/z = 867.02($C_{63}H_{38}N_4O$, 866.30) |
| 229 | m/z = 714.83($C_{51}H_{30}N_4O$, 714.24) | 230 | m/z = 714.83($C_{51}H_{30}N_4O$, 714.24) |
| 231 | m/z = 790.93($C_{57}H_{34}N_4O$, 790.27) | 232 | m/z = 740.87($C_{53}H_{32}N_4O$, 740.26) |
| 233 | m/z = 816.96($C_{59}H_{36}N_4O$, 816.29) | 234 | m/z = 893.06($C_{65}H_{40}N_4O$, 892.32) |
| 235 | m/z = 690.81($C_{49}H_{30}N_4O$, 690.24) | 236 | m/z = 690.81($C_{49}H_{30}N_4O$, 690.24) |
| 237 | m/z = 766.90($C_{55}H_{34}N_4O$, 766.27) | 238 | m/z = 690.81($C_{49}H_{30}N_4O$, 690.24) |
| 239 | m/z = 766.90($C_{55}H_{34}N_4O$, 766.27) | 240 | m/z = 790.93($C_{57}H_{34}N_4O$, 790.27) |
| 241 | m/z = 867.02($C_{63}H_{38}N_4O$, 866.30) | 242 | m/z = 943.12($C_{69}H_{42}N_4O$, 942.34) |
| 243 | m/z = 740.87($C_{53}H_{32}N_4O$, 740.26) | 244 | m/z = 816.96($C_{59}H_{36}N_4O$, 816.29) |
| 245 | m/z = 816.96($C_{59}H_{36}N_4O$, 816.29) | 246 | m/z = 816.96($C_{59}H_{36}N_4O$, 816.29) |
| 247 | m/z = 740.87($C_{53}H_{32}N_4O$, 740.26) | 248 | m/z = 816.96($C_{59}H_{36}N_4O$, 816.29) |
| 249 | m/z = 740.87($C_{53}H_{32}N_4O$, 740.26) | 250 | m/z = 816.96($C_{59}H_{36}N_4O$, 816.29) |
| 251 | m/z = 816.96($C_{59}H_{36}N_4O$, 816.29) | 252 | m/z = 614.71($C_{43}H_{26}N_4O$, 614.21) |
| 253 | m/z = 693.82($C_{48}H_{27}N_3OS$, 693.19) | 254 | m/z = 769.92($C_{54}H_{31}N_3OS$, 769.22) |
| 255 | m/z = 643.76($C_{44}H_{25}N_3OS$, 643.17) | 256 | m/z = 719.86($C_{50}H_{29}N_3OS$, 719.20) |
| 257 | m/z = 719.86($C_{50}H_{29}N_3OS$, 719.20) | 258 | m/z = 795.96($C_{56}H_{33}N_3OS$, 795.23) |
| 259 | m/z = 643.76($C_{44}H_{25}N_3OS$, 643.17) | 260 | m/z = 719.86($C_{50}H_{29}N_3OS$, 719.20) |
| 261 | m/z = 643.76($C_{44}H_{25}N_3OS$, 643.17) | 262 | m/z = 719.86($C_{50}H_{29}N_3OS$, 719.20) |
| 263 | m/z = 743.88($C_{52}H_{29}N_3OS$, 743.20) | 264 | m/z = 819.98($C_{58}H_{33}N_3OS$, 819.23) |
| 265 | m/z = 769.92($C_{54}H_{31}N_3OS$, 769.22) | 266 | m/z = 769.92($C_{54}H_{31}N_3OS$, 769.22) |
| 267 | m/z = 693.82($C_{48}H_{27}N_3OS$, 693.19) | 268 | m/z = 769.92($C_{54}H_{31}N_3OS$, 769.22) |
| 269 | m/z = 693.82($C_{48}H_{27}N_3OS$, 693.19) | 270 | m/z = 769.92($C_{54}H_{31}N_3OS$, 769.22) |
| 271 | m/z = 769.92($C_{54}H_{31}N_3OS$, 769.22) | 272 | m/z = 719.86($C_{50}H_{29}N_3OS$, 719.20) |
| 273 | m/z = 795.96($C_{56}H_{33}N_3OS$, 795.23) | 274 | m/z = 872.06($C_{62}H_{37}N_3OS$, 871.27) |
| 275 | m/z = 719.86($C_{50}H_{29}N_3OS$, 719.20) | 276 | m/z = 795.96($C_{56}H_{33}N_3OS$, 795.23) |
| 277 | m/z = 719.86($C_{50}H_{29}N_3OS$, 719.20) | 278 | m/z = 795.96($C_{56}H_{33}N_3OS$, 795.23) |
| 279 | m/z = 795.96($C_{56}H_{33}N_3OS$, 795.23) | 280 | m/z = 693.82($C_{48}H_{27}N_3OS$, 693.19) |
| 281 | m/z = 627.70($C_{44}H_{25}N_3O_2$, 627.19) | 282 | m/z = 769.92($C_{54}H_{31}N_3OS$, 769.22) |
| 283 | m/z = 769.92($C_{54}H_{31}N_3OS$, 769.22) | 284 | m/z = 677.76($C_{48}H_{27}N_3O_2$, 677.21) |
| 285 | m/z = 677.76($C_{48}H_{27}N_3O_2$, 677.21) | 286 | m/z = 779.90($C_{56}H_{33}N_3O_2$, 779.26) |
| 287 | m/z = 643.76($C_{44}H_{25}N_3OS$, 643.17) | 288 | m/z = 719.86($C_{50}H_{29}N_3OS$, 719.20) |
| 289 | m/z = 664.77($C_{47}H_{28}N_4O$, 664.23) | 290 | m/z = 816.96($C_{59}H_{36}N_4O$, 816.29) |
| 291 | m/z = 614.71($C_{43}H_{26}N_4O$, 614.21) | 292 | m/z = 690.81($C_{49}H_{30}N_4O$, 690.24) |
| 293 | m/z = 690.81($C_{49}H_{30}N_4O$, 690.24) | 294 | m/z = 766.90($C_{55}H_{34}N_4O$, 766.27) |
| 295 | m/z = 614.71($C_{43}H_{26}N_4O$, 614.21) | 296 | m/z = 690.81($C_{49}H_{30}N_4O$, 690.24) |
| 297 | m/z = 614.71($C_{43}H_{26}N_4O$, 614.21) | 298 | m/z = 690.81($C_{49}H_{30}N_4O$, 690.24) |
| 299 | m/z = 690.81($C_{49}H_{30}N_4O$, 690.24) | 300 | m/z = 714.83($C_{51}H_{30}N_4O$, 714.24) |
| 301 | m/z = 664.76($C_{47}H_{28}N_4O$, 664.22) | 302 | m/z = 740.86($C_{53}H_{32}N_4O$, 740.25) |
| 303 | m/z = 740.86($C_{53}H_{32}N_4O$, 740.25) | 304 | m/z = 816.96($C_{59}H_{36}N_4O$, 816.28) |
| 305 | m/z = 664.76($C_{47}H_{28}N_4O$, 664.22) | 306 | m/z = 740.86($C_{53}H_{32}N_4O$, 740.25) |
| 307 | m/z = 664.76($C_{47}H_{28}N_4O$, 664.22) | 308 | m/z = 740.86($C_{53}H_{32}N_4O$, 740.25) |
| 309 | m/z = 740.86($C_{53}H_{32}N_4O$, 740.25) | 310 | m/z = 764.88($C_{55}H_{32}N_4O$, 764.25) |
| 311 | m/z = 714.82($C_{51}H_{30}N_4O$, 714.24) | 312 | m/z = 790.92($C_{57}H_{34}N_4O$, 790.27) |

TABLE 8-continued

| Compound | FD-Mass | Compound | FD-Mass |
|---|---|---|---|
| 313 | m/z = 790.92($C_{57}H_{34}N_4O$, 790.27) | 314 | m/z = 714.82($C_{51}H_{30}N_4O$, 714.24) |
| 315 | m/z = 790.92($C_{57}H_{34}N_4O$, 790.27) | 316 | m/z = 714.82($C_{51}H_{30}N_4O$, 714.24) |
| 317 | m/z = 714.82($C_{51}H_{30}N_4O$, 714.24) | 318 | m/z = 740.86($C_{53}H_{32}N_4O$, 740.25) |
| 319 | m/z = 740.86($C_{53}H_{32}N_4O$, 740.25) | 320 | m/z = 740.86($C_{53}H_{32}N_4O$, 740.25) |
| 321 | m/z = 766.90($C_{55}H_{34}N_4O$, 766.27) | 322 | m/z = 766.90($C_{55}H_{34}N_4O$, 766.27) |
| 323 | m/z = 843.00($C_{61}H_{38}N_4O$, 842.30) | 324 | m/z = 690.80($C_{49}H_{30}N_4O$, 690.24) |
| 325 | m/z = 690.80($C_{49}H_{30}N_4O$, 690.24) | 326 | m/z = 816.96($C_{59}H_{36}N_4O$, 816.28) |
| 327 | m/z = 816.96($C_{59}H_{36}N_4O$, 816.28) | 328 | m/z = 843.00($C_{61}H_{38}N_4O$, 842.30) |
| 329 | m/z = 740.86($C_{53}H_{32}N_4O$, 740.25) | 330 | m/z = 740.86($C_{53}H_{32}N_4O$, 740.25) |
| 331 | m/z = 740.86($C_{53}H_{32}N_4O$, 740.25) | 332 | m/z = 816.96($C_{59}H_{36}N_4O$, 816.28) |
| 333 | m/z = 693.82($C_{48}H_{27}N_3OS$, 693.18) | 334 | m/z = 643.76($C_{44}H_{25}N_3OS$, 643.17) |
| 335 | m/z = 719.86($C_{50}H_{29}N_3OS$, 719.20) | 336 | m/z = 643.76($C_{44}H_{25}N_3OS$, 643.17) |
| 337 | m/z = 693.82($C_{48}H_{27}N_3OS$, 693.18) | 338 | m/z = 719.86($C_{50}H_{29}N_3OS$, 719.20) |
| 339 | m/z = 769.92($C_{54}H_{31}N_3OS$, 769.21) | 340 | m/z = 693.82($C_{48}H_{27}N_3OS$, 693.18) |
| 341 | m/z = 693.82($C_{48}H_{27}N_3OS$, 693.18) | 342 | m/z = 769.92($C_{54}H_{31}N_3OS$, 769.21) |
| 343 | m/z = 846.02($C_{60}H_{35}N_3OS$, 845.25) | 344 | m/z = 795.96($C_{56}H_{33}N_3OS$, 795.23) |
| 345 | m/z = 719.86($C_{50}H_{29}N_3OS$, 719.20) | 346 | m/z = 693.82($C_{48}H_{27}N_3OS$, 693.18) |
| 347 | m/z = 703.80($C_{50}H_{29}N_3O_2$, 703.22) | 348 | m/z = 703.80($C_{50}H_{29}N_3O_2$, 703.22) |
| 349 | m/z = 664.76($C_{47}H_{28}N_4O$, 664.22) | 350 | m/z = 664.76($C_{47}H_{28}N_4O$, 664.22) |
| 351 | m/z = 614.70($C_{43}H_{26}N_4O$, 614.21) | 352 | m/z = 690.80($C_{49}H_{30}N_4O$, 690.24) |
| 353 | m/z = 690.80($C_{49}H_{30}N_4O$, 690.24) | 354 | m/z = 614.70($C_{43}H_{26}N_4O$, 614.21) |
| 355 | m/z = 614.70($C_{43}H_{26}N_4O$, 614.21) | 356 | m/z = 714.82($C_{51}H_{30}N_4O$, 714.24) |
| 357 | m/z = 664.76($C_{47}H_{28}N_4O$, 664.22) | 358 | m/z = 664.76($C_{47}H_{28}N_4O$, 664.22) |
| 359 | m/z = 664.76($C_{47}H_{28}N_4O$, 664.22) | 360 | m/z = 764.88($C_{55}H_{32}N_4O$, 764.25) |
| 361 | m/z = 714.82($C_{51}H_{30}N_4O$, 714.24) | 362 | m/z = 714.82($C_{51}H_{30}N_4O$, 714.24) |
| 363 | m/z = 714.82($C_{51}H_{30}N_4O$, 714.24) | 364 | m/z = 740.86($C_{53}H_{32}N_4O$, 740.25) |
| 365 | m/z = 790.92($C_{57}H_{34}N_4O$, 790.27) | 366 | m/z = 690.80($C_{49}H_{30}N_4O$, 690.24) |
| 367 | m/z = 690.80($C_{49}H_{30}N_4O$, 690.24) | 368 | m/z = 740.86($C_{53}H_{32}N_4O$, 740.25) |
| 369 | m/z = 693.82($C_{48}H_{27}N_3OS$, 693.18) | 370 | m/z = 643.76($C_{44}H_{25}N_3OS$, 643.17) |
| 371 | m/z = 643.76($C_{44}H_{25}N_3OS$, 643.17) | 372 | m/z = 693.82($C_{48}H_{27}N_3OS$, 693.18) |
| 373 | m/z = 769.92($C_{54}H_{31}N_3OS$, 769.21) | 374 | m/z = 719.86($C_{50}H_{29}N_3OS$, 719.20) |
| 375 | m/z = 643.76($C_{44}H_{25}N_3OS$, 643.17) | 376 | m/z = 719.86($C_{50}H_{29}N_3OS$, 719.20) |
| 377 | m/z = 688.79($C_{49}H_{28}N_4O$, 688.23) | 378 | m/z = 664.77($C_{47}H_{28}N_4O$, 664.23) |
| 379 | m/z = 769.92($C_{54}H_{31}N_3OS$, 769.22) | 380 | m/z = 769.92($C_{54}H_{31}N_3OS$, 769.22) |

1) Manufacture of Organic Light Emitting Device

<Experimental Example 1>—Manufacture of Organic Light Emitting Device

1) Manufacture of Organic Light Emitting Device (Red Single Host)

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treated for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris [2-naphthyl (phenyl) amino] triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 500 Å using the compound described in the following Table 9 as a red host and (piq)$_2$(Ir) (acac) as a red phosphorescent dopant by 3% doping (piq)$_2$(Ir) (acac) to the host. After that, BCP was deposited to 60 Å as a hole blocking layer, and Alq$_3$ was deposited to 200 Å thereon as an electron transfer layer. After that, BCP was deposited to 60 Å as a hole blocking layer, and Alq$_3$ was deposited to 200 Å thereon as, an electron transfer layer. Lastly, an electron injection layer was formed on the electron transfer layer by depositing lithium fluoride (LiF) to a thickness of 10 Å, and an aluminum (Al) cathode was deposited to a thickness of 1,200 Å on the electron injection layer, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

For the organic electroluminescent device manufactured as above, electroluminescent (EL) properties were measured using M7000 manufactured by McScience Inc., and with the measurement results, T90 was measured when standard luminance was 6,000 cd/m$^2$ using a lifetime measurement system (M6000) manufactured by McScience Inc. Properties of the organic electro luminescent device of the present disclosure are as shown in the following Table 9.

TABLE 9

| | Compound | Driving Voltage (V) | Efficiency (cd/A) | Color Coordinate (x, y) | Lifetime ($T_{90}$) |
|---|---|---|---|---|---|
| Comparative Example 1 | Comparative Compound A | 5.74 | 14.2 | 0.691, 0.309 | 42 |
| Comparative Example 2 | Comparative Compound B | 5.22 | 13.1 | 0.688, 0.312 | 63 |
| Comparative Example 3 | Comparative Compound C | 5.52 | 13.7 | 0.689, 0.310 | 57 |
| Comparative Example 4 | Comparative Compound D | 5.62 | 14.5 | 0.691, 0.309 | 73 |
| Comparative Example 5 | Comparative Compound E | 5.82 | 12.5 | 0.689, 0.310 | 64 |

TABLE 9-continued

| Compound | | Driving Voltage (V) | Efficiency (cd/A) | Color Coordinate (x, y) | Lifetime ($T_{90}$) |
|---|---|---|---|---|---|
| Comparative Example 6 | Comparative Compound F | 5.78 | 14.2 | 0.672, 0.327 | 48 |
| Comparative Example 7 | Comparative Compound G | 5.32 | 14.9 | 0.684, 0.315 | 73 |
| Comparative Example 8 | Comparative Compound H | 5.02 | 13.1 | 0.678, 0.321 | 63 |
| Comparative Example 9 | Comparative Compound I | 4.99 | 11.0 | 0.676, 0.324 | 75 |
| Comparative Example 10 | Comparative Compound J | 5.19 | 12.7 | 0.680, 0.319 | 79 |
| Example 1 | Compound 1 | 4.26 | 24.2 | 0.676, 0.324 | 99 |
| Example 2 | Compound 4 | 4.09 | 18.7 | 0.678, 0.322 | 112 |
| Example 3 | Compound 10 | 4.18 | 25.7 | 0.691, 0.309 | 111 |
| Example 4 | Compound 11 | 4.27 | 22.0 | 0.681, 0.319 | 100 |
| Example 5 | Compound 21 | 4.20 | 25.2 | 0.678, 0.321 | 101 |
| Example 6 | Compound 25 | 4.10 | 21.0 | 0.678, 0.321 | 127 |
| Example 7 | Compound 26 | 3.97 | 22.7 | 0.679, 0.321 | 111 |
| Example 8 | Compound 28 | 4.06 | 20.2 | 0.685, 0.314 | 118 |
| Example 9 | Compound 29 | 4.05 | 17.2 | 0.674, 0.325 | 101 |
| Example 10 | Compound 36 | 4.10 | 21.6 | 0.689, 0.310 | 109 |
| Example 11 | Compound 37 | 4.10 | 21.0 | 0.689, 0.310 | 103 |
| Example 12 | Compound 44 | 3.94 | 23.8 | 0.689, 0.310 | 89 |
| Example 13 | Compound 46 | 4.19 | 18.4 | 0.676, 0.324 | 120 |
| Example 14 | Compound 49 | 3.96 | 18.9 | 0.684, 0.315 | 129 |
| Example 15 | Compound 68 | 4.12 | 21.2 | 0.685, 0.314 | 122 |
| Example 16 | Compound 74 | 3.91 | 24.0 | 0.688, 0.312 | 86 |
| Example 17 | Compound 76 | 3.89 | 17.1 | 0.691, 0.309 | 98 |
| Example 18 | Compound 80 | 3.92 | 22.0 | 0.687, 0.313 | 96 |
| Example 19 | Compound 81 | 3.97 | 23.5 | 0.682, 0.317 | 108 |
| Example 20 | Compound 89 | 4.10 | 21.0 | 0.684, 0.316 | 94 |
| Example 21 | Compound 95 | 3.93 | 20.7 | 0.681, 0.319 | 129 |
| Example 22 | Compound 97 | 4.09 | 20.9 | 0.687, 0.313 | 89 |
| Example 23 | Compound 101 | 4.18 | 19.8 | 0.681, 0.319 | 121 |
| Example 24 | Compound 105 | 3.99 | 20.7 | 0.682, 0.318 | 109 |
| Example 25 | Compound 114 | 3.80 | 22.9 | 0.684, 0.316 | 102 |
| Example 26 | Compound 119 | 4.02 | 19.9 | 0.682, 0.317 | 125 |
| Example 27 | Compound 125 | 4.04 | 20.7 | 0.678, 0.322 | 132 |
| Example 28 | Compound 130 | 3.97 | 19.4 | 0.682, 0.317 | 128 |
| Example 29 | Compound 136 | 4.00 | 17.6 | 0.682, 0.317 | 127 |
| Example 30 | Compound 140 | 4.01 | 19.6 | 0.679, 0.321 | 128 |
| Example 31 | Compound 142 | 4.22 | 20.9 | 0.680, 0.319 | 118 |
| Example 32 | Compound 147 | 3.95 | 18.9 | 0.680, 0.319 | 132 |
| Example 33 | Compound 156 | 4.11 | 19.9 | 0.685, 0.314 | 127 |
| Example 34 | Compound 160 | 3.89 | 20.9 | 0.683, 0.317 | 127 |
| Example 35 | Compound 161 | 3.96 | 22.9 | 0.672, 0.327 | 111 |
| Example 36 | Compound 169 | 3.90 | 19.9 | 0.685, 0.314 | 134 |
| Example 37 | Compound 175 | 3.97 | 20.8 | 0.682, 0.317 | 129 |
| Example 38 | Compound 179 | 4.44 | 22.5 | 0.678, 0.321 | 98 |
| Example 39 | Compound 185 | 4.01 | 19.8 | 0.678, 0.321 | 109 |
| Example 40 | Compound 195 | 3.88 | 20.5 | 0.682, 0.317 | 114 |
| Example 41 | Compound 200 | 4.23 | 19.9 | 0.689, 0.310 | 105 |
| Example 42 | Compound 201 | 3.93 | 20.4 | 0.687, 0.313 | 97 |
| Example 43 | Compound 204 | 3.99 | 19.9 | 0.680, 0.319 | 98 |
| Example 44 | Compound 210 | 4.02 | 20.9 | 0.687, 0.313 | 119 |
| Example 45 | Compound 221 | 4.16 | 19.9 | 0.688, 0.312 | 129 |
| Example 46 | Compound 232 | 4.12 | 21.7 | 0.676, 0.324 | 123 |
| Example 47 | Compound 236 | 4.25 | 22.9 | 0.678, 0.321 | 119 |
| Example 48 | Compound 238 | 4.19 | 20.6 | 0.683, 0.317 | 103 |
| Example 49 | Compound 240 | 3.99 | 21.6 | 0.674, 0.325 | 103 |
| Example 50 | Compound 252 | 4.37 | 21.8 | 0.672, 0.327 | 100 |
| Example 51 | Compound 253 | 3.99 | 22.5 | 0.681, 0.319 | 112 |
| Example 52 | Compound 259 | 3.93 | 21.2 | 0.684, 0.315 | 98 |
| Example 53 | Compound 271 | 4.12 | 21.7 | 0.691, 0.309 | 97 |
| Example 54 | Compound 277 | 4.18 | 21.9 | 0.689, 0.310 | 87 |
| Example 55 | Compound 280 | 3.90 | 20.2 | 0.685, 0.314 | 117 |
| Example 56 | Compound 288 | 4.14 | 21.3 | 0.691, 0.309 | 102 |
| Example 57 | Compound 289 | 4.11 | 20.3 | 0.680, 0.319 | 131 |
| Example 58 | Compound 297 | 4.13 | 21.7 | 0.674, 0.325 | 111 |
| Example 59 | Compound 307 | 4.11 | 22.9 | 0.687, 0.313 | 109 |
| Example 60 | Compound 318 | 4.08 | 19.2 | 0.684, 0.316 | 112 |
| Example 61 | Compound 320 | 3.99 | 22.9 | 0.688, 0.312 | 128 |
| Example 62 | Compound 324 | 4.16 | 22.7 | 0.674, 0.325 | 106 |
| Example 63 | Compound 325 | 4.00 | 21.9 | 0.684, 0.316 | 111 |
| Example 64 | Compound 330 | 4.02 | 19.9 | 0.678, 0.322 | 113 |
| Example 65 | Compound 333 | 4.00 | 21.6 | 0.688, 0.312 | 98 |
| Example 66 | Compound 340 | 4.12 | 21.0 | 0.679, 0.321 | 122 |
| Example 67 | Compound 342 | 4.19 | 20.8 | 0.691, 0.309 | 123 |
| Example 68 | Compound 345 | 4.21 | 20.9 | 0.674, 0.325 | 114 |
| Example 69 | Compound 349 | 3.95 | 18.9 | 0.682, 0.318 | 131 |
| Example 70 | Compound 354 | 4.38 | 20.9 | 0.676, 0.324 | 96 |
| Example 71 | Compound 355 | 4.32 | 21.9 | 0.689, 0.310 | 98 |
| Example 72 | Compound 359 | 4.58 | 22.0 | 0.679, 0.321 | 121 |
| Example 73 | Compound 364 | 4.12 | 20.2 | 0.672, 0.327 | 114 |
| Example 74 | Compound 367 | 4.34 | 18.6 | 0.685, 0.314 | 94 |
| Example 75 | Compound 373 | 4.49 | 21.9 | 0.684, 0.315 | 101 |
| Example 76 | Compound 374 | 3.97 | 19.9 | 0.680, 0.319 | 88 |
| Example 77 | Compound 376 | 4.33 | 20.2 | 0.680, 0.319 | 99 |

Comparative Compound A

Comparative Compound B

Comparative Compound C

TABLE 9-continued

| Compound | Driving Voltage (V) | Efficiency (cd/A) | Color Coordinate (x, y) | Life-time ($T_{90}$) |
|---|---|---|---|---|
| Comparative Compound D | | | | |

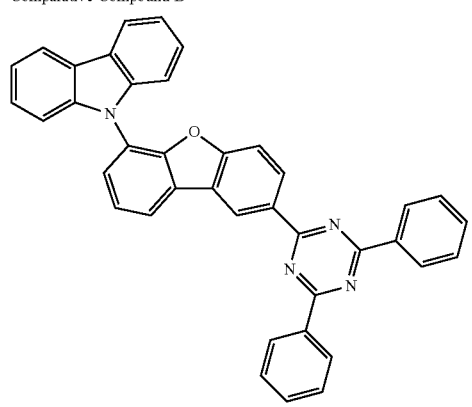

Comparative Compound E

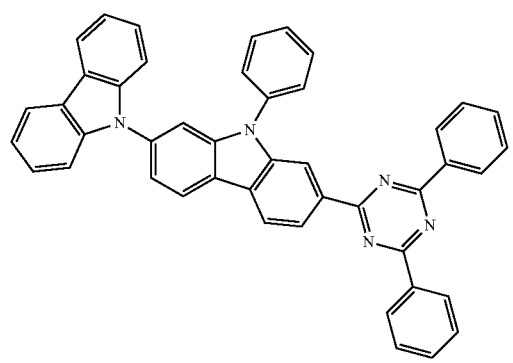 [SMILES: c1ccc(-c2nc(-c3ccccc3)nc(-c3ccc4c5ccc(-n6c7ccccc7c7ccccc76)cc5n(-c5ccccc5)c4c3)n2)cc1]

Comparative Compound F

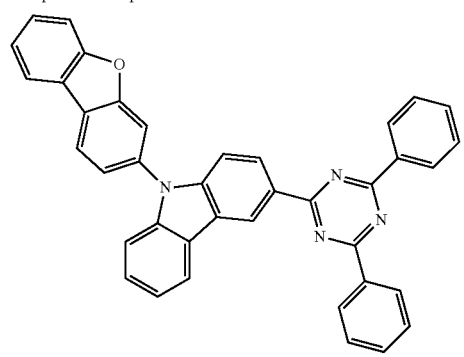

Comparative Compound G

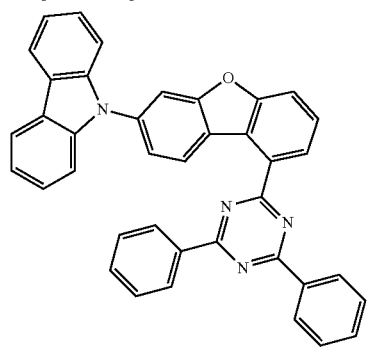

Comparative Compound H

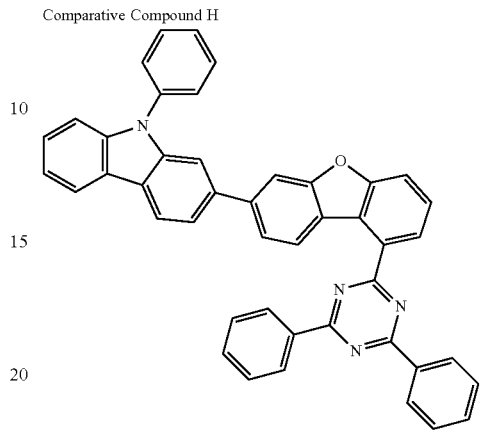

Comparative Compound I

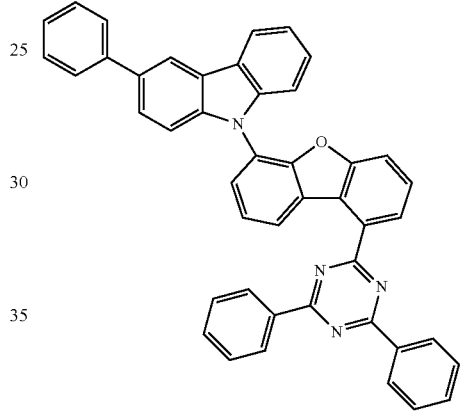

Comparative Compound J

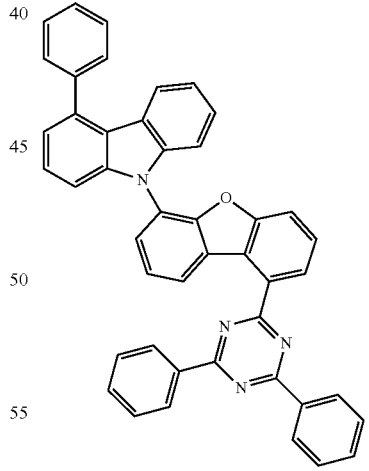

<Experimental Example 2>—Manufacture of Organic Light Emitting Device (Red N+N Mixed Host)

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris [2-naphthyl (phenyl) amino] triphenylamine) and a hole transfer layer NPB (N,N'-di (1-naphthyl)-N,N'-diphenyl-(1,1'-biphenyl)-4,4'-diamine), which are common layers, were formed.

A light emitting layer was thermal vacuum deposited thereon as follows. As the light emitting layer, two types of the compound described in Chemical Formula 1 were pre-mixed as described in the following Table 10 and deposited to 400 Å in one supply source as a red host, and $(piq)_2(Ir)$ (acac) was 3% doped and deposited as a red phosphorescent dopant. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

For the organic electroluminescent devices manufactured as above, electroluminescent (EL) properties were measured using M7000 manufactured by McScience Inc., and with the measurement results, $T_{90}$ was measured when standard luminance was 6,000 $cd/m^2$ using a lifetime measurement system (M6000) manufactured by McScience Inc.

<Experimental Example 3>—Manufacture of Organic Light Emitting Device (Red N+P Mixed Host)

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl (phenyl) amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As the light emitting layer, one type of the compound described in Chemical Formula 1 and one type of the compound described in Chemical Formula 14 were pre-mixed as described in the following Table 11 and deposited to 400 Å in one supply source as a red host, and $(piq)_2(Ir)$ (acac) was 3% doped and deposited as a red phosphorescent dopant. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

TABLE 10

| | Light Emitting Layer Compound | Ratio (N:N) | Driving Voltage (V) | Efficiency (cd/A) | Color Coordinate (x, y) | Lifetime ($T_{90}$) |
|---|---|---|---|---|---|---|
| Example 1 | Compound 1:Compound 105 | 1:1 | 4.12 | 24.5 | 0.685, 0.314 | 373 |
| Example 2 | Compound 46:Compound 114 | 1:1 | 4.28 | 24.9 | 0.680, 0.319 | 369 |
| Example 3 | Compound 136:Compound 232 | 1:1 | 4.03 | 25.5 | 0.674, 0.325 | 348 |
| Example 4 | Compound 89:Compound 169 | 1:1 | 4.29 | 24.9 | 0.685, 0.314 | 396 |
| Example 5 | Compound 236:Compound 238 | 1:1 | 4.38 | 26.8 | 0.681, 0.319 | 408 |
| Example 6 | Compound 277:Compound 288 | 1:1 | 4.18 | 24.6 | 0.691, 0.309 | 389 |
| Example 7 | Compound 119:Compound 201 | 1:1 | 4.32 | 27.9 | 0.678, 0.321 | 377 |
| Example 8 | Compound 36:Compound 333 | 1:1 | 4.26 | 24.2 | 0.681, 0.319 | 414 |
| Example 9 | Compound 297:Compound 354 | 1:1 | 4.49 | 26.8 | 0.682, 0.317 | 399 |
| Example 10 | Compound 324:Compound 374 | 1:1 | 4.10 | 27.0 | 0.691, 0.309 | 326 |

Meanwhile, all the organic compounds required to manufacture the OLED were vacuum sublimation purified under $10^{-6}$ torr to $10^{-8}$ torr for each material to be used in the OLED manufacture.

For the organic electroluminescent devices manufactured as above, electroluminescent (EL) properties were measured using M7000 manufactured by McScience Inc., and with the measurement results, $T_{90}$ was measured when standard luminance was 6,000 cd/m² using a lifetime measurement system (M6000)

TABLE 11

| | Light Emitting Layer Compound | Ratio (N:P) | Driving Voltage (V) | Efficiency (cd/A) | Color Coordinate (x, y) | Lifetime ($T_{90}$) |
|---|---|---|---|---|---|---|
| Example 1 | Compound 29:P-Host A | 3:1 | 4.15 | 27.9 | 0.672, 0.327 | 394 |
| Example 2 | | 2:1 | 4.20 | 25.0 | 0.691, 0.309 | 366 |
| Example 3 | | 1:1 | 4.25 | 23.6 | 0.674, 0.325 | 348 |
| Example 4 | | 1:2 | 4.43 | 22.7 | 0.679, 0.321 | 346 |
| Example 5 | | 1:3 | 4.70 | 20.2 | 0.678, 0.322 | 340 |
| Example 6 | Compound 46:P-Host B | 3:1 | 4.17 | 28.4 | 0.674, 0.325 | 426 |
| Example 7 | | 2:1 | 4.18 | 28.2 | 0.687, 0.313 | 419 |
| Example 8 | | 1:1 | 4.22 | 24.2 | 0.681, 0.319 | 371 |
| Example 9 | | 1:2 | 4.45 | 22.4 | 0.680, 0.319 | 354 |
| Example 10 | | 1:3 | 4.86 | 22.1 | 0.682, 0.317 | 324 |
| Example 11 | Compound 81:P-Host C | 3:1 | 4.20 | 26.5 | 0.682, 0.317 | 402 |
| Example 12 | Compound 125:P-Host D | 3:1 | 4.23 | 27.2 | 0.682, 0.317 | 388 |
| Example 13 | Compound 140:P-Host E | 3:1 | 4.11 | 28.8 | 0.678, 0.322 | 390 |
| Example 14 | Compound 156:P-Host F | 3:1 | 4.23 | 27.4 | 0.679, 0.321 | 376 |
| Example 15 | Compound 179:P-Host G | 3:1 | 4.19 | 27.8 | 0.678, 0.321 | 398 |
| Example 16 | Compound 195:P-Host H | 3:1 | 4.22 | 28.9 | 0.680, 0.319 | 418 |
| Example 17 | Compound 210:P-Host I | 3:1 | 4.23 | 27.5 | 0.679, 0.321 | 356 |
| Example 18 | Compound 259:P-Host A | 3:1 | 4.21 | 29.9 | 0.681, 0.319 | 376 |
| Example 19 | Compound 307:P-Host B | 3:1 | 4.28 | 26.2 | 0.685, 0.314 | 384 |
| Example 20 | Compound 320:P-Host C | 3:1 | 4.24 | 26.9 | 0.676, 0.324 | 396 |
| Example 21 | Compound 340:P-Host D | 3:1 | 4.18 | 27.3 | 0.678, 0.322 | 374 |
| Example 22 | Compound 345:P-Host E | 3:1 | 4.20 | 28.8 | 0.680, 0.319 | 390 |
| Example 23 | Compound 349:P-Host F | 3:1 | 4.29 | 28.6 | 0.682, 0.317 | 382 |
| Example 24 | Compound 355:P-Host G | 3:1 | 4.10 | 27.2 | 0.678, 0.322 | 396 |
| Example 25 | Compound 367:P-Host H | 3:1 | 4.29 | 29.9 | 0.688, 0.312 | 382 |
| Example 26 | Compound 376:P-Host I | 3:1 | 4.15 | 26.4 | 0.680, 0.319 | 379 |

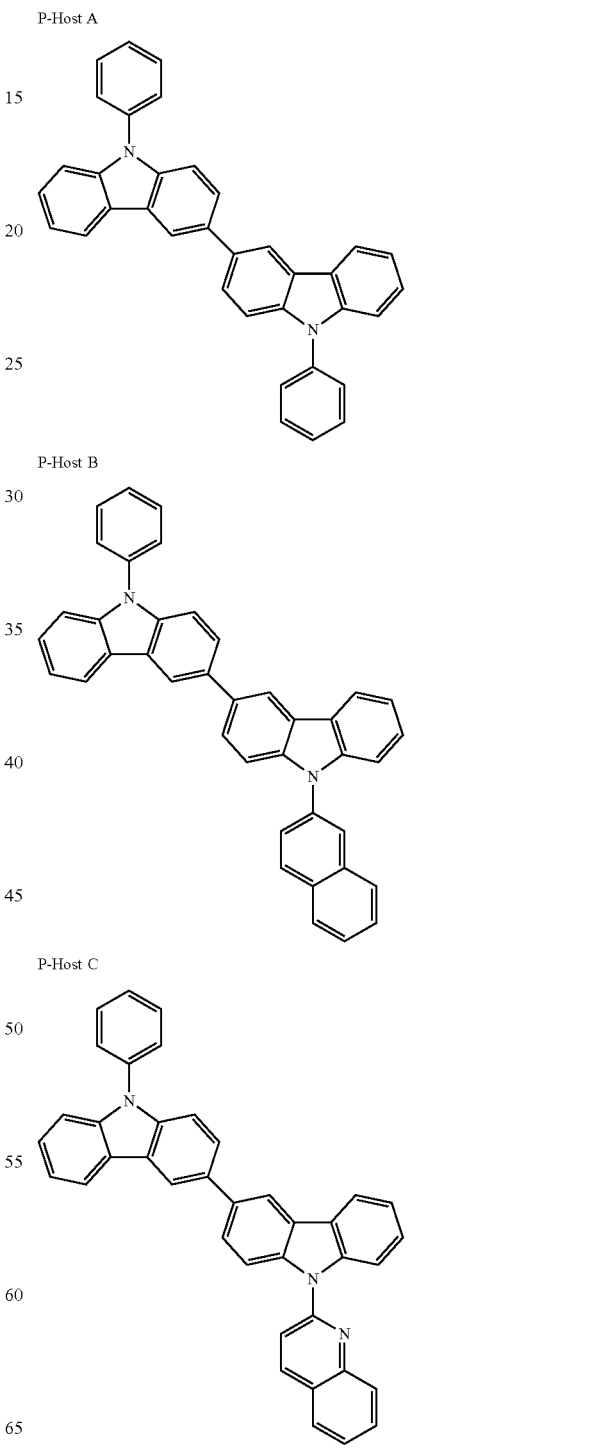

P-Host A

P-Host B

P-Host C

TABLE 11-continued

| Light Emitting Layer Compound | Ratio (N:P) | Driving Voltage (V) | Efficiency (cd/A) | Color Coordinate (x, y) | Lifetime ($T_{90}$) |
|---|---|---|---|---|---|

P-Host D

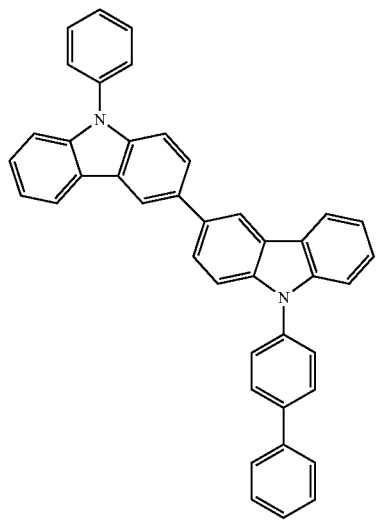 [SMILES: c1ccc(-c2ccc(-n3c4ccccc4c4cc(-c5ccc6c(c5)c5ccccc5n6-c5ccccc5)ccc43)cc2)cc1]

P-Host E

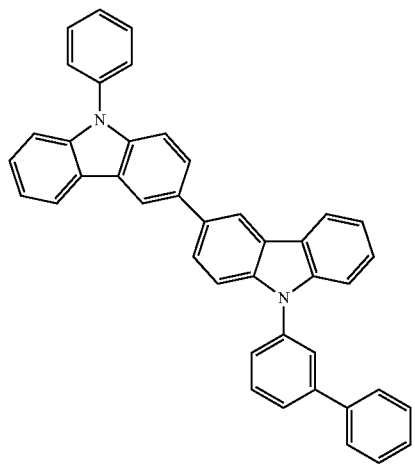 [SMILES: c1ccc(-c2cccc(-n3c4ccccc4c4cc(-c5ccc6c(c5)c5ccccc5n6-c5ccccc5)ccc43)c2)cc1]

P-Host F

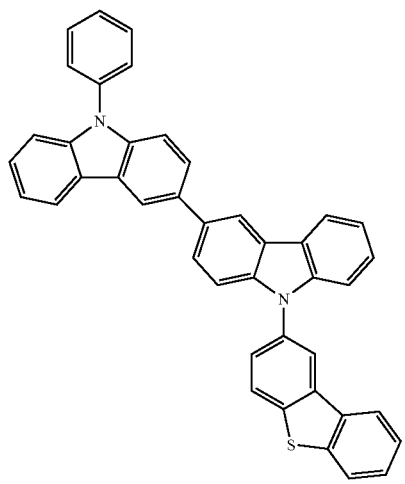 [SMILES: c1ccc(-n2c3ccccc3c3cc(-c4ccc5c(c4)c4ccccc4n5-c4ccc5oc6ccccc6c5c4)ccc32)cc1]

TABLE 11-continued

| Light Emitting Layer Compound | Ratio (N:P) | Driving Voltage (V) | Efficiency (cd/A) | Color Coordinate (x, y) | Lifetime ($T_{90}$) |
|---|---|---|---|---|---|

P-Host G

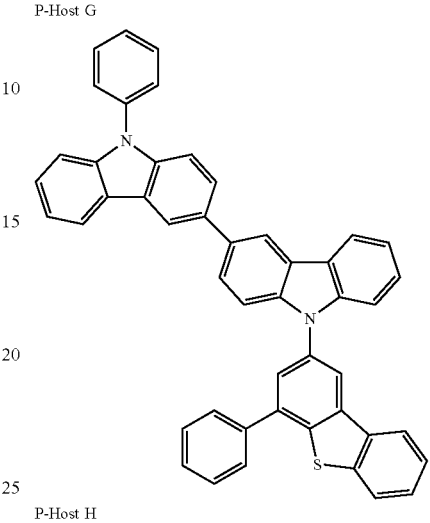

P-Host H

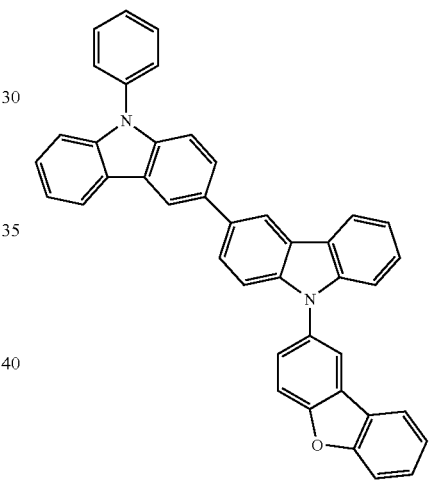

P-Host I

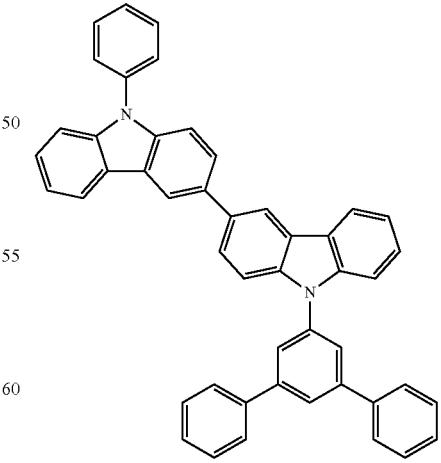

As shown in Table 9, it was identified that superior effects were obtained in terms of lifetime, efficiency and driving voltage properties when using the compound corresponding to Chemical Formula 1 in a light emitting layer of an organic light emitting device compared to when the compound was not used.

Particularly, in the compound of Chemical Formula 1, one side benzene ring in the dibenzofuran structure is substituted with an N-containing ring, and the other side benzene ring not substituted with the N-containing ring in the dibenzofuran structure is substituted with a carbazole structure, and as a result, it was identified that a structure of more stable electron stability was obtained, and a proper energy level and thermal stability were provided to the device, and an organic light emitting device having improved lifetime, driving stability and efficiency was manufactured using the compounds of Chemical Formula 1.

In addition, as identified in Table 10 and Table 11, more superior effects were obtained in efficiency and lifetime when comprising two types of the compound corresponding to Chemical Formula 1 of the present application (N+N Compound), or comprising two types of one type of the compound corresponding to Chemical Formula 1 of the present application and one type of the Compound corresponding to Chemical Formula 14 of the present application (N+P Compound) in the organic material layer of the organic light emitting device. Such results may lead to a forecast that an exciplex phenomenon occurred when comprising the two compounds at the same time.

Particularly, the exciplex phenomenon when comprising two types of one type of the compound corresponding to Chemical Formula 1 of the present application and one type of the Compound corresponding to Chemical Formula 14 of the present application (N+P Compound) in the organic material layer of the organic light emitting device is a phenomenon of releasing energy having sizes of a donor (p-host) HOMO level and an acceptor (n-host) LUMO level due to electron exchanges between the two molecules. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with enhancement in the lifetime.

The invention claimed is:

1. A heterocyclic compound represented by any one of the following Chemical Formulae 2 to 5, 10 and 11:

[Chemical Formula 2]

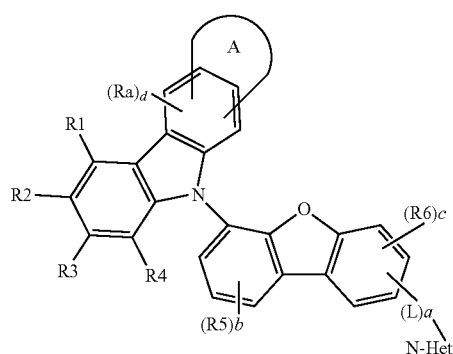

[Chemical Formula 3]

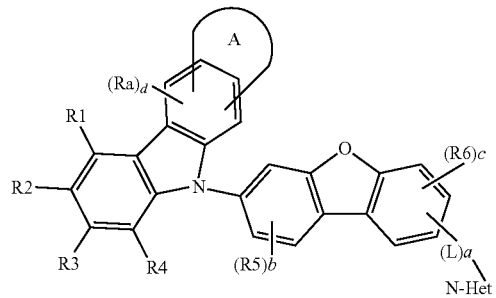

[Chemical Formula 4]

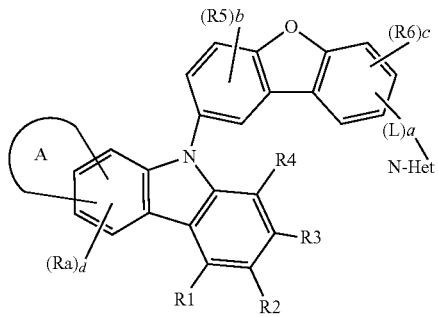

[Chemical Formula 5]

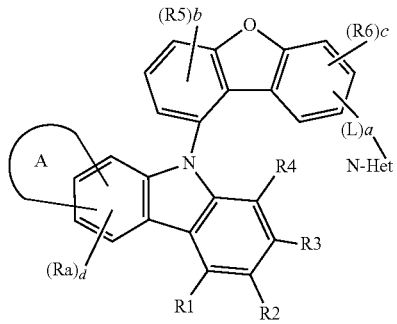

[Chemical Formula 10]

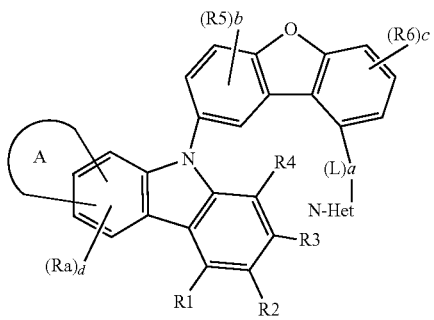

[Chemical Formula 11]

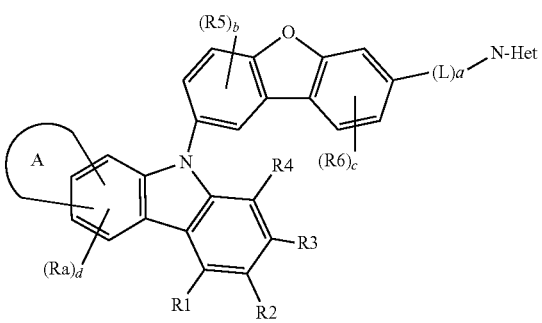

[Chemical Formula 10]

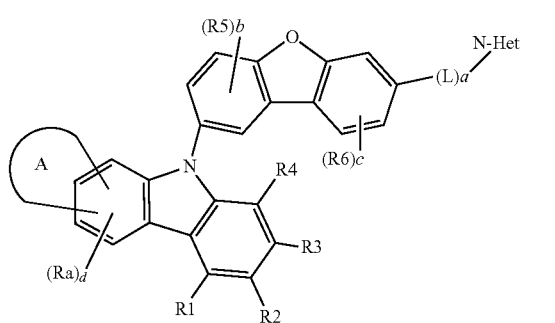

wherein, in Chemical Formulae 2 to 5, 10 and 11,

N-Het is a monocyclic or polycyclic heterocyclic group substituted or unsubstituted, and comprising one or more Ns;

L is a direct bond; a substituted or unsubstituted arylene group; or a substituted or unsubstituted heteroarylene group, a is an integer of 1 to 3, and when a is 2 or greater, Ls are the same as or different from each other;

A is a substituted or unsubstituted aryl ring; or a substituted or unsubstituted heteroaryl ring;

Ra is selected from the group consisting of hydrogen; a substituted or unsubstituted aryl group; and a substituted or unsubstituted heteroaryl group, or two or more groups adjacent to each other bond to each other to form a substituted or unsubstituted aliphatic or aromatic hydrocarbon ring or heteroring, d is an integer of 0 to 2, and when d is 2, two or more Ras are the same as or different from each other; and R5 and R6 are the same as or different from each other, and each independently selected from the group consisting of hydrogen and deuterium;

R1 to R4 are the same as or different from each other, and each independently selected from the group consisting of hydrogen: deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, b and c are each an integer of 1 to 3, and when b is 2 or greater, R5s are the same as or different from each other, and when c is 2 or greater, R6s are the same as or different from each other.

2. The heterocyclic compound of claim 1, wherein

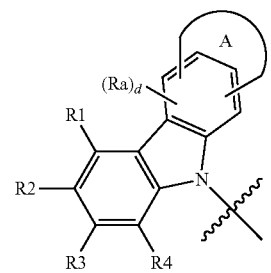

is represented by any one of the following Chemical Formulae 1-1 to 1-5:

[Chemical Formula 1-1]

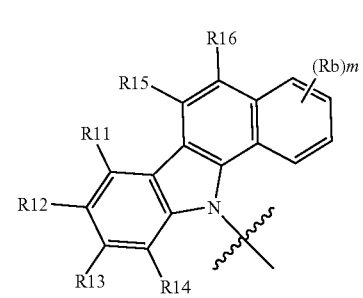

[Chemical Formula 1-2]

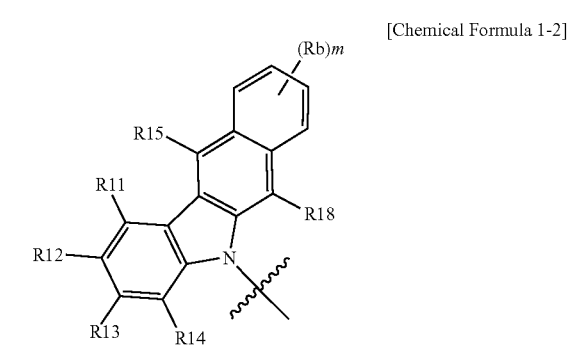

[Chemical Formula 1-3]

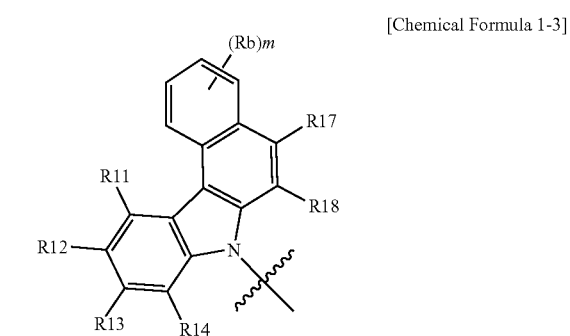

[Chemical Formula 1-4]

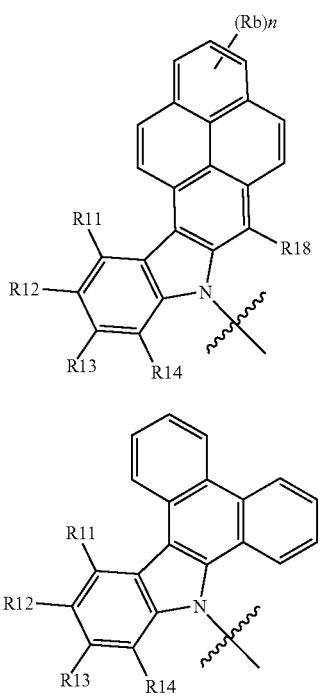

[Chemical Formula 1-5]

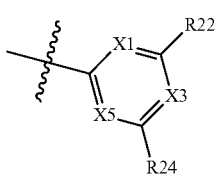

in Chemical Formulae 1-1 to 1-5,

R11 to R14 are the same as or different from each other, and each independently selected from the group consisting of hydrogen; a substituted or unsubstituted alkyl group; a substituted or unsubstituted aryl group; and a substituted or unsubstituted heteroaryl group, or two or more groups adjacent to each other bond to each other to form a substituted or unsubstituted aliphatic or aromatic hydrocarbon ring or heteroring;

R15 to R18 are the same as or different from each other, and each independently hydrogen; a substituted or unsubstituted alkyl group; a substituted or unsubstituted aryl group, or a substituted or unsubstituted heteroaryl group; and Rb is selected from the group consisting of hydrogen; and a substituted or unsubstituted aryl group, or two or more groups adjacent to each other bond to each other to form a substituted or unsubstituted aliphatic or aromatic hydrocarbon ring or heteroring, m is an integer of 1 to 4, n is an integer of 1 to 3, and when m and n are 2 or greater, Rbs are the same as or different from each other.

3. The heterocyclic compound of claim 1, wherein N-Het is represented by any one of the following Chemical Formulae 2-1 to 2-3:

[Chemical Formula 2-1]

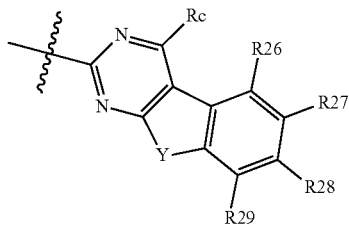

[Chemical Formula 2-2]

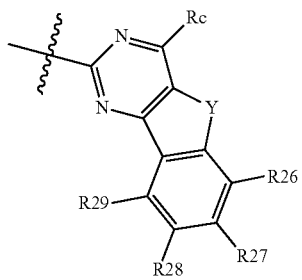

[Chemical Formula 2-3]

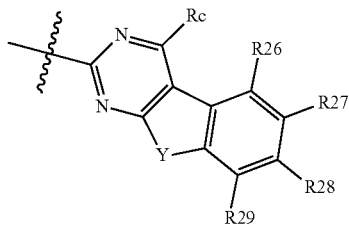

in Chemical Formulae 2-1 to 2-3,

X1 is N or CR21, X3 is N or CR23, and X5 is N or CR25;

at least one of X1 to X3 is N;

Y is O; or S;

Rc is hydrogen; or a substituted or unsubstituted aryl group; and

R21 to R29 are the same as or different from each other, and each independently hydrogen; a substituted or unsubstituted alkyl group; a substituted or unsubstituted aryl group; or a substituted or unsubstituted heteroaryl group.

4. The heterocyclic compound of claim 3, wherein Chemical Formula 2-1 is any one of the following structural formulae:

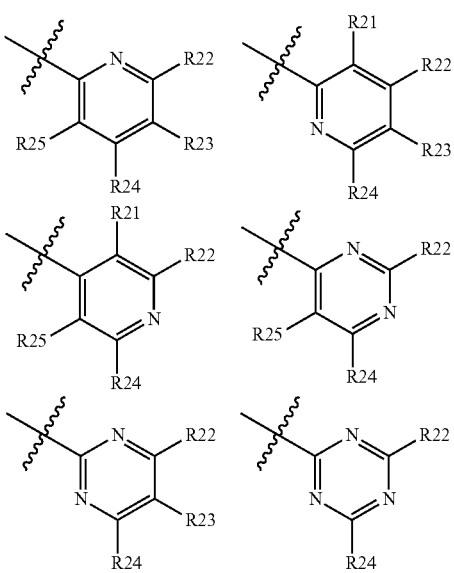

in the structural formulae,

R21 to R25 have the same definitions as in Chemical Formula 2-1.

5. The heterocyclic compound of claim 1, wherein any one of Chemical Formulae 2 to 5, 10 and 11 is represented by any one of the following compounds:
1
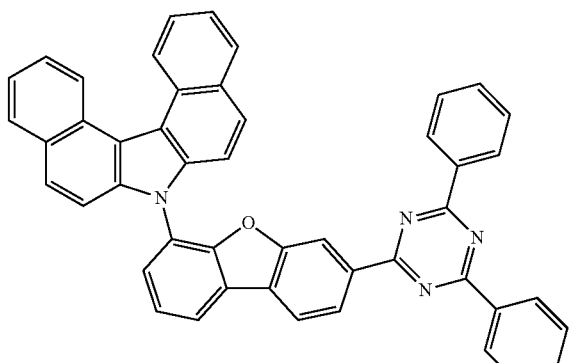
2
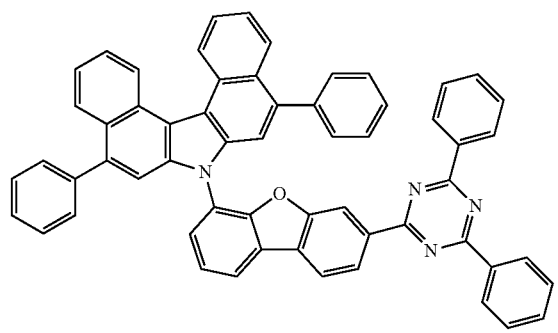
3
4
5
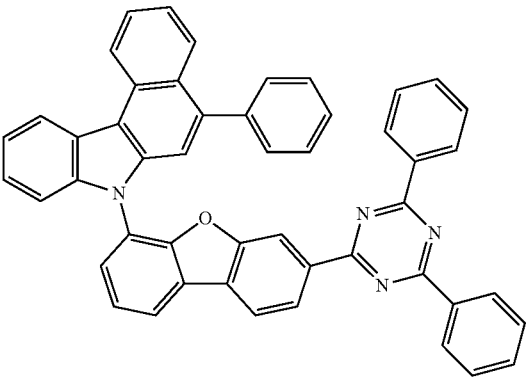
6
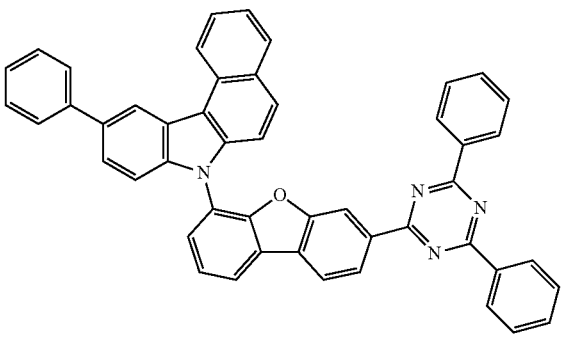
7
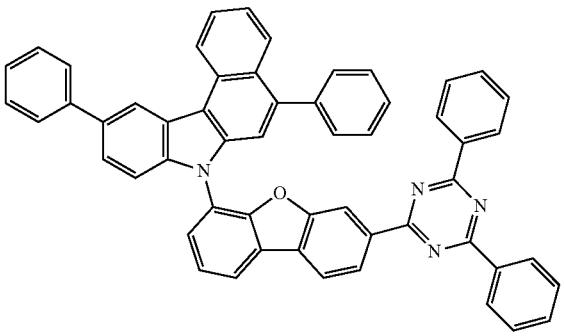
8
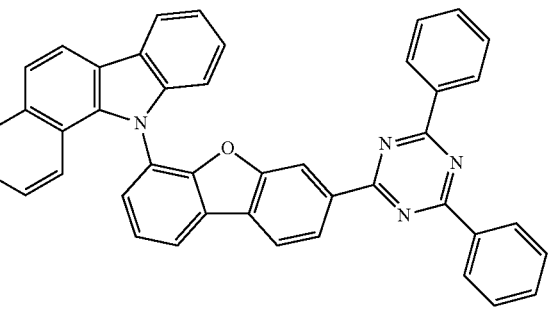

245
-continued
9
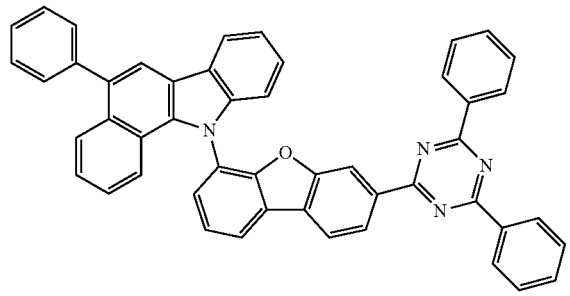
10
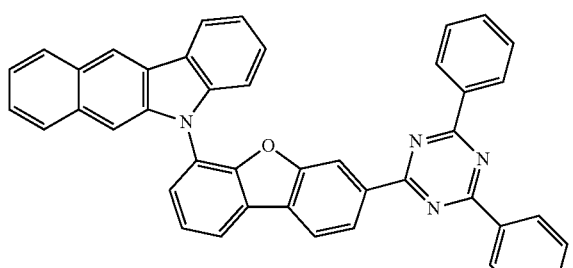
11
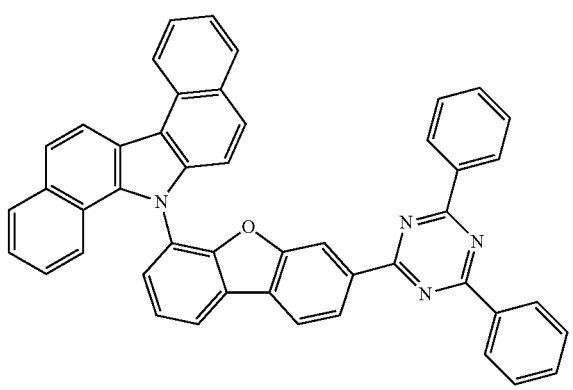
12
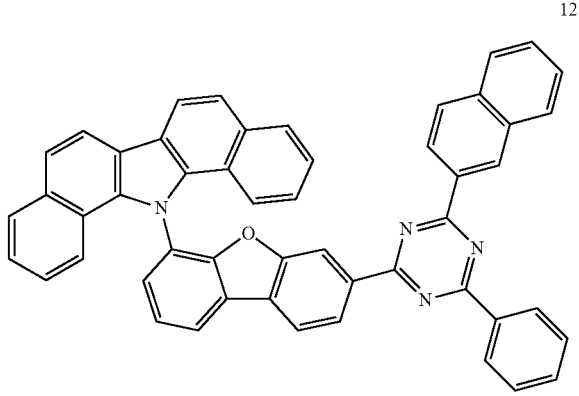
246
-continued
13
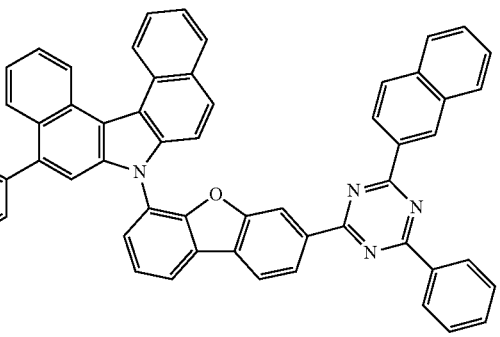
14
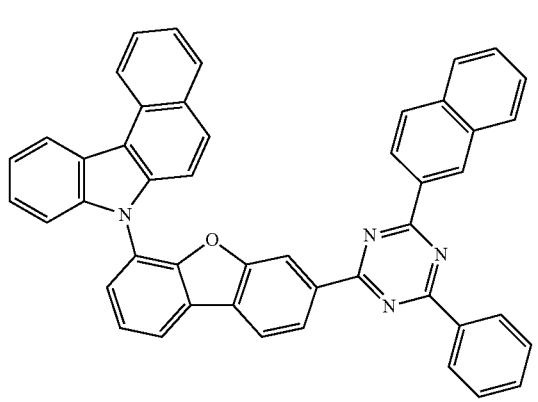
15
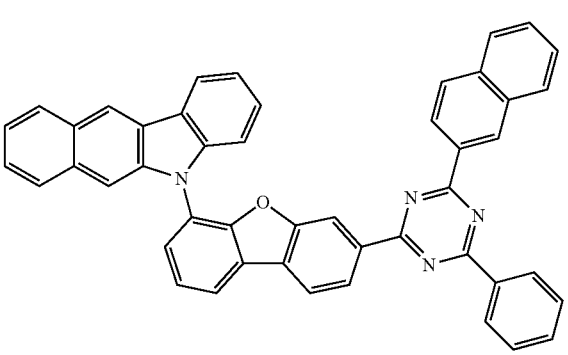
16
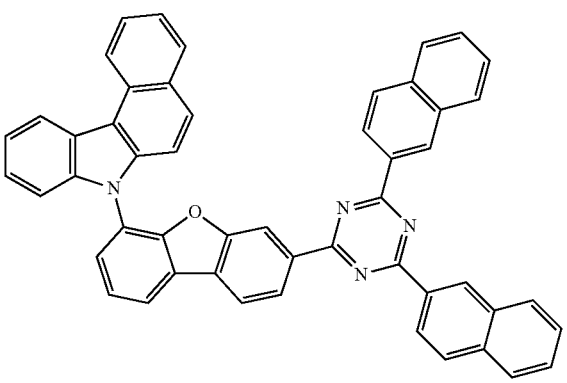

-continued
17
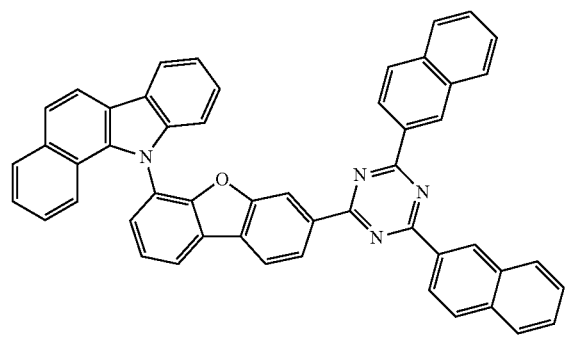
18
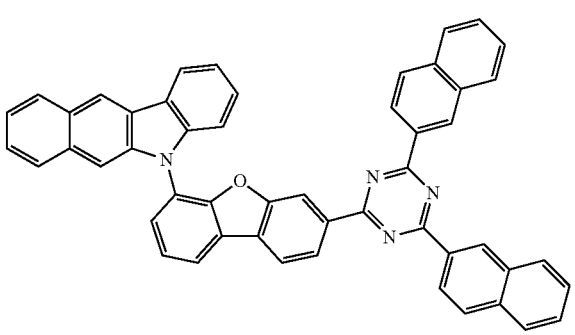
19
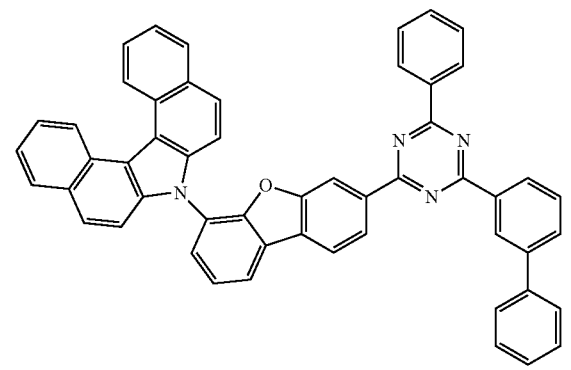
20
-continued
21
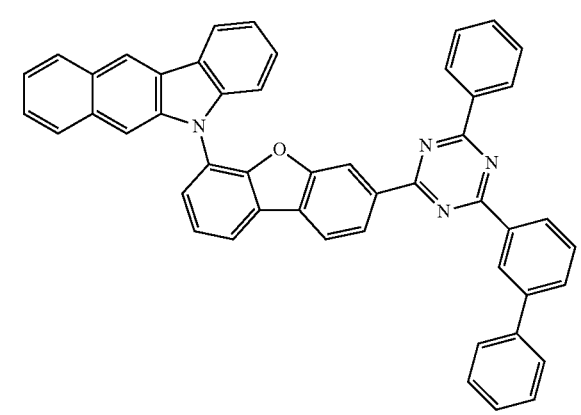
22
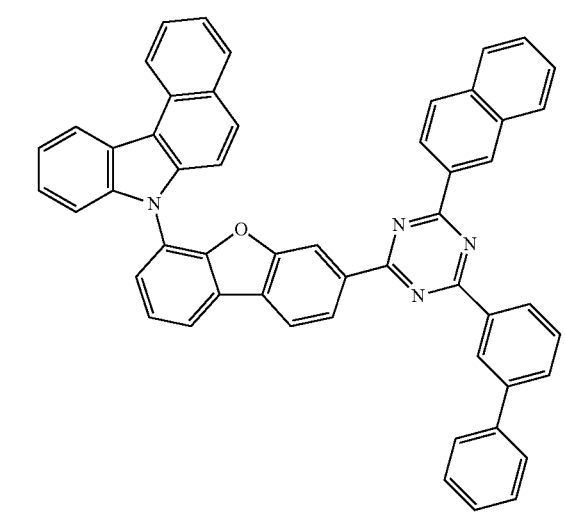
23
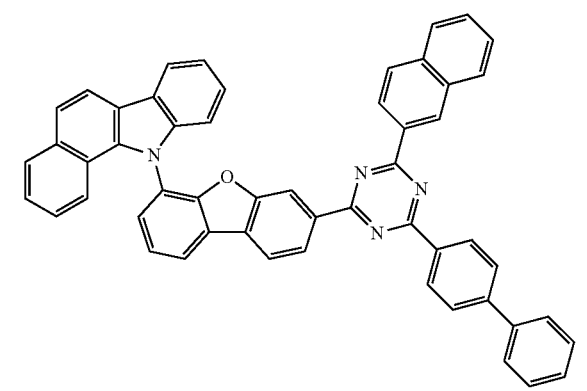

24
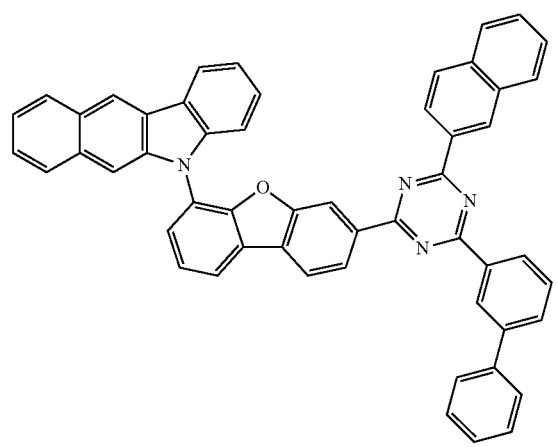
25
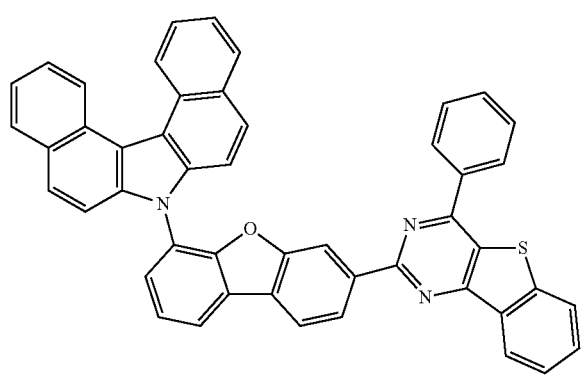
26
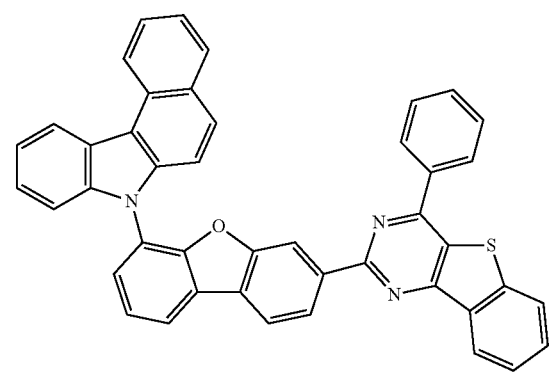
27
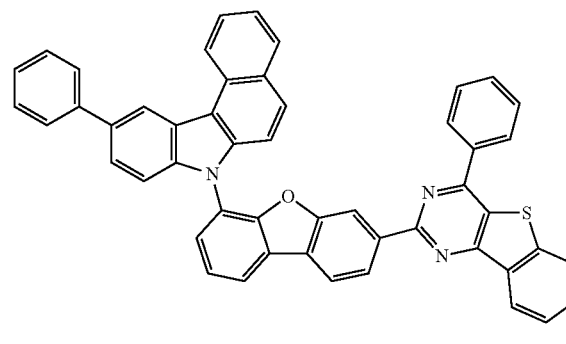
28
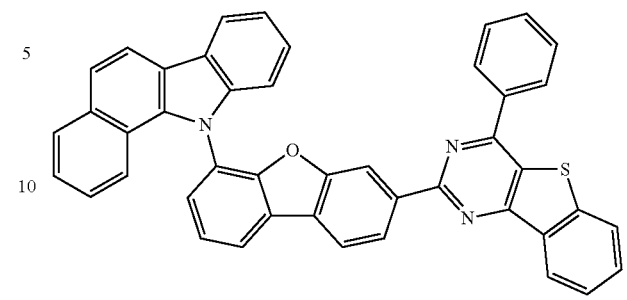
29
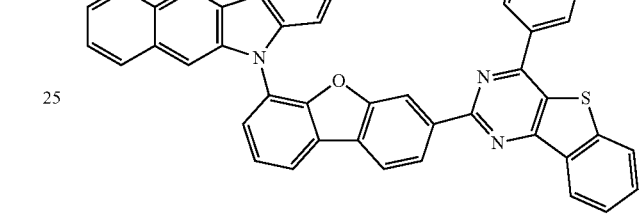
30
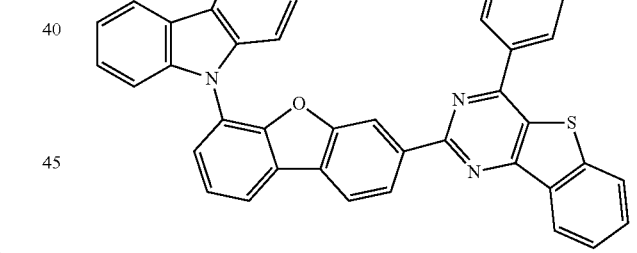
31
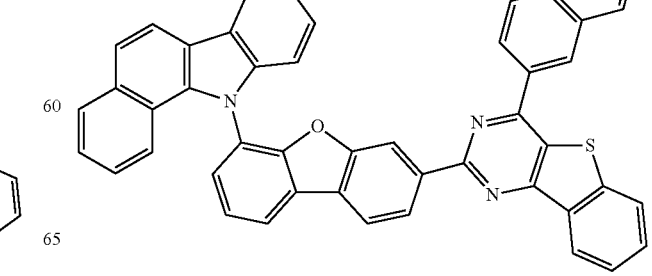

32
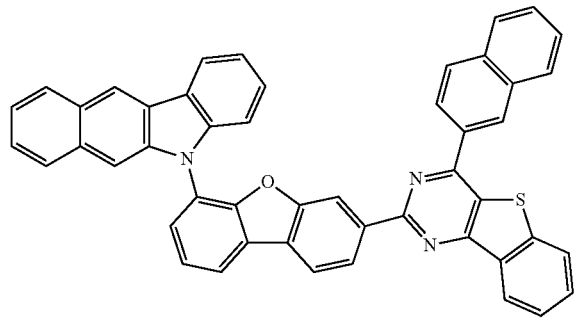
33
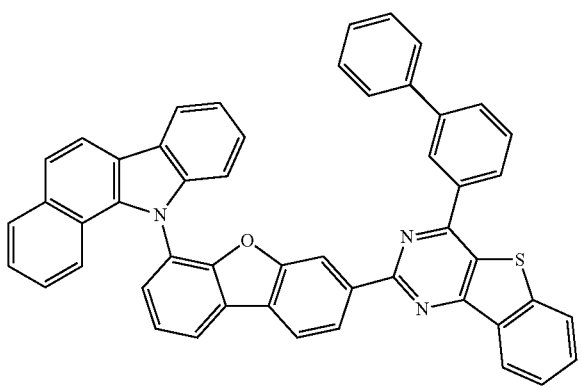
34
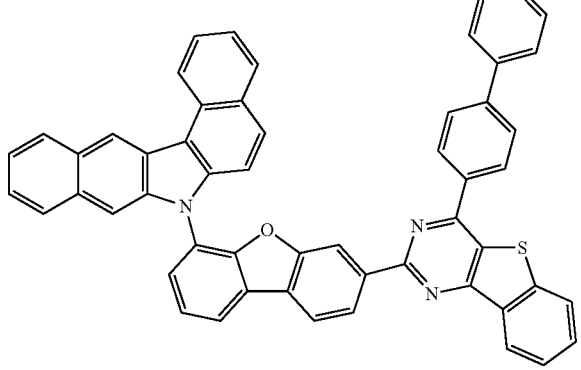
35
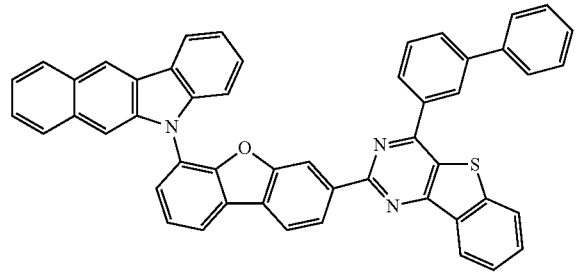
36
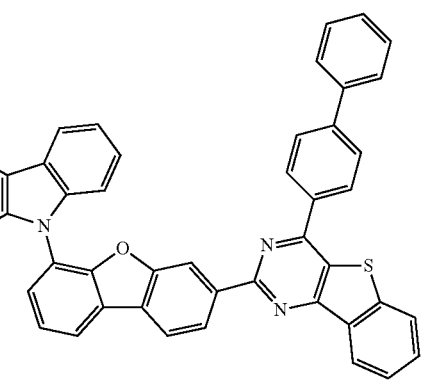
37
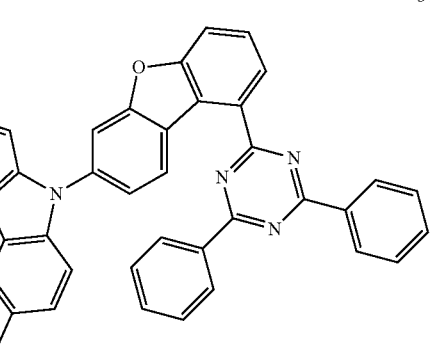
38
39
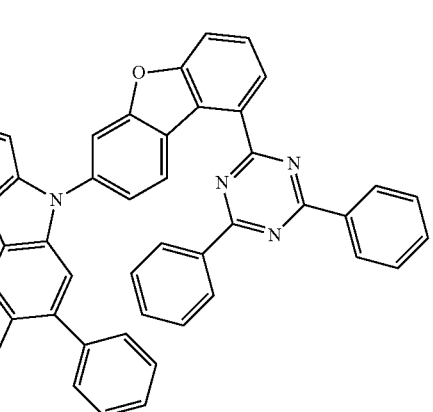

40
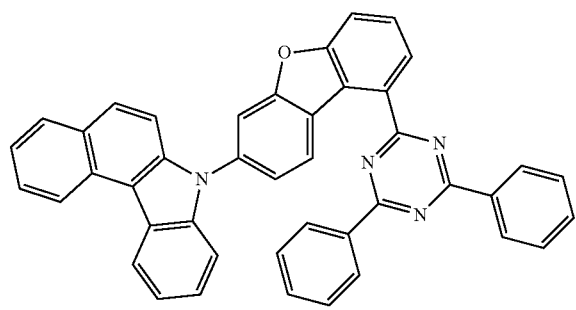
41
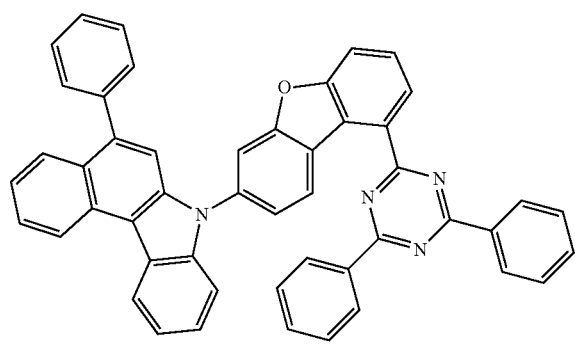
42
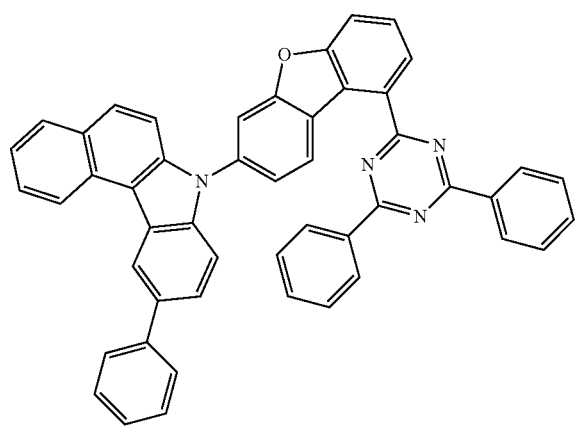
43
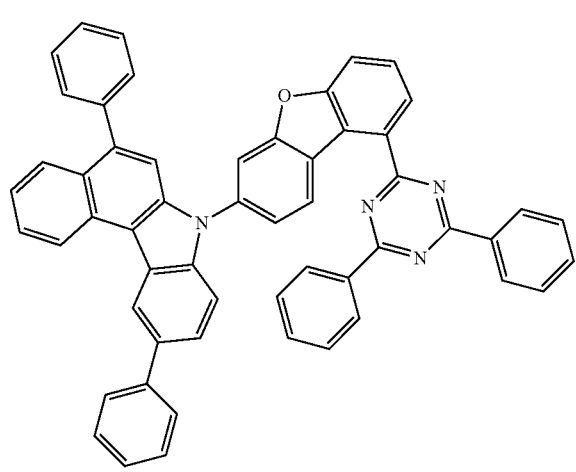
44
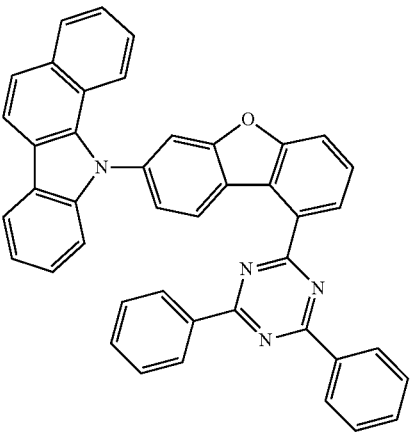
45
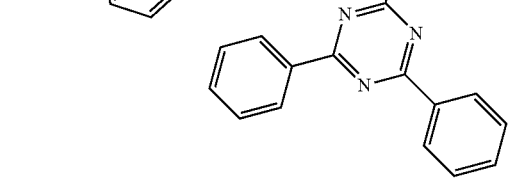
46
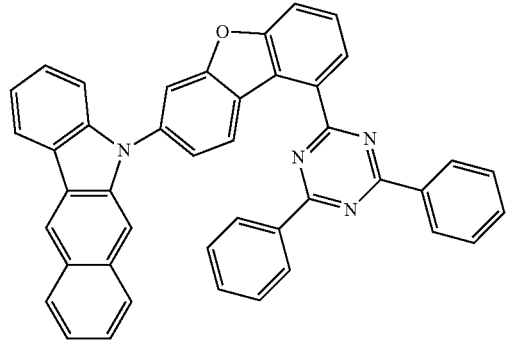
47
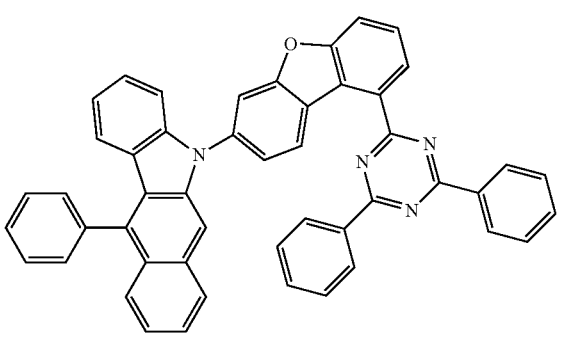

48
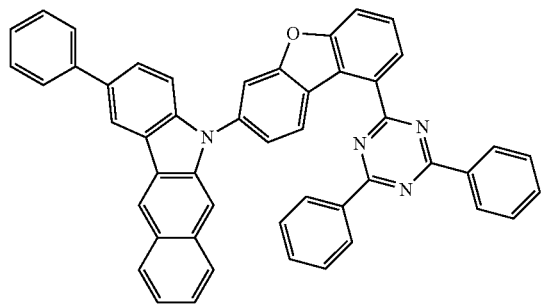
49
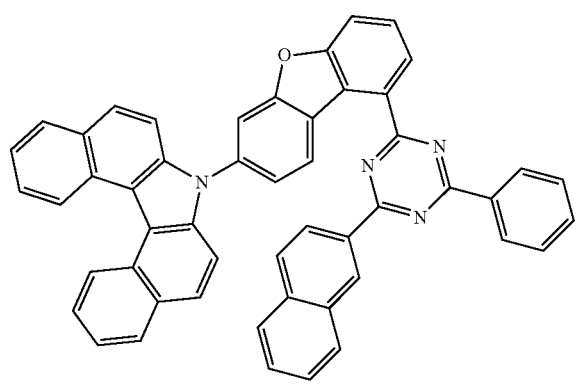
50
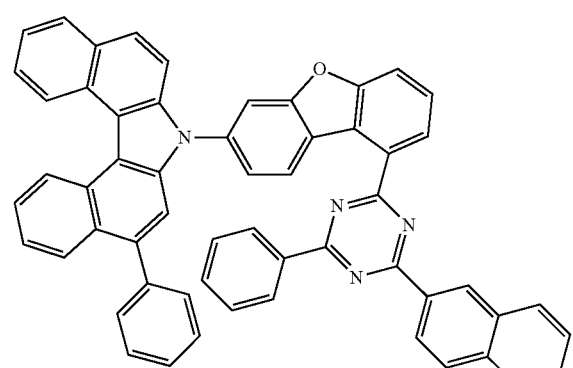
51
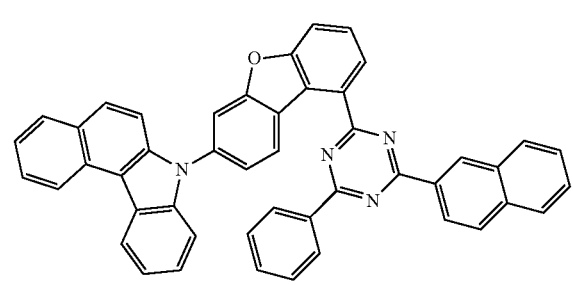
52
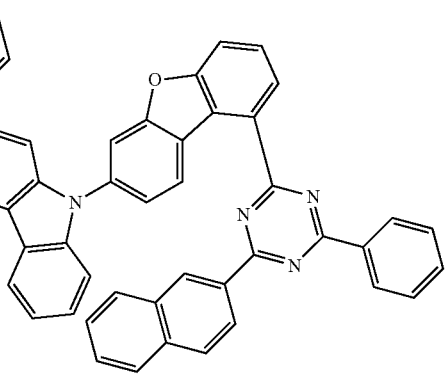
53
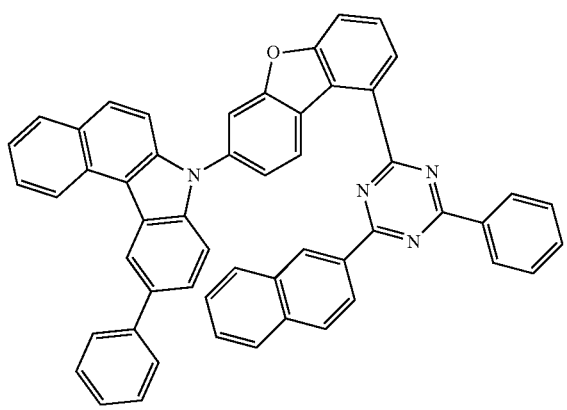
54
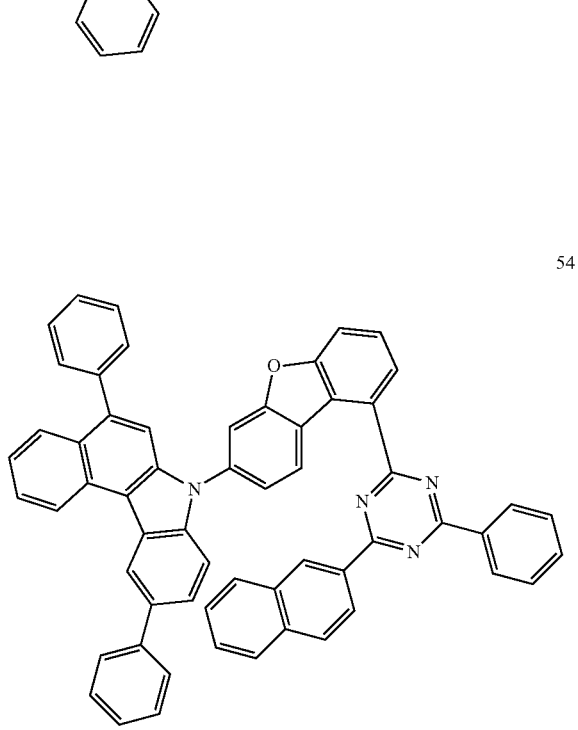

55
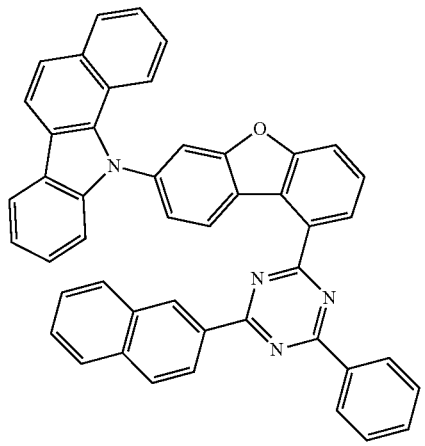
56
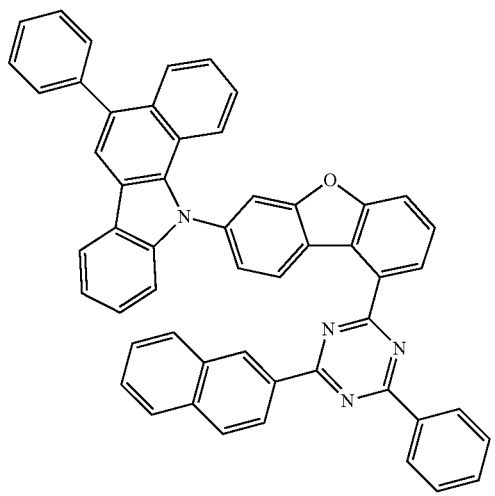
57
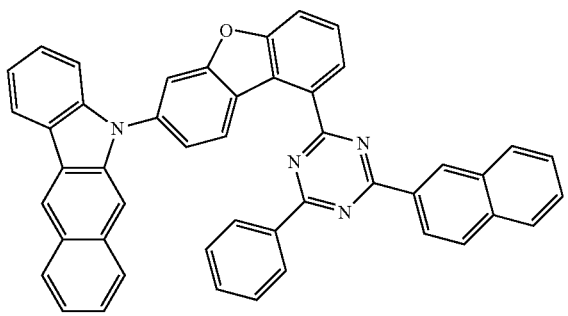
58
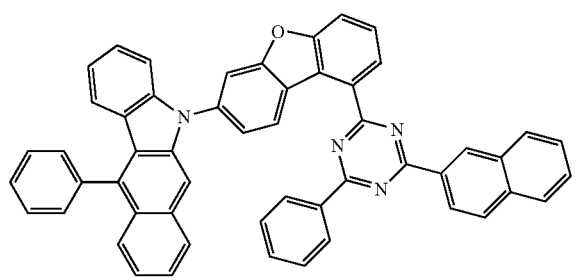
59
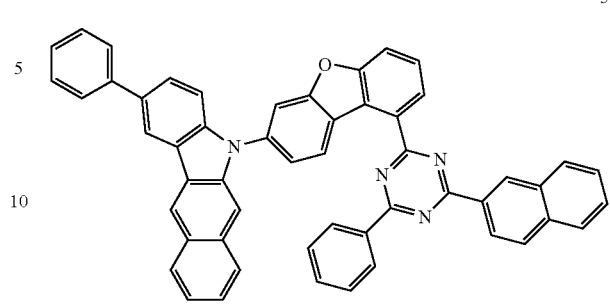
60
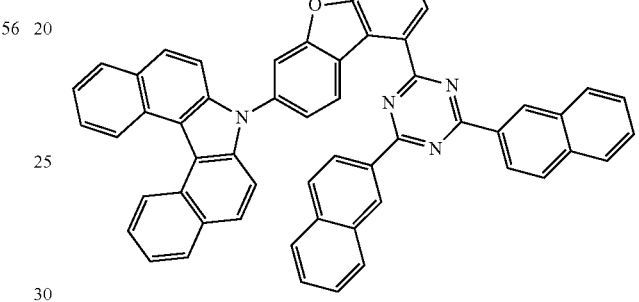
61
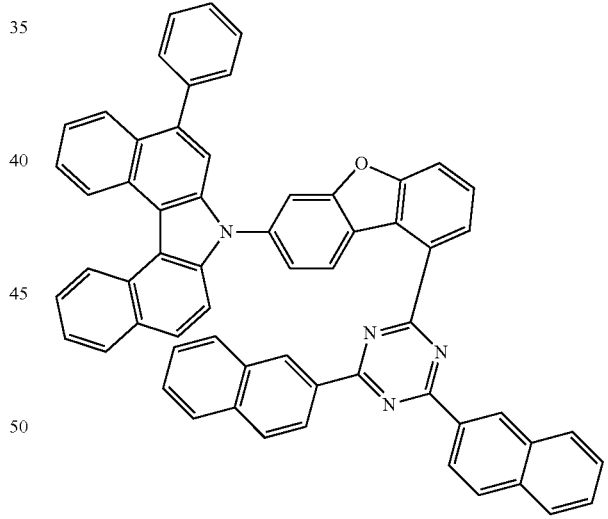
62
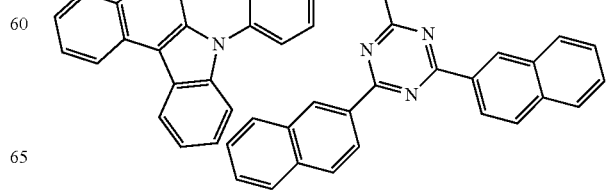

259
-continued
63
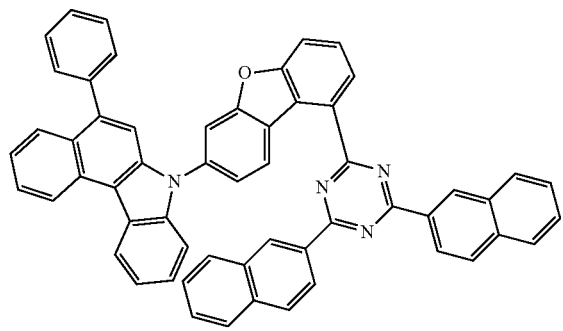
64
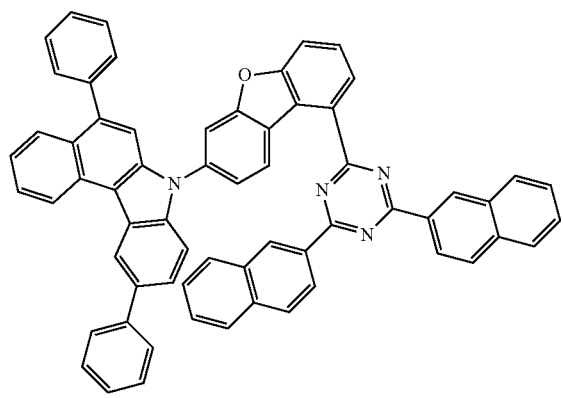
65
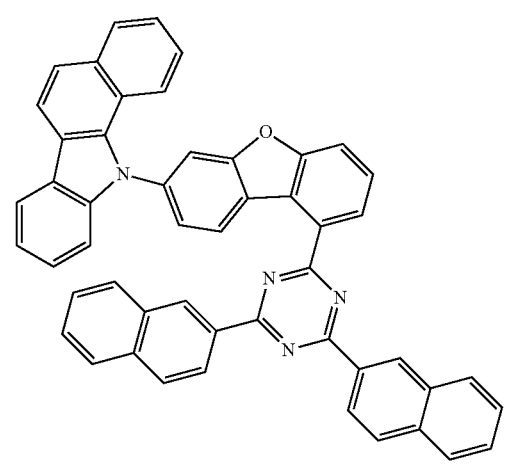
260
-continued
66
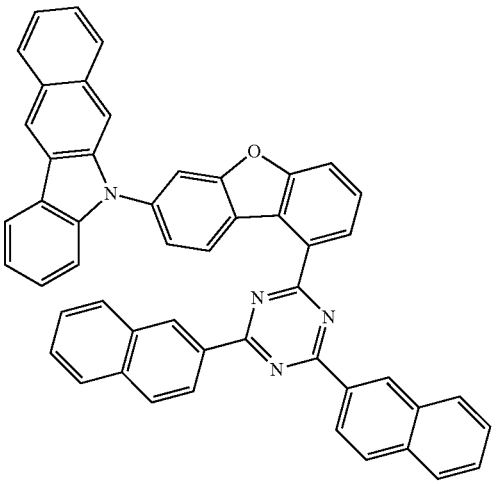
67
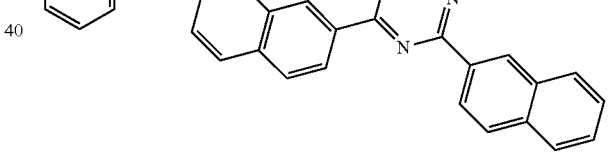
68
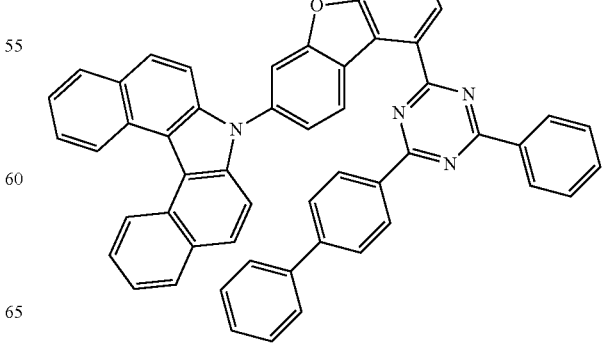

-continued
69
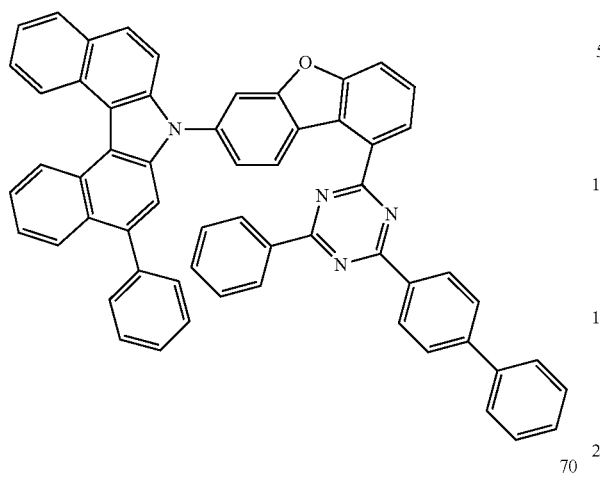
70
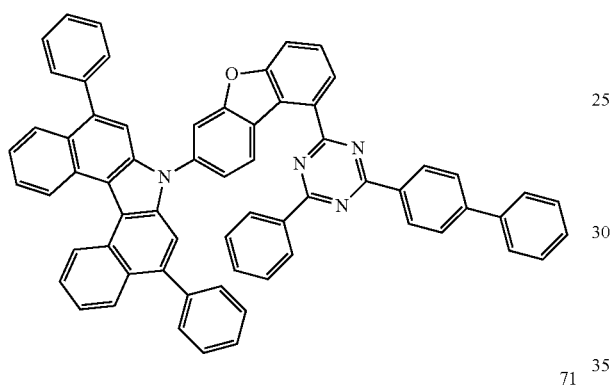
71
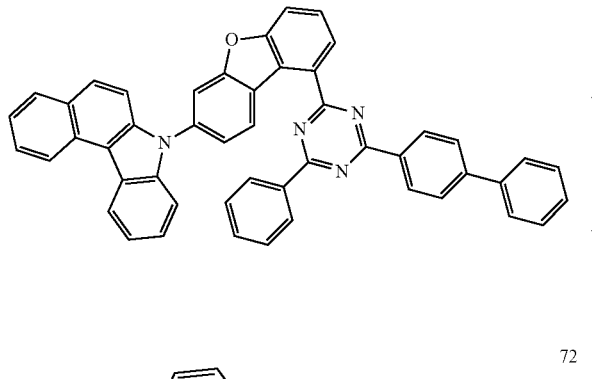
72
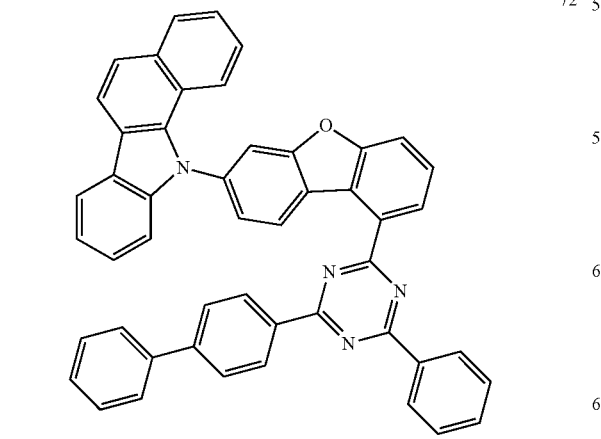
-continued
73
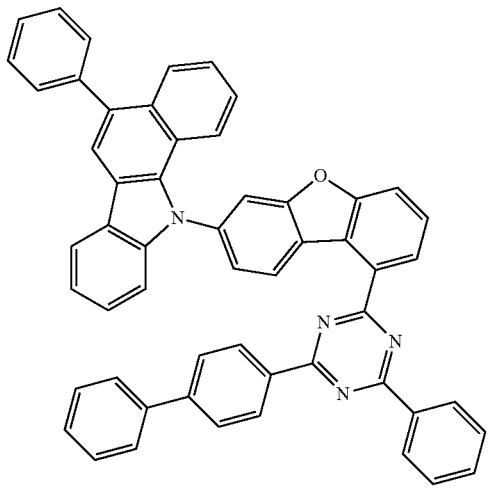
74
75
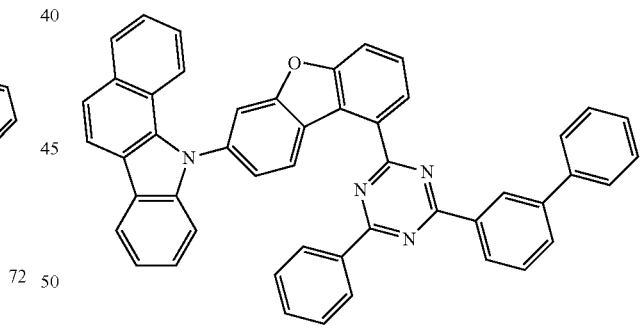
76
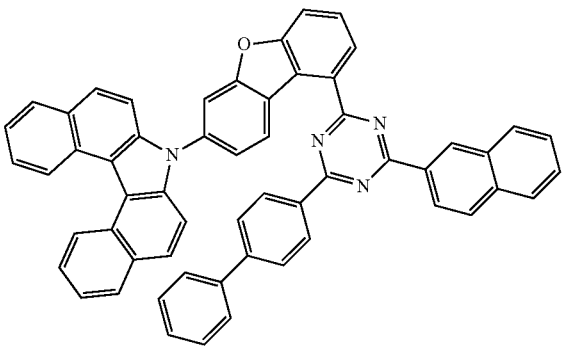

-continued
77
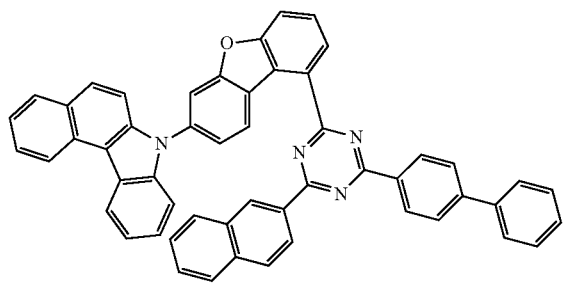
78
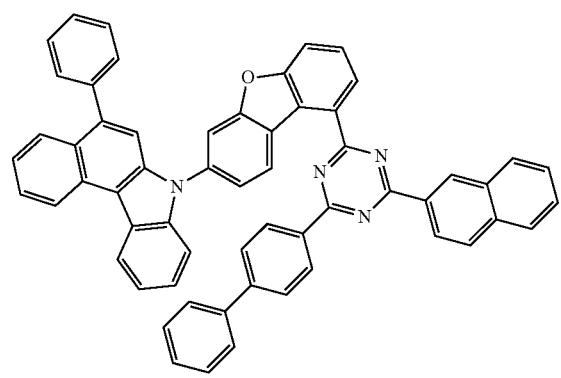
79
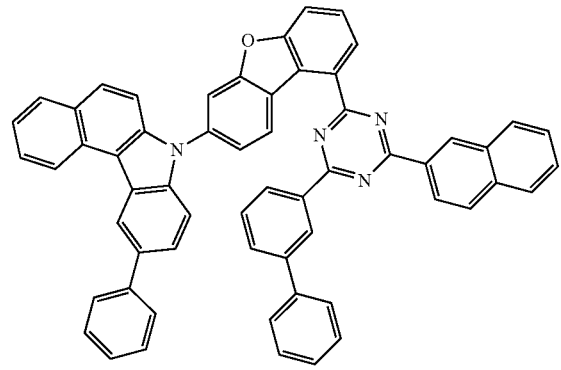
80
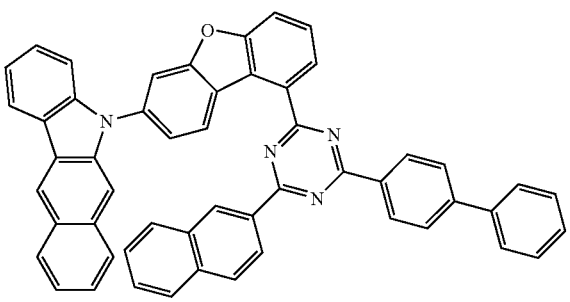
-continued
81
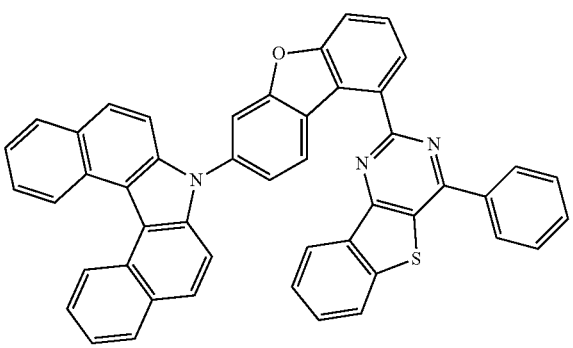
82
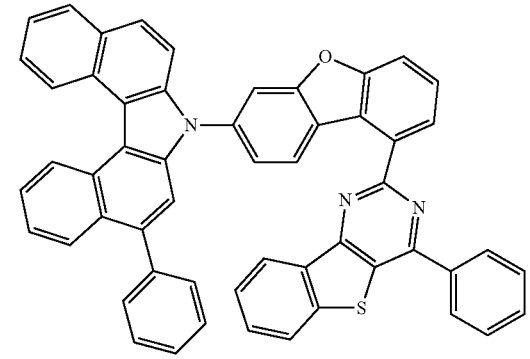
83
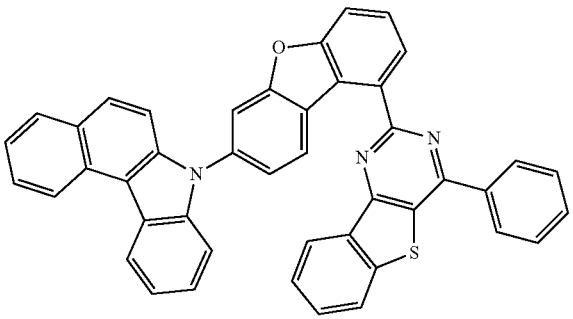
84
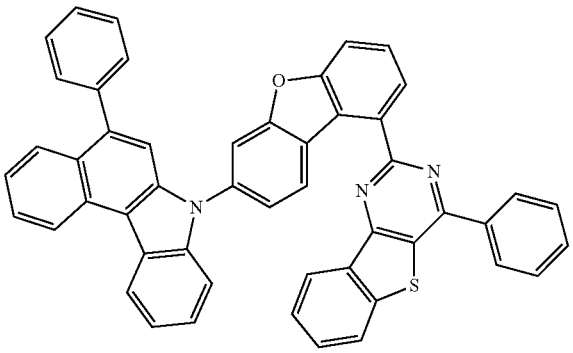

-continued
85
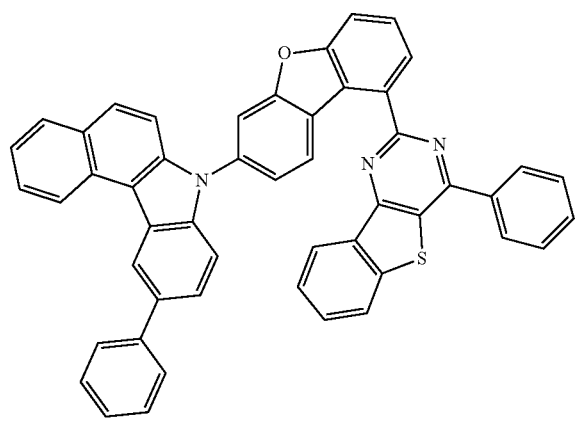
86
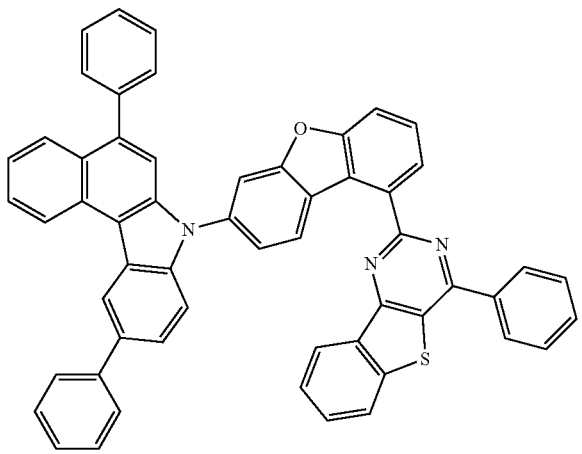
87
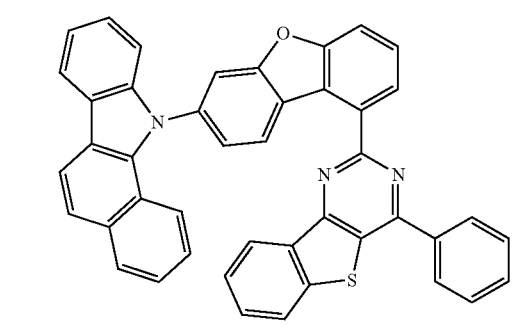
88
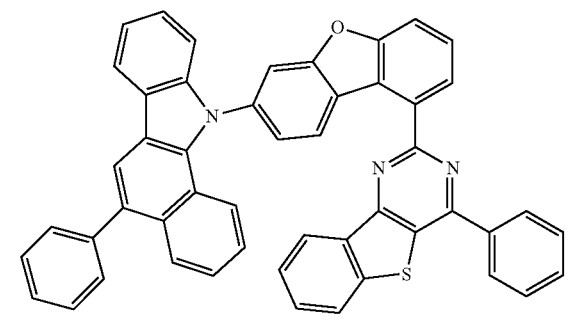
-continued
89
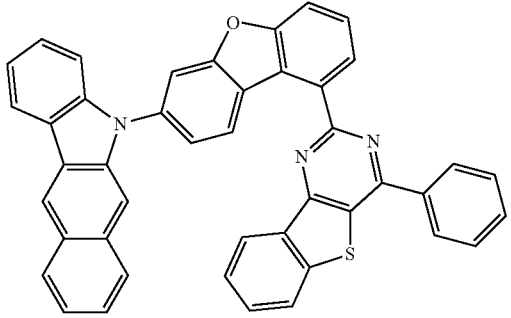
90
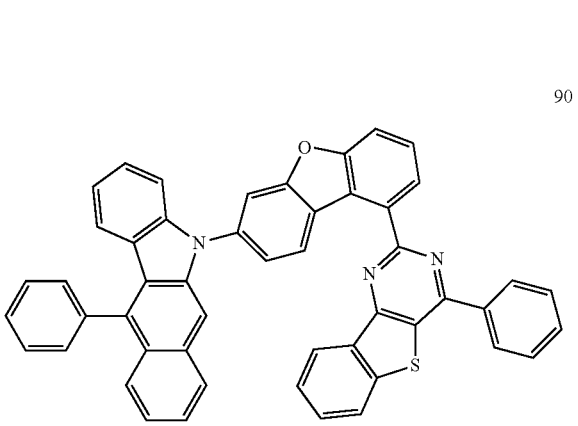
91
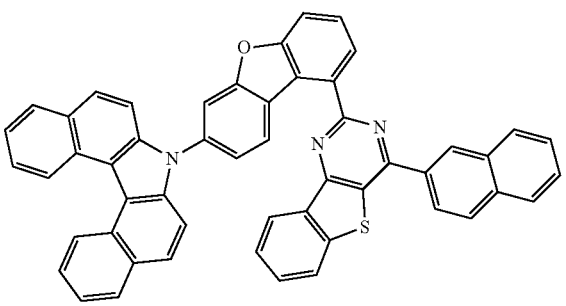
92
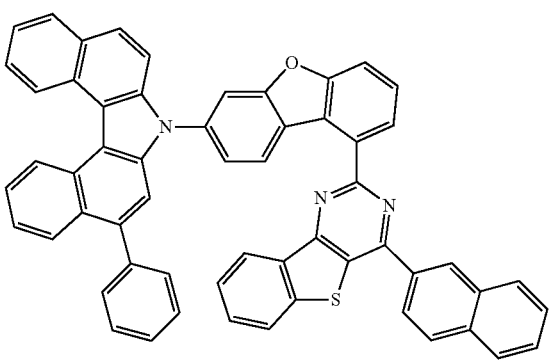

93
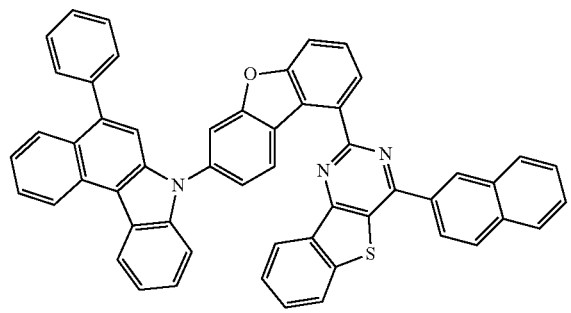
94
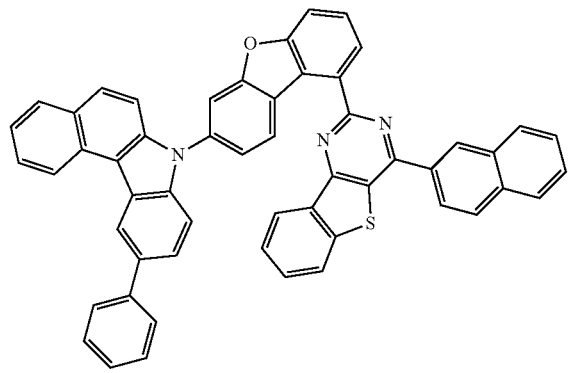
95
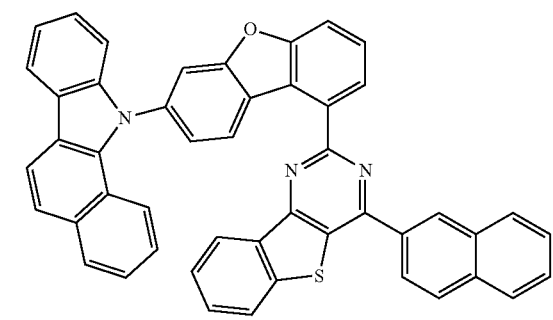
96
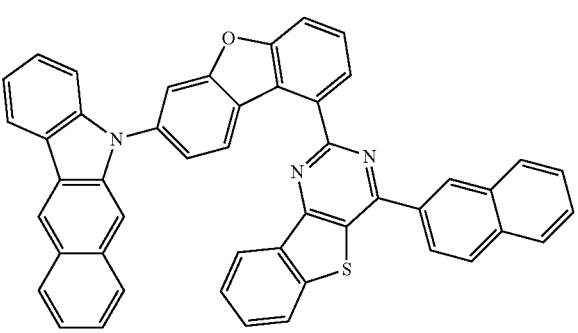
97
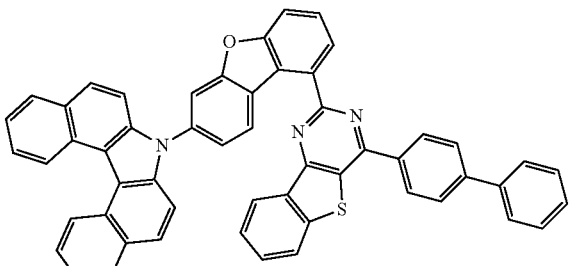
98
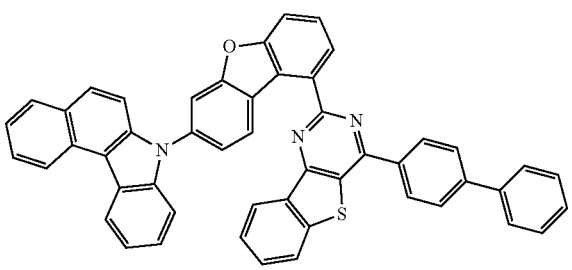
99
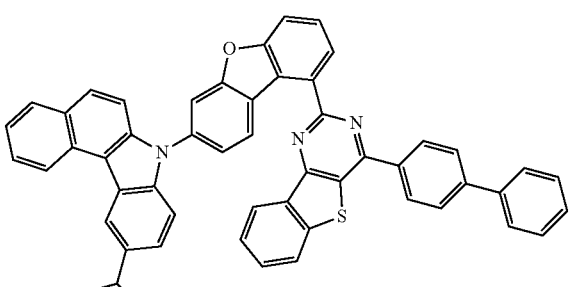
100
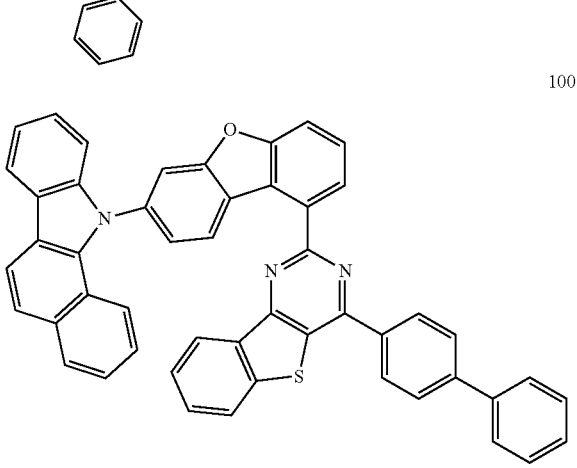
101
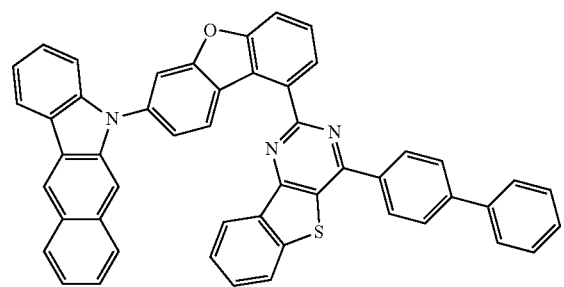

269
-continued
102
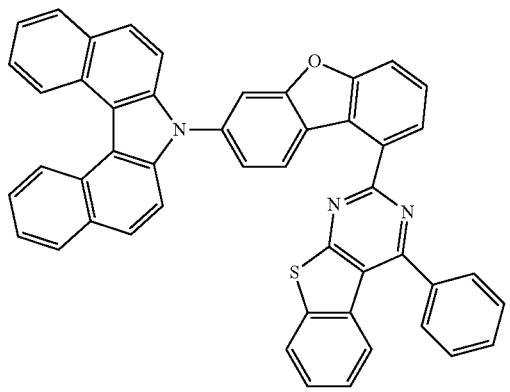
103
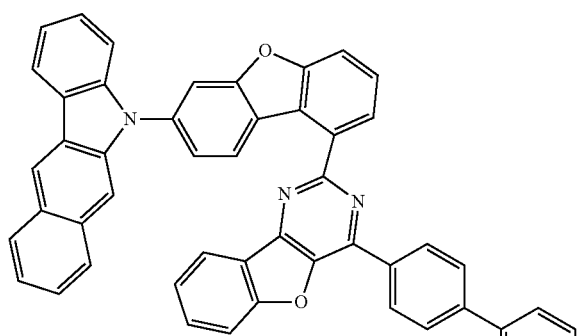
104
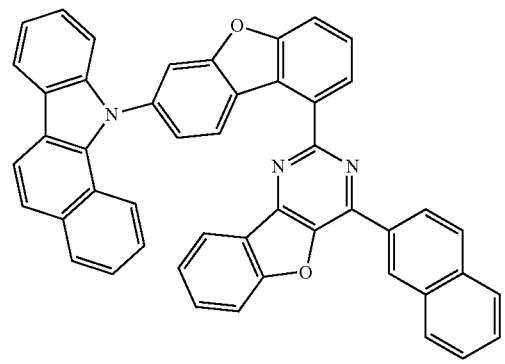
105
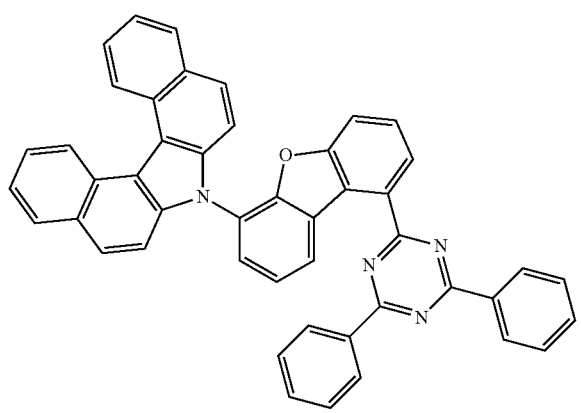
270
-continued
106
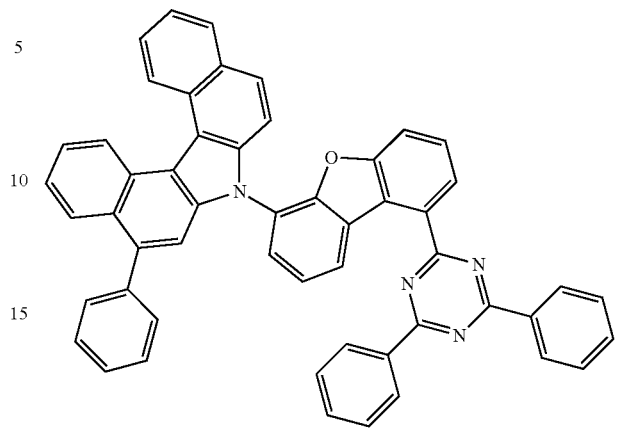
107
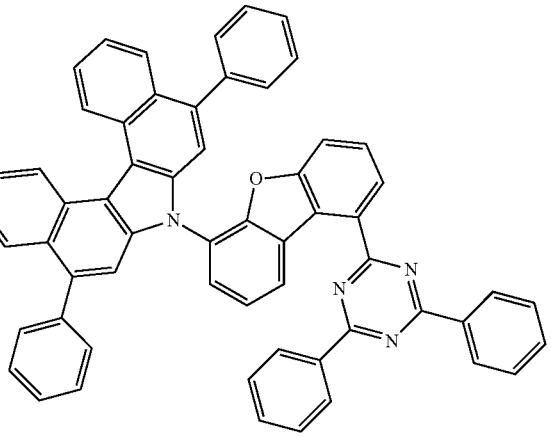
108
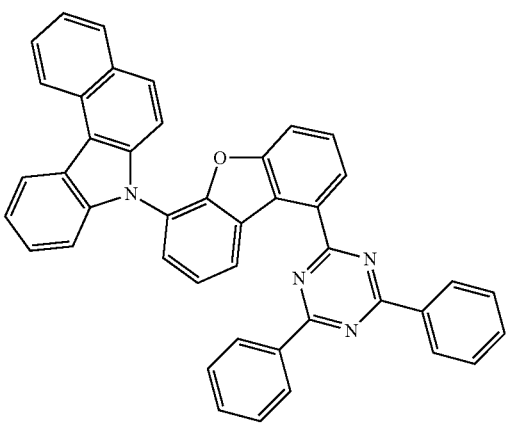

109
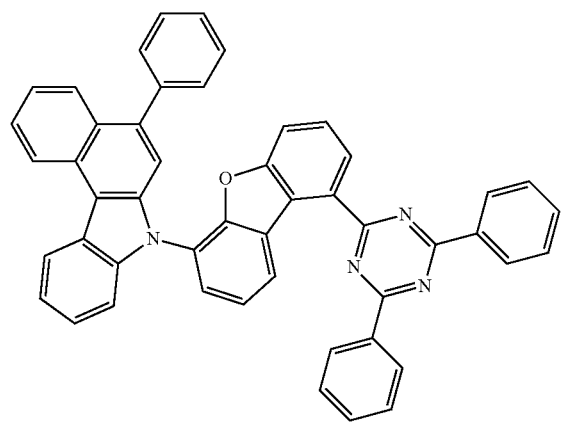
110
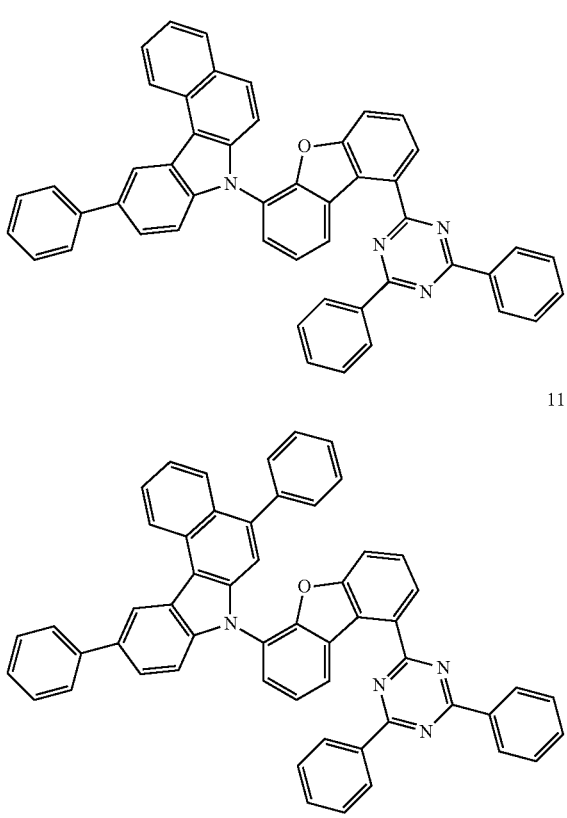
111
112
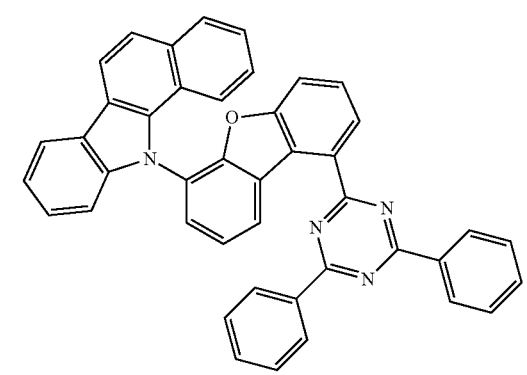
113
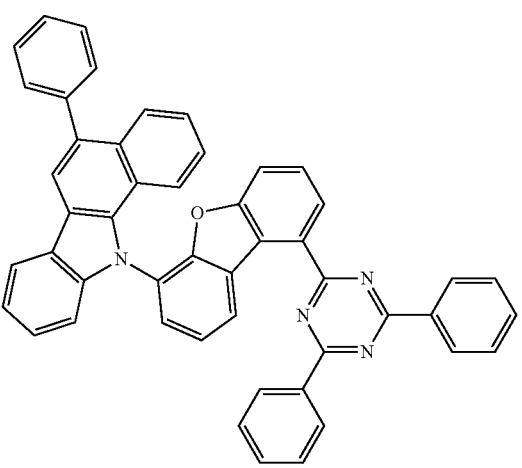
114
115

116
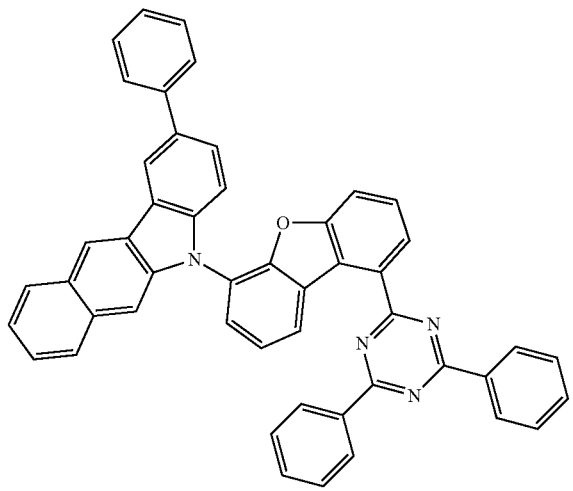
117
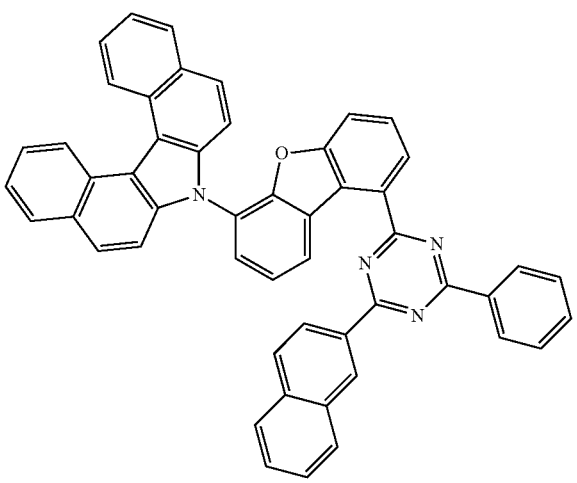
118
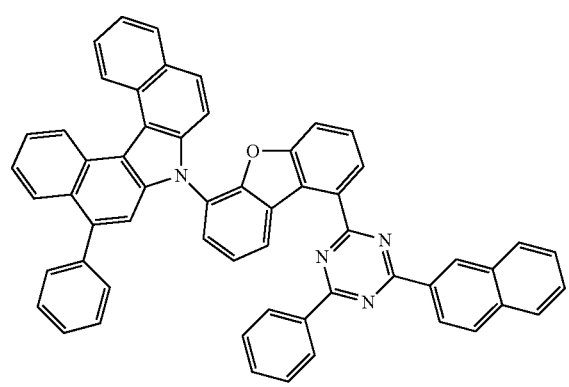
119
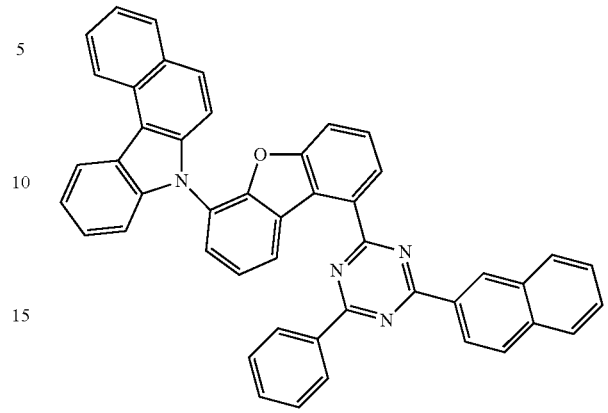
120
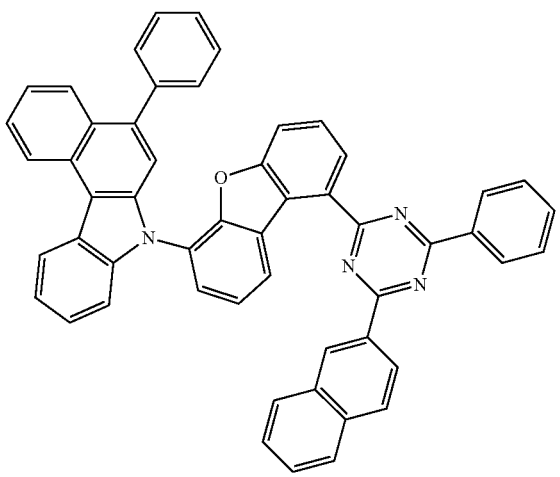
121
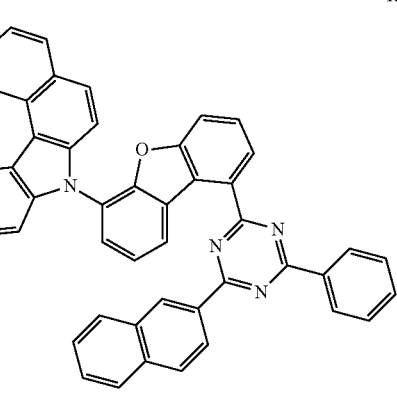

122
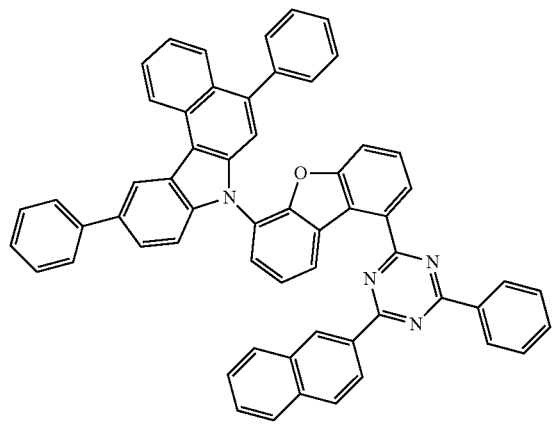
123
125
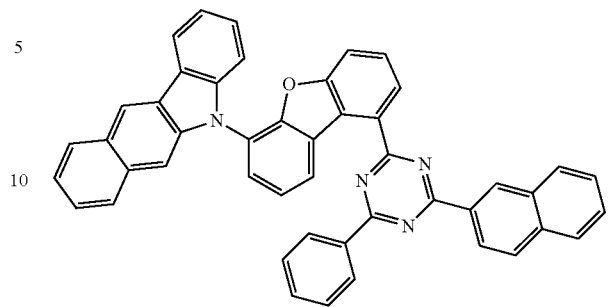
126
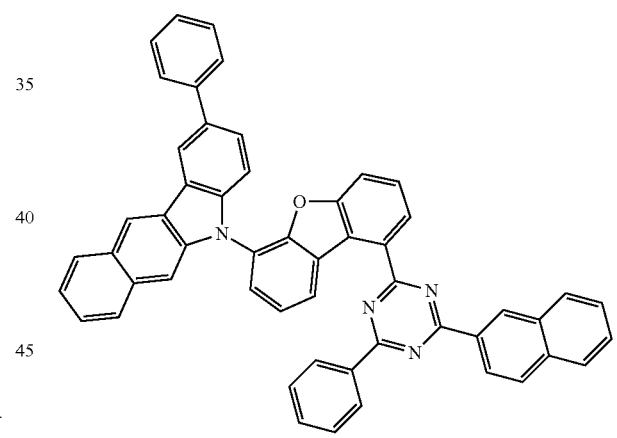
127
124
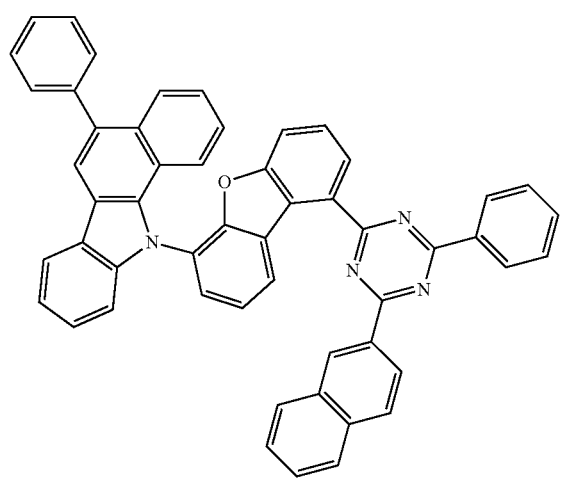
128
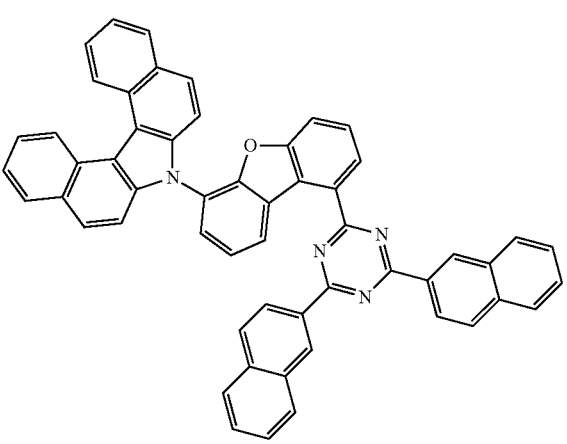

-continued
129
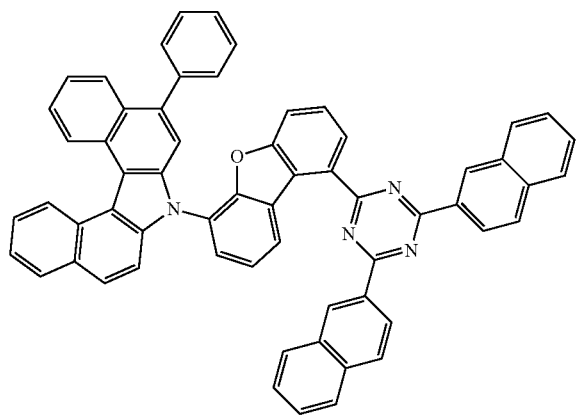
130
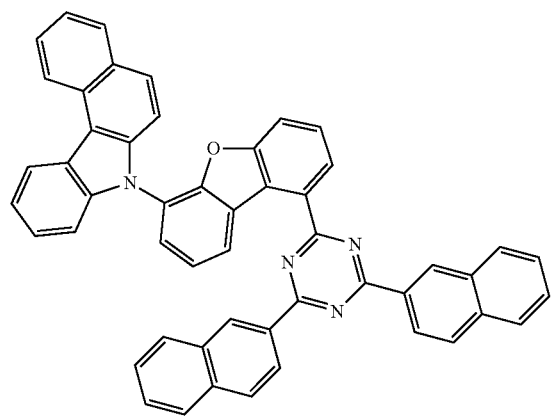
131
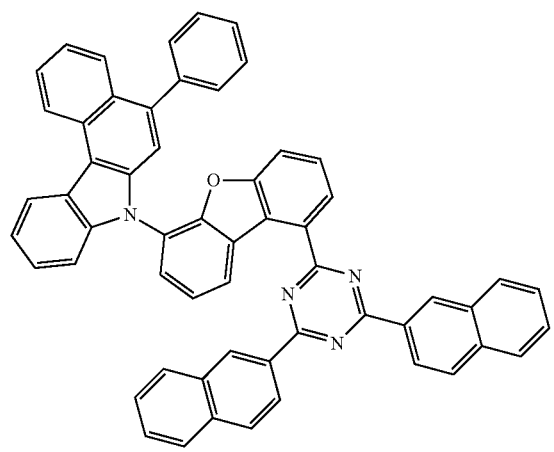
-continued
132
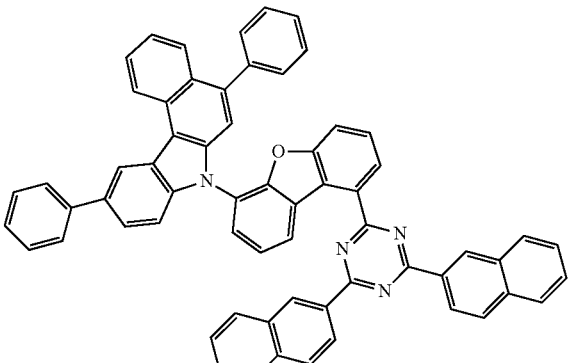
133
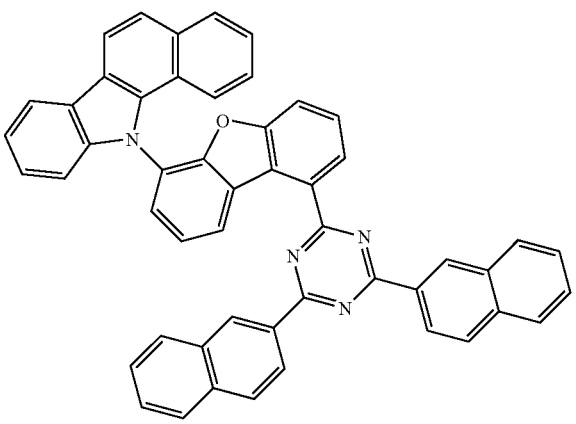
134
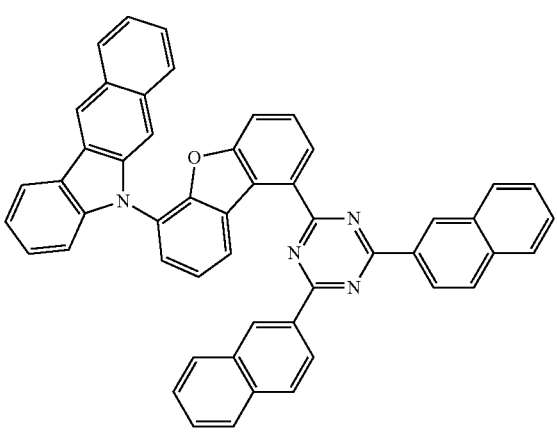

135
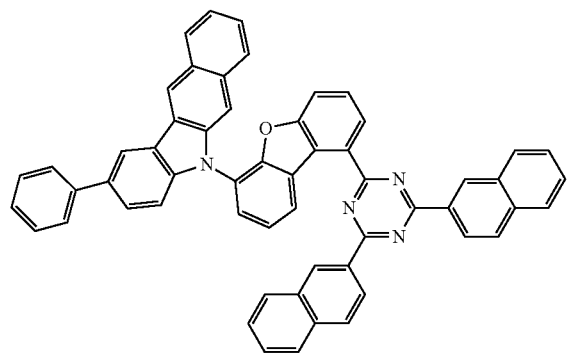
136
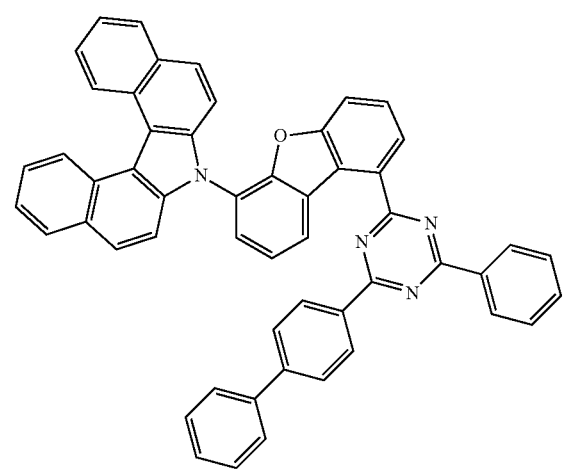
137
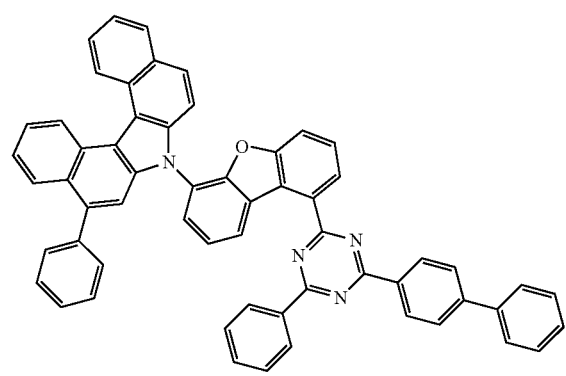
138
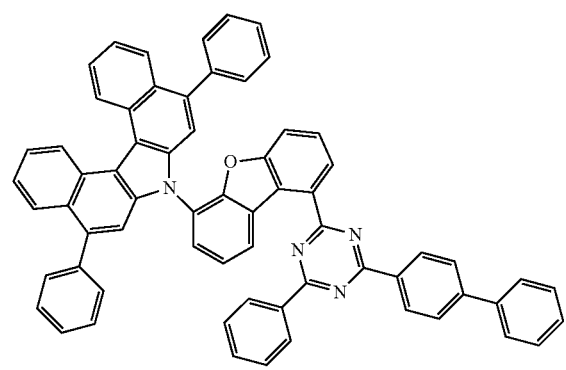
139
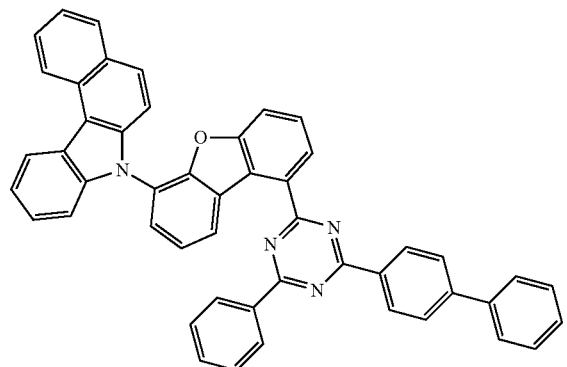
140
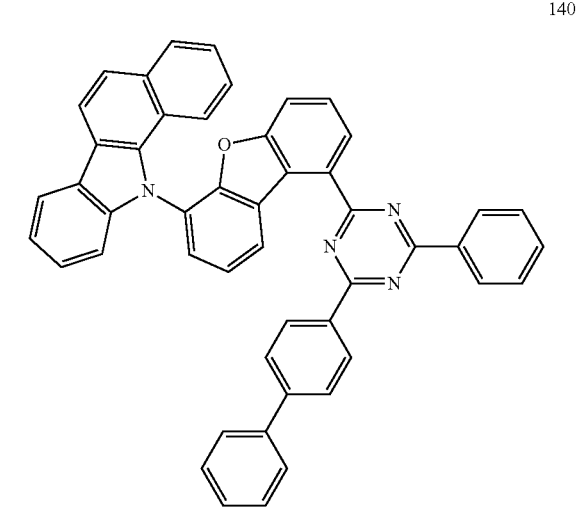
141
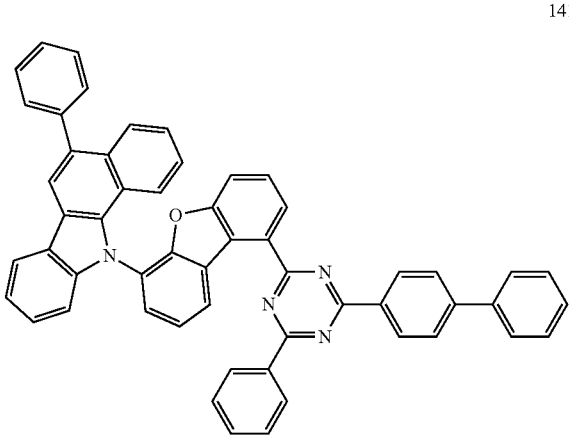
142
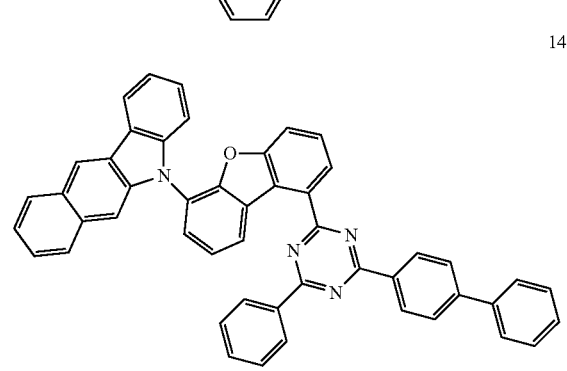

143
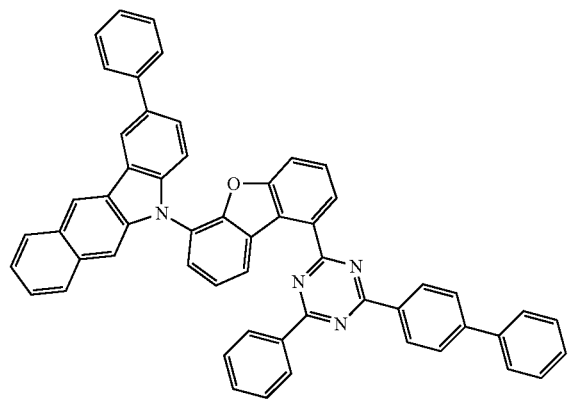
144
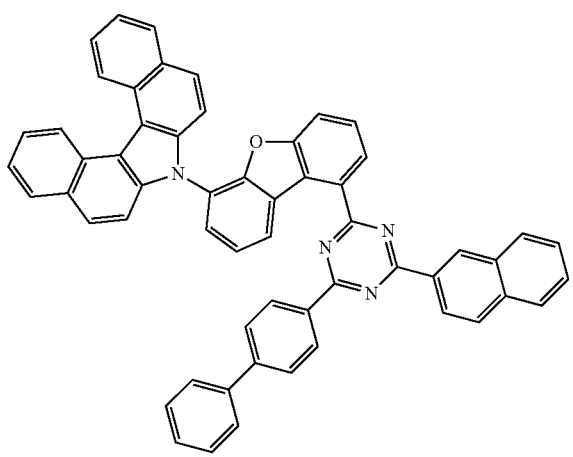
145
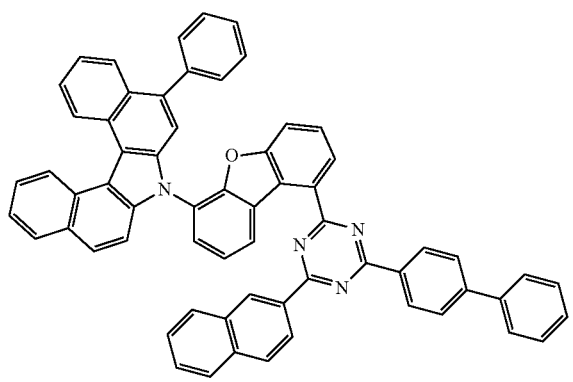
146
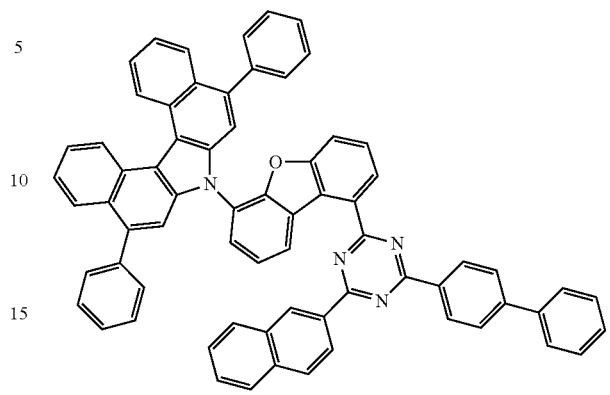
147
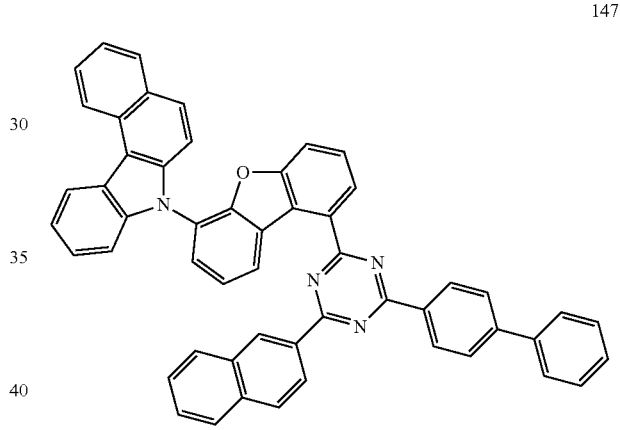
148
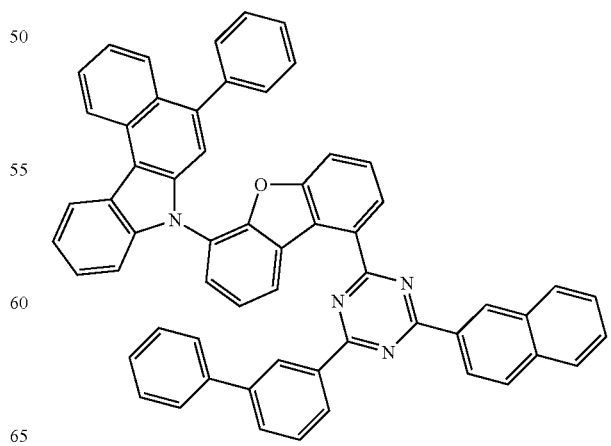

149
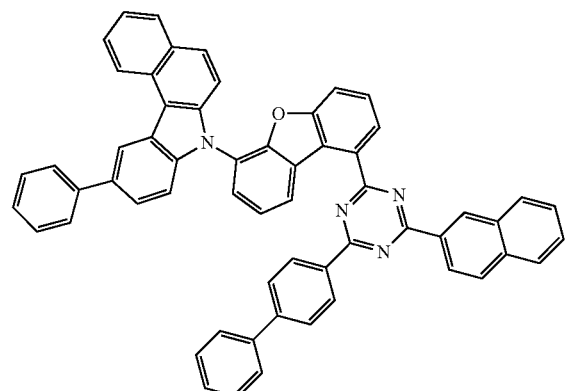
150
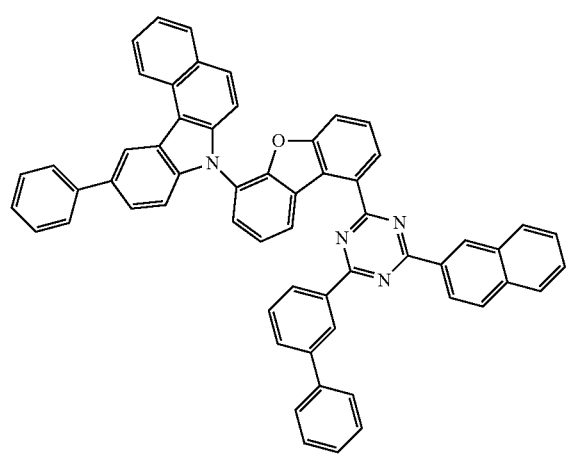
151
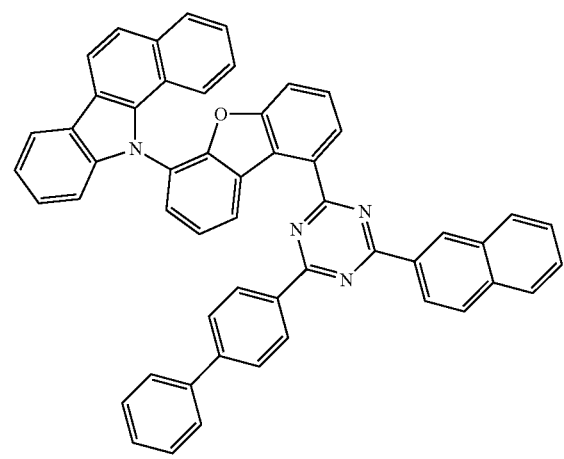
152
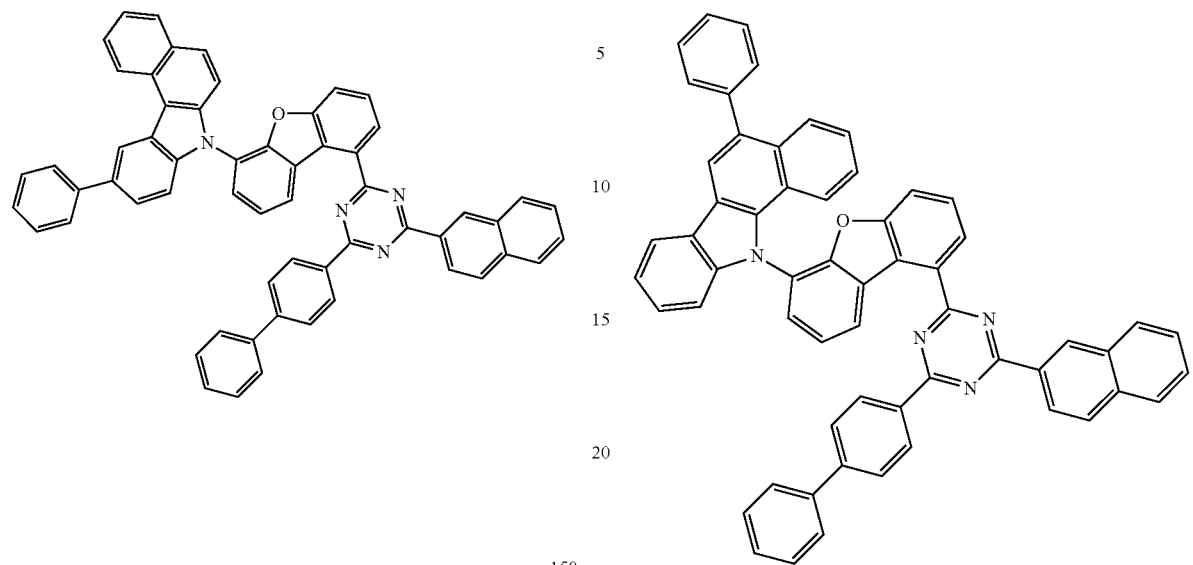
153
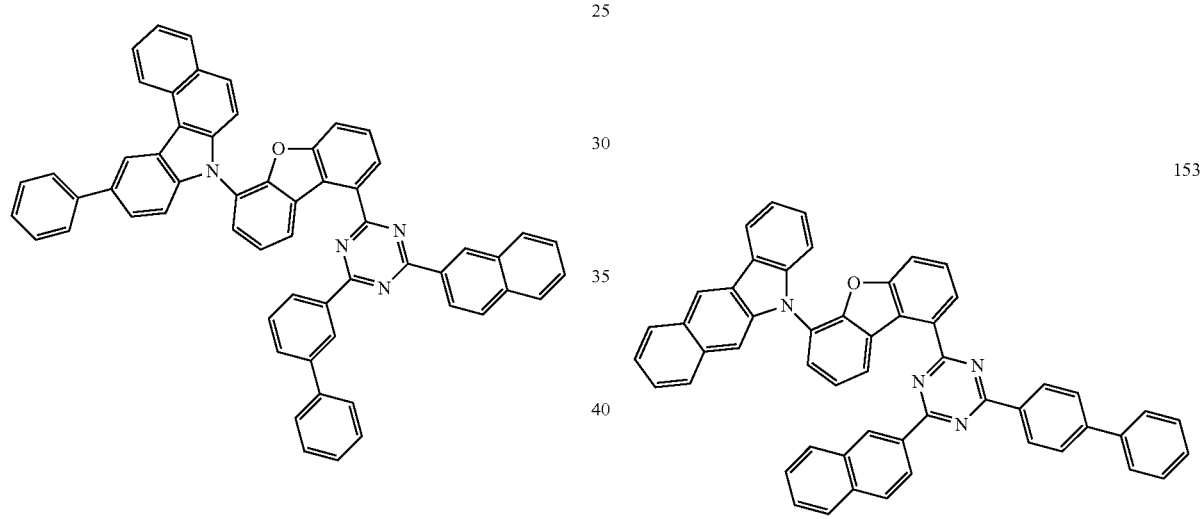
154
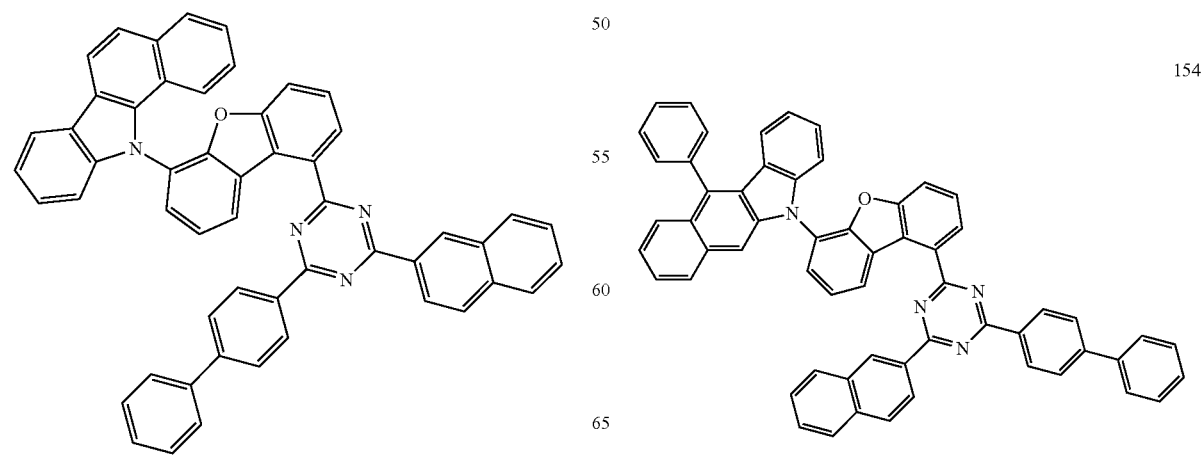

155 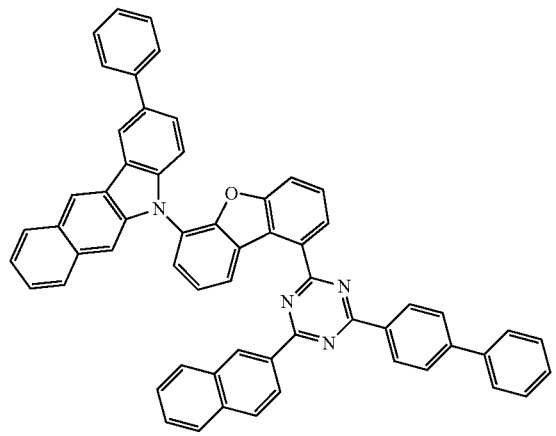
158 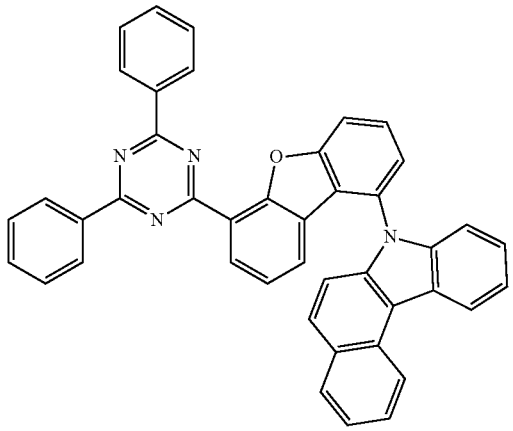
156 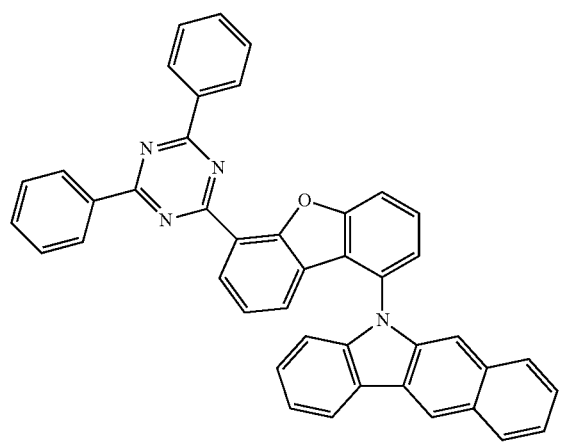
159
157 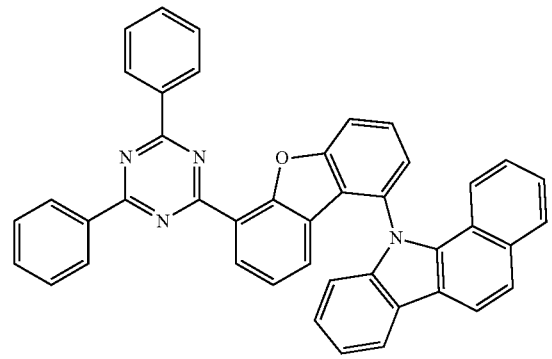
160 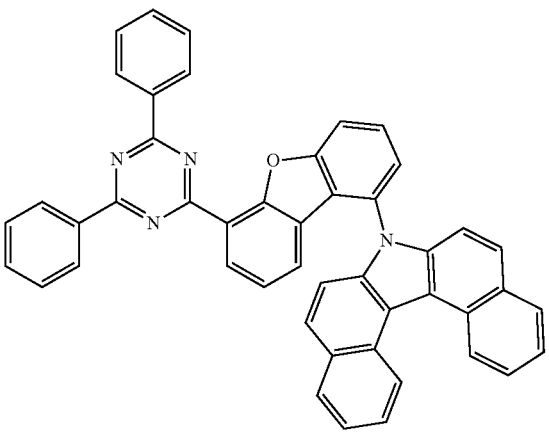

161
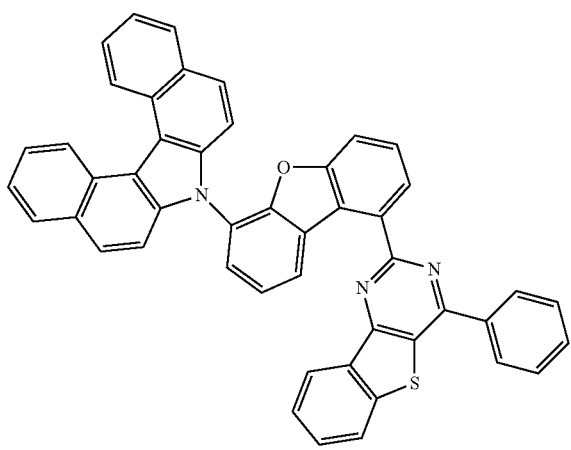
162
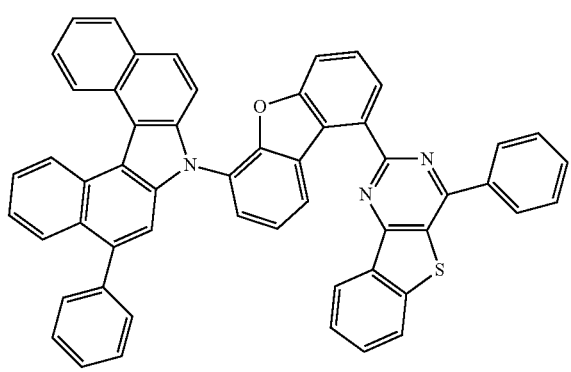
163
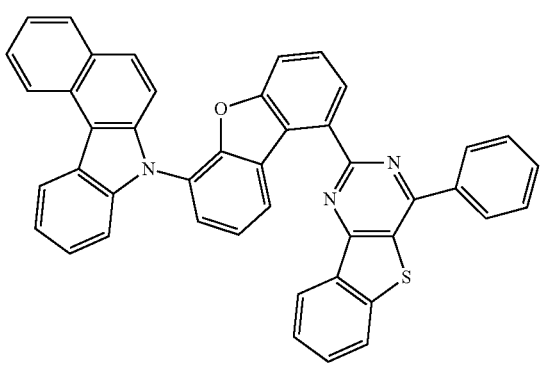
164
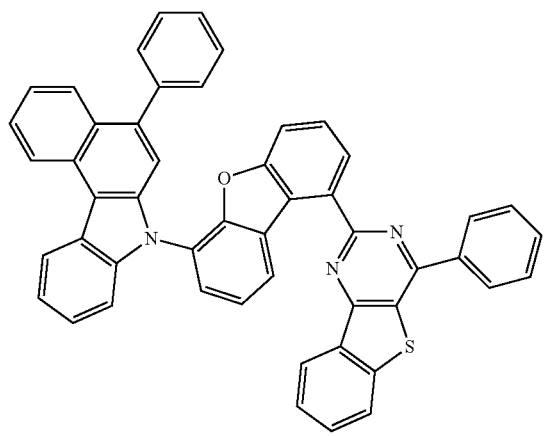
165
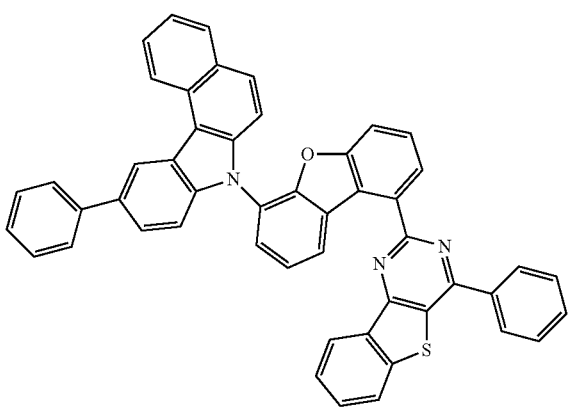
166
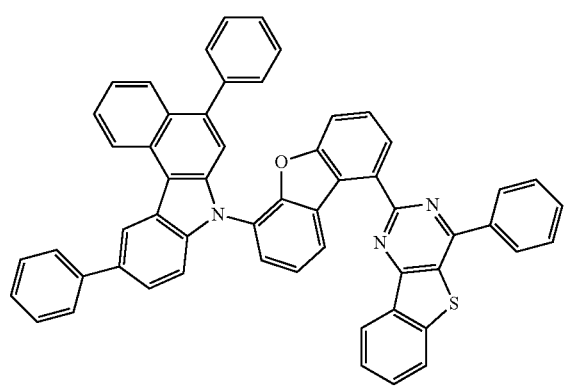

167
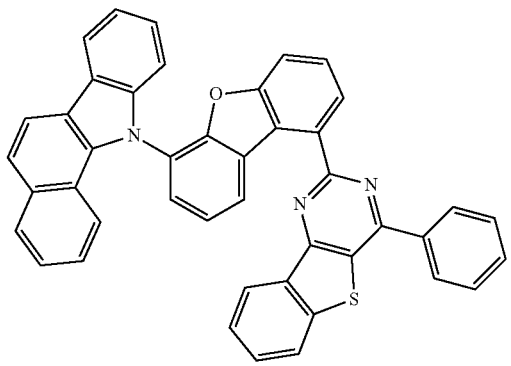
168
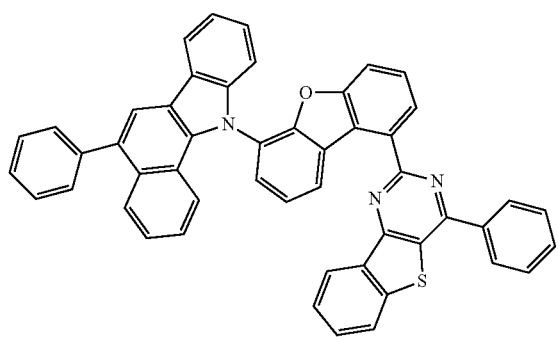
169
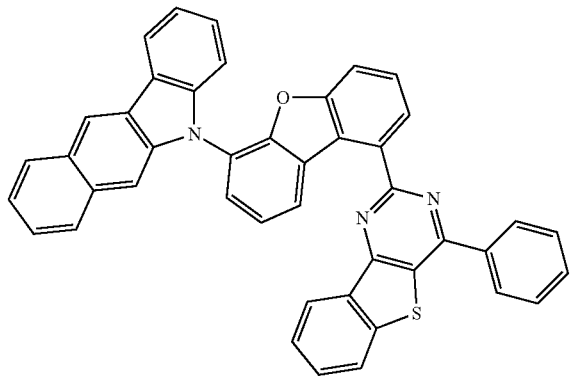
170
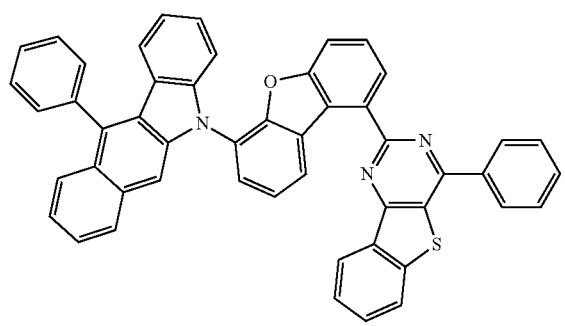
171
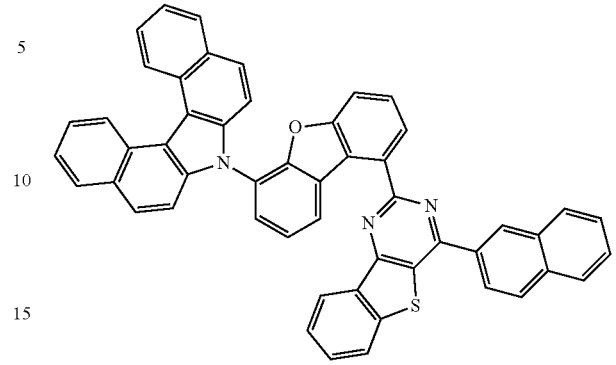
172
173
174
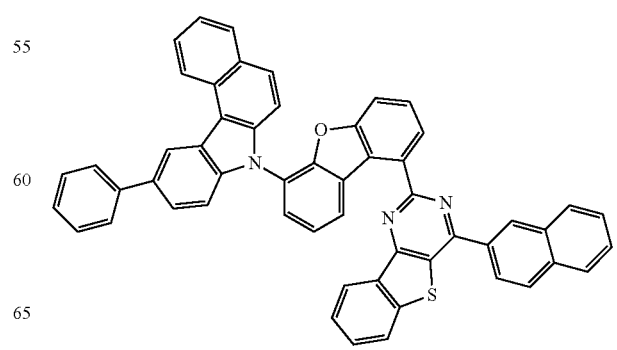

291
-continued
175
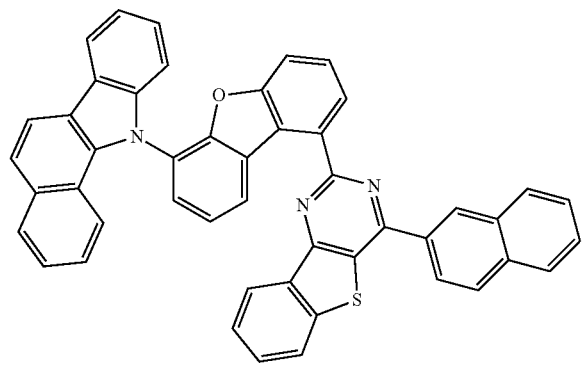
176
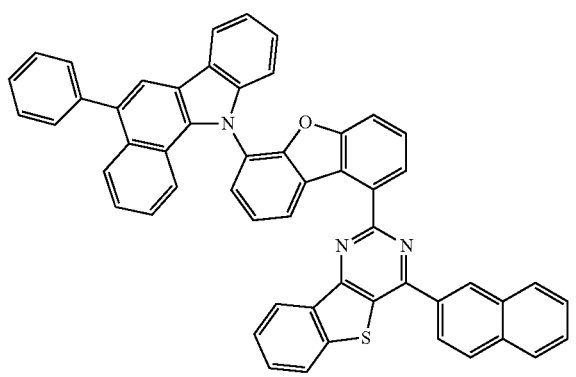
177
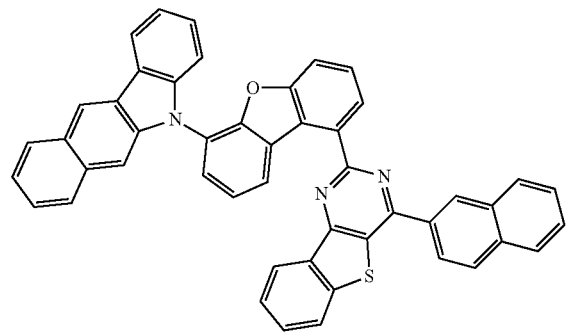
178
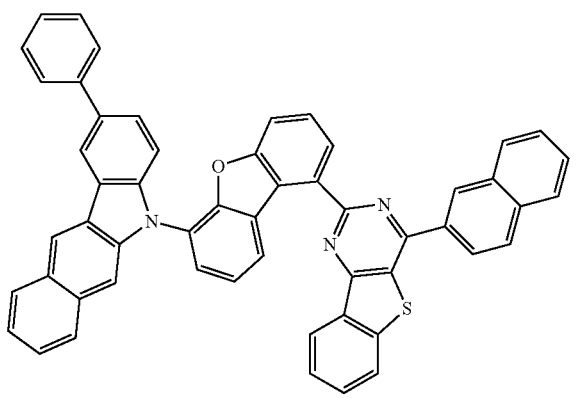
292
-continued
179
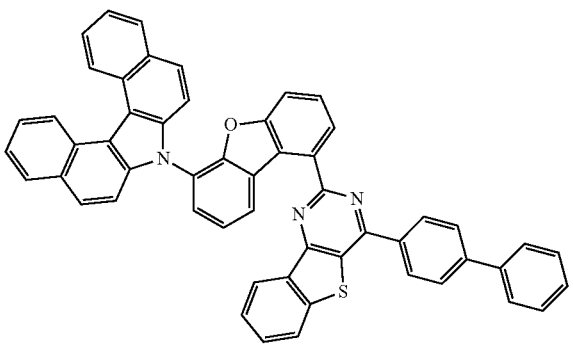
180
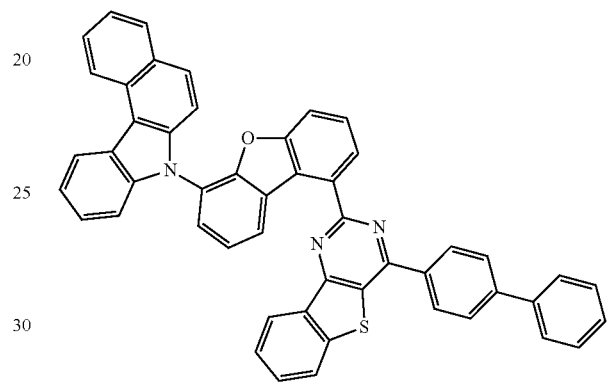
181
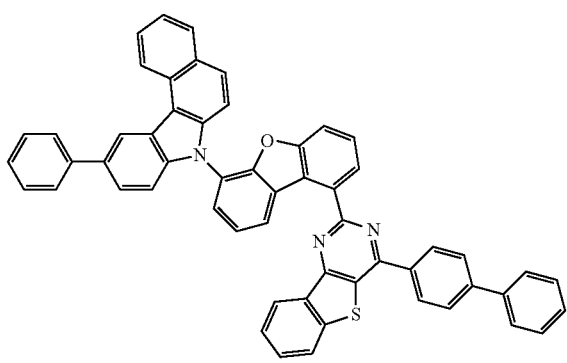
182
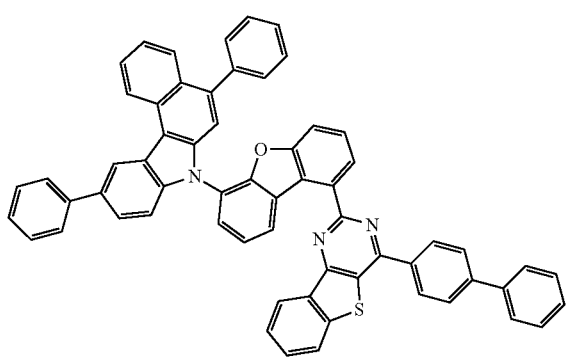

183
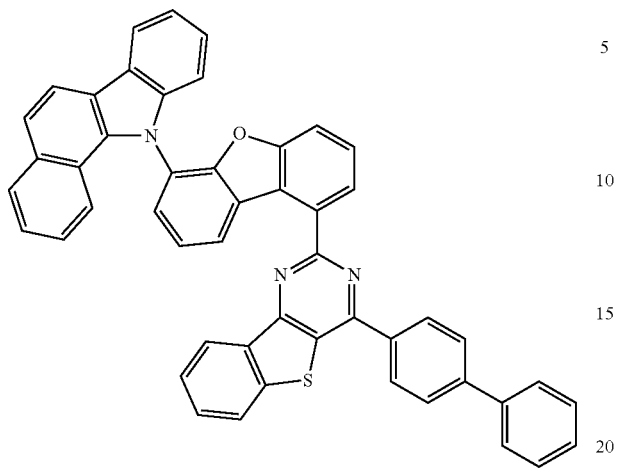
184
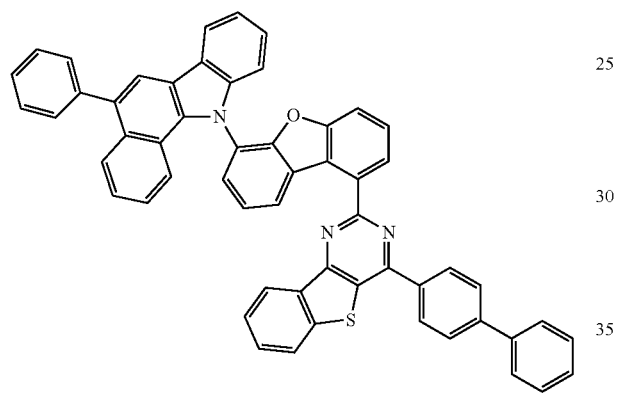
185
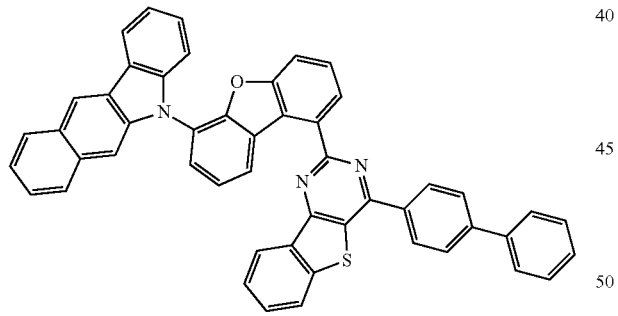
186
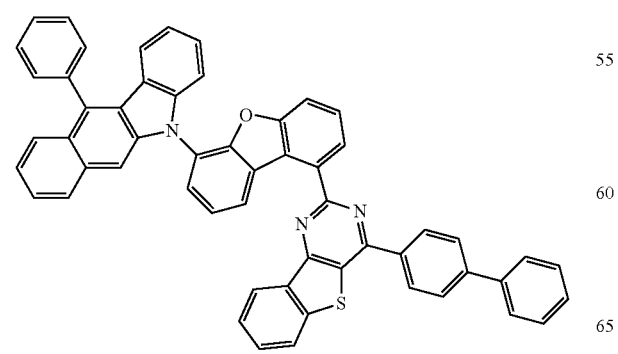
187
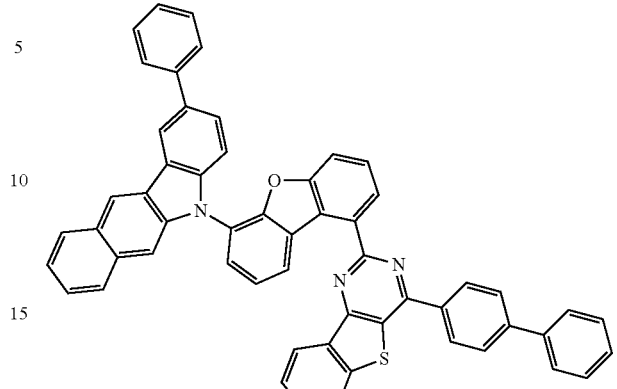
188
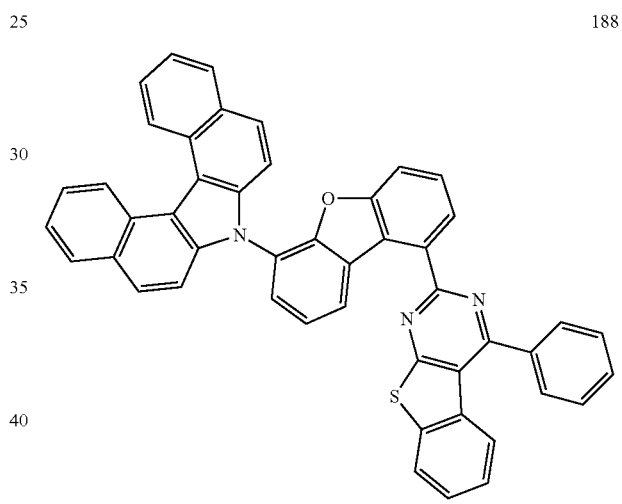
189
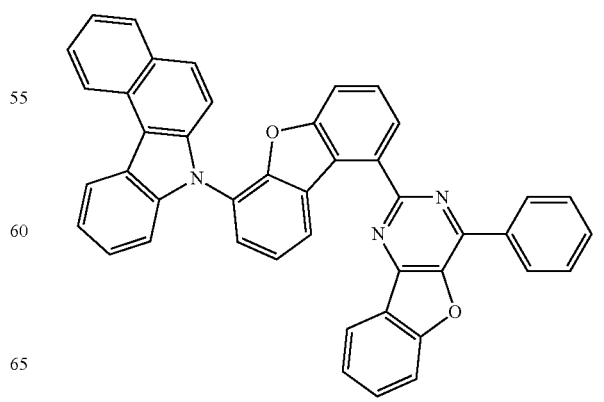

190
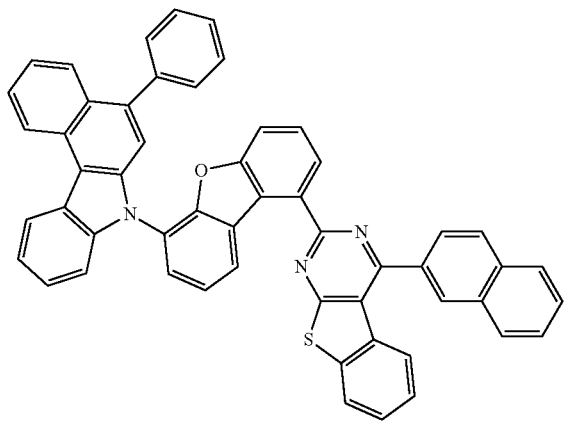
191
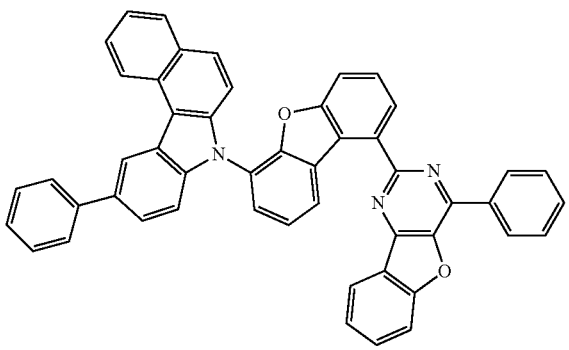
192
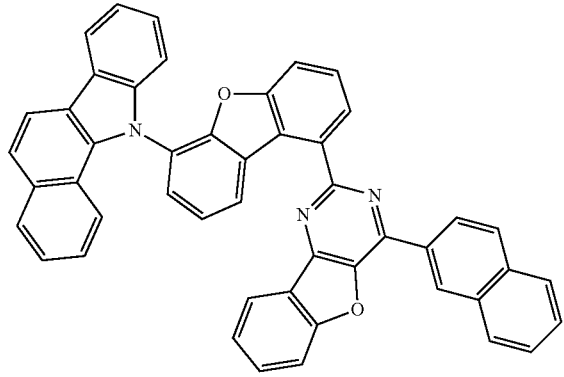
193
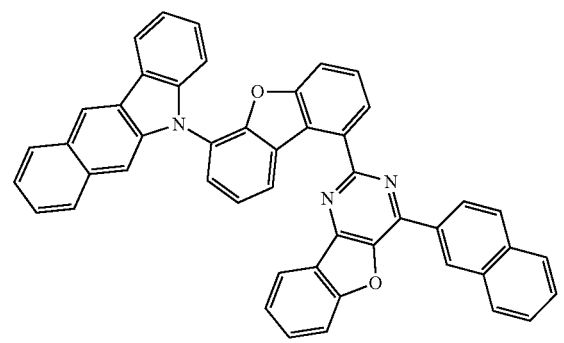
194
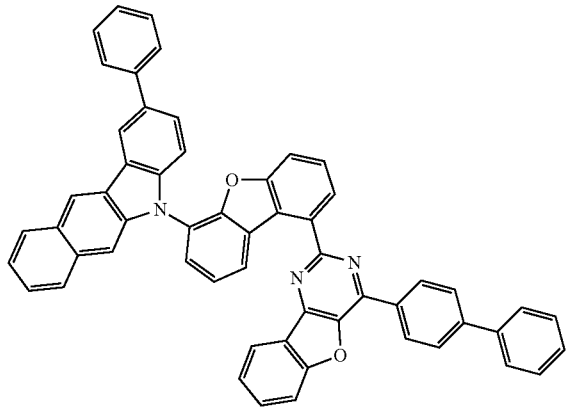
195
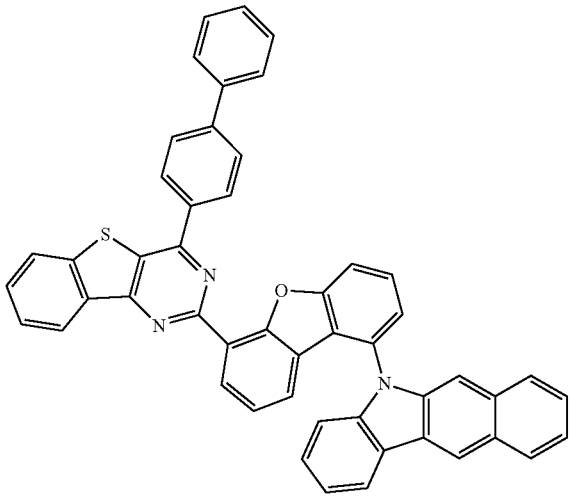
196

297
-continued
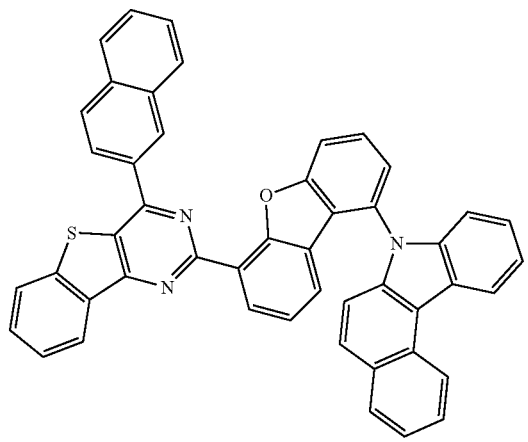
197
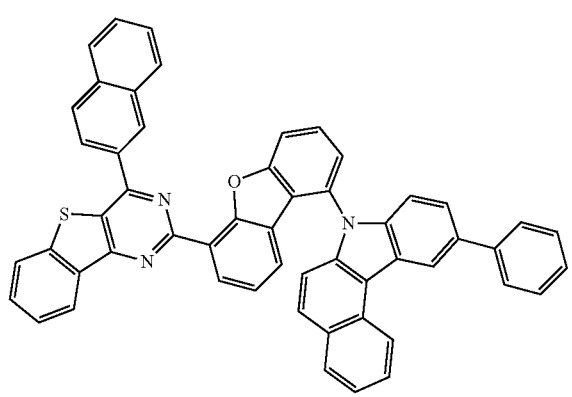
198
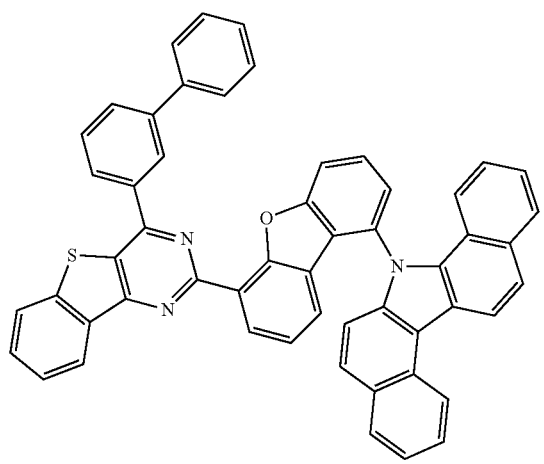
199
298
-continued
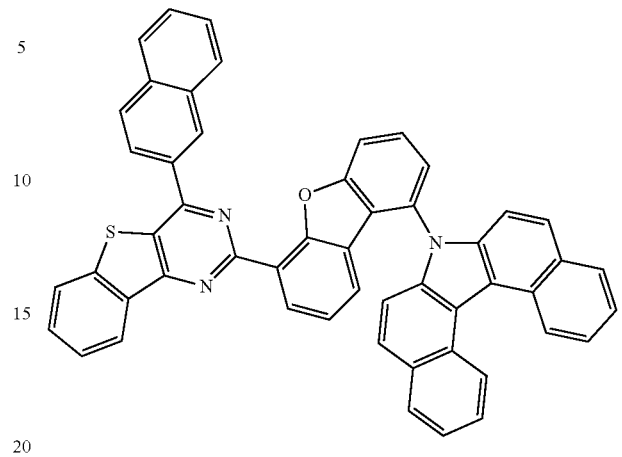
200
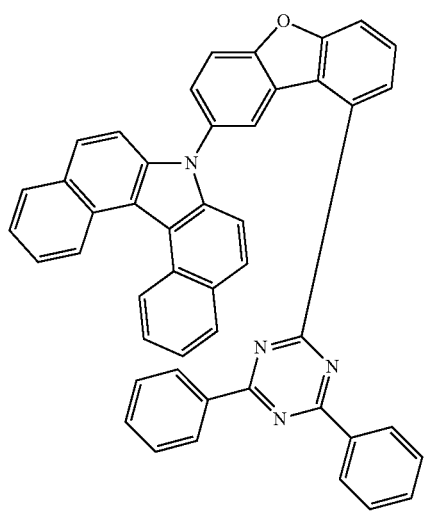
201
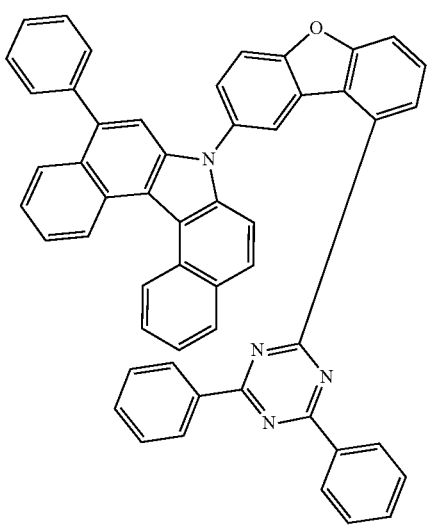
202

-continued
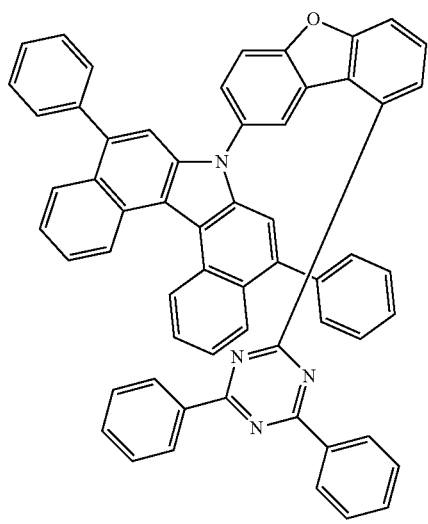
203
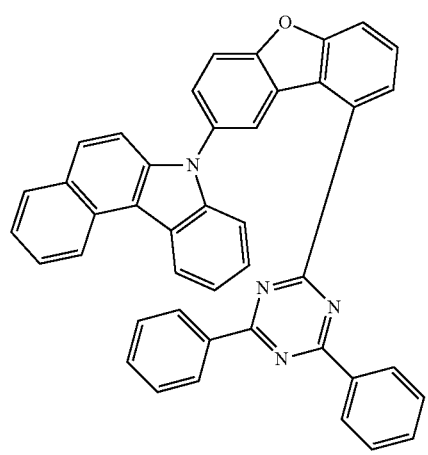
204
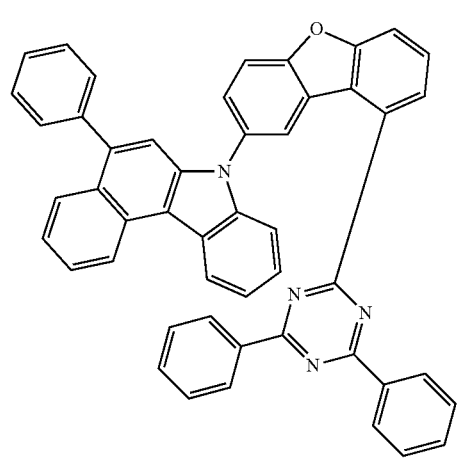
205
-continued
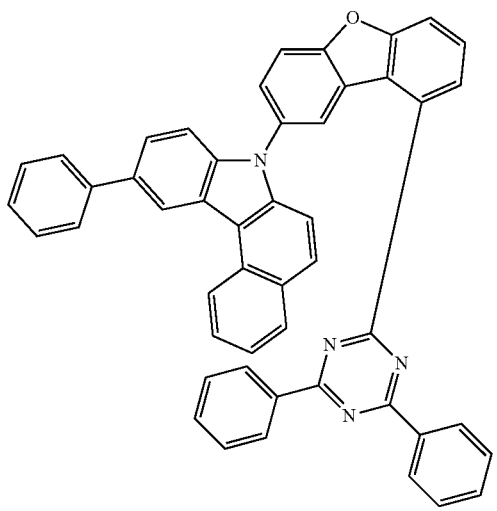
206
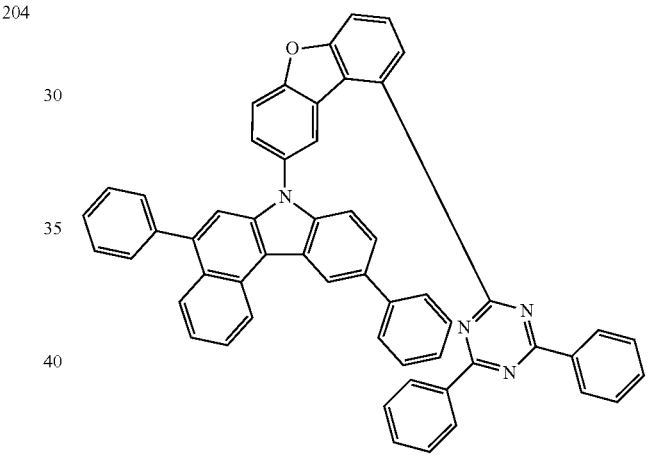
207
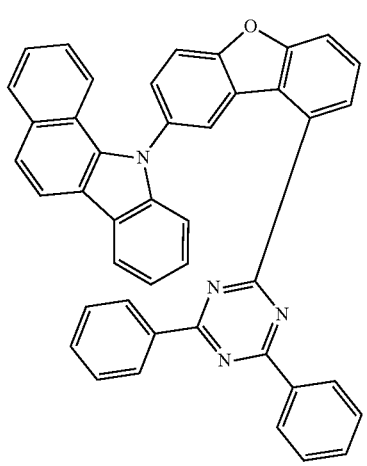
208

301
209
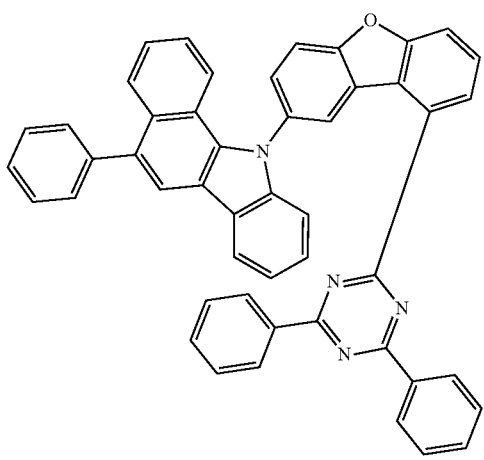
210
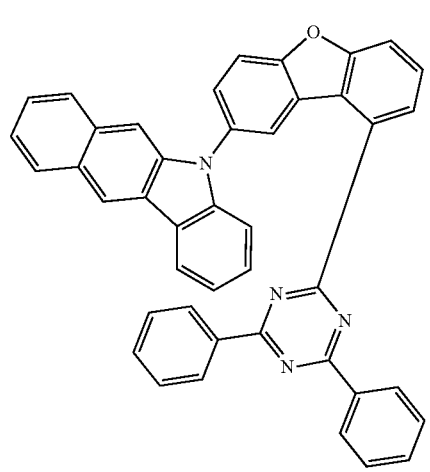
211
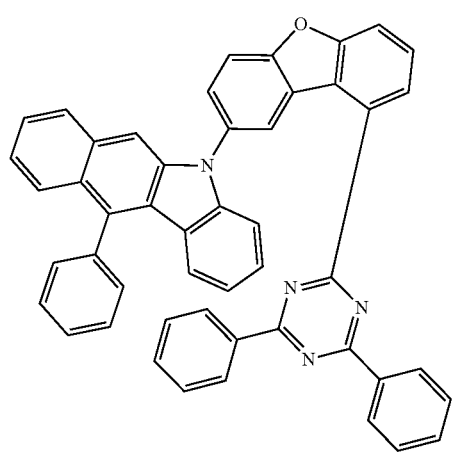
302
212
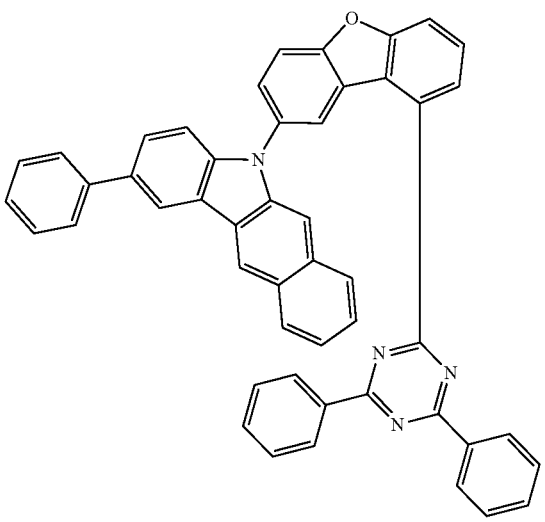
213
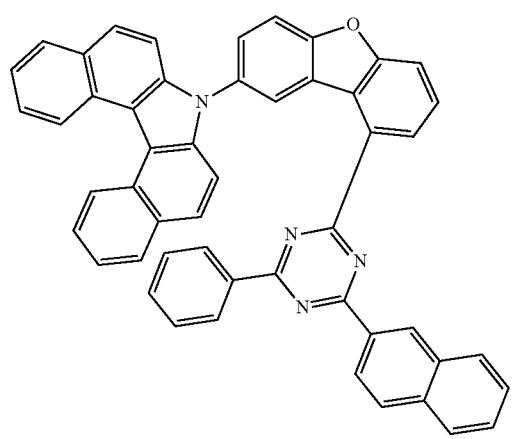
214
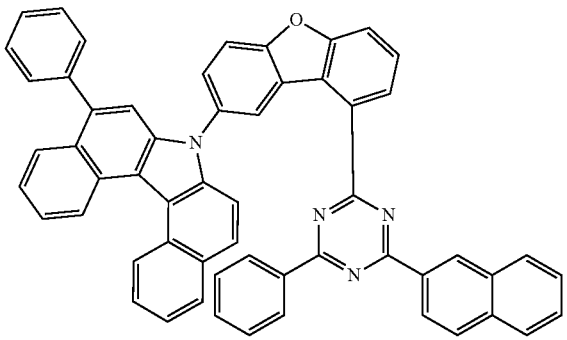

-continued
215
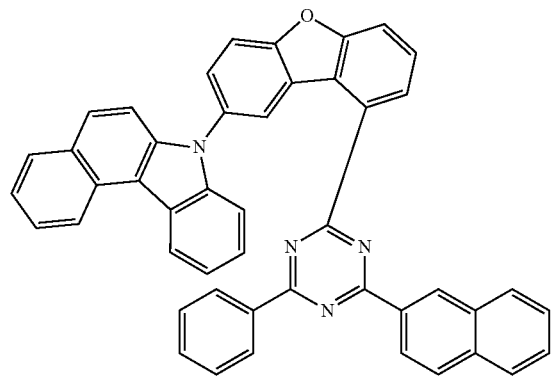
216
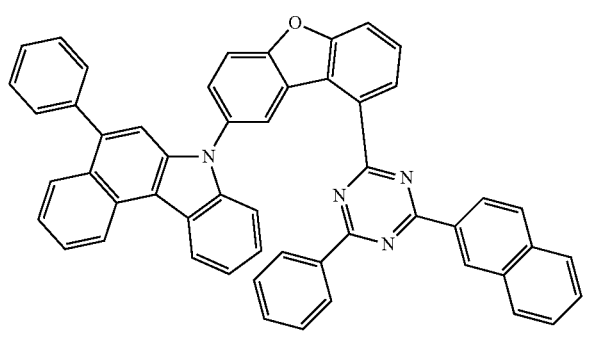
217
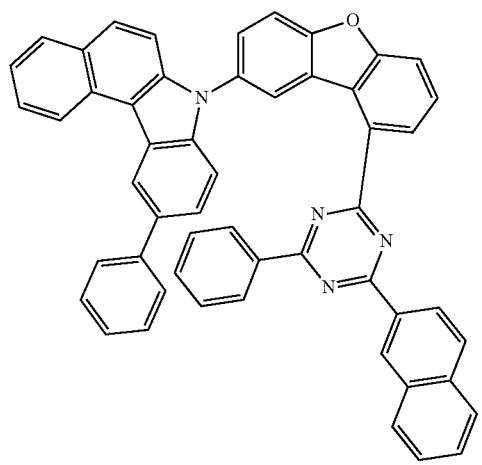
218
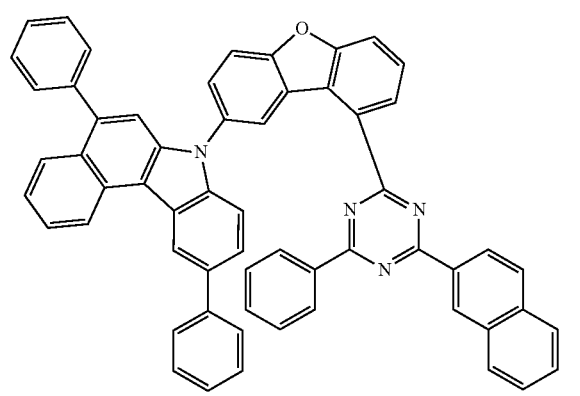
-continued
219
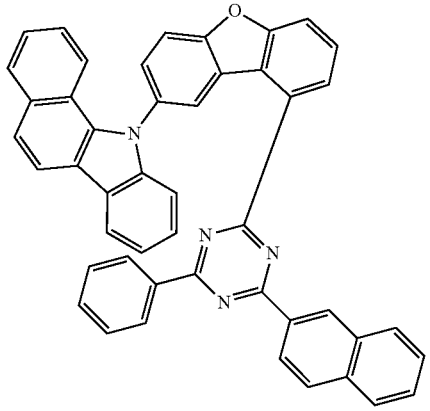
220
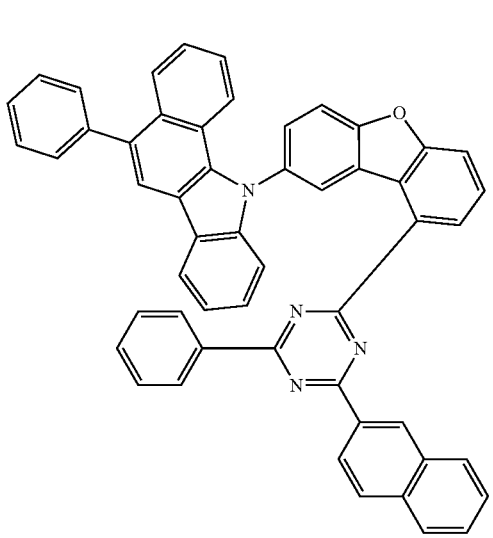
221
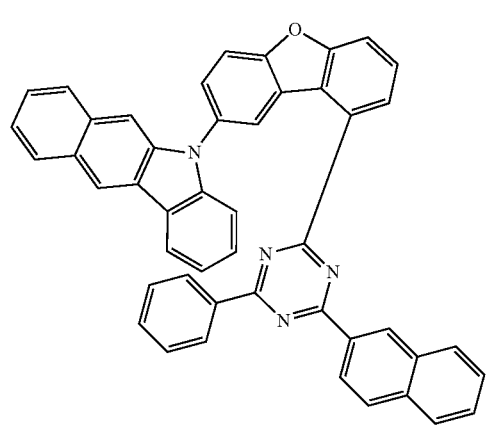

222
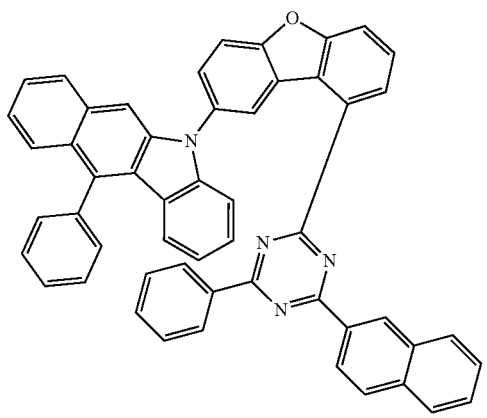
225
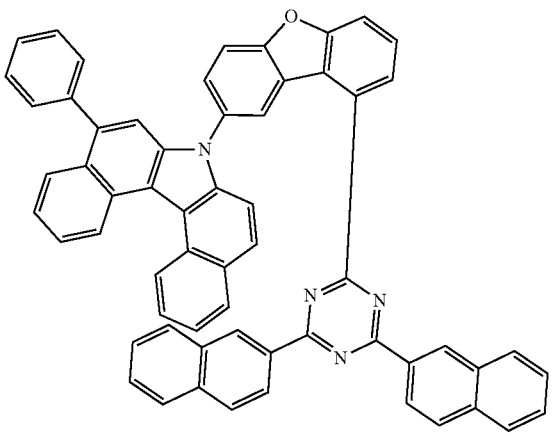
223
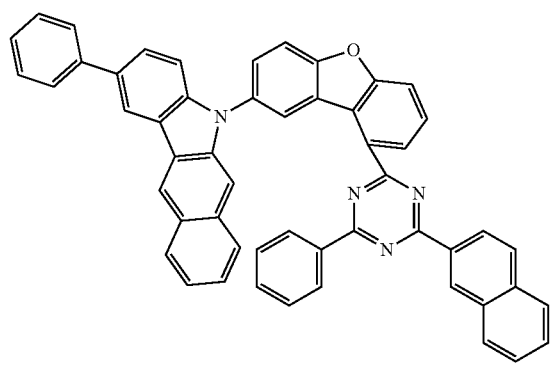
226
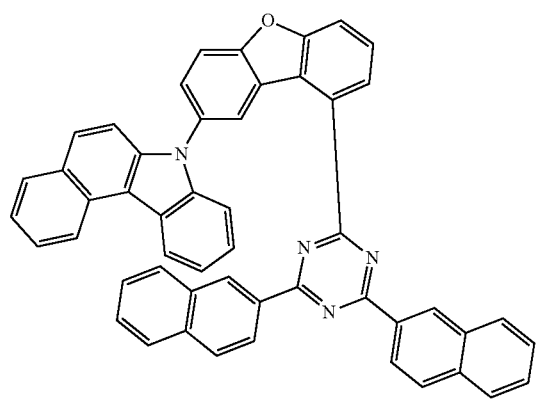
224
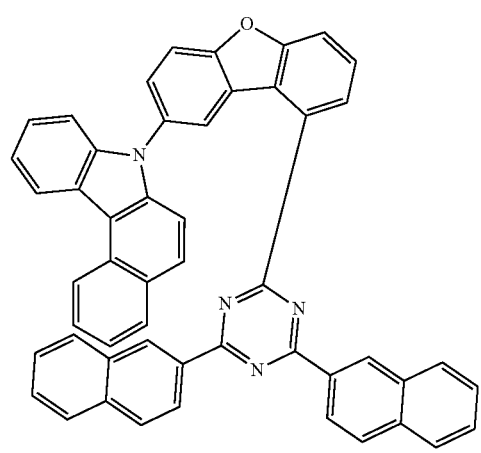
227
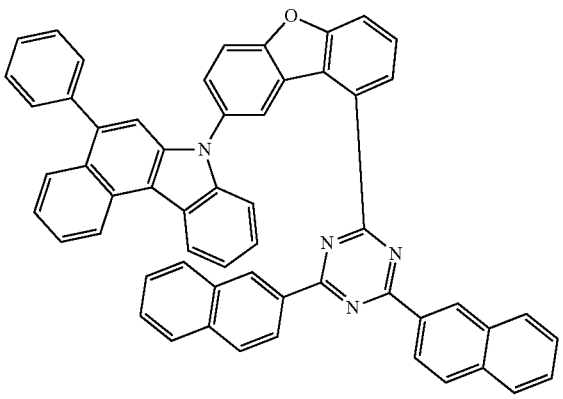

228
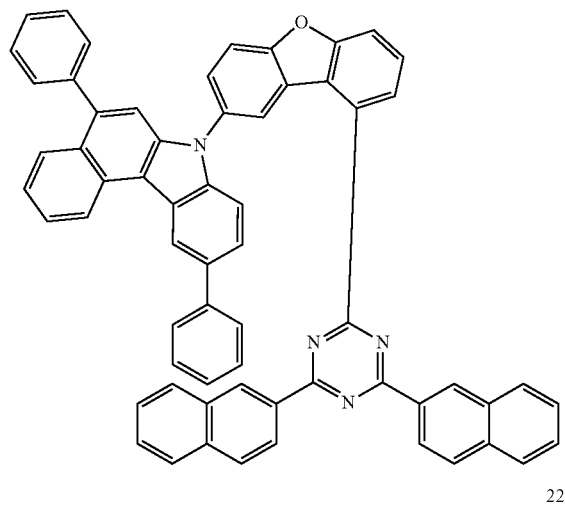
229
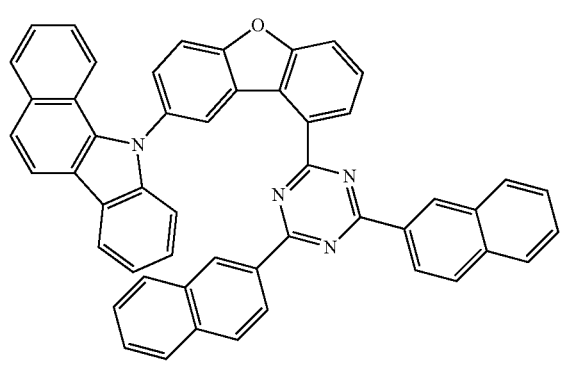
230
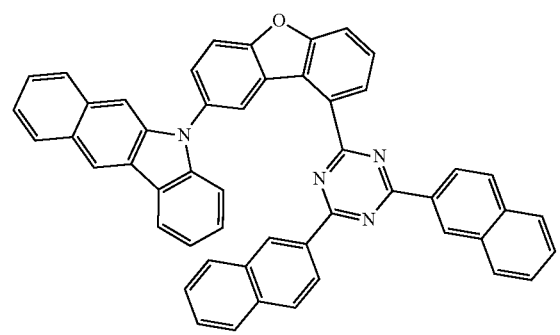
231
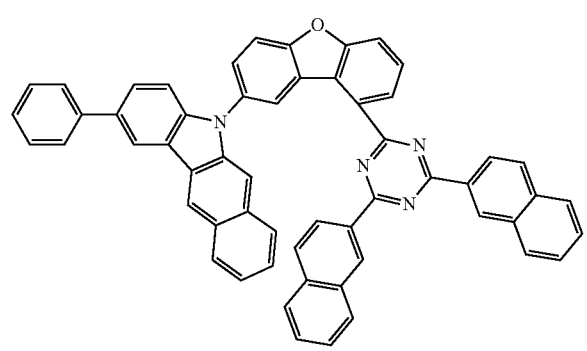
232
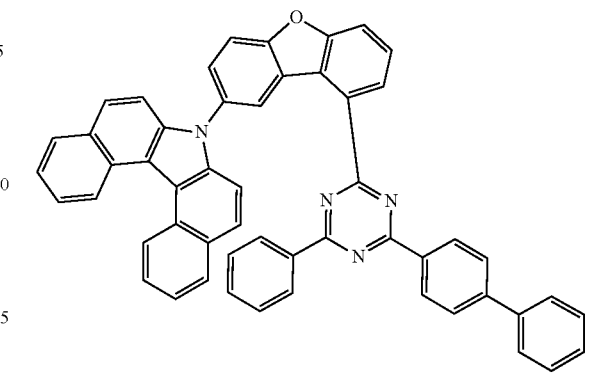
233
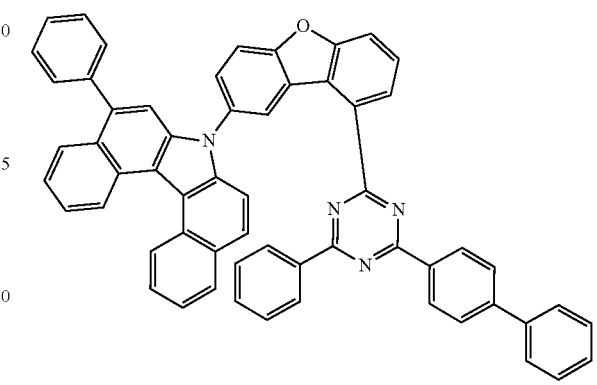
234
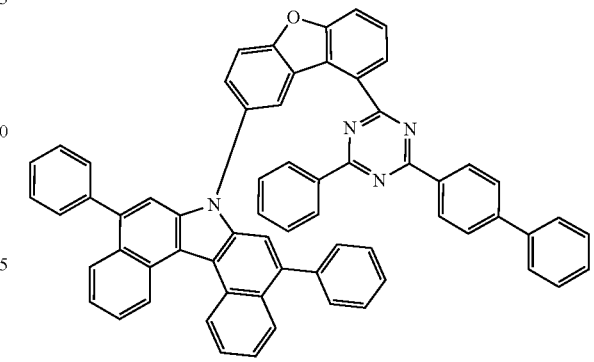
235
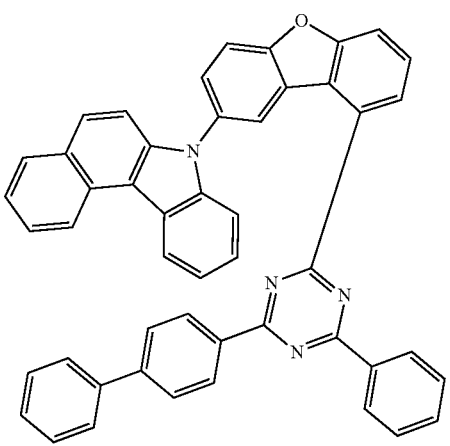

236
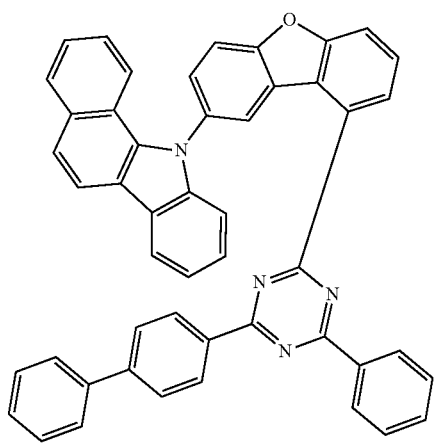
239
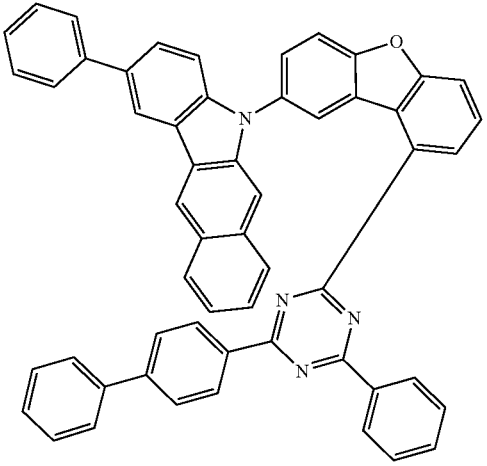
237
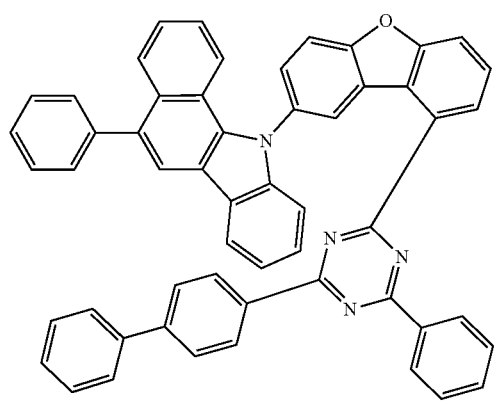
240
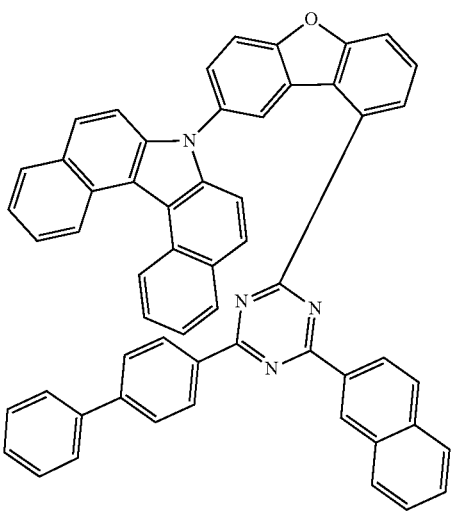
238
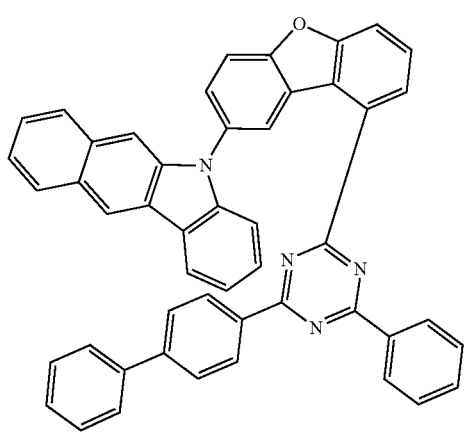
241
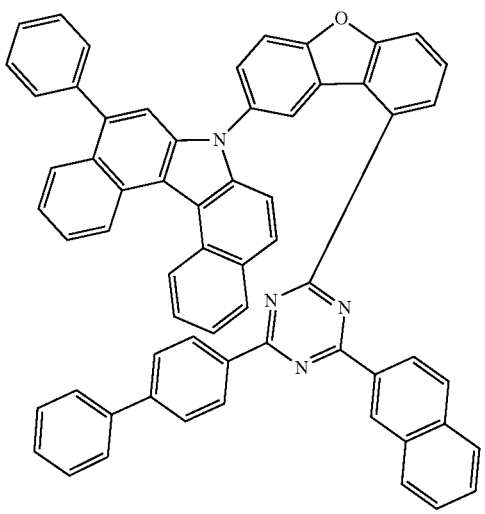

311
-continued
242
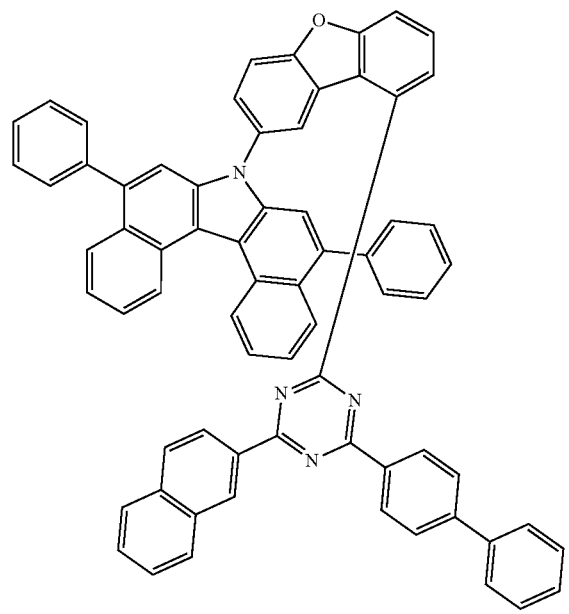
243
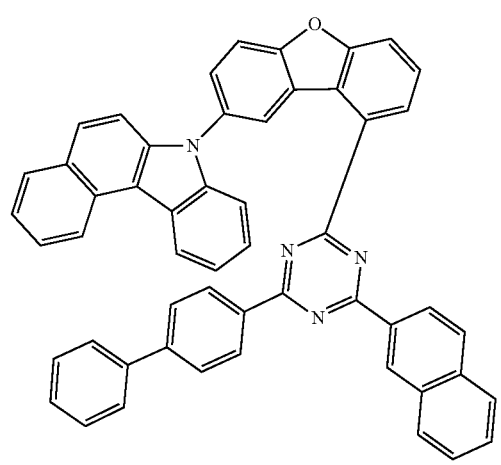
244
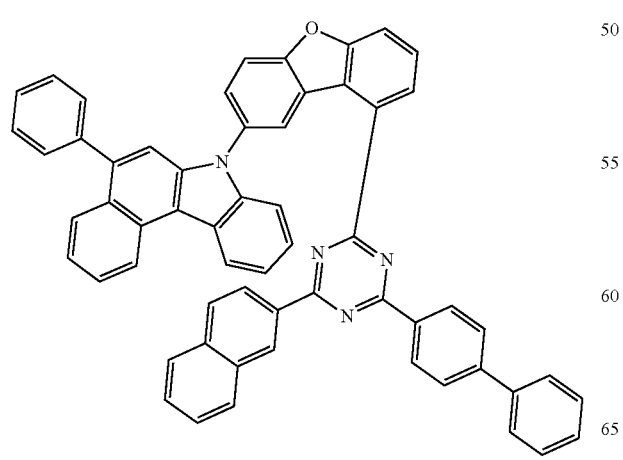
312
-continued
245
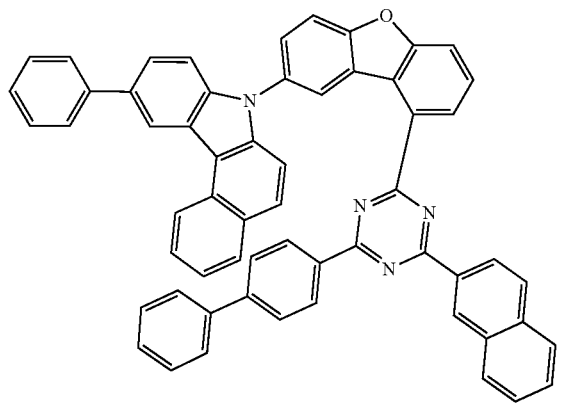
246
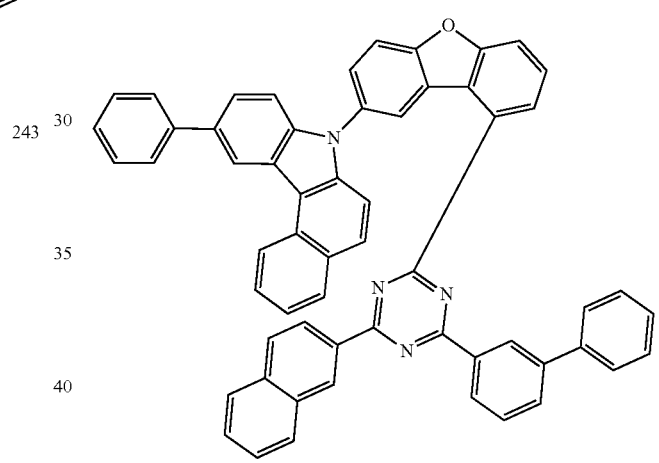
247
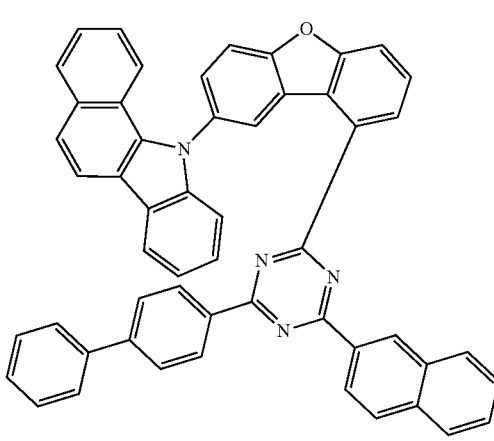

-continued
248
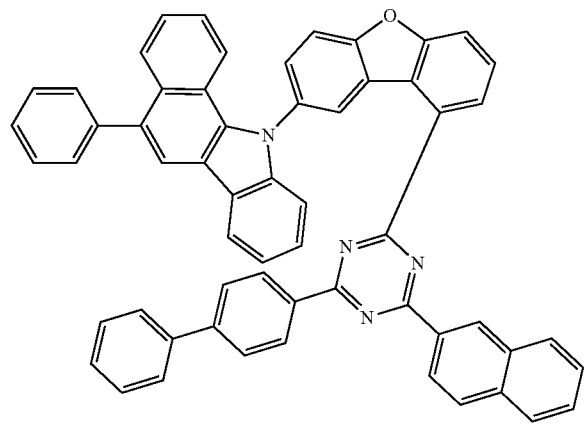
249
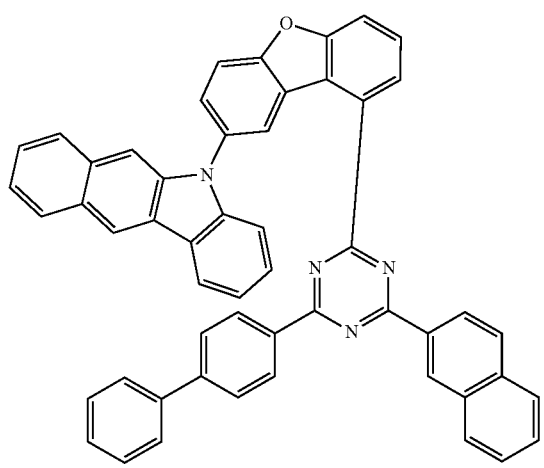
250
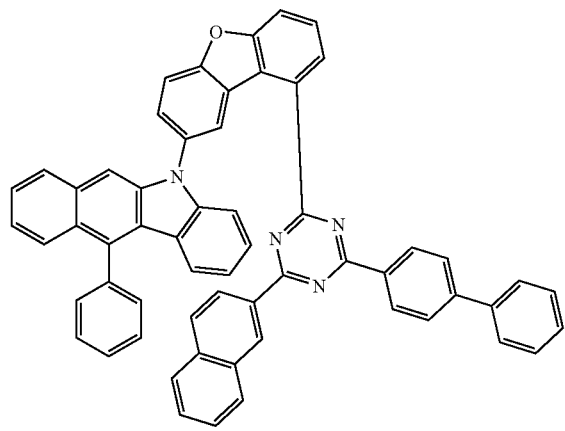
-continued
251
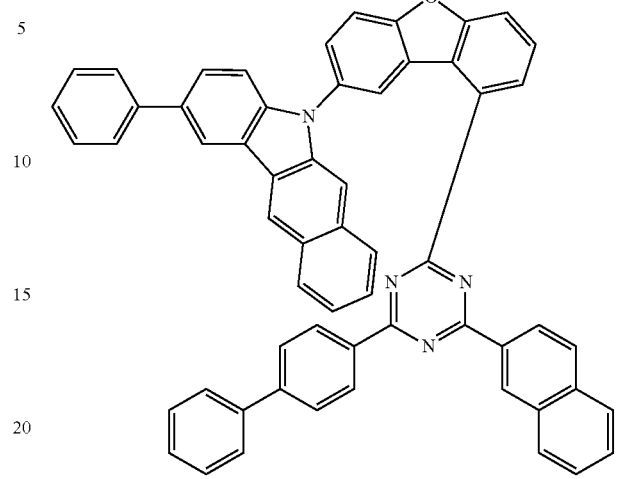
252
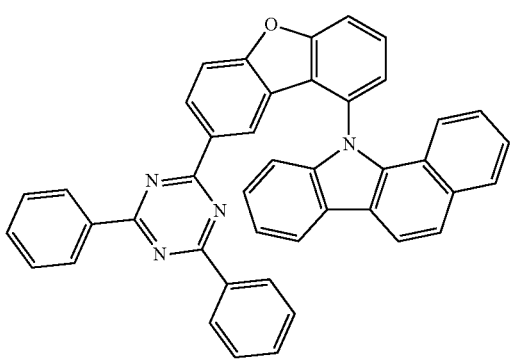
253
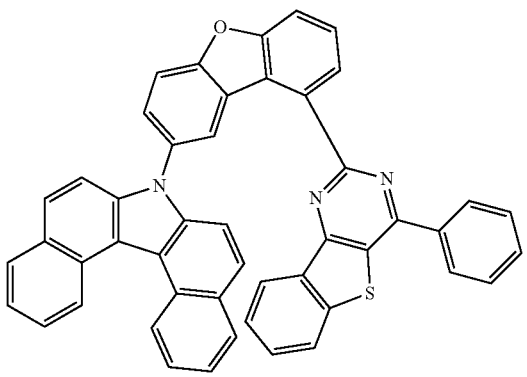

254
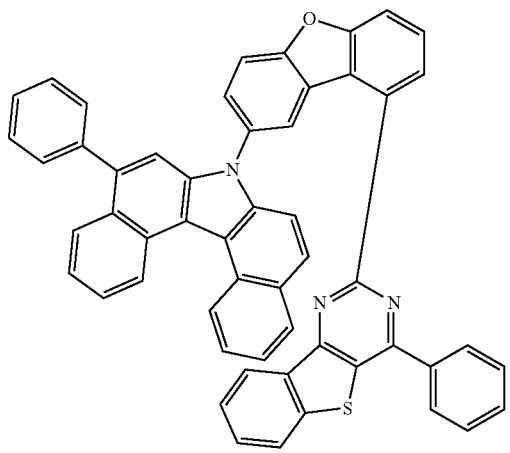
255
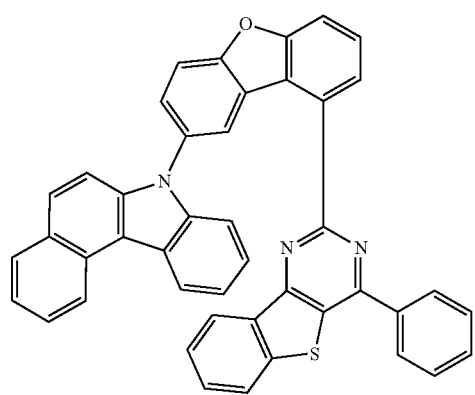
256
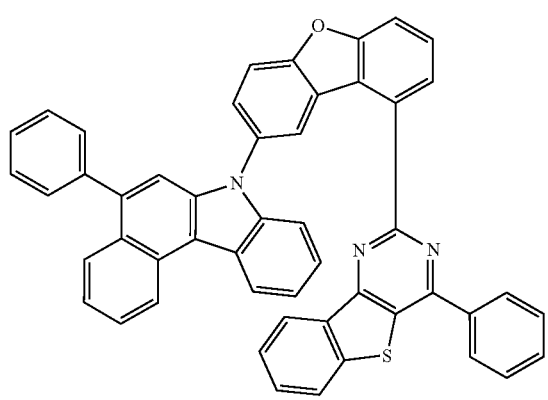
257
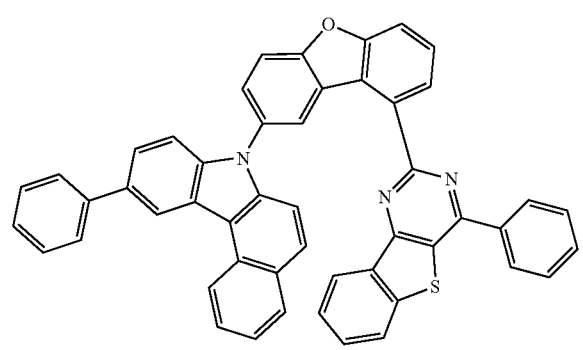
258
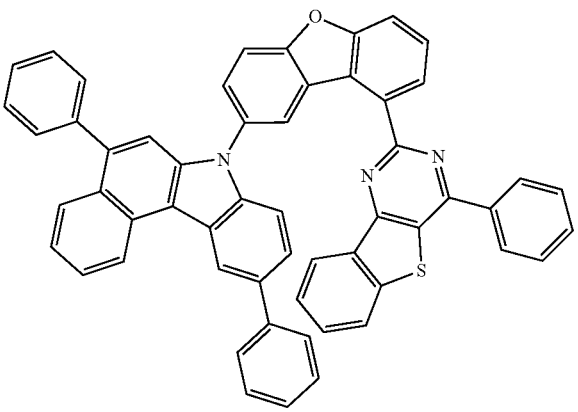
259
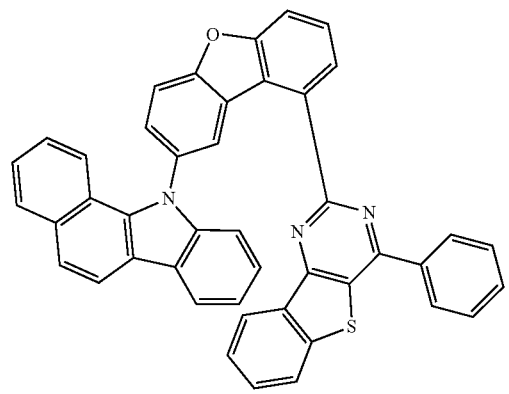
260
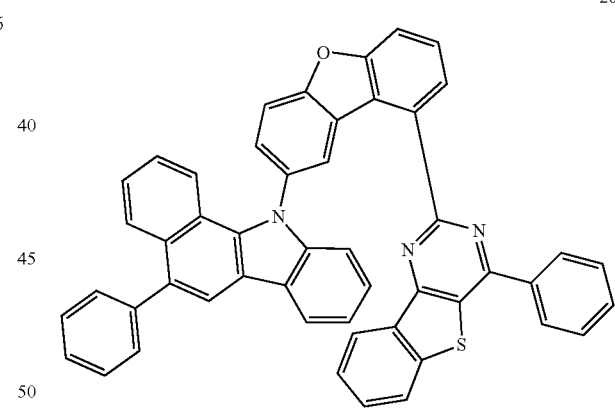
261
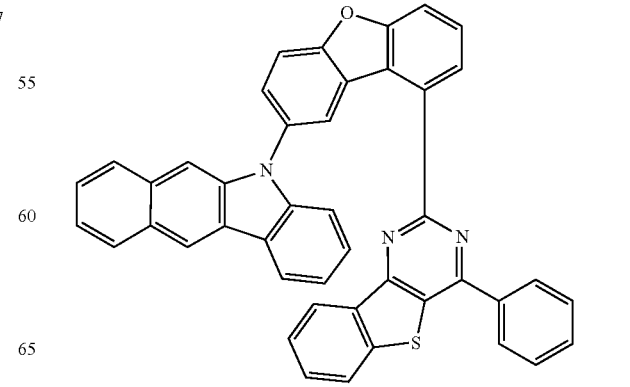

262
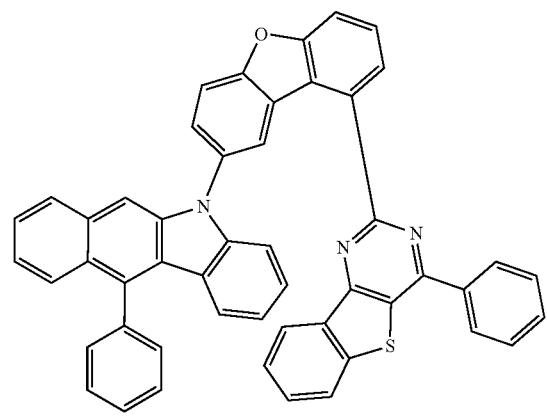
263
266
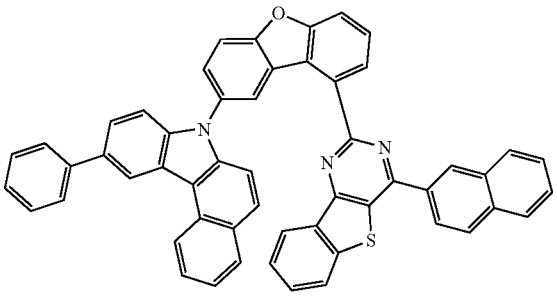
267
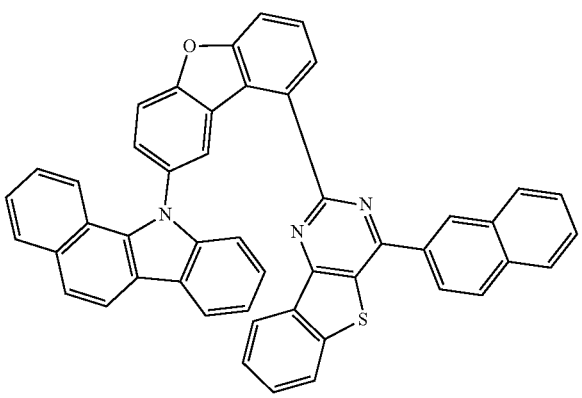
264
268
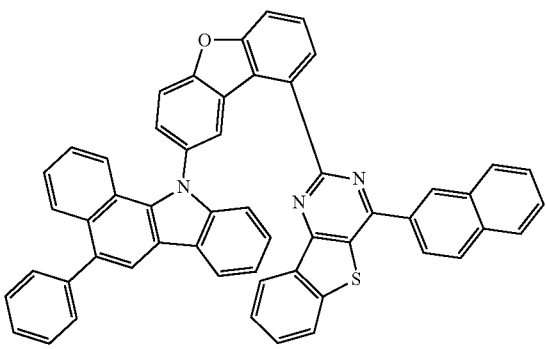
265
269
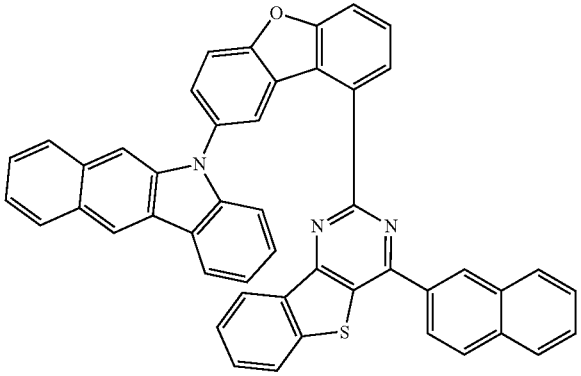

270
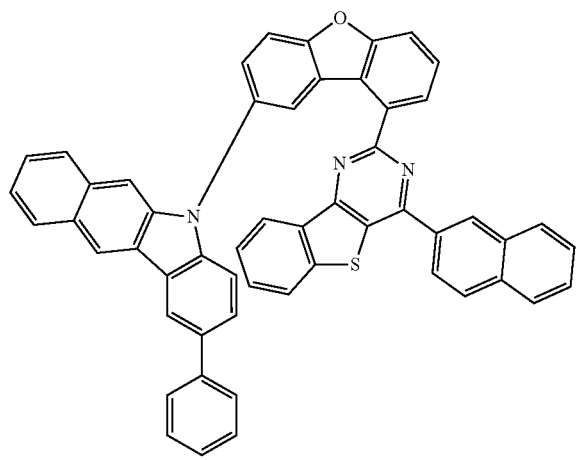
271
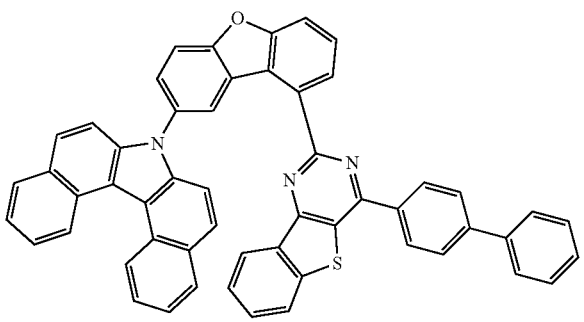
272
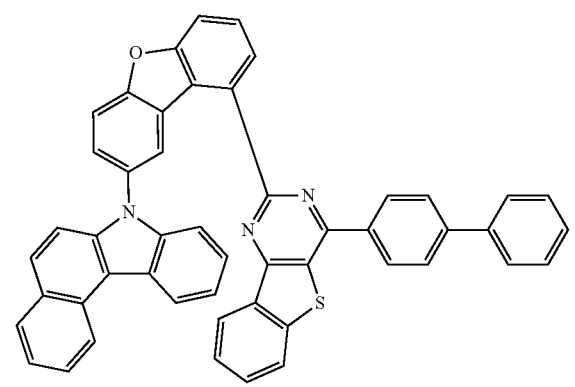
273
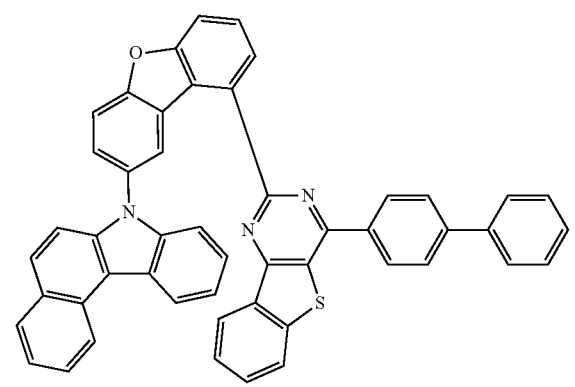
274
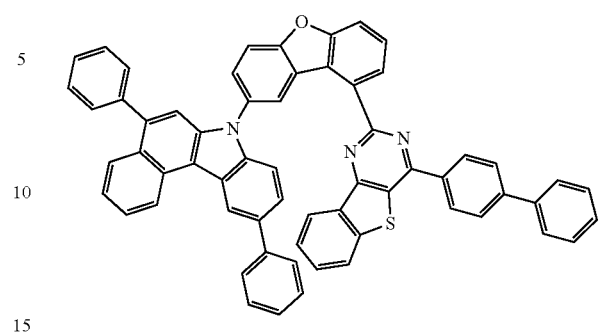
275
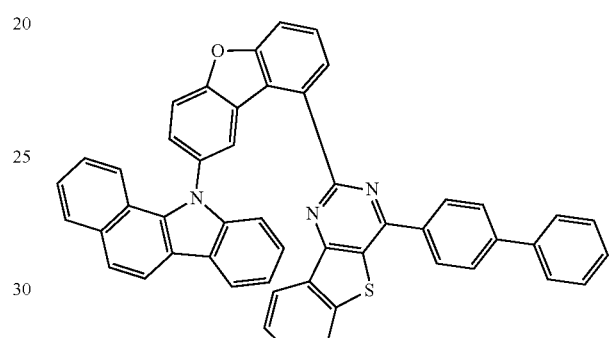
276
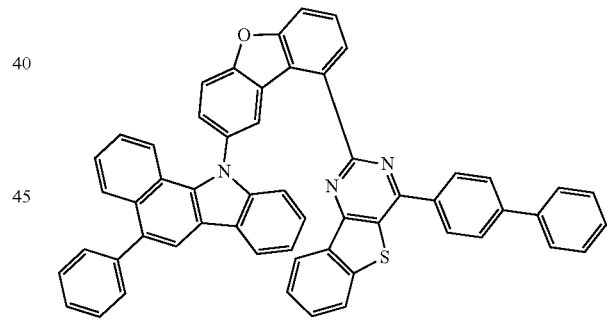
277
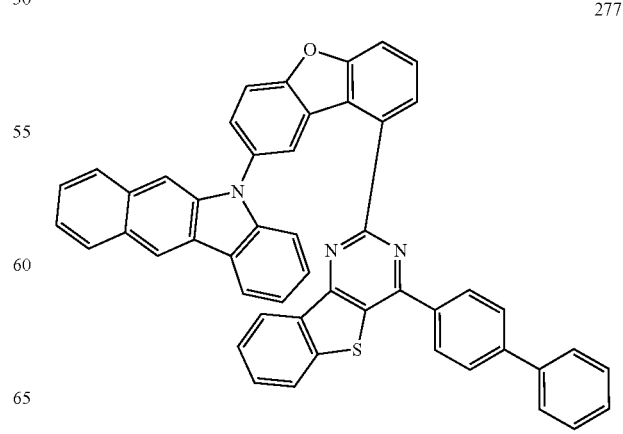

-continued
278
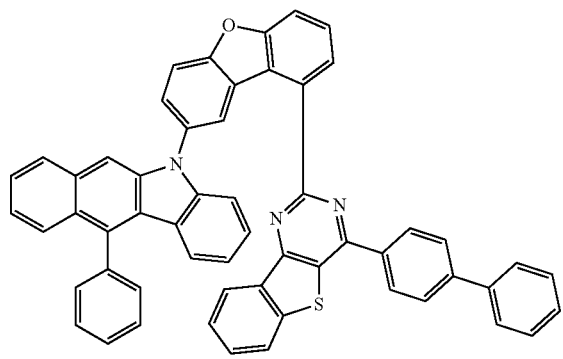
279
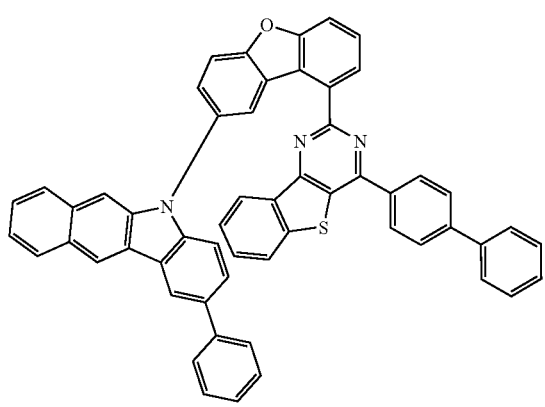
280
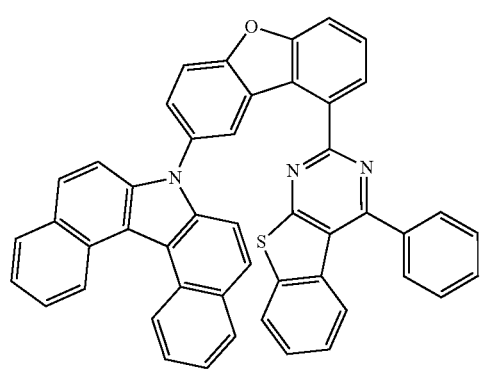
281
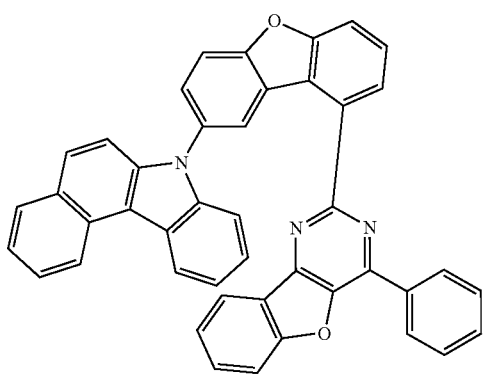
-continued
282
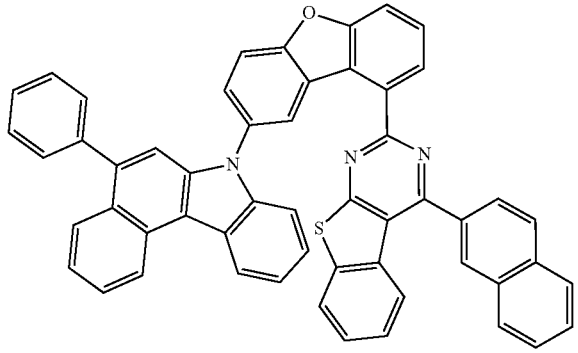
283
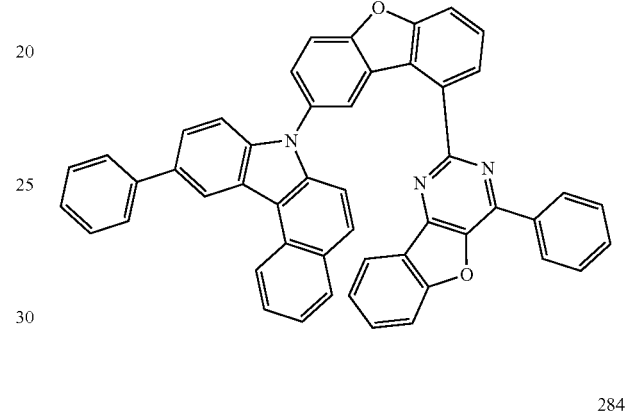
284
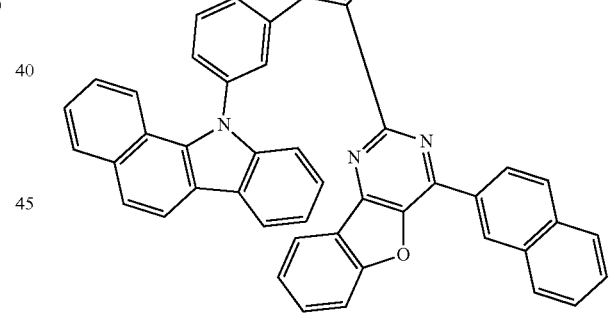
285
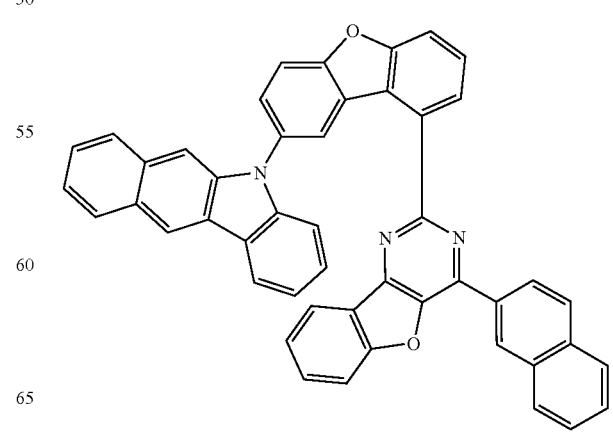

286
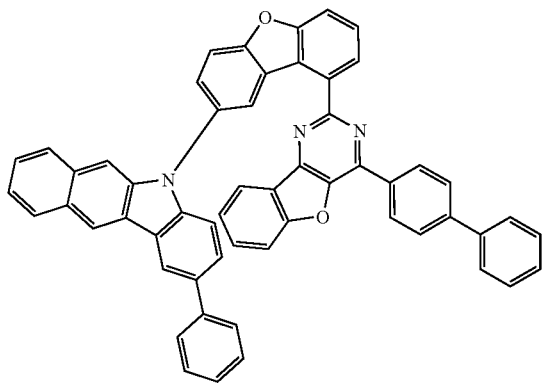
287
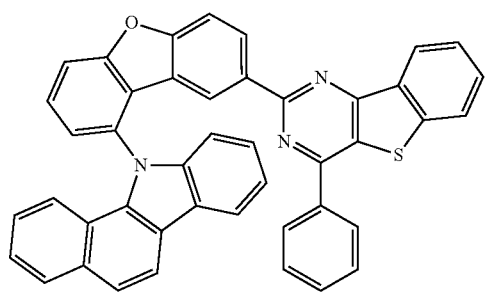
288
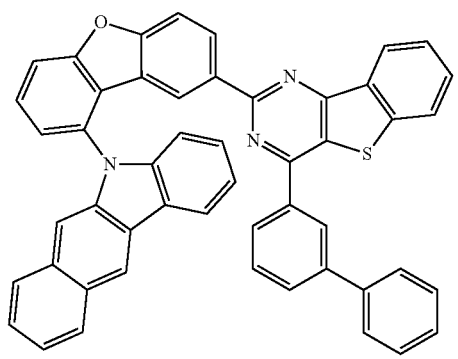
289
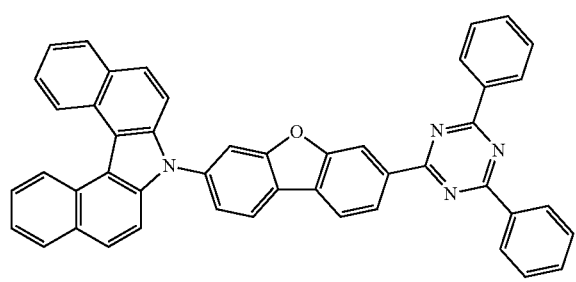
290
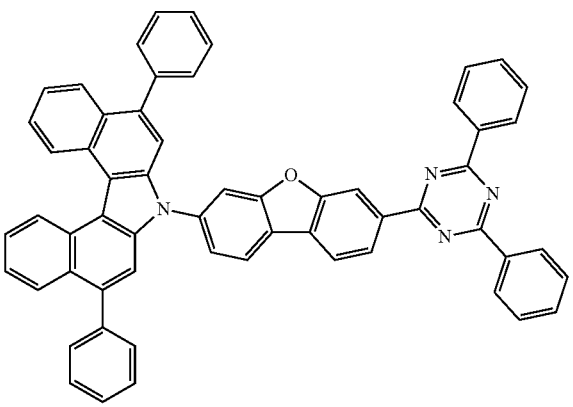
291
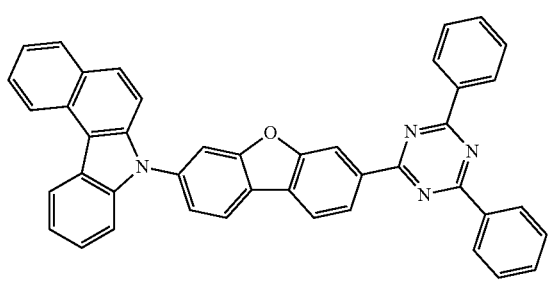
292
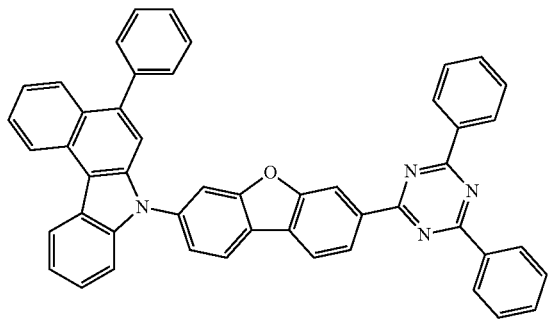
293
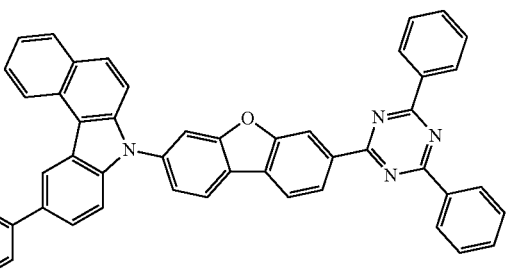

294
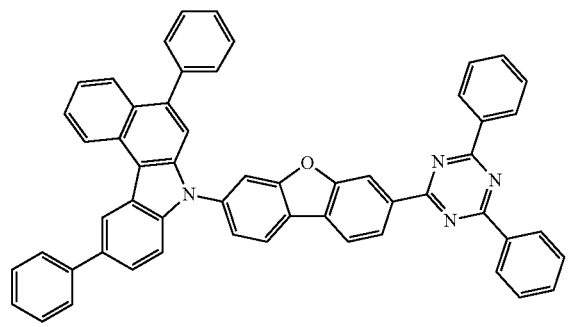
295
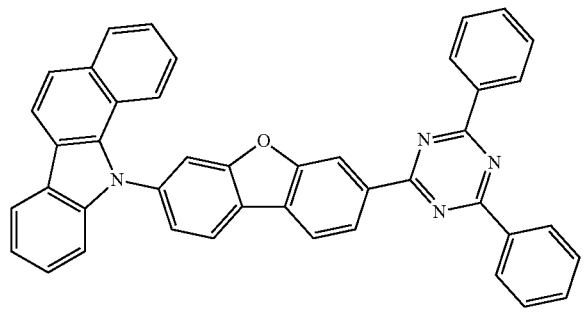
296
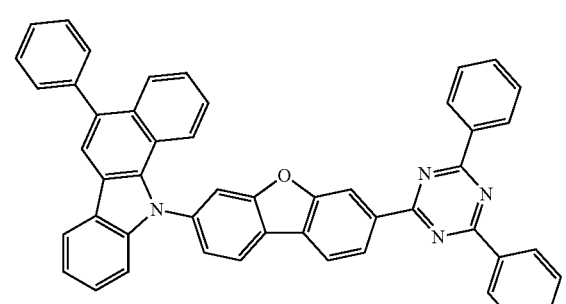
297
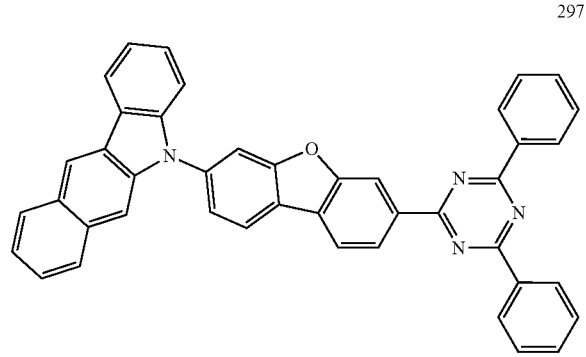
298
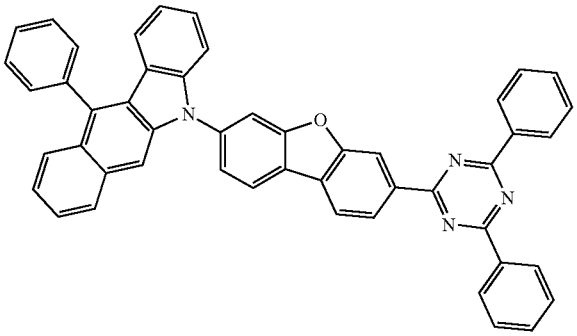
299
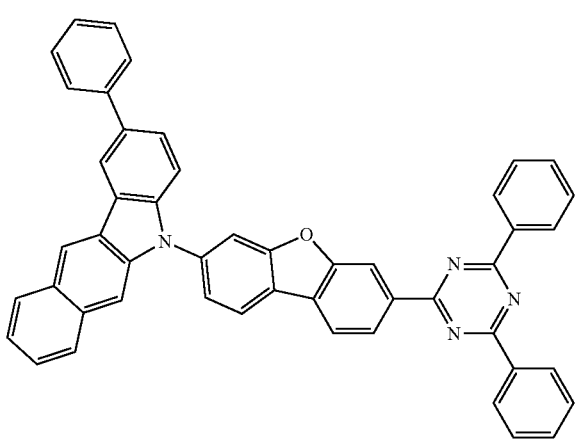
300
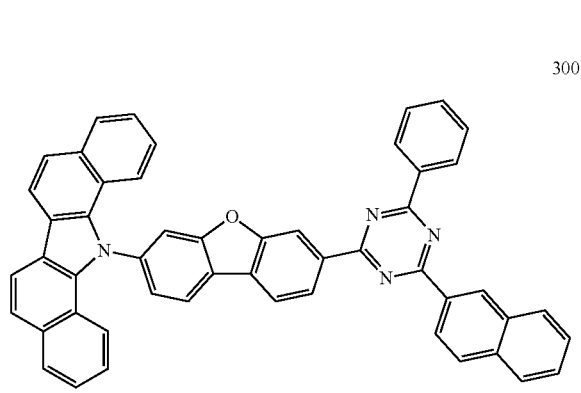
301
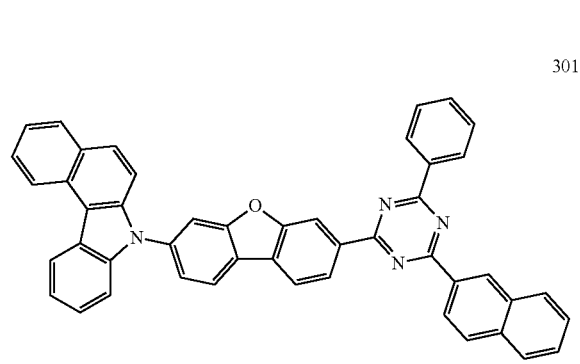

327
-continued
302
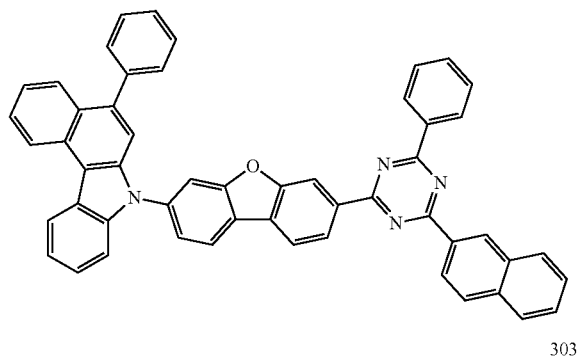
303
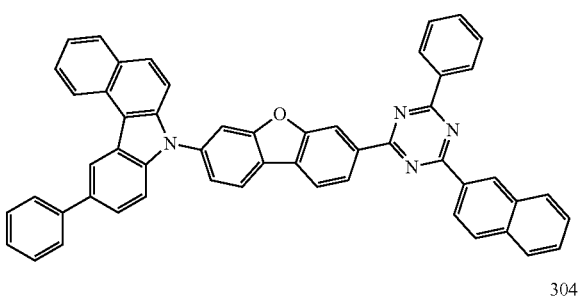
304
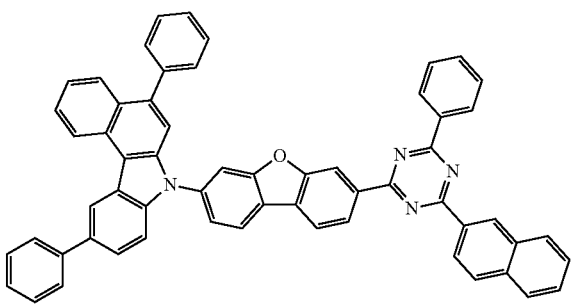
305
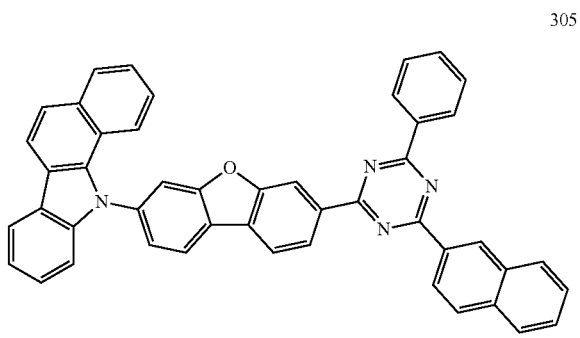
306
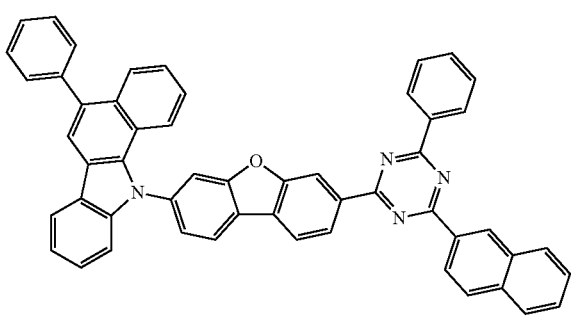
328
-continued
307
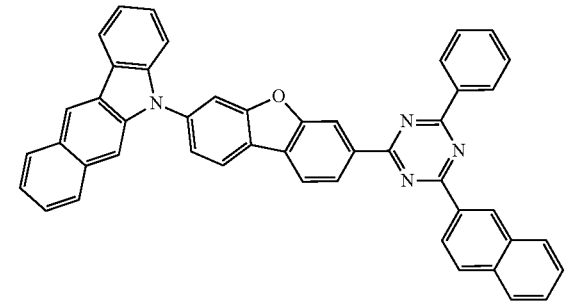
308
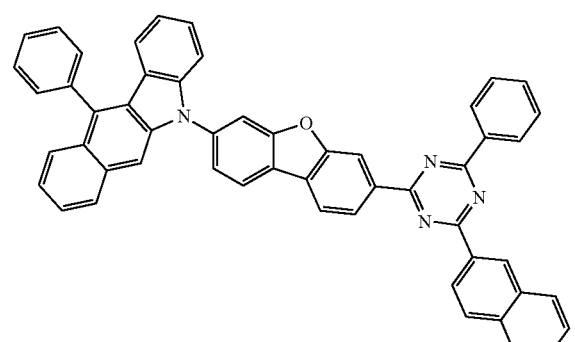
309
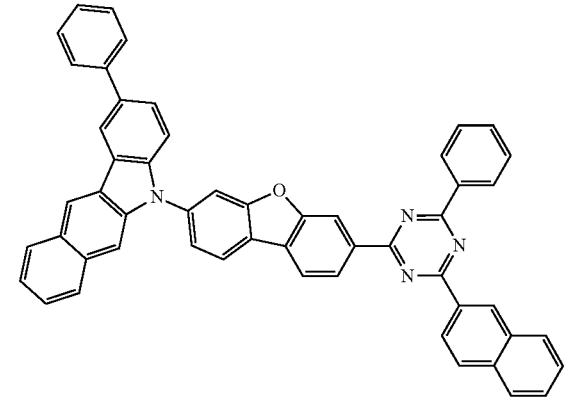
310
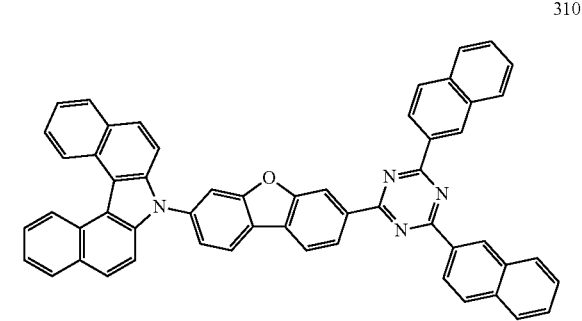

311
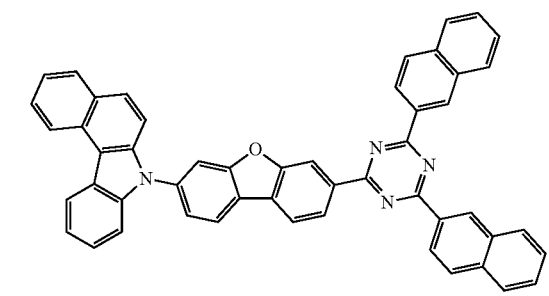
312
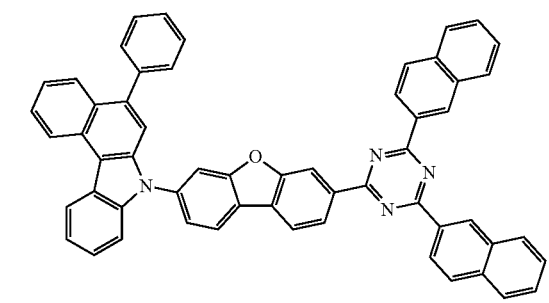
313
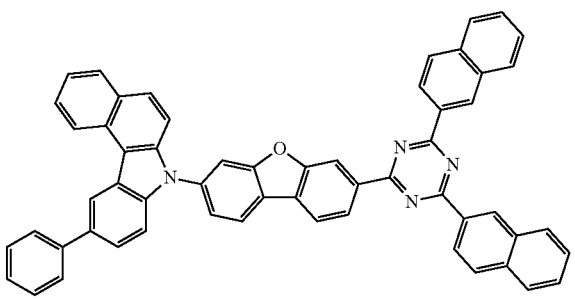
314
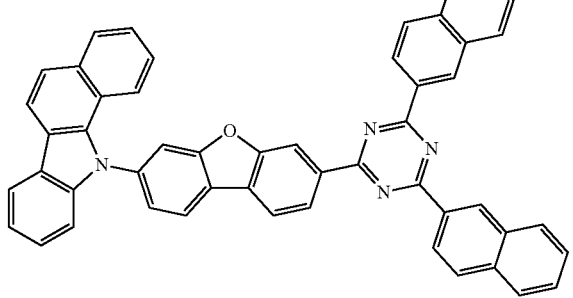
315
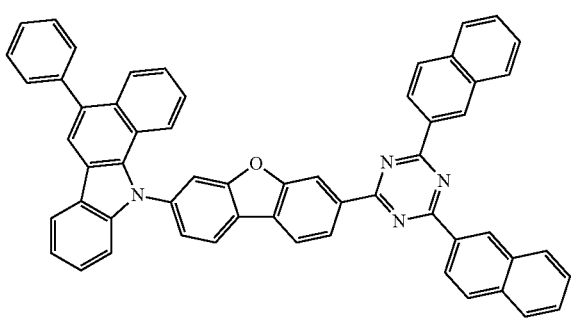
316
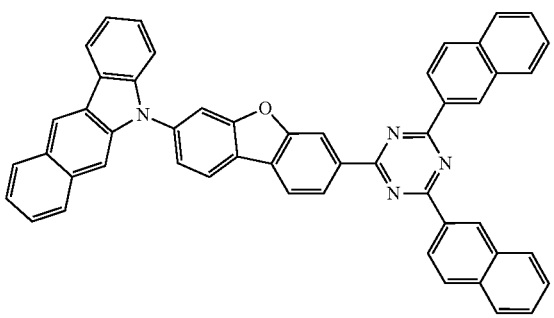
317
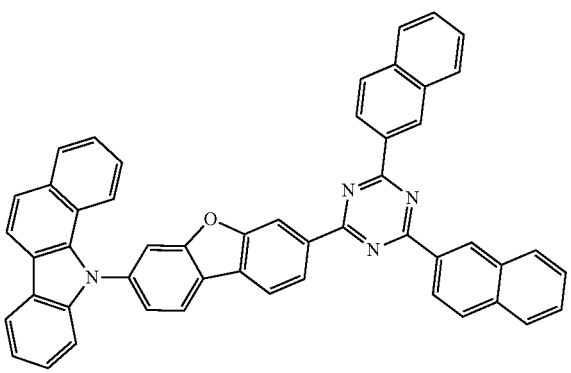
318
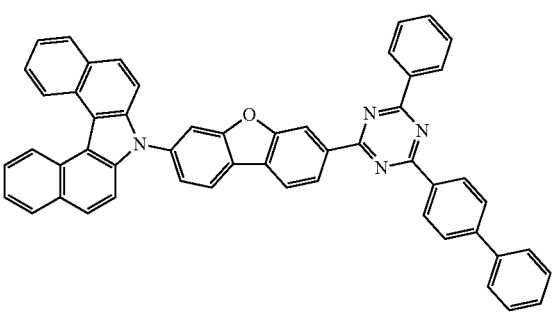
319
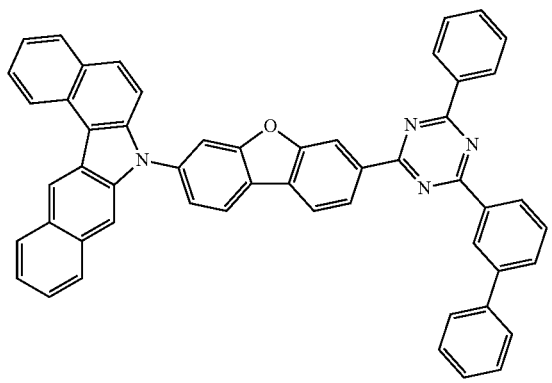

-continued
320
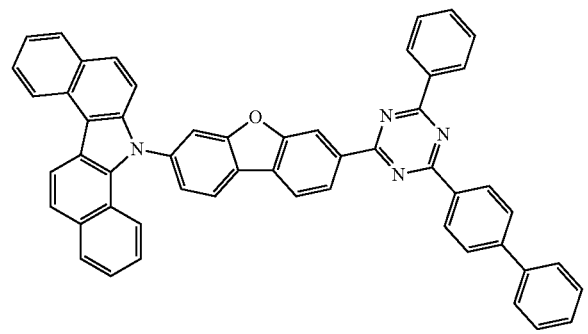
321
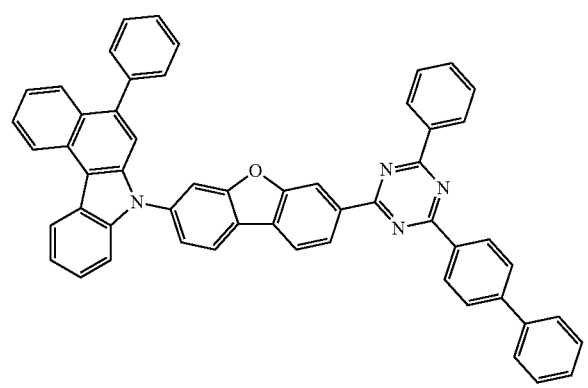
322
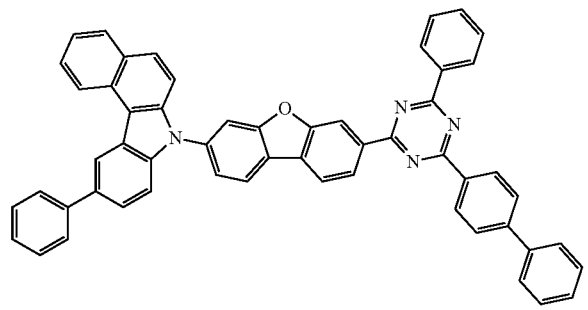
323
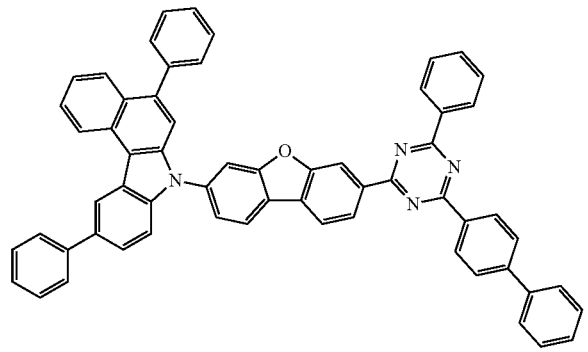
-continued
324
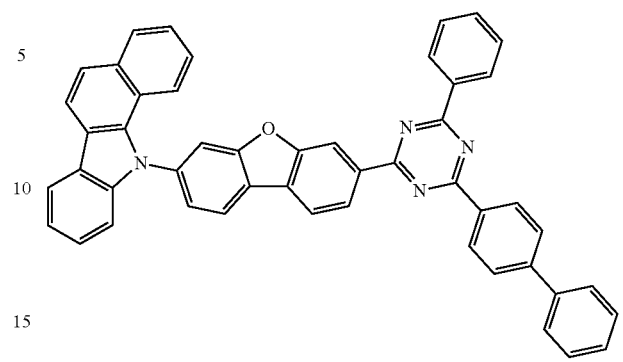
325
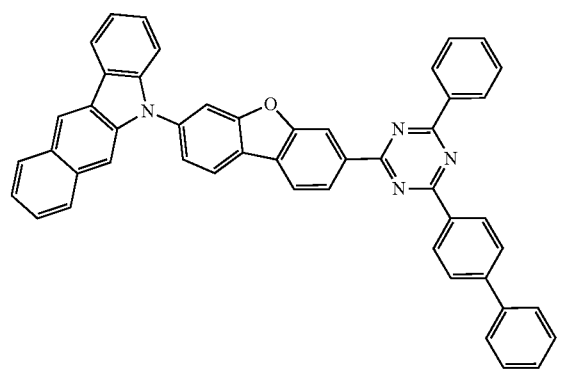
326
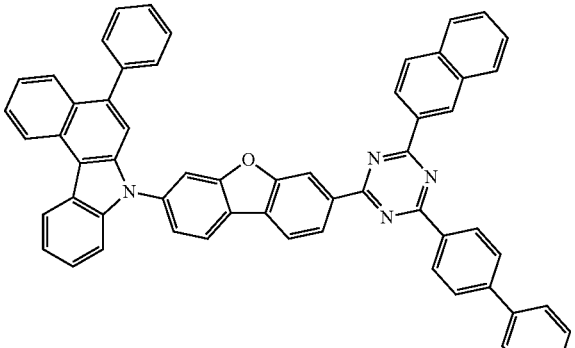
327
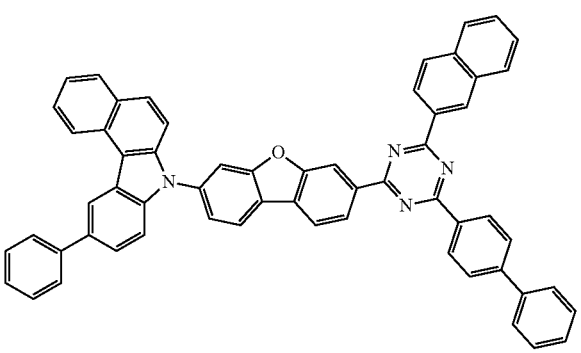

333 -continued
328
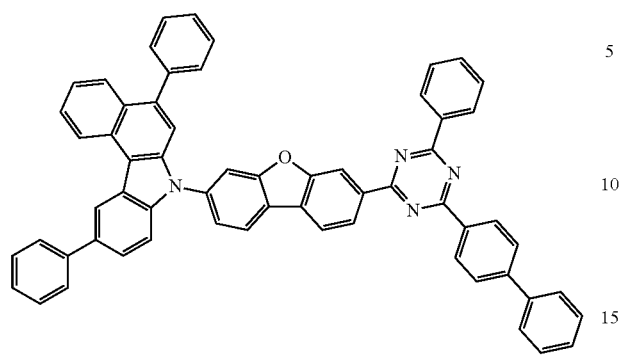
329
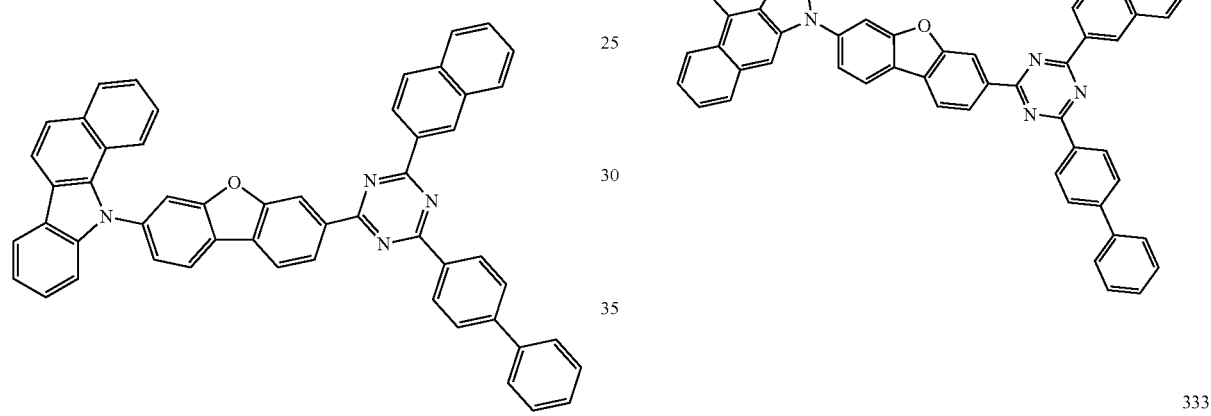
330
334 -continued
331
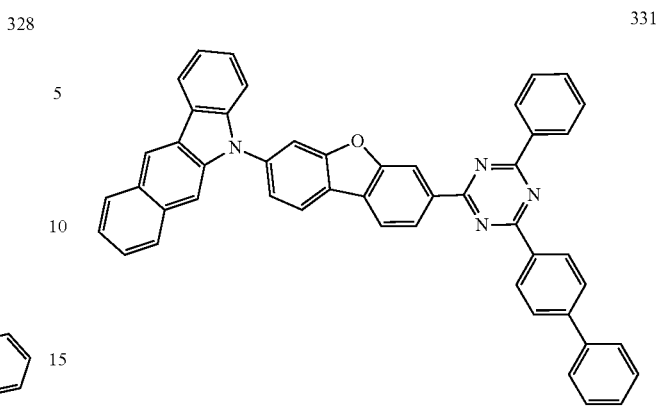
332
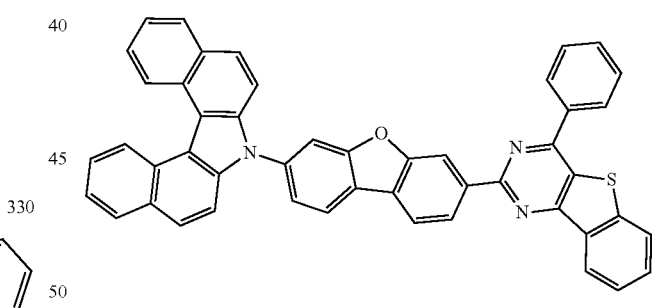
333
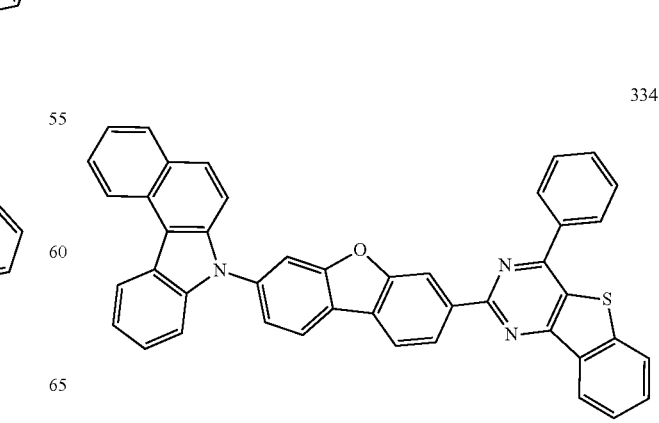
334

335
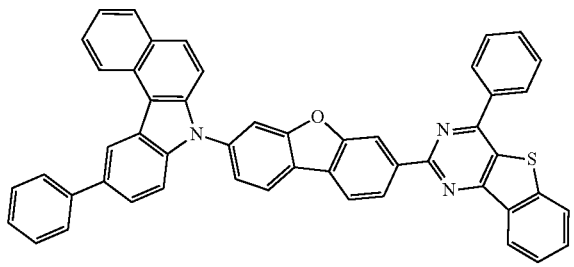
336
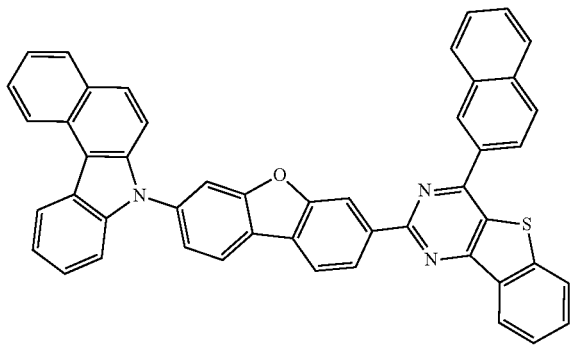
337
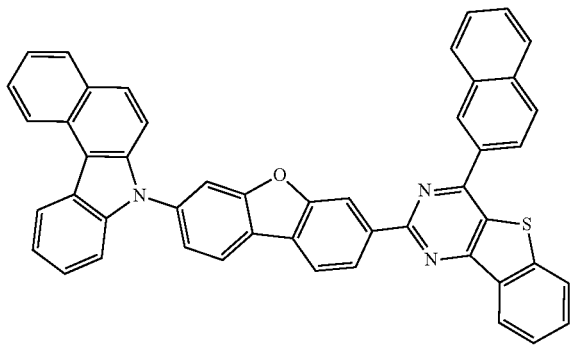
338
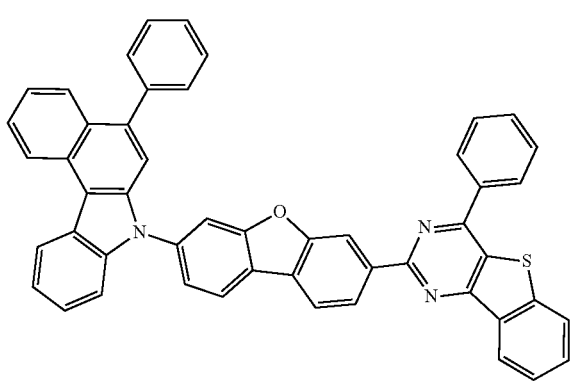
336
339
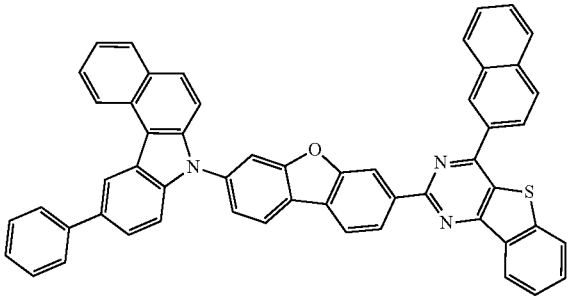
340
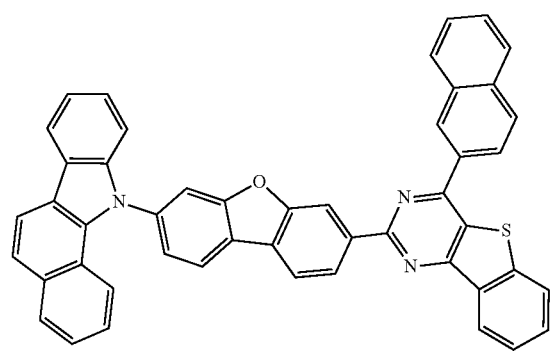
341
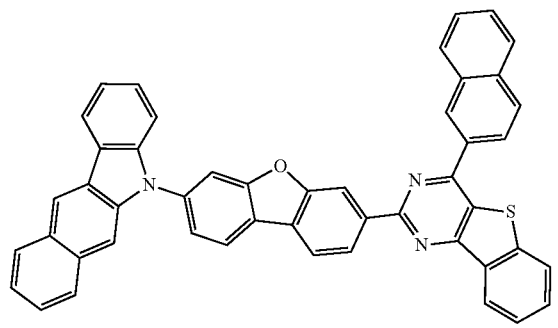
342
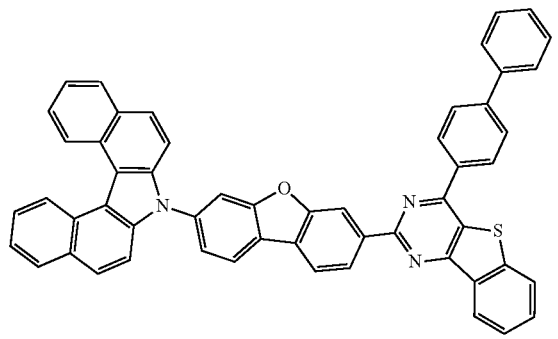

343
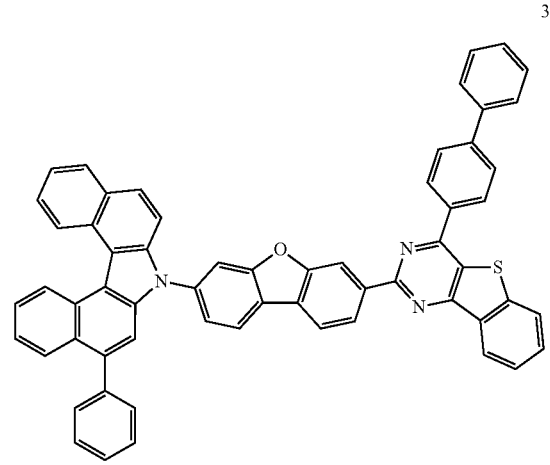
344
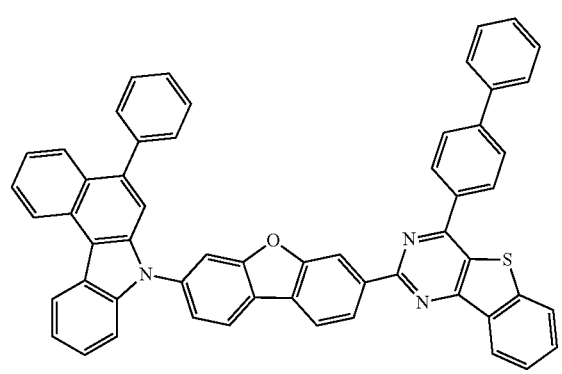
345
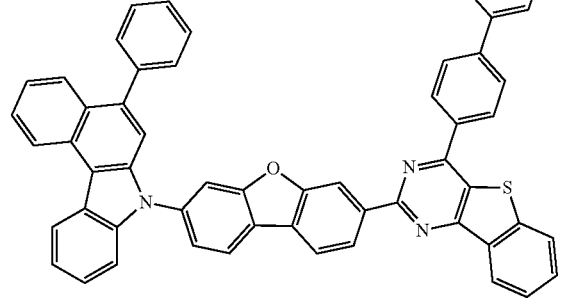
346
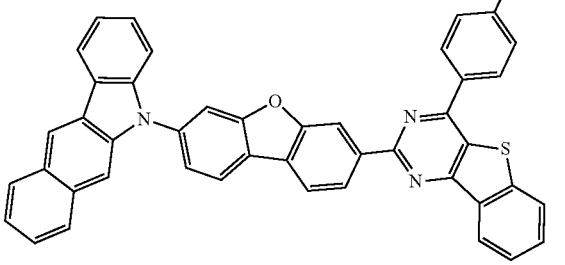
347
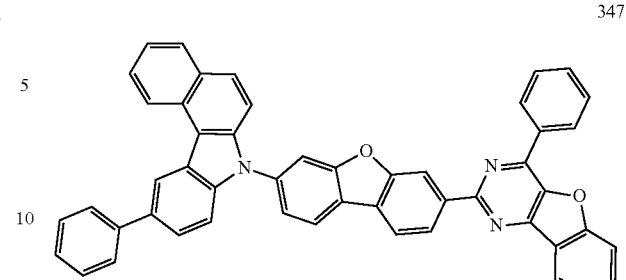
348
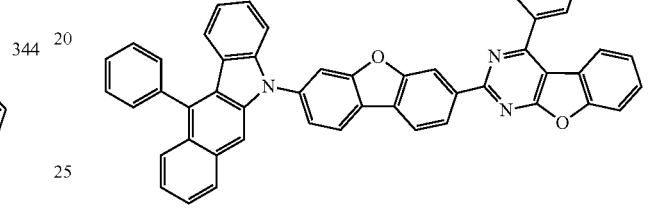
349
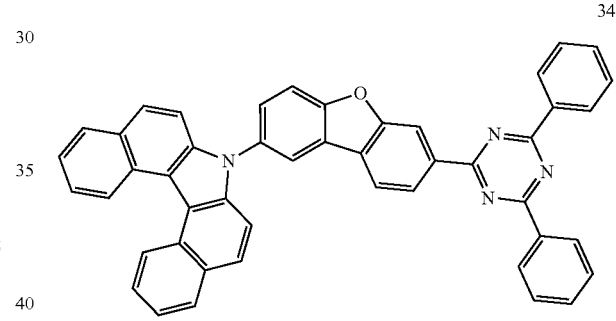
350
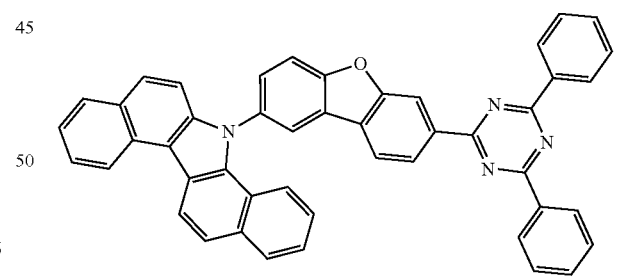
351
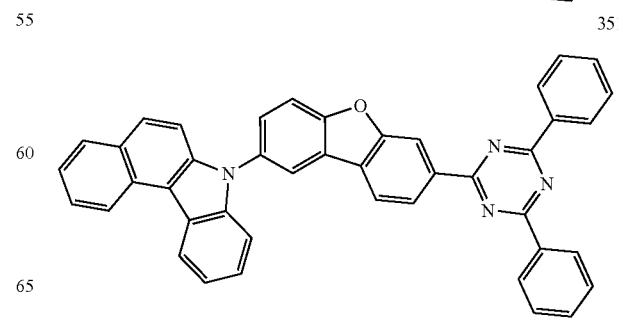

352
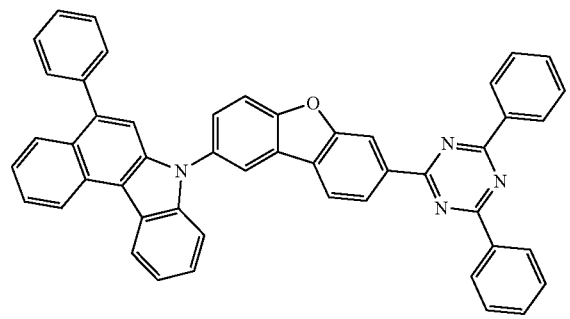
353
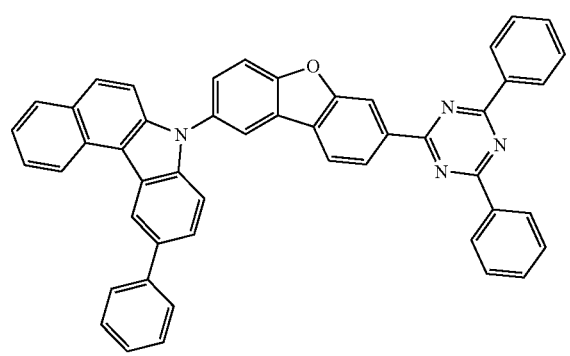
354
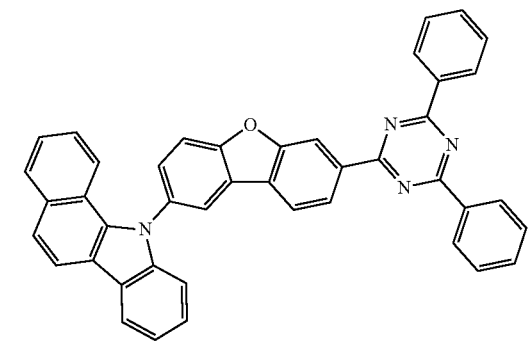
355
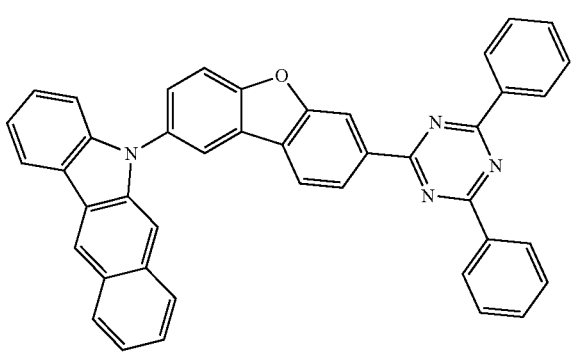
356
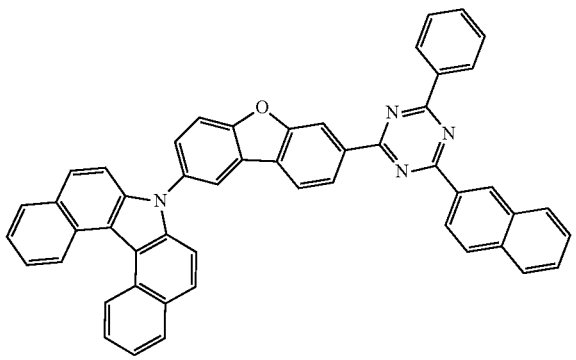
357
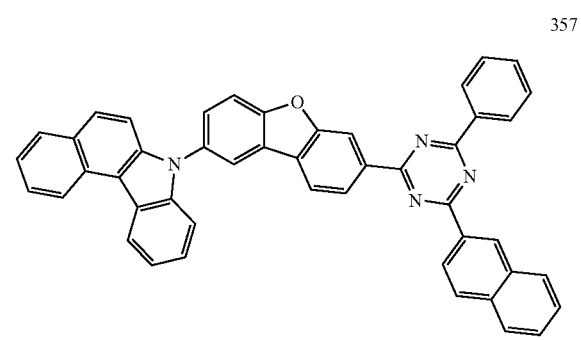
358
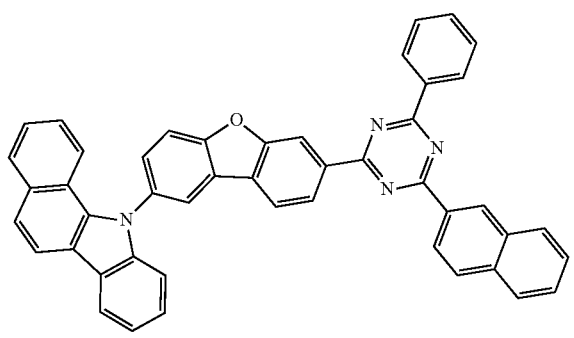
359
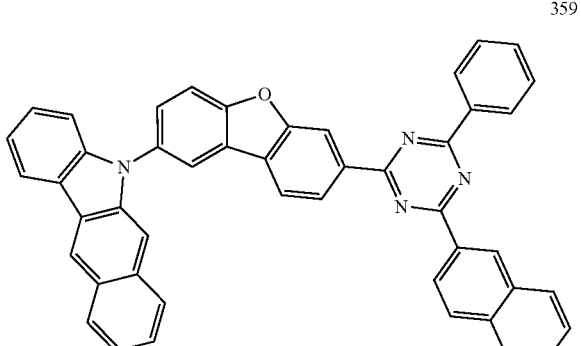

341
-continued
360
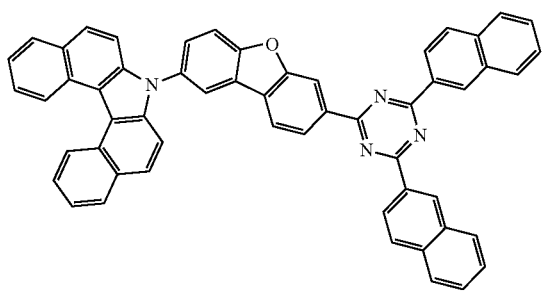
361
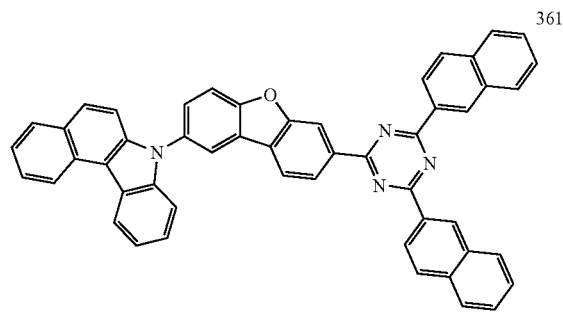
362
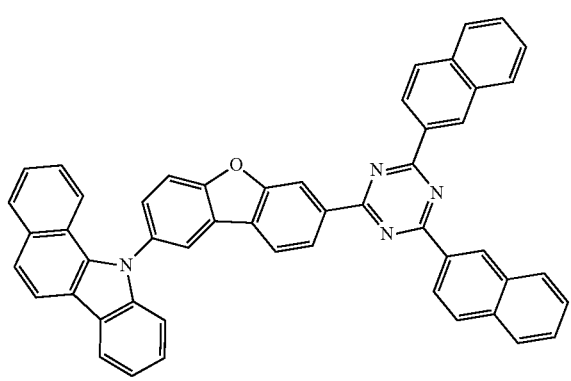
363
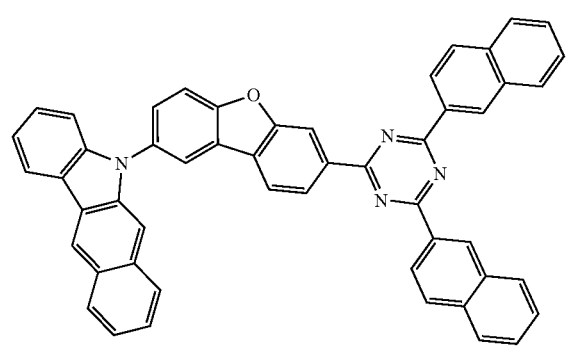
342
-continued
364
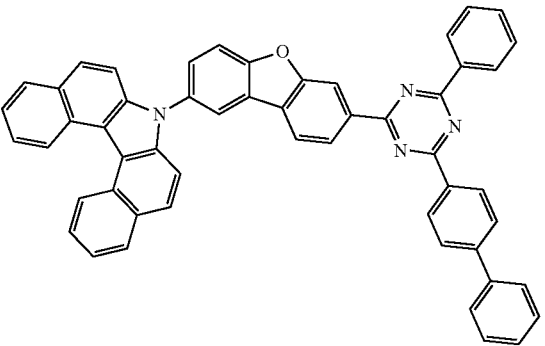
365
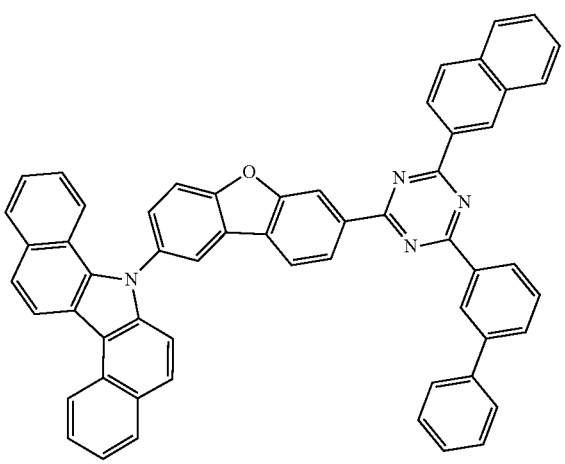
366
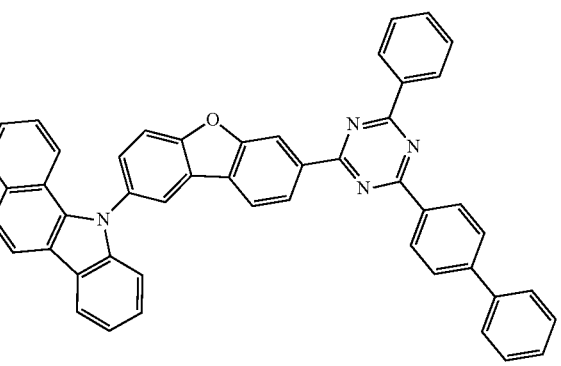
367
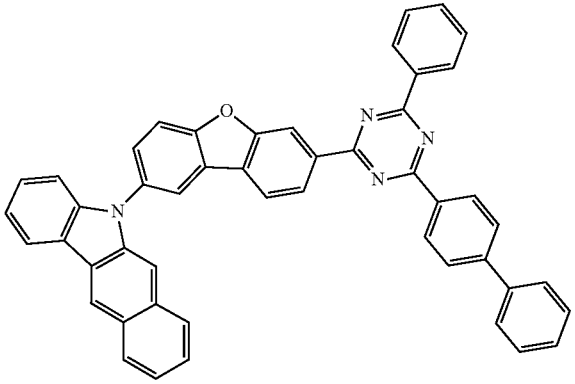

368
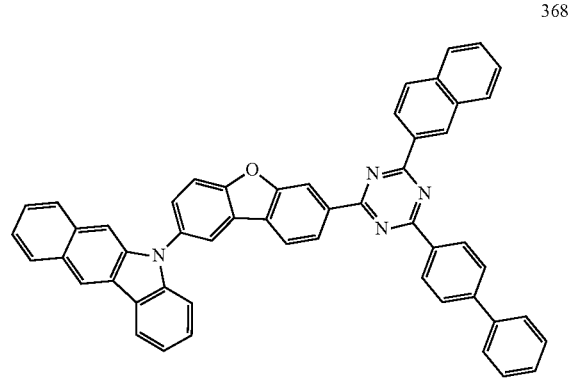
369
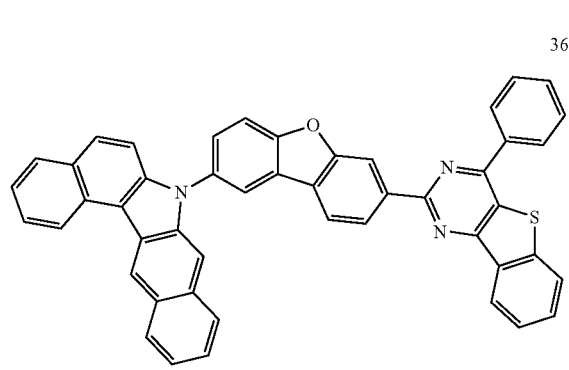
370
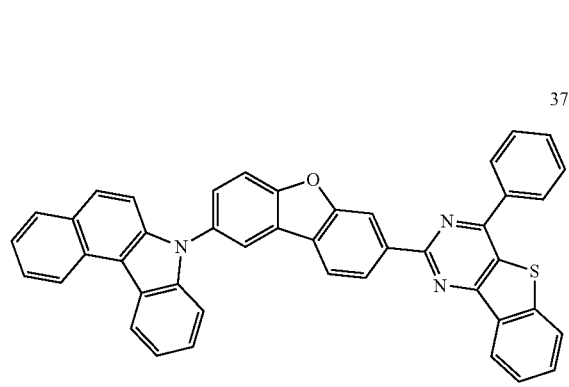
371
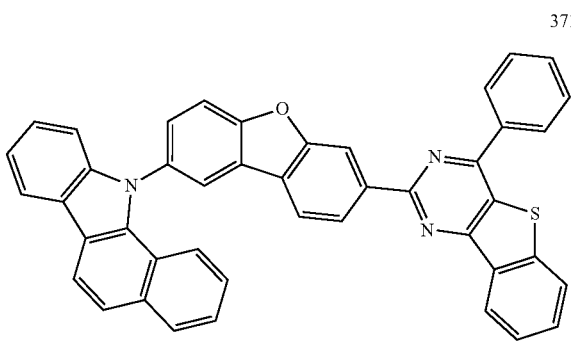
372
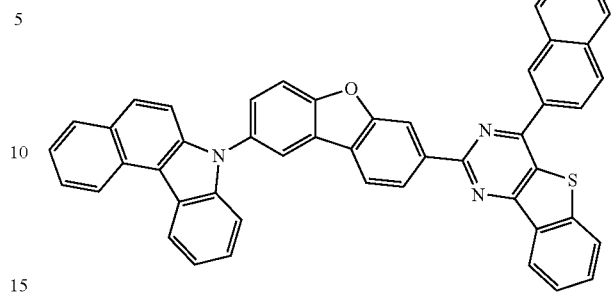
373
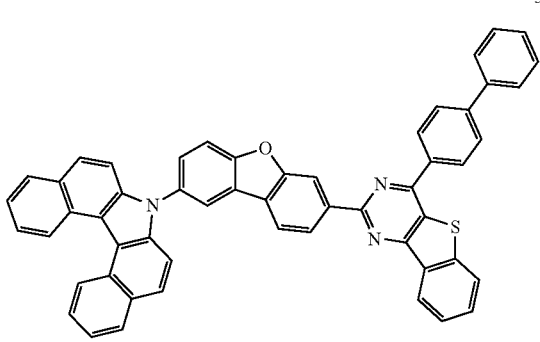
374
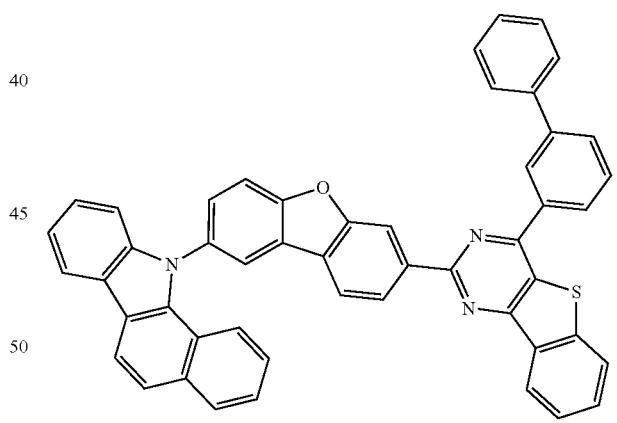
375
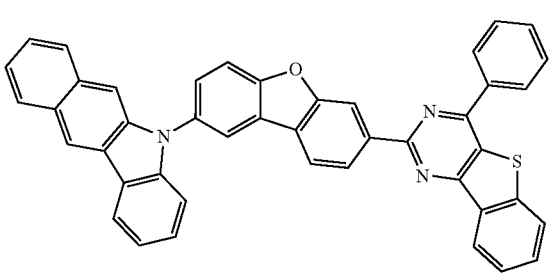

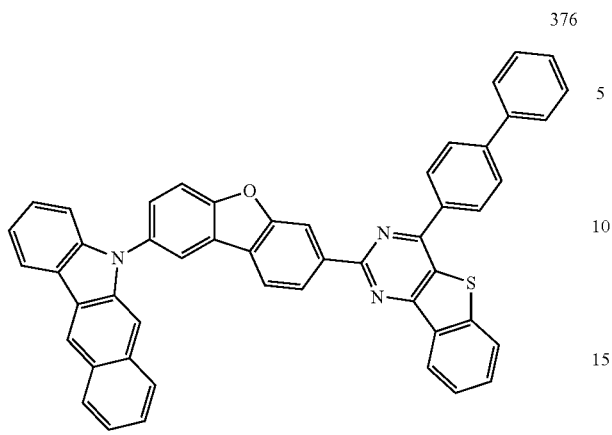

376

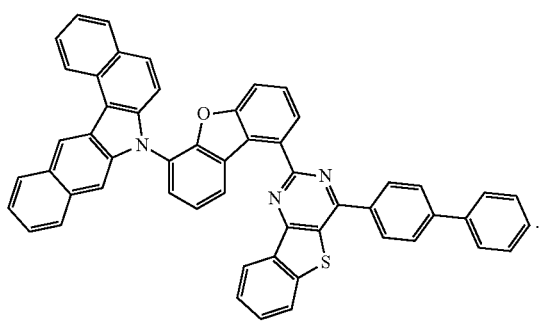

380

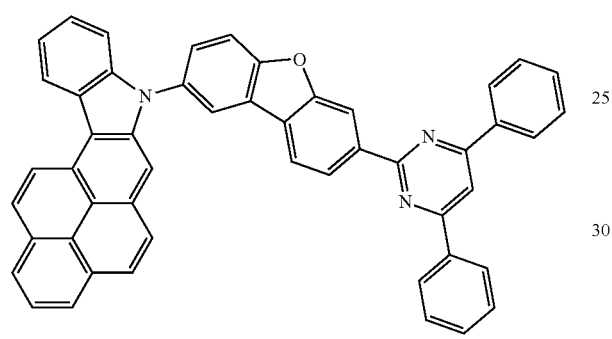

377

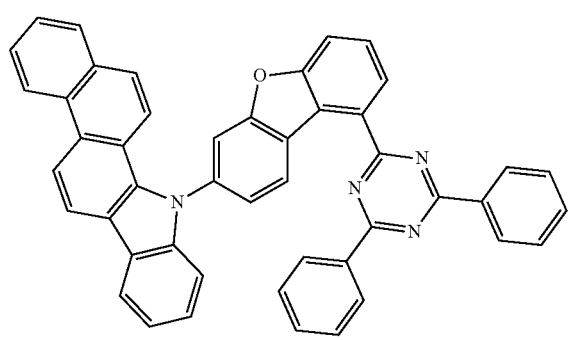

378

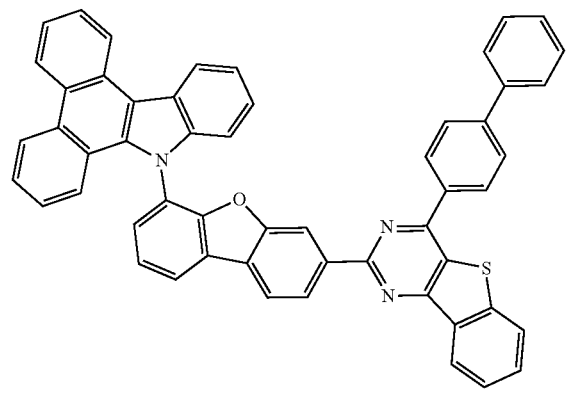

379

6. An organic light emitting device comprising:
a first electrode;
a second electrode provided opposite to the first electrode; and
one or more organic material layers provided between the first electrode and the second electrode,
wherein one or more layers of the organic material layers comprise one or more of the heterocyclic compound of claim 1.

7. The organic light emitting device of claim 6, wherein the organic material layer comprises a light emitting layer, and the light emitting layer comprises the heterocyclic compound.

8. The organic light emitting device of claim 6, wherein the organic material layer comprises a light emitting layer, the light emitting layer comprises a host material, and the host material comprises the heterocyclic compound.

9. The organic light emitting device of claim 6, wherein the organic material layer comprises an electron injection layer or an electron transfer layer, and the electron transfer layer or the electron injection layer comprises the heterocyclic compound.

10. The organic light emitting device of claim 6, wherein the organic material layer comprises an electron blocking layer or a hole blocking layer, and the electron blocking layer or the hole blocking layer comprises the heterocyclic compound.

11. The organic light emitting device of claim 6, further comprising one, two or more layers selected from the group consisting of a light emitting layer, a hole injection layer, a hole transfer layer, an electron injection layer, an electron transfer layer, an electron blocking layer and a hole blocking layer.

12. The organic light emitting device of claim 6, wherein the organic material layer further comprises a compound of the following Chemical Formula 14:

[Chemical Formula 14]

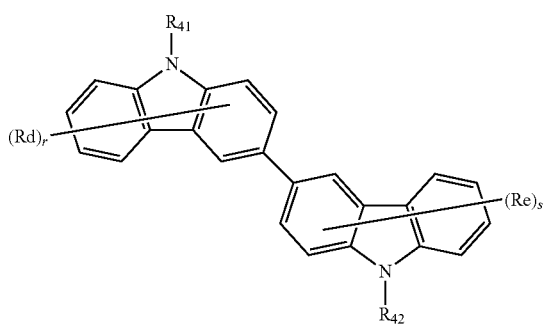

in Chemical Formula 14, $R_{41}$ and $R_{42}$ are the same as or different from each other, and each independently a substituted or unsubstituted aryl group; or a substituted or unsubstituted heteroaryl group;

Rd and Re are the same as or different from each other, and each independently hydrogen; or a substituted or unsubstituted aryl group; and r and s are an integer of 0 to 7.

13. A composition for an organic material layer of an organic light emitting device, the composition comprising the heterocyclic compound represented by any one of Chemical Formulae 2 to 5, 10 and 11 in claim 1 and a compound represented by the following Chemical Formula 14; or two types of the heterocyclic compound represented by any one of Chemical Formulae 2 to 5, 10 and 11:

[Chemical Formula 14]

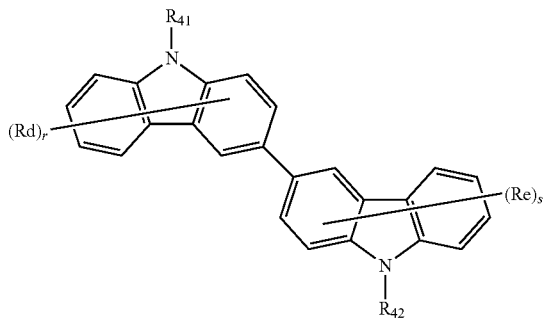

wherein, in Chemical Formula 14, $R_{41}$ and $R_{42}$ are the same as or different from each other, and each independently a substituted or unsubstituted aryl group; or a substituted or unsubstituted heteroaryl group;

Rd and Re are the same as or different from each other, and each independently hydrogen; or a substituted or unsubstituted aryl group; and r and s are an integer of 0 to 7.

14. The composition for an organic material layer of an organic light emitting device of claim 13, wherein a weight ratio of the heterocyclic compound represented by any one of Chemical Formulae 2 to 5, 10 and 11:the heterocyclic compound represented by any one of Chemical Formulae 2 to 5, 10 and 11 in the composition is from 1:10 to 10:1.

15. The composition for an organic material layer of an organic light emitting device of claim 13, wherein a weight ratio of the heterocyclic compound represented by any one of Chemical Formulae 2 to 5, 10 and 11:the heterocyclic compound represented by Chemical Formula 14 in the composition is from 1:10 to 10:1.

16. A method for manufacturing an organic light emitting device, the method comprising:

preparing a substrate;

forming a first electrode on the substrate;

forming one or more organic material layers on the first electrode; and forming a second electrode on the organic material layer, wherein the forming of organic material layers comprises forming one or more organic material layers using the composition for an organic material layer of claim 13.

17. The method for manufacturing an organic light emitting device of claim 16, wherein the forming of organic material layers is forming by premixing the heterocyclic compound of any one of Chemical Formulae 2 to 5, 10 and 11 and the heterocyclic compound of Chemical Formula 14 and using a thermal vacuum deposition method.

\* \* \* \* \*